(12) United States Patent
Armstrong et al.

(10) Patent No.: US 8,008,317 B2
(45) Date of Patent: *Aug. 30, 2011

(54) INHIBITORS OF AKT ACTIVTIY

(75) Inventors: Donna J. Armstrong, Harleysville, PA (US); Essa H. Hu, Camarillo, CA (US); Michael J. Kelly, III, Wayne, PA (US); Mark E. Layton, Harleysville, PA (US); Yiwei Li, San Diego, CA (US); Jun Liang, Palo Alto, CA (US); Kevin J. Rodzinak, Schwenksville, PA (US); Michael J. Rossi, Limerick, PA (US); Philip E. Sanderson, Valley Forge, PA (US); Jiabing Wang, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 930 days.

This patent is subject to a terminal disclaimer.

(21) Appl. No.: 11/921,352

(22) PCT Filed: Jun. 7, 2006

(86) PCT No.: PCT/US2006/022079
§ 371 (c)(1),
(2), (4) Date: Nov. 30, 2007

(87) PCT Pub. No.: WO2006/135627
PCT Pub. Date: Dec. 21, 2006

(65) Prior Publication Data
US 2010/0222321 A1    Sep. 2, 2010

Related U.S. Application Data

(60) Provisional application No. 60/689,726, filed on Jun. 10, 2005, provisional application No. 60/734,188, filed on Nov. 7, 2005.

(51) Int. Cl.
*A61K 31/437* (2006.01)
*A61K 31/4375* (2006.01)
*C07D 471/14* (2006.01)
*C07D 471/16* (2006.01)
(52) U.S. Cl. .......................... 514/290; 546/81
(58) Field of Classification Search ............ 546/81; 514/290
See application file for complete search history.

(56) References Cited

U.S. PATENT DOCUMENTS

| | | | |
|---|---|---|---|
| 7,034,026 B2 | 4/2006 | Barnett et al. |
| 7,576,209 B2 | 8/2009 | Kelly, III et al. |
| 2003/0199511 A1 | 10/2003 | Li et al. |
| 2005/0130977 A1 | 6/2005 | Lindsley et al. |
| 2005/0159422 A1 | 7/2005 | Lindsley et al. |
| 2005/0182256 A1 | 8/2005 | Duggan et al. |
| 2005/0222155 A1 | 10/2005 | Bilodeau et al. |
| 2005/0288294 A1 | 12/2005 | Duggan et al. |
| 2006/0270673 A1 | 11/2006 | Duggan et al. |
| 2007/0043001 A1 | 2/2007 | Bilodeau et al. |
| 2007/0082906 A1 | 4/2007 | Bilodeau et al. |
| 2007/0254901 A1 | 11/2007 | Bilodeau et al. |
| 2008/0009507 A1 | 1/2008 | Cosford et al. |
| 2008/0015212 A1 | 1/2008 | Barnett et al. |
| 2008/0280899 A1 | 11/2008 | Bilodeau et al. |

FOREIGN PATENT DOCUMENTS

| | | |
|---|---|---|
| EP | 1 679 308 | 7/2006 |
| WO | WO 2004/096130 | 11/2004 |
| WO | WO 2005/007099 | 1/2005 |
| WO | WO 2005/100356 | 10/2005 |
| WO | WO 2006/036395 | 4/2006 |
| WO | WO 2006/065601 | 6/2006 |
| WO | WO 2006/110638 | 10/2006 |
| WO | WO 2006/135627 | 12/2006 |

OTHER PUBLICATIONS

Notice of Allowance mailed Apr. 17, 2009 in U.S. Appl. No. 11/999,234, 5 pages.
Response to Non-Final Office Action mailed Nov. 12, 2008 in U.S. Appl. No. 11/999,234, 35 pages.
Non-Final Office Action mailed Sep. 16, 2008 in U.S. Appl. No. 11/999,234, 14 pages.
Basso, et al., Oncogene, vol. 21, pp. 1159-1166 (2002).
Frogne, et al., Endocrine-Related Cancer, vol. 12, pp. 599-614 (2005).
Koul, et al., Mol. Cancer Ther., vol. 5, pp. 637-644 (2006).
Beresford, et al., Journal of Interferon & Cytokine Res., vol. 21, pp. 313-322 (2001).
Altomare, et al., Oncogene, vol. 23, pp. 5853-5857 (2004).

*Primary Examiner* — Rita Desai
(74) *Attorney, Agent, or Firm* — Matthew A. Leff; David A. Mutard

(57) ABSTRACT

The instant invention provides for substituted naphthyridine compounds that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

4 Claims, No Drawings

US 8,008,317 B2

INHIBITORS OF AKT ACTIVTIY

PRIORITY CLAIM

This application is a §371 application of PCT/US06/022079 that was filed on Jun. 7, 2006, which claims priority from the U.S. Provisional Application Nos. 60/689,726, filed on Jun. 10, 2005, and 60/734,188, filed on Nov. 7, 2005, now expired.

BACKGROUND OF THE INVENTION

The present invention relates to substituted naphthyridine compounds which are inhibitors of the activity of one or more of the isoforms of the serine/threonine kinase, Akt (also known as PKB; hereinafter referred to as "Akt"). The present invention also relates to pharmaceutical compositions comprising such compounds and methods of using the instant compounds in the treatment of cancer.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt pathway appears important for regulating cell survival/cell death (Kulik et al. *Mol. Cell. Biol.* 17:1595-1606 (1997); Franke et al, *Cell*, 88:435-437 (1997); Kauffmann-Zeh et al. *Nature* 385:544-548 (1997) Hemmings *Science*, 275:628-630 (1997); Dudek et al., *Science*, 275:661-665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns(3,4,5)-P3), which in turn binds to, and promotes the activation of, the serine/threonine kinase Akt, which contains a pleckstrin homology (PH)-domain (Franke et al *Cell*, 81:727-736 (1995); Hemmings *Science*, 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt mutants abolish survival-promoting activities of these growth factors or cytokines. It has been previously disclosed that inhibitors of PI3K (LY294002 or wortmannin) blocked the activation of Akt by upstream kinases. In addition, introduction of constitutively active PI3K or Akt mutants promotes cell survival under conditions in which cells normally undergo apoptotic cell death (Kulik et al. 1997, Dudek et al. 1997).

Three members of the Akt subfamily of second-messenger regulated serine/threonine protein kinases have been identified and termed Akt1/PKBα, Akt2/PKBβ, and Akt3/PKBγ (hereinafter referred to as "Akt1", "Akt2" and "Akt3"), respectively. The isoforms are homologous, particularly in regions encoding the catalytic domains. Akts are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt. The current model of Akt activation proposes recruitment of the enzyme to the membrane by 3'-phosphorylated phosphoinositides, where phosphorylation of the regulatory sites of Akt by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1 occurs on two regulatory sites, $Thr^{308}$ in the catalytic domain activation loop and on $Ser^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2 and Akt3. The upstream kinase, which phosphorylates Akt at the activation loop site has been cloned and termed 3'-phosphoinositide dependent protein kinase 1 (PDK1). PDK1 phosphorylates not only Akt, but also p70 ribosomal S6 kinase, p90RSK, serum and glucocorticoid-regulated kinase (SGK), and protein kinase C. The upstream kinase phosphorylating the regulatory site of Akt near the carboxy terminus has not been identified yet, but recent reports imply a role for the integrin-linked kinase (ILK-1), a serine/threonine protein kinase, or autophosphorylation.

Analysis of Akt levels in human tumors showed that Akt2 is overexpressed in a significant number of ovarian (J. Q. Cheng et al. *Proc. Natl. Acad. Sci. U.S.A.* 89:9267-9271 (1992)) and pancreatic cancers (J. Q. Cheng et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. No specific PDK1 inhibitors have been disclosed. Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

It is an object of the instant invention to provide novel compounds that are inhibitors of Akt.

It is also an object of the present invention to provide pharmaceutical compositions that comprise the novel compounds that are inhibitors of Akt.

It is also an object of the present invention to provide a method for treating cancer that comprises administering such inhibitors of Akt activity.

SUMMARY OF THE INVENTION

The instant invention provides for substituted naphthyridine compounds that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

DETAILED DESCRIPTION OF THE INVENTION

The compounds of the instant invention are useful in the inhibition of the activity of the serine/threonine kinase Akt. In a first embodiment of this invention, the inhibitors of Akt activity are illustrated by the Formula A:

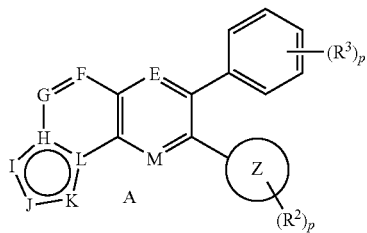

A wherein:

E, F, G, H, I, J, K, L and M are independently selected from: C or N, wherein each E, F, G, H, I, J, K, L and M is optionally substituted with $R^1$;

a is 0 or 1; b is 0 or 1; m is 0, 1 or 2; p is independently 0, 1, 2, 3, 4 or 5;

Ring Z is selected from: $(C_3-C_8)$cycloalkyl, aryl, heteroaryl and heterocyclyl;

$R^1$ is selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;

$R^2$ is independently selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, SH, $S(O)_mNR^7R^8$, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;

$R^3$ is independently selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one or more substituents selected from $R^6$;

$R^6$ is: $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_bNR^7R^8$, oxo, CHO, $(N=O)R^7R^8$, $S(O)_mNR^7R^8$, SH, $S(O)_m-(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one or more substituents selected from $R^{6a}$;

$R^{6a}$ is selected from: $(C=O)_aO_b(C_1-C_{10})$alkyl, $O_a(C_1-C_3)$ perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(R^b)_2$, $C(O)R^a$, $(C_0-C_6)$alkylene-$CO_2R^a$, C(O)H, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$;

$R^7$ and $R^8$ are independently selected from: H, $(C=O)_aO_b(C_1-C_{10})$alkyl, $(C=O)_aO_b(C_3-C_8)$cycloalkyl, $(C=O)_aO_b$-aryl, $(C=O)_aO_b$-heterocyclyl, $(C_2-C_{10})$alkenyl, $(C_2-C_{10})$alkynyl, SH, $SO_2R^a$, and $(C=O)_aNR_2^b$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{6a}$;

$R^a$ is $(C_1-C_6)$alkyl, $(C_3-C_6)$cycloalkyl, aryl, or heterocyclyl; and $R^b$ is independently: H, $(C_1-C_6)$alkyl, aryl, heterocyclyl, $(C_3-C_6)$cycloalkyl, $(C=O)_aO_b(C_1-C_6)$alkyl, or $S(O)_mR^a$;

or a pharmaceutically acceptable salt or a stereoisomer thereof.

In a second embodiment of this invention, the inhibitors of Akt activity are illustrated by the Formula B:

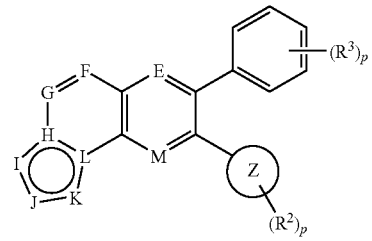

B wherein:

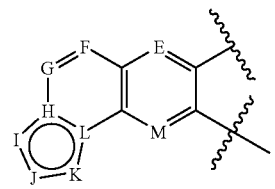

is selected from:
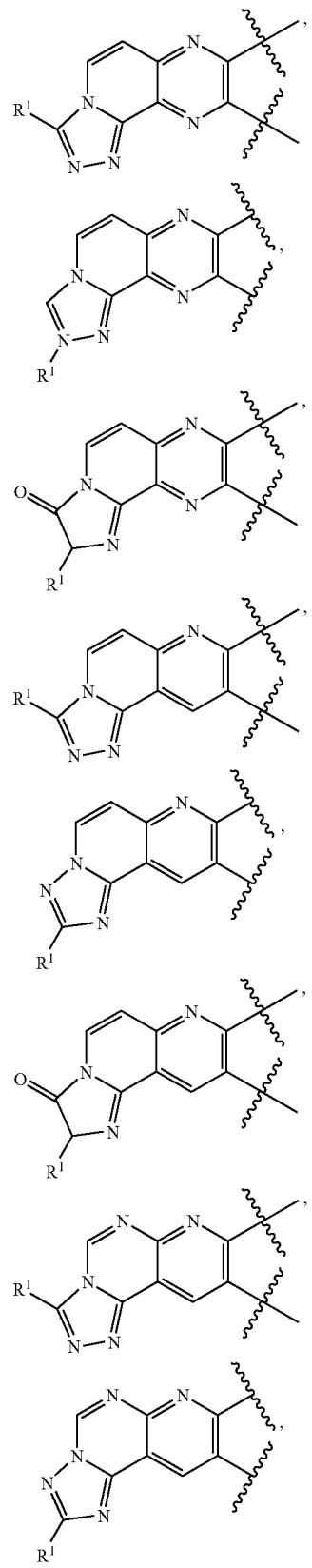
-continued
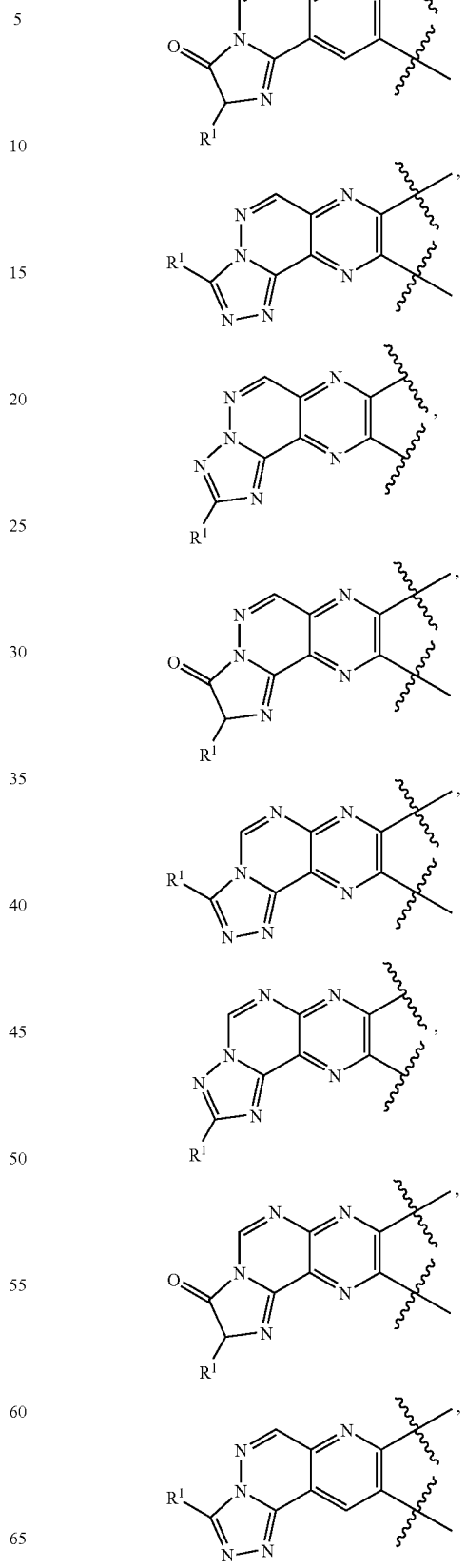

-continued

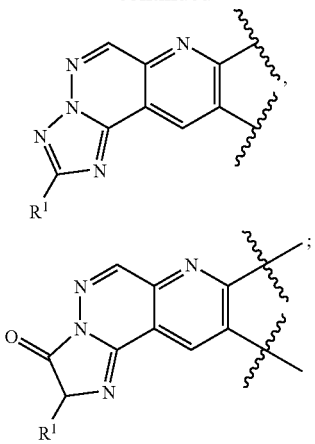

In a fourth embodiment the inhibitors of the instant invention are illustrated by the Formula D:

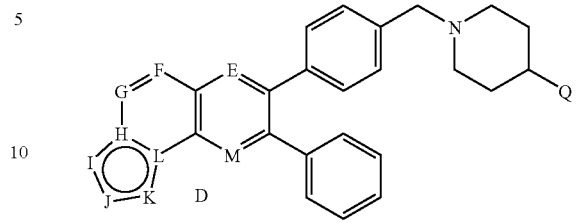

wherein:
all other substituents and variables are as defined in the third embodiment;
or a pharmaceutically acceptable salt or a stereoisomer thereof.

$R^1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;
and all other substituents and variables are as defined in the first embodiment;
or a pharmaceutically acceptable salt or a stereoisomer thereof.

In a third embodiment of this invention, the inhibitors of Akt activity are illustrated by the Formula C:

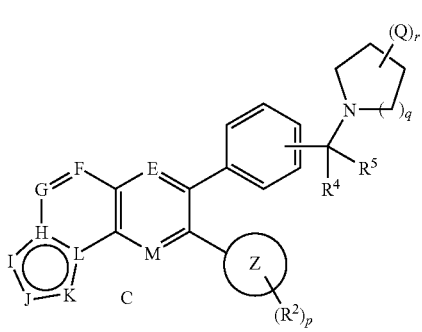

wherein:
q is 0, 1, 2, 3 or 4; r is 0, 1, 2, 3, 4 or 5; t is 2, 3, 4, 5 or 6;
Q is independently selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^{6a}$;
$R^4$ and $R^5$ are independently selected from: H, $(C_1-C_6)$alkyl and $(C_1-C_6)$perfluoroalkyl, or $R^4$ and $R^5$ are combined to form $—(CH_2)_t—$ wherein one of the carbon atoms is optionally replaced by a moiety selected from O, $S(O)_m$, $—N(R^b)C(O)—$, and $—N(COR^a)—$;
and all other substituents and variables are as defined in the second embodiment;
or a pharmaceutically acceptable salt or a stereoisomer thereof.

In a fifth embodiment the inhibitors of the instant invention are illustrated by the Formula E:

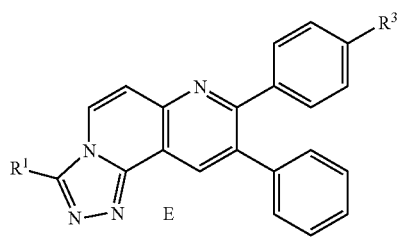

wherein:
a is 0 or 1; b is 0 or 1; m is 0, 1 or 2;
$R^1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;
$R^3$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one or more substituents selected from $R^6$;
$R^6$ is: $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_bNR^7R^8$, oxo, CHO, $(N=O)R^7R^8$, $S(O)_mNR^7R^8$, SH, $S(O)_m-(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one or more substituents selected from $R^{6a}$;
$R^{6a}$ is selected from: $(C=O)_aO_b(C_1-C_{10})$alkyl, $O_a(C_1-C_3)$perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(R^b)_2$, $C(O)R^a$, $(C_0-C_6)$alkylene-$CO_2R^a$, $C(O)H$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$;

$R^7$ and $R^8$ are independently selected from: H, $(C=O)_aO_b$ $(C_1-C_{10})$alkyl, $(C=O)_aO_b(C_3-C_8)$cycloalkyl, $(C=O)_aO_b$-aryl, $(C=O)_aO_b$-heterocyclyl, $(C_2-C_{10})$alkenyl, $(C_2-C_{10})$alkynyl, SH, $SO_2R^a$, and $(C=O)_aNR^b{}_2$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{6a}$;

$R^a$ is $(C_1-C_6)$alkyl, $(C_3-C_6)$cycloalkyl, aryl, or heterocyclyl; and $R^b$ is independently: H, $(C_1-C_6)$alkyl, aryl, heterocyclyl, $(C_3-C_6)$cycloalkyl, $(C=O)_aO_b(C_1-C_6)$alkyl, or $S(O)_mR^a$;

or a pharmaceutically acceptable salt or a stereoisomer thereof.

In a sixth embodiment the inhibitors of the instant invention are illustrated by the Formula F:

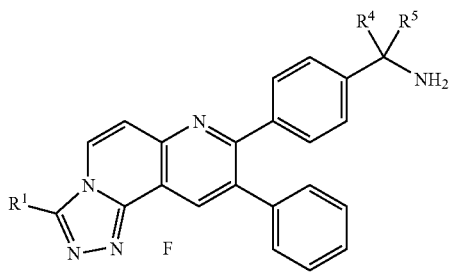

wherein:
$R^4$ and $R^5$ are independently: H and $(C_1-C_6)$alkyl, wherein said alkyl is optionally substituted with up to three substituents selected from: OH and halo; and wherein $R^4$ and $R^5$ may be joined to form a $(C_3-C_7)$cycloalkyl; and all other substituents and variables are as defined in the fifth embodiment;

or a pharmaceutically acceptable salt or a stereoisomer thereof.

In a seventh embodiment the inhibitors of the instant invention are illustrated by the Formula F:
wherein:
$R^1$ is selected from: H, $NH_2$, OH and $(C_1-C_6)$alkyl;
$R^4$ and $R^5$ are independently: H and $(C_1-C_6)$alkyl;
or a pharmaceutically acceptable salt or a stereoisomer thereof.

In an eighth embodiment the inhibitors of the instant invention are illustrated by the Formula G:

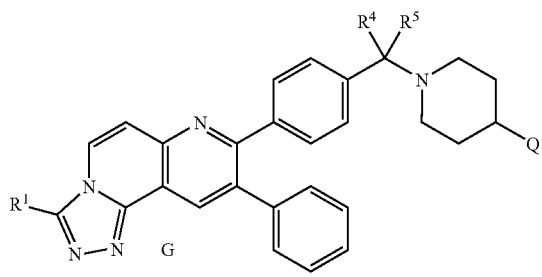

wherein:
a is 0 or 1; b is 0 or 1; m is 0, 1 or 2;
Q is selected from: heterocyclyl, which is optionally substituted with one or more substituents selected from $R^{6a}$;
$R^1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_m$ $NR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;

$R^4$ and $R^5$ are independently: H, $(C_1-C_6)$alkyl, $(C_1-C_6)$alkenyl, $(C_1-C_6)$alkynyl, wherein said alkyl is optionally substituted with up to three substituents selected from: OH and halo; and wherein $R^4$ and $R^5$ can be taken together to form a $(C_3-C_7)$cycloalkyl, wherein said cycloalkyl is optionally substituted with up to three substituents selected from $R^6$;

$R^6$ is: $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_bNR^7R^8$, oxo, CHO, $(N=O)R^7R^8$, $S(O)_mNR^7R^8$, SH, $S(O)_m-(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one or more substituents selected from $R^{6a}$;

$R^{6a}$ is selected from: $(C=O)_aO_b(C_1-C_{10})$alkyl, $O_a(C_1-C_3)$ perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(R^b)_2$, $C(O)R^a$, $(C_0-C_6)$alkylene-$CO_2R^a$, $C(O)H$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$ alkyl, oxo, and $N(R^b)_2$;

$R^7$ and $R^8$ are independently selected from: H, $(C=O)_aO_b$ $(C_1-C_{10})$alkyl, $(C=O)_aO_b(C_3-C_8)$cycloalkyl, $(C=O)_aO_b$-aryl, $(C=O)_aO_b$-heterocyclyl, $(C_2-C_{10})$alkenyl, $(C_2-C_{10})$ alkynyl, SH, $SO_2R^a$, and $(C=O)_aNR_2{}^b$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{6a}$;

$R^a$ is $(C_1-C_6)$alkyl, $(C_3-C_6)$cycloalkyl, aryl, or heterocyclyl; and $R^b$ is independently: H, $(C_1-C_6)$alkyl, aryl, heterocyclyl, $(C_3-C_6)$cycloalkyl, $(C=O)_aO_b(C_1-C_6)$alkyl, or $S(O)_mR^a$;

or a pharmaceutically acceptable salt or a stereoisomer thereof.

In a ninth embodiment the inhibitors of the instant invention are illustrated by the Formula H:

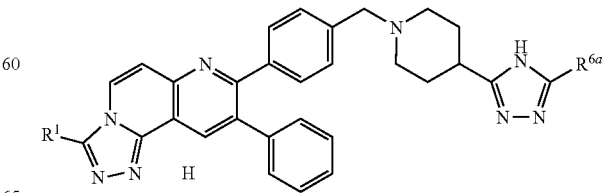

wherein:

R¹ is heterocyclyl, said heterocyclyl optionally substituted with from one to three substituents selected from: $(C_1-C_6)$ alkyl, OH, halo, and $NH_2$;

$R^{6a}$ is selected from:

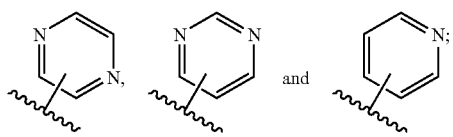

and or a pharmaceutically acceptable salt or a stereoisomer thereof.

In a tenth embodiment the inhibitors of the instant invention are illustrated by the Formula H:

wherein:
R¹ is selected from:

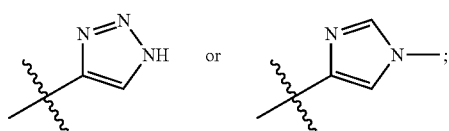

and all other substituents and variables are as defined in the ninth embodiment;

or a pharmaceutically acceptable salt or a stereoisomer thereof.

In an eleventh embodiment the inhibitors of the instant invention are illustrated by the Formula J:

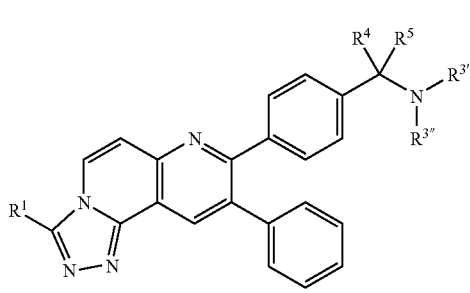

J wherein:

a is 0 or 1; b is 0 or 1; m is 0, 1 or 2;

R¹ is selected from: $CF^3$, H, oxo, $(C=O)_aO_b(C_1-C_{10})$alkyl, $(C=O)_aO_b$-aryl, $(C=O)_aO_b(C_2-C_{10})$alkenyl, $(C=O)_a O_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl is optionally substituted with one to six substituents selected from $R^6$;

$R^{3'}$ and $R^{3''}$ are independently selected from: $CF^3$, H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m$—$(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one to five substituents selected from $R^6$; or $R^{3'}$ and $R^{3''}$ can be taken together with the nitrogen to which they are attached to form a piperidine or pyrrolidine which may be optionally substituted with one to five substituents selected from $R^6$;

$R^4$ and $R^5$ are independently: H, $(C_1-C_6)$alkyl, $(C_1-C_6)$alkenyl, $(C_1-C_6)$alkynyl, wherein said alkyl is optionally substituted with up to three substituents selected from: OH and halo; and wherein $R^4$ and $R^5$ can be taken together to form a $(C_3-C_7)$cycloalkyl, wherein said cycloalkyl is optionally substituted with up to three substituents selected from $R^6$;

$R^6$ is: $CF^3$, $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_b$ $NR^7R^8$, oxo, CHO, $(N=O)R^7R^8$, $S(O)_mNR^7R^8$, SH, $S(O)_m$—$(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one to five substituents selected from $R^{6a}$;

$R^{6a}$ is selected from: $CF^3$, $(C=O)_aO_b(C_1-C_{10})$alkyl, $O_a(C_1-C_3)$perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(R^b)_2$, $(C=O)_aNR_2^b$, $C(O)R^a$, $(C_0-C_6)$alkylene-$CO_2R^a$, $C(O)H$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$;

$R^7$ and $R^8$ are independently selected from: $CF^3$, H, $(C=O)_aO_b(C_1-C_{10})$alkyl, $(C=O)_aO_b(C_3-C_8)$cycloalkyl, $(C=O)_aO_b$-aryl, $(C=O)_aO_b$-heterocyclyl, $(C_2-C_{10})$alkenyl, $(C_2-C_{10})$alkynyl, SH, $SO_2R^a$, and $(C=O)_aNR_2^b$, said alkyl, cycloalkyl, aryl, heterocylyl, alkenyl, and alkynyl is optionally substituted with one to five substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to six substituents selected from $R^{6a}$;

$R^a$ is $(C_1-C_6)$alkyl, $NR_2^b$, $(C_3-C_6)$cycloalkyl, aryl, or heterocyclyl; and $R^b$ is independently: H, $(C_1-C_6)$alkyl, $NH_2$, aryl, heterocyclyl, $(C_3-C_6)$cycloalkyl, $(C=O)_aO_b(C_1-C_6)$alkyl, or $S(O)_m R^a$;

or a pharmaceutically acceptable salt or a stereoisomer thereof.

Specific compounds of the instant invention include:

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-amine (1-4);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol (1-5);

9-phenyl-8-(4-{[4-(4-pyridin-2-yl-1H-imidazol-1-yl)piperidin-1-yl]methyl}phenyl)[1,2,4]triazolo[3,4-f]-1,6-naphthyridin-3-amine (1-6);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol (1-7);

3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-2);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-3);

3-(chloromethyl)-9-phenyl-8-(4-{[4-(4-pyridin-2-yl-1H-imidazol-1-yl)piperidin-1-yl]methyl}phenyl)[1,2,4]triazolo[3,4-f]-1,6-naphthyridine (2-4);

3-[(4-methylpiperazin-1-yl)methyl]-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-5); and 2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol (2-6);

or a pharmaceutically acceptable salt or stereoisomer thereof.

Examples of the compounds of the instant invention include TFA salts of the following compounds:

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-amine (1-4);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol (1-5);

9-phenyl-8-(4-{[4-(4-pyridin-2-yl-1H-imidazol-1-yl)piperidin-1-yl]methyl}phenyl)[1,2,4]triazolo[3,4-f]-1,6-naphthyridin-3-amine (1-6);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol (1-7);

3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-2);

9-phenyl-8-(4-{[4-(5-pyridin-2-yl-1H-1,2,4-triazol-3-yl)piperidin-1-yl]methyl}-phenyl)[1,2,4]triazolo[3,4-f]-1,6-naphthyridine (2-3);

3-(chloromethyl)-9-phenyl-8-(4-{[4-(4-pyridin-2-yl-1H-imidazol-1-yl)piperidin-1-yl]methyl}phenyl)[1,2,4]triazolo[3,4-f]-1,6-naphthyridine (2-4);

3-[(4-methylpiperazin-1-yl)methyl]-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-5);

2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol (2-6);

3-(3-methyl-1H-1,2,4-triazol-5-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-9);

3-imidazo[2,1-b][1,3]thiazol-6-yl-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine (9-10);

9-phenyl-8-(4-{[4-(5-pyridin-2-yl-4H-1,2,4-triazol-3-yl)piperidin-1-yl]methyl}phenyl)-3-[1,2,4]triazolo[1,5-a]pyrimidin-2-yl[1,2,4]triazolo[3,4-f]-1,6-naphthyridine (9-11);

3-imidazo[1,2-a]pyridin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-12);

3-(1-methyl-1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (13-3);

5-[({4-[3-(1-methyl-1H-imidazol-4-yl)-9-phenyl[1,2,4]triazolo[3,4-f]-1,6-naphthyridin-8-yl]benzyl}amino)methyl]pyridin-2-ol (13-8);

N¹,N¹,2,2-tetramethyl-N³-{4-[3-(1-methyl-1H-imidazol-4-yl)-9-phenyl[1,2,4]triazolo[3,4-f]-1,6-naphthyridin-8-yl]benzyl}propane-1,3-diamine (13-9);

N³-{4-[3-(hydroxymethyl)-9-phenyl[1,2,4]triazolo[3,4-f]-1,6-naphthyridin-8-yl]benzyl}-N¹-(4-hydroxyphenyl)-beta-alaninamide (14-6);

1-[4-(9-phenyl-3-pyridin-2-yl[1,2,4]triazolo[3,4-f]-1,6-naphthyridin-8-yl)phenyl]methanamine (16-13);

4-[3-(1-methyl-5-phenyl-1H-pyrazol-4-yl)-9-phenyl[1,2,4]triazolo[3,4-f]-1,6-naphthyridin-8-yl]benzylamine (16-41);

1-{4-[9-phenyl-3-(4,5,6,7-tetrahydro-1-benzothien-3-yl)[1,2,4]triazolo[3,4-f]-1,6-naphthyridin-8-yl]phenyl}methanamine (16-42);

1-{4-[3-(1-isopropyl-1H-pyrazol-4-yl)-9-phenyl[1,2,4]triazolo[3,4-f]-1,6-naphthyridin-8-yl]phenyl}methanamine (16-43);

1-{4-[9-phenyl-3-(1,4,5,6-tetrahydrocyclopenta[c]pyrazol-3-yl)[1,2,4]triazolo[3,4-f]-1,6-naphthyridin-8-yl]phenyl}methanamine (16-44);

1-[4-(3-cyclopropyl-9-phenyl[1,2,4]triazolo[3,4-f]-1,6-naphthyridin-8-yl)phenyl]methanamine (16-48);

1-{4-[9-phenyl-3-(trifluoromethyl)[1,2,4]triazolo[3,4-f]-1,6-naphthyridin-8-yl]phenyl}methanamine (16-49);

1-{4-[3-(5-methyl-1H-pyrazol-3-yl)-9-phenyl[1,2,4]triazolo[3,4-f]-1,6-naphthyridin-8-yl]phenyl}methanamine (16-50);

1-{4-[3-(1,5-dimethyl-1H-pyrazol-3-yl)-9-phenyl[1,2,4]triazolo[3,4-f]-1,6-naphthyridin-8-yl]phenyl}methanamine (16-51);

4-[3-(1H-indol-2-yl)-9-phenyl[1,2,4]triazolo[3,4-f]-1,6-naphthyridin-8-yl]benzylaminen (16-52);

1-{-4-[3-(1-methyl-1H-imidazol-2-yl)-9-phenyl[1,2,4]triazolo[3,4-f]-1,6-naphthyridin-8-yl]phenyl}methanamine (16-53);

1-{4-[3-(3-methyl-2H-3lambda~5~-imidazol-4-yl)-9-phenyl[1,2,4]triazolo[3,4-f]-1,6-naphthyridin-8-yl]phenyl}methanamine (16-54);

4-[3-(6-chloroimidazo[1,2-a]pyridin-2-yl)-9-phenyl[1,2,4]triazolo[3,4-f]-1,6-naphthyridin-8-yl]benzylamine (16-55);

1-{4-[3-(1H-benzimidazol-2-yl)-9-phenyl[1,2,4]triazolo[3,4-f]-1,6-naphthyridin-8-yl]phenyl}methanamine (16-56);

4-[3-(5-cyclopropyl-4H-pyrazol-3-yl)-9-phenyl[1,2,4]triazolo[3,4-f]-1,6-naphthyridin-8-yl]benzylamine (16-57);

1-{4-[9-phenyl-3-(4,5,6,7-tetrahydro-1H-indazol-3-yl)[1,2,4]triazolo[3,4-f]-1,6-naphthyridin-8-yl]phenyl}methanamine (16-58);

4-[9-phenyl-3-(3-phenyl-1H-pyrazol-5-yl)[1,2,4]triazolo[3,4-f]-1,6-naphthyridin-8-yl]benzylamine (16-59);

1-(4-{9-phenyl-3-[3-(trifluoromethyl)-1H-pyrazol-5-yl][1,2,4]triazolo[3,4-f]-1,6-naphthyridin-8-yl}phenyl)methanamine (16-60);

1-[4-(9-phenyl-3-pyrazolo[1,5-a]pyrimidin-2-yl[1,2,4]triazolo[3,4-f]-1,6-naphthyridin-8-yl)phenyl]methanamine (16-61);

1-{4-[3-(1-benzyl-1H-pyrazol-4-yl)-9-phenyl[1,2,4]triazolo[3,4-f]-1,6-naphthyridin-8-yl]phenyl}methanamine (16-62);

1-[4-(9-phenyl-3-[1,2,4]triazolo[1,5-a]pyrimidin-2-yl[1,2,4]triazolo[3,4-f]-1,6-naphthyridin-8-yl)phenyl]methanamine (16-63);

4-[9-phenyl-3-(1-phenyl-1H-pyrazol-4-yl)[1,2,4]triazolo[3,4-f]-1,6-naphthyridin-8-yl]benzylamine (16-64);

1-{4-[9-phenyl-3-(4,5,6,7-tetrahydro-2-benzothien-1-yl)[1,2,4]triazolo[3,4-f]-1,6-naphthyridin-8-yl]phenyl}methanamine (16-65);

1-{8-[4-(aminomethyl)phenyl]-9-phenyl[1,2,4]triazolo[3,4-f]-1,6-naphthyridin-3-yl}ethane-1,2-diol (16-68);

4-{8-[4-(aminomethyl)phenyl]-9-phenyl[1,2,4]triazolo[3,4-f]-1,6-naphthyridin-3-yl}imidazolidin-2-one (16-69);
(2R)-2-amino-2-{8-[4-(aminomethyl)phenyl]-9-phenyl[1,2,4]triazolo[3,4-f]-1,6-naphthyridin-3-yl}ethanol (16-70);
(2R)-2-{8-[4-(aminomethyl)phenyl]-9-phenyl[1,2,4]triazolo[3,4-f]-1,6-naphthyridin-3-yl}-2-(methylamino)ethanol (16-71);
1-[4-(3-ethyl-9-phenyl[1,2,4]triazolo[3,4-f]-1,6-naphthyridin-8-yl)phenyl]methanamine (17-6);
1-[4-(9-phenyl-3-propyl[1,2,4]triazolo[3,4-f]-1,6-naphthyridin-8-yl)phenyl]methanamine (17-7);
1-[4-(3-Methyl-9-phenyl[1,2,4]triazolo[3,4-f]-1,6-naphthyridin-8-yl)phenyl]cyclopropanamine (33-5);
1-{4-[3-(1-methyl-1H-imidazol-4-yl)-9-phenyl[1,2,4]triazolo[3,4-f]-1,6-naphthyridin-8-yl]phenyl}cyclo propanamine (33-6);
1-[4-(9-phenyl-3-[1,2,4] triazolo[1,5-a]pyrimidin-2-yl[1,2,4]triazolo[3,4-f]-1,6-naphthyridin-8-yl)phenyl]cyclopropanamine (33-7);
N-[4-(3-methyl-9-phenyl[1,2,4]triazolo[3,4-f]-1,6-naphthyridin-8-yl)benzyl]-5-pyridin-4-yl-2-furamide (39-2);
(3-methyl-9-phenyl-8-(4-{1-[(pyridin-3-ylacetyl)amino]cyclopropyl}-phenyl)[1,2,4]triazolo[3,4-f]-1,6-naphthyridine (39-43);
3-methyl-9-phenyl-8-(4-{1-[(quinolin-3-yl carbonyl)amino]cyclopropyl}phenyl)[1,2,4]triazolo[3,4-f]-1,6-naphthyridine (39-44);
3-(1-methyl-1H-imidazol-4-yl)-9-phenyl-8-(4-{1-[(pyridin-3-ylacetyl)amino]cyclopropyl}phenyl)[1,2,4]triazolo[3,4-f]-1,6-naphthyridine (39-46);
1-[4-(9-ethyl-2-phenyl[1,2,4]triazolo[4',3':1,6]pyrido[2,3-b]pyrazin-3-yl)phenyl]cyclopropanamine (42-6); and
1-[4-(9-ethyl-3-phenyl[1,2,4]triazolo[4',3':1,6]pyrido[2,3-b]pyrazin-2-yl)phenyl]cyclopropanamine (42-7);
or a stereoisomer thereof.

Examples of the compounds of the instant invention include formic acid salts of the following compounds:
9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-amine (1-4); and
9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol (1-5);
or a stereoisomer thereof.

Specific compounds of the instant invention include:
9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-amine (1-4);
9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol (1-5);
9-phenyl-8-(4-{[4-(4-pyridin-2-yl-1H-imidazol-1-yl)piperidin-1-yl]methyl}phenyl)[1,2,4]triazolo[3,4-f]-1,6-naphthyridin-3-amine (1-6);
9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol (1-7);
3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-2);
9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-3);
3-(chloromethyl)-9-phenyl-8-(4-{[4-(4-pyridin-2-yl-1H-imidazol-1-yl)piperidin-1-yl]methyl}phenyl)[1,2,4]triazolo[3,4-f]-1,6-naphthyridine (2-4);
3-[(4-methylpiperazin-1-yl)methyl]-9-phenyl-8-(4-{[4-(5-pyridin-2-yl-1H-1,2,4-triazol-3-yl)piperidin-1-yl]methyl}-phenyl)[1,2,4]triazolo[3,4-f]-1,6-naphthyridine (2-5);
2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol (2-6);
8-(4-Aminomethyl-phenyl)-9-phenyl-[1,2,4]triazolo[3,4-f][1,6]naphthyridin-3-ol (3-8);
1-[4-(9-Phenyl[1,2,4]triazolo[3,4-f]-1,6-naphthyridin-8-yl)phenyl]methanamine (4-3);
4-(3-Methyl-9-phenyl-[1,2,4]triazolo[3,4-f][1,6]naphthyridin-8-yl)-benzylamine (5-3);
8-[4-(Aminomethyl)phenyl]-9-phenyl[1,2,4]triazolo[3,4-f]-1,6-naphthyridin-3-amine (6-2);
1-[4-(9-Phenyl[1,2,4]triazolo[3,4-f]-1,6-naphthyridin-8-yl)phenyl]ethanamine (7-4); and
9-Phenyl-8-{-4-[4-(5-pyridin-2-yl-4H-[1,2,4]triazol-3-yl)-piperidin-1-ylmethyl]-phenyl}-[1,2,4]triazolo[3,4-f][1,6]naphthyridine (8-10)
or a pharmaceutically acceptable salt or stereoisomer thereof.

Examples of the compounds of the instant invention include HCl salts of the following compounds:
8-(4-Aminomethyl-phenyl)-9-phenyl-[1,2,4]triazolo[3,4-f][1,6]naphthyridin-3-ol (3-8);
1-[4-(9-Phenyl[1,2,4]triazolo[3,4-f]-1,6-naphthyridin-8-yl)phenyl]methanamine (4-3);
4-(3-Methyl-9-phenyl-[1,2,4]triazolo[3,4-f][1,6]naphthyridin-8-yl)-benzylamine (5-3);
8-[4-(Aminomethyl)phenyl]-9-phenyl[1,2,4]triazolo[3,4-f]-1,6-naphthyridin-3-amine (6-2); and
1-[4-(9-Phenyl[1,2,4]triazolo[3,4-f]-1,6-naphthyridin-8-yl)phenyl]ethanamine (7-4);
3-(1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-5);
tert-butyl[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]methylcarbamate (9-6);
[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanol (9-7);
5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]-2,4-dihydro-3H-1,2,4-triazol-3-one (9-8);
9-phenyl-8-(4-{[4-(5-pyridin-2-yl-4H-1,2,4-triazol-3-yl)piperidin-1-yl]methyl}phenyl)-3-(1H-1,2,4-triazol-5-yl)[1,2,4]triazolo[3,4-f]-1,6-naphthyridine (9-13);
3-(1H-benzimidazol-6-yl)-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine (9-14);
3-(1,5-dimethyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-15);
3-imidazo[1,2-a]pyrimidin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-16);
5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine (9-17);
9-phenyl-3-pyrazolo[1,5-a]pyrimidin-3-yl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-18);

3-(5-methyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-19);

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine (9-20);

4-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-21);

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-22);

2-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-23);

1-{4-[3-(5-oxo-4,5-dihydro-1H-1,2,4-triazol-3-yl)-9-phenyl[1,2,4]triazolo[3,4-f]-1,6-naphthyridin-8-yl]benzyl}piperidine-4-carboxamide (9-24);

1-[4-(3-imidazo[1,2-a]pyridin-2-yl-9-phenyl[1,2,4]triazolo[3,4-f]-1,6-naphthyridin-8-yl)benzyl]piperidine-4-carboxamide (9-25);

3-(1-methyl-1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (13-3);

3-(1-methyl-1H-imidazol-4-yl)-9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (13-4);

N-[2-(4-methyl-1H-imidazol-2-yl)ethyl]-N-{4-[3-(1-methyl-1H-imidazol-4-yl)-9-phenyl[1,2,4]triazolo[3,4-f]-1,6-naphthyridin-8-yl]benzyl}amine (13-5);

$N^1$-(2-hydroxyphenyl)-$N^3$-{4-[3-(1-methyl-1H-imidazol-4-yl)-9-phenyl[1,2,4]triazolo[3,4-f]-1,6-naphthyridin-8-yl]benzyl}-beta-alaninamide (13-6);

1-{4-[3-(1-methyl-1H-imidazol-4-yl)-9-phenyl[1,2,4]triazolo[3,4-f]-1,6-naphthyridin-8-yl]benzyl}piperidine-4-carboxamide (13-7);

3-hydroxy-2,2-dimethyl-N-[4-(3-methyl-9-phenyl[1,2,4]triazolo[3,4-f]-1,6-naphthyridin-8-yl)benzyl]propan-1-amine (13-10);

2-fluoro-3-hydroxy-N-[4-(3-methyl-9-phenyl[1,2,4]triazolo[3,4-f]-1,6-naphthyridin-8-yl)benzyl]propan-1-amine (13-11);

2,2-difluoro-3-hydroxy-N-[4-(3-methyl-9-phenyl[1,2,4]triazolo[3,4-f]-1,6-naphthyridin-8-yl)benzyl]propan-1-amine (13-12);

2,3-dihydroxy-N-[4-(3-methyl-9-phenyl[1,2,4]triazolo[3,4-f]-1,6-naphthyridin-8-yl)benzyl]propan-1-amine (13-13);

4-hydroxy-N-[4-(3-methyl-9-phenyl[1,2,4]triazolo[3,4-f]-1,6-naphthyridin-8-yl)benzyl]cyclohexanamine (13-14);

4-hydroxy-N-[4-(3-methyl-9-phenyl[1,2,4]triazolo[3,4-f]-1,6-naphthyridin-8-yl)benzyl]cyclohexanamine (13-15);

3-hydroxy-2,2-dimethyl-N-{4-[3-(1-methyl-1H-imidazol-4-yl)-9-phenyl[1,2,4]triazolo[3,4-f]-1,6-naphthyridin-8-yl]benzyl}propan-1-amine (13-16);

3-hydroxy-2,2-dimethyl-N-[4-(9-phenyl-3-[1,2,4]triazolo[1,5-a]pyrimidin-2-yl[1,2,4]triazolo[3,4-f]-1,6-naphthyridin-8-yl)benzyl]propan-1-amine (13-17);

3-hydroxy-2,2-dimethyl-N-[4-(9-phenyl-3-pyrazolo[1,5-a]pyrimidin-2-yl[1,2,4]triazolo[3,4-f]-1,6-naphthyridin-8-yl)benzyl]propan-1-amine (13-18);

3-hydroxy-2,2-dimethyl-N-{4-[9-phenyl-3-(1H-1,2,3-triazol-4-yl) [1,2,4]triazolo[3,4-f]-1,6-naphthyridin-8-yl]benzyl}propan-1-amine (13-19);

N-{4-[3-(ammoniomethyl)-9-phenyl[1,2,4]triazolo[3,4-f]-1,6-naphthyridin-8-yl]benzyl}-3-hydroxy-2,2-dimethylpropan-1-amine (13-21);

$N^3$-{4-[3-(hydroxymethyl)-9-phenyl[1,2,4]triazolo[3,4-f]-1,6-naphthyridin-8-yl]benzyl}-$N^1$-(2-hydroxyphenyl)-beta-alaninamide (14-4);

(8-{4-[(cyclohexylamino)methyl]phenyl}-9-phenyl[1,2,4]triazolo[3,4-f]-1,6-naphthyridin-3-yl)methanol (14-5);

[9-phenyl-8-(4-{[4-(5-pyridin-3-yl-4H-1,2,4-triazol-3-yl)piperidin-1-yl]methyl}phenyl)[1,2,4]triazolo[3,4-f]-1,6-naphthyridin-3-yl]methanol (14-7);

1-{4-[3-(hydroxymethyl)-9-phenyl[1,2,4]triazolo[3,4-f]-1,6-naphthyridin-8-yl]benzyl}piperidine-4-carboxamide (14-8);

1-{4-[3-(1-oxidopyridin-3-yl)-9-phenyl[1,2,4]triazolo[3,4-f]-1,6-naphthyridin-8-yl]phenyl}methanamine (16-4);

1-[4-(3,9-diphenyl[1,2,4]triazolo[3,4-f]-1,6-naphthyridin-8-yl)phenyl]methanamine (16-5);

1-{4-[3-(4-fluorophenyl)-9-phenyl[1,2,4]triazolo[3,4-f]-1,6-naphthyridin-8-yl]phenyl}methanamine (16-6);

4-{8-[4-(aminomethyl)phenyl]-9-phenyl[1,2,4]triazolo[3,4-f]-1,6-naphthyridin-3-yl}benzonitrile (16-7);

4-(9-phenyl-3-pyrimidin-4-yl[1,2,4]triazolo[3,4-f]-1,6-naphthyridin-8-yl)benzylamine (16-8);

1-{4-[3-(1-oxidopyridin-2-yl)-9-phenyl[1,2,4]triazolo[3,4-f]-1,6-naphthyridin-8-yl]phenyl}methanamine (16-9);

5-{8-[4-(aminomethyl)phenyl]-9-phenyl[1,2,4]triazolo[3,4-f]-1,6-naphthyridin-3-yl}yridine-2-ol (16-10);

1-[4-(9-phenyl-3-pyridin-3-yl[1,2,4]triazolo[3,4-f]-1,6-naphthyridin-8-yl)phenyl]methanamine (16-11);

4-(9-phenyl-3-pyrimidin-2-yl[1,2,4]triazolo[3,4-f]-1,6-naphthyridin-8-yl)benzylamine (16-12);

1-[4-(9-phenyl-3-pyrazin-2-yl[1,2,4]triazolo[3,4-f]-1,6-naphthyridin-8-yl)phenyl]methanamine (16-14);

1-{4-[9-phenyl-3-(1H-1,2,4-triazol-3-yl)[1,2,4]triazolo[3,4-f]-1,6-naphthyridin-8-yl]phenyl}methanamine (16-15);

1-{4-[9-phenyl-3-(1,3-thiazol-4-yl)[1,2,4]triazolo[3,4-f]-1,6-naphthyridin-8-yl]phenyl}methanamine (16-16);

1-{4-[9-phenyl-3-(1H-pyrazol-4-yl)[1,2,4]triazolo[3,4-f]-1,6-naphthyridin-8-yl]phenyl}methanamine (16-17);

1-{4-[3-(3-methyl-1H-pyrazol-4-yl)-9-phenyl[1,2,4]triazolo[3,4-f]-1,6-naphthyridin-8-yl]phenyl}methanamine (16-18);

1-{-4-[3-(3-methyl-1H-1,2,4-triazol-5-yl)-9-phenyl[1,2,4]triazolo[3,4-f]-1,6-naphthyridin-8-yl]phenyl}methanamine (16-19);

1-{4-[3-(1-methyl-1H-pyrazol-4-yl)-9-phenyl[1,2,4]triazolo[3,4-f]-1,6-naphthyridin-8-yl]phenyl}methanamine (16-20);

1-{4-[9-phenyl-3-(1,2,5-thiadiazol-3-yl)[1,2,4]triazolo[3,4-f]-1,6-naphthyridin-8-yl]phenyl}methanamine (16-21);

1-{4-[9-phenyl-3-(1,2,3-thiadiazol-4-yl)[1,2,4]triazolo[3,4-f]-1,6-naphthyridin-8-yl]phenyl}methanamine (16-22);

1-[4-(9-phenyl-3-pyrazolo[1,5-a]pyrimidin-3-yl[1,2,4]triazolo[3,4-f]-1,6-naphthyridin-8-yl)phenyl]methanamine (16-23);

{8-[4-(aminomethyl)phenyl]-9-phenyl[1,2,4]triazolo[3,4-f]-1,6-naphthyridin-3-yl}methanamine (16-24);

{8-[4-(aminomethyl)phenyl]-9-phenyl[1,2,4]triazolo[3,4-f]-1,6-naphthyridin-3-yl}methanol (16-25);

1-{4-[9-phenyl-3-(2,2,2-trifluoroethyl)[1,2,4]triazolo[3,4-f]-1,6-naphthyridin-8-yl]phenyl}methanamine (16-26);

1-{4-[9-phenyl-3-(1H-tetraazol-1-ylmethyl)[1,2,4]triazolo[3,4-f]-1,6-naphthyridin-8-yl]phenyl}methanamine (16-27);

8-[4-(aminomethyl)phenyl]-9-phenyl[1,2,4]triazolo[3,4-f]-1,6-naphthyridine-3-carboxamide (16-28);

1-{4-[3-(1H-imidazol-1-ylmethyl)-9-phenyl[1,2,4]triazolo[3,4-f]-1,6-naphthyridin-8-yl]phenyl}methanamine (16-29);
1-(4-{3-[(methylsulfonyl)methyl]-9-phenyl[1,2,4]triazolo[3,4-f]-1,6-naphthyridin-8-yl}phenyl)methanamine (16-30);
{8-[4-(aminomethyl)phenyl]-9-phenyl[1,2,4]triazolo[3,4-f]-1,6-naphthyridin-3-yl}acetonitrile (16-31);
2-{8-[4-(aminomethyl)phenyl]-9-phenyl[1,2,4]triazolo[3,4-f]-1,6-naphthyridin-3-yl}ethanol (16-32);
N-({8-[4-(aminomethyl)phenyl]-9-phenyl[1,2,4]triazolo[3,4-f]-1,6-naphthyridin-3-yl}methyl)acetamide (16-33);
1-[4-(3-imidazo[1,2-a]pyridin-2-yl-9-phenyl[1,2,4]triazolo[3,4-f]-1,6-naphthyridin-8-yl)phenyl]methanamine (16-36);
1-[4-(3-imidazo[2,1-b][1,3]thiazol-6-yl-9-phenyl[1,2,4]triazolo[3,4-f]-1,6-naphthyridin-8-yl)phenyl]methanamine (16-38);
1-{4-[3-(1-methyl-1H-imidazol-4-yl)-9-phenyl[1,2,4]triazolo[3,4-f]-1,6-naphthyridin-8-yl]phenyl}methanamine (16-40);
1-(4-{9-phenyl-3-[(2R)-pyrrolidin-2-yl][1,2,4]triazolo[3,4-f]-1,6-naphthyridin-8-yl}phenyl)methanamine (16-44);
1-(4-{9-phenyl-3-[(2S)-pyrrolidin-2-yl][1,2,4]triazolo[3,4-f]-1,6-naphthyridin-8-yl}phenyl)methanamine (16-45);
4-[3-(1-aminoethyl)-9-phenyl[1,2,4]triazolo[3,4-f]-1,6-naphthyridin-8-yl]benzylamine (16-46);
1-{4-[3-(1H-imidazol-2-yl)-9-phenyl[1,2,4]triazolo[3,4-f]-1,6-naphthyridin-8-yl]phenyl}methanamine (16-47);
1-{4-[9-phenyl-3-(5,6,7,8-tetrahydroimidazo-[1,2-a]pyridin-2-yl)[1,2,4]triazolo[3,4-f]-1,6-naphthyridin-8-yl]phenyl}methanamine (16-66);
2-{8-[4-(aminomethyl)phenyl]-9-phenyl[1,2,4]triazolo[3,4-f]-1,6-naphthyridin-3-yl}propan-2-amine (16-67);
1-{4-[3-(5-ethylisoxazol-3-yl)-9-phenyl[1,2,4]triazolo[3,4-f]-1,6-naphthyridin-8-yl]phenyl}methanamine (16-72);
5-{8-[4-(aminomethyl)phenyl]-9-phenyl[1,2,4]triazolo[3,4-f]-1,6-naphthyridin-3-yl}-2,4-dihydro-3H-1,2,4-triazol-3-one (16-73);
6-{8-[4-(aminomethyl)phenyl]-9-phenyl[1,2,4]triazolo[3,4-f]-1,6-naphthyridin-3-yl}-4,5-dihydropyridazin-3(2H)-one (16-74);
6-{8-[4-(aminomethyl)phenyl]-9-phenyl[1,2,4]triazolo[3,4-f]-1,6-naphthyridin-3-yl}pyridazin-3(2H)-one (16-75);
N-(4-{8-[4-(aminomethyl)phenyl]-9-phenyl[1,2,4]triazolo[3,4-f]-1,6-naphthyridin-3-yl}phenyl)acetamide (16-76);
1-{4-[3-(4-phenoxyphenyl)-9-phenyl[1,2,4]triazolo[3,4-f]-1,6-naphthyridin-8-yl]phenyl}methanamine (16-77);
1-[4-(3-(1H-benzimidazol-5-yl)-9-phenyl[1,2,4]triazolo[3,4-f]-1,6-naphthyridin-8-yl)phenyl]methanamine (16-78);
(4-{8-[4-(aminomethyl)phenyl]-9-phenyl[1,2,4]triazolo[3,4-f]-1,6-naphthyridin-3-yl}phenyl)methanol (16-79);
4-[3-(4-cyclohexylphenyl)-9-phenyl[1,2,4]triazolo[3,4-f]-1,6-naphthyridin-8-yl]benzylamine (16-80);
4-{8-[4-(aminomethyl)phenyl]-9-phenyl[1,2,4]triazolo[3,4-f]-1,6-naphthyridin-3-yl}-1,3-dihydro-2H-imidazol-2-one (16-81);
1-{-4-[3-(4-methyl-1H-imidazol-5-yl)-9-phenyl[1,2,4]triazolo[3,4-f]-1,6-naphthyridin-8-yl]phenyl}methanamine (16-82);
4-[9-phenyl-3-(1-propyl-1H-imidazol-4-yl)[1,2,4]triazolo[3,4-f]-1,6-naphthyridin-8-yl]benzylamine (16-83);
1-{4-[3-(1-isopropyl-1H-imidazol-4-yl)-9-phenyl[1,2,4]triazolo[3,4-f]-1,6-naphthyridin-8-yl]phenyl}methanamine (16-84);
1-{4-[3-(1-butyl-1H-imidazol-4-yl)-9-phenyl[1,2,4]triazolo[3,4-f]-1,6-naphthyridin-8-yl]phenyl}methanamine (16-85);
1-[4-(3-imidazo[1,2-a]pyrimidin-2-yl-9-phenyl[1,2,4]triazolo[3,4-f]-1,6-naphthyridin-8-yl)phenyl]methanamine (16-86);
1-(6-methoxypyridin-3-yl)-N-[4-(3-methyl-9-phenyl[1,2,4]triazolo[3,4-f]-1,6-naphthyridin-8-yl)benzyl]methanamine (17-4);
N-[(2-methoxypyrimidin-5-yl)methyl]-N-[4-(3-methyl-9-phenyl[1,2,4]triazolo[3,4-f]-1,6-naphthyridin-8-yl)benzyl]amine (17-5);
9-phenyl-3-(1H-1,2,3-triazol-4-yl)-8-(4-{[4-(4H-1,2,4-triazol-3-yl)piperidin-1-yl]methyl}phenyl) [1,2,4]triazolo[3,4-f]-1,6-naphthyridine (21-4);
1-{4-[9-phenyl-3-(3H-1lambda$^4$,3-thiazol-5-yl)[1,2,4]triazolo[3,4-f]-1,6-naphthyridin-8-yl]phenyl}methanamine (22-4);
1-{4-[9-phenyl-3-(1H-pyrazol-3-yl)-2H-4lambda$^{5[}$1,2,4]triazolo[3,4-f]-1,6-naphthyridin-8-yl]phenyl}methanamine (22-5);
1-{4-[9-phenyl-3-(1,3-thiazol-4-yl)[1,2,4]triazolo[3,4-f]-1,6-naphthyridin-8-yl]phenyl}methanamine (22-6);
1-{4-[3-(azetidin-1-ylmethyl)-9-phenyl[1,2,4]triazolo[3,4-f]-1,6-naphthyridin-8-yl]phenyl}methanamine (26-3);
1-({8-[4-(aminomethyl)phenyl]-9-phenyl[1,2,4]triazolo[3,4-f]-1,6-naphthyridin-3-yl}methyl)piperidine-4-carboxamide (26-4);
1-{4-[3-(morpholin-4-ylmethyl)-9-phenyl[1,2,4]triazolo[3,4-f]-1,6-naphthyridin-8-yl]phenyl}methanamine (26-5);
2-[({8-[4-(aminomethyl)phenyl]-9-phenyl[1,2,4]triazolo[3,4-f]-1,6-naphthyridin-3-yl}methyl)amino]ethanol (26-6);
1-(4-{3-[(4-methyl piperazin-1-yl)methyl]-9-phenyl[1,2,4]triazolo[3,4-f]-1,6-naphthyridin-8-yl}phenyl)methanamine (26-7);
4-[9-phenyl-3-(piperazin-1-ylmethyl)[1,2,4]triazolo[3,4-f]-1,6-naphthyridin-8-yl]benzylamine (26-8);
N-({8-[4-(aminomethyl)phenyl]-9-phenyl[1,2,4]triazolo[3,4-f]-1,6-naphthyridin-3-yl}methyl)-N-methylamine (26-9);
N-({8-[4-(aminomethyl)phenyl]-9-phenyl[1,2,4]triazolo[3,4-f]-1,6-naphthyridin-3-yl}methyl)-N,N-dimethylamine (26-10);
3-methyl-9-phenyl-8-(4-{[4-(4H-1,2,4-triazol-3-yl)piperidin-1-yl]methyl}phenyl)[1,2,4]triazolo[3,4-f]-1,6-naphthyridine (31-1);
1-{4-[9-phenyl-3-(5,6,7,8-tetrahydro imidazo[1,2-a]pyridin-2-yl)[1,2,4]triazolo[3,4-f]-1,6-naphthyridin-8-yl]phenyl}cyclopropanamine (33-8);
1-[4-(9-phenyl-3-pyrimidin-2-yl[1,2,4]triazolo[3,4-f]-1,6-naphthyridin-8-yl)phenyl]cyclopropanamine (33-9);
1-{4-[3-(1,5-dimethyl-1H-pyrazol-3-yl)-9-phenyl[1,2,4]triazolo[3,4-f]-1,6-naphthyridin-8-yl]phenyl}cyclopropanamine (33-10);
(1R)-1-[4-(3-Methyl-9-phenyl[1,2,4]triazolo[3,4-f]-1,6-naphthyridin-8-yl)phenyl]ethanamine (34-5);
(1R)-1-[4-(9-phenyl[1,2,4]triazolo[3,4-f]-1,6-naphthyridin-8-yl)phenyl]ethanamine (34-6);
(1R)-1-{4-[9-Phenyl-3-(5-pyridin-2-yl-1H-pyrazol-3-yl)[1,2,4]triazolo[3,4-f]-1,6-naphthyridin-8-yl]phenyl}ethanamine (35-1);
(1R)-1-{4-[3-(hydroxymethyl)-9-phenyl[1,2,4]triazolo[3,4-f]-1,6-naphthyridin-8-yl]phenyl}ethanamine (35-2);
(1R)-1-{4-[3-(1-methyl-1H-imidazol-4-yl)-9-phenyl[1,2,4]triazolo[3,4-f]-1,6-naphthyridin-8-yl]phenyl}ethanamine (35-3);

(1R)-1-[4-(9-phenyl-3-[1,2,4]triazolo[1,5-a]pyrimidin-2-yl [1,2,4]triazolo[3,4-f]-1,6-naphthyridin-8-yl)phenyl]ethanamine (35-4);

(1R)-1-[4-(3-imidazo[2,1-b][1,3]thiazol-6-yl-9-phenyl[1,2,4]triazolo[3,4-f]-1,6-naphthyridin-8-yl)phenyl]ethanamine (35-5);

(1R)-1-[4-(9-phenyl-3-pyrimidin-2-yl[1,2,4]triazolo[3,4-f]-1,6-naphthyridin-8-yl)phenyl]ethanamine (35-6);

(1R)-1-[4-(9-Phenyl[1,2,4]triazolo[3,4-f]-1,6-naphthyridin-8-yl)phenyl]propan-1-amine (36-1);

2-[4-(3-methyl-9-phenyl[1,2,4]triazolo[3,4-f]-1,6-naphthyridin-8-yl)phenyl]propan-2-amine (37-4)

2-[4-(9-phenyl[1,2,4]triazolo[3,4-f]-1,6-naphthyridin-8-yl)phenyl]propan-2-amine (38-1);

3-(2-{[4-(3-methyl-9-phenyl[1,2,4]triazolo[3,4-f]-1,6-naphthyridin-8-yl)benzyl]amino}-2-oxoethyl)pyridine (39-1);

N-[4-(3-methyl-9-phenyl[1,2,4]triazolo[3,4-f]-1,6-naphthyridin-8-yl)benzyl]-5-pyridin-3-yl-2-furamide (39-3);

N-[4-(3-methyl-9-phenyl[1,2,4]triazolo[3,4-f]-1,6-naphthyridin-8-yl)benzyl]-5-pyridin-3-yl-1H-pyrrole-3-carboxamide (39-4);

4-(2-{[4-(3-methyl-9-phenyl[1,2,4]triazolo[3,4-f]-1,6-naphthyridin-8-yl)benzyl]amino}-2-oxoethyl)morpholine (39-7);

2-{[4-(3-methyl-9-phenyl[1,2,4]triazolo[3,4-f]-1,6-naphthyridin-8-yl)benzyl]amino}-2-oxoethanamine (39-8);

4-(2-{[4-(3-methyl-9-phenyl[1,2,4]triazolo[3,4-f]-1,6-naphthyridin-8-yl)benzyl]amino}-2-oxoethyl)pyridine (39-9);

2,4-dihydroxy-6-(2-{[4-(3-methyl-9-phenyl[1,2,4]triazolo[3,4-f]-1,6-naphthyridin-8-yl)benzyl]amino}-2-oxoethyl)pyrimidine (39-10);

2-(2-{[4-(3-methyl-9-phenyl[1,2,4]triazolo[3,4-f]-1,6-naphthyridin-8-yl)benzyl]amino}-2-oxoethyl)pyridine (39-11);

3-(2-{[4-(3-methyl-9-phenyl[1,2,4]triazolo[3,4-f]-1,6-naphthyridin-8-yl)benzyl]amino}-2-oxoethyl)pyridine (39-12);

3-methyl-9-phenyl-8-[4-({[(pyridin-3-ylamino) carbonyl]amino}methyl)phenyl][1,2,4]triazolo[3,4-f]-1,6-naphthyridine (39-14);

3-methyl-9-phenyl-8-(4-{[(pyridin-3-ylcarbonyl)amino]methyl}phenyl)[1,2,4]triazolo[3,4-f]-1,6-naphthyridine (39-20);

3-methyl-9-phenyl-8-(4-{[(quinolin-3-ylcarbonyl)amino]methyl}phenyl)[1,2,4]triazolo[3,4-f]-1,6-naphthyridine (39-26);

8-(4-{[(1H-benzimidazol-1-ylacetyl)amino]methyl}phenyl)-3-methyl-9-phenyl[1,2,4]triazolo[3,4-f]-1,6-naphthyridine (39-29);

8-(4-{[(1H-benzimidazol-2-ylacetyl)amino]methyl}phenyl)-3-methyl-9-phenyl[1,2,4]triazolo[3,4-f]-1,6-naphthyridine (39-30);

3-methyl-8-[4-({[(6-morpholin-4-ylpyridin-3-yl)carbonyl]amino}methyl)phenyl]-9-phenyl[1,2,4]triazolo[3,4-f]-1,6-naphthyridine (39-34);

3-methyl-9-phenyl-8-(4-{[((3-pyridin-3-yl propanoyl)amino]methyl}phenyl)[1,2,4]triazolo[3,4-f]-1,6-naphthyridine (39-37);

3-(1-methyl-1H-imidazol-4-yl)-9-phenyl-8-(4-{[(pyridin-3-ylacetyl)amino]methyl}phenyl)[1,2,4]triazolo[3,4-f]-1,6-naphthyridine (39-38);

9-phenyl-3-pyrazolo[1,5-a]pyrimidin-3-yl-8-(4-{[(pyridin-3-ylacetyl)amino]methyl}phenyl)[1,2,4]triazolo[3,4-f]-1,6-naphthyridine (39-39);

N-{(1R)-[4-(3-methyl-9-phenyl[1,2,4]triazolo[3,4-f]-1,6-naphthyridin-8-yl)phenyl]ethyl}-2-pyridin-3-ylacetamide (39-47); and N-((1R)-1-{4-[3-(hydroxymethyl)-9-phenyl[1,2,4]triazolo[3,4-f]-1,6-naphthyridin-8-yl]phenyl}ethyl)-2-pyridin-3-ylacetamide (39-49);

or a stereoisomer thereof.

Further specific compounds of the instant invention include:

9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-amine (1-4);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol (1-5);

9-phenyl-8-(4-{[4-(4-pyridin-2-yl-1H-imidazol-1-yl)piperidin-1-yl]methyl}phenyl)[1,2,4]triazolo[3,4-f]-1,6-naphthyridin-3-amine (1-6);

9-phenyl-8-(4-{[4-(5-pyridin-2-yl-1H-1,2,4-triazol-3-yl)piperidin-1-yl]methyl}phenyl)[1,2,4]triazolo[3,4f]-1,6-naphthyridin-3-thiol (1-7);

3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-2);

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-3);

3-(chloromethyl)-9-phenyl-8-(4-{[4-(4-pyridin-2-yl-1H-imidazol-1-yl)piperidin-1-yl]methyl}phenyl) [1,2,4]triazolo[3,4-f]-1,6-naphthyridine (2-4);

3-[(4-methylpiperazin-1-yl)methyl]-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-5);

2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol (2-6);

8-(4-Aminomethyl-phenyl)-9-phenyl-[1,2,4]triazolo[3,4-f][1,6]naphthyridin-3-ol (3-8);

1-[4-(9-Phenyl[1,2,4]triazolo[3,4-f]-1,6-naphthyridin-8-yl)phenyl]methanamine (4-3);

4-(3-Methyl-9-phenyl-[1,2,4]triazolo[1,6]naphthyridin-8-yl)-benzylamine (5-3);

8-[4-(Aminomethyl)phenyl]-9-phenyl[1,2,4]triazolo[3,4-f]-1,6-naphthyridin-3-amine (6-2);

1-[4-(9-Phenyl[1,2,4]triazolo[3,4-f]-1,6-naphthyridin-8-yl)phenyl]ethanamine (7-4);

9-Phenyl-8-{4-[4-(5-pyridin-2-yl-4H-[1,2,4]triazol-3-yl)-piperidin-1-ylmethyl]-phenyl}-[1,2,4]triazolo[3,4-f][1,6]naphthyridine (8-10);

9-phenyl-8-(4-{[4-(5-pyridin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine (9-4);

3-(1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-5);

tert-butyl[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]methylcarbamate (9-6);

[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanol (9-7);

5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]-2,4-dihydro-3H-1,2,4-triazol-3-one (9-8);

3-(3-methyl-1H-1,2,4-triazol-5-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-9);

3-imidazo[2,1-b][1,3]thiazol-6-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-10);

9-phenyl-8-(4-{[4-(5-pyridin-2-yl-4H-1,2,4-triazol-3-yl)piperidin-1-yl]methyl}phenyl)-3-[1,2,4]triazolo[1,5-a]pyrimidin-2-yl[1,2,4]triazolo[3,4-f]-1,6-naphthyridine (9-11);

3-imidazo[1,2-a]pyridin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-12);

9-phenyl-8-(4-{[4-(5-pyridin-2-yl-4H-1,2,4-triazol-3-yl)piperidin-1-yl]methyl}phenyl)-3-(1H-1,2,4-triazol-5-yl)[1,2,4]triazolo[3,4-f]-1,6-naphthyridine (9-13);

3-(1H-benzimidazol-6-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-14);

3-(1,5-dimethyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-15);

3-imidazo[1,2-a]pyrimidin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-16);

5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine (9-17);

9-phenyl-3-pyrazolo[1,5-a]pyrimidin-3-yl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-18);

3-(5-methyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (9-19);

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine (9-20);

4-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-21);

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-22);

2-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol (9-23);

1-{4-[3-(5-oxo-4,5-dihydro-1H-1,2,4-triazol-3-yl)-9-phenyl[1,2,4]triazolo[3,4-f]-1,6-naphthyridin-8-yl]benzyl}piperidine-4-carboxamide (9-24);

1-[4-(3-imidazo[1,2-a]pyridin-2-yl-9-phenyl[1,2,4]triazolo[3,4-f]-1,6-naphthyridin-8-yl)benzyl]piperidine-4-carboxamide (9-25);

9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (10-4);

9-phenyl-8-(4-{[4-(5-pyrimidin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine (11-4);

3-(1-methyl-1H-imidazol-4-yl)-9-phenyl-8-(4-{[4-(5-pyrimidin-2-yl-4H-1,2,4-triazol-3-yl)piperidin-1-yl]methyl}phenyl)[1,2,4]triazolo[3,4-f]-1,6-naphthyridine (12-1);

3-(1-methyl-1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (13-3);

3-(1-methyl-1H-imidazol-4-yl)-9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (13-4);

N-[2-(4-methyl-1H-imidazol-2-yl)ethyl]-N-{4-[3-(1-methyl-1H-imidazol-4-yl)-9-phenyl[1,2,4]triazolo[3,4-f]-1,6-naphthyridin-8-yl]benzyl}amine (13-5);

$N^1$-(2-hydroxyphenyl)-$N^3$-{4-[3-(1-methyl-1H-imidazol-4-yl)-9-phenyl[1,2,4]triazolo[3,4-f]-1,6-naphthyridin-8-yl]benzyl}-beta-alaninamide (13-6);

1-{4-[3-(1-methyl-1H-imidazol-4-yl)-9-phenyl[1,2,4]triazolo[3,4-f]-1,6-naphthyridin-8-yl]benzyl}piperidine-4-carboxamide (13-7);

5-[({-4-[3-(1-methyl-1H-imidazol-4-yl)-9-phenyl[1,2,4]triazolo[3,4-f]-1,6-naphthyridin-8-yl]benzyl}amino)methyl]pyridin-2-ol (13-8);

$N^1,N^1$,2,2-tetramethyl-$N^3$-{4-[3-(1-methyl-1H-imidazol-4-yl)-9-phenyl[1,2,4]triazolo[3,4-f]-1,6-naphthyridin-8-yl]benzyl}propane-1,3-diamine (13-9);

3-hydroxy-2,2-dimethyl-N-[4-(3-methyl-9-phenyl[1,2,4]triazolo[3,4-f]-1,6-naphthyridin-8-yl)benzyl]propan-1-amine (13-10);

2-fluoro-3-hydroxy-N-[4-(3-methyl-9-phenyl[1,2,4]triazolo[3,4-f]-1,6-naphthyridin-8-yl)benzyl]propan-1-amine (13-11);

2,2-difluoro-3-hydroxy-N-[4-(3-methyl-9-phenyl[1,2,4]triazolo[3,4-f]-1,6-naphthyridin-8-yl)benzyl]propan-1-amine (13-12);

2,3-dihydroxy-N-[4-(3-methyl-9-phenyl[1,2,4]triazolo[3,4-f]-1,6-naphthyridin-8-yl)benzyl]propan-1-amine (13-13);

4-hydroxy-N-[4-(3-methyl-9-phenyl[1,2,4]triazolo[3,4-f]-1,6-naphthyridin-8-yl)benzyl]cyclohexanamine (13-14);

4-hydroxy-N-[4-(3-methyl-9-phenyl[1,2,4]triazolo[3,4-f]-1,6-naphthyridin-8-yl)benzyl]cyclohexanamine (13-15);

3-hydroxy-2,2-dimethyl-N-{4-[3-(1-methyl-1H-imidazol-4-yl)-9-phenyl[1,2,4]triazolo[3,4-f]-1,6-naphthyridin-8-yl]benzyl}propan-1-amine (13-16);

3-hydroxy-2,2-dimethyl-N-[4-(9-phenyl-3-[1,2,4]triazolo[1,5-a]pyrimidin-2-yl[1,2,4]triazolo[3,4-f]-1,6-naphthyridin-8-yl)benzyl]propan-1-amine (13-17);

3-hydroxy-2,2-dimethyl-N-[4-(9-phenyl-3-pyrazolo[1,5-a]pyrimidin-2-yl[1,2,4]triazolo[3,4-f]-1,6-naphthyridin-8-yl)benzyl]propan-1-amine (13-18);

3-hydroxy-2,2-dimethyl-N-{4-[9-phenyl-3-(1H-1,2,3-triazol-4-yl) [1,2,4]triazolo[3,4-f]-1,6-naphthyridin-8-yl]benzyl}propan-1-amine (13-19);

tert-butyl {[8-(4-{[(3-hydroxy-2,2-dimethylpropyl)amino]methyl}phenyl)-9-phenyl[1,2,4]triazolo[3,4-f]-1,6-naphthyridin-3-yl]methyl}carbamate (13-20);

N-{4-[3-(ammoniomethyl)-9-phenyl[1,2,4]triazolo[3,4-f]-1,6-naphthyridin-8-yl]benzyl}-3-hydroxy-2,2-dimethyl-propan-1-amine (13-21);

[9-phenyl-8-(4-{[4-(5-pyrazin-2-yl-4H-1,2,4-triazol-3-yl)piperidin-1yl]methyl}phenyl)[1,2,4]triazolo[3,4-f]-1,6-naphthyridin-3-yl]methanol (14-3);

$N^3$-{4-[3-(hydroxymethyl)-9-phenyl[1,2,4]triazolo[3,4-f]-1,6-naphthyridin-8-yl]benzyl}-$N^1$-(2-hydroxyphenyl)-beta-alaninamide (14-4);

(8-{4-[(cyclohexylamino)methyl]phenyl}-9-phenyl[1,2,4]triazolo[3,4-f]-1,6-naphthyridin-3-yl)methanol (14-5);

$N^3$-{4-[3-(hydroxymethyl)-9-phenyl[1,2,4]triazolo[3,4-f]-1,6-naphthyridin-8-yl]benzyl}-$N^1$-(4-hydroxyphenyl)-beta-alaninamide (14-6);

[9-phenyl-8-(4-{[4-(5-pyridin-3-yl-4H-1,2,4-triazol-3-yl)piperidin-1-yl]methyl}phenyl)[1,2,4]triazolo[3,4-f]-1,6-naphthyridin-3-yl]methanol (14-7);

1-{4-[3-(hydroxymethyl)-9-phenyl[1,2,4]triazolo[3,4-f]-1,6-naphthyridin-8-yl]benzyl}piperidine-4-carboxamide (14-8);
{8-[4-(1-aminocyclopropyl)phenyl]-9-phenyl[1,2,4]triazolo[3,4-f]-1,6-naphthyridin-3-yl}methanol (15-2);
1-[4-(9-phenyl-3-pyridin-4-yl[1,2,4]triazolo[3,4-f]-1,6-naphthyridin-8-yl)phenyl]methanamine (16-3);
1-{4-[3-(1-oxidopyridin-3-yl)-9-phenyl[1,2,4]triazolo[3,4-f]-1,6-naphthyridin-8-yl]phenyl}methanamine (16-4);
1-[4-(3,9-diphenyl[1,2,4]triazolo[3,4-f]-1,6-naphthyridin-8-yl)phenyl]methanamine (16-5);
1-{4-[3-(4-fluorophenyl)-9-phenyl[1,2,4]triazolo[3,4-f]-1,6-naphthyridin-8-yl]phenyl}methanamine (16-6);
4-{8-[4-(aminomethyl)phenyl]-9-phenyl[1,2,4]triazolo[3,4-f]-1,6-naphthyridin-3-yl}benzonitrile (16-7);
4-(9-phenyl-3-pyrimidin-4-yl[1,2,4]triazolo[3,4-f]-1,6-naphthyridin-8-yl)benzylamine (16-8);
1-{4-[3-(1-oxidopyridin-2-yl)-9-phenyl[1,2,4]triazolo[3,4-f]-1,6-naphthyridin-8-yl]phenyl}methanamine (16-9);
5-{8-[4-(aminomethyl)phenyl]-9-phenyl[1,2,4]triazolo[3,4-f]-1,6-naphthyridin-3-yl}yridine-2-ol (16-10);
1-[4-(9-phenyl-3-pyridin-3-yl[1,2,4]triazolo[3,4-f]-1,6-naphthyridin-8-yl)phenyl]methanamine (16-11);
4-(9-phenyl-3-pyrimidin-2-yl[1,2,4]triazolo[3,4-f]-1,6-naphthyridin-8-yl)benzylamine (16-12);
1-[4-(9-phenyl-3-pyridin-2-yl[1,2,4]triazolo[3,4-f]-1,6-naphthyridin-8-yl)phenyl]methanamine (16-13);
1-[4-(9-phenyl-3-pyrazin-2-yl[1,2,4]triazolo[3,4-f]-1,6-naphthyridin-8-yl)phenyl]methanamine (16-14);
1-{4-[9-phenyl-3-(1H-1,2,4-triazol-3-yl)[1,2,4]triazolo[3,4-f]-1,6-naphthyridin-8-yl]phenyl}methanamine (16-15);
1-{4-[9-phenyl-3-(1,3-thiazol-4-yl)[1,2,4]triazolo[3,4-f]-1,6-naphthyridin-8-yl]phenyl}methanamine (16-16);
1-{1-[9-phenyl-3-(1H-pyrazol-4-yl)[1,2,4]triazolo[3,4-f]-1,6-naphthyridin-8-yl]phenyl}methanamine (16-17);
1-{4-[3-(3-methyl-1H-pyrazol-4-yl)-9-phenyl[1,2,4]triazolo[3,4-f]-1,6-naphthyridin-8-yl]phenyl}methanamine (16-18);
1-{4-[3-(3-methyl-1H-1,2,4-triazol-5-yl)-9-phenyl[1,2,4]triazolo[3,4-f]-1,6-naphthyridin-8-yl]phenyl}methanamine (16-19);
1-{4-[3-(1-methyl-1H-pyrazol-4-yl)-9-phenyl[1,2,4]triazolo[3,4-f]-1,6-naphthyridin-8-yl]phenyl}methanamine (16-20);
1-{4-[9-phenyl-3-(1,2,5-thiadiazol-3-yl)[1,2,4]triazolo[3,4-f]-1,6-naphthyridin-8-yl]phenyl}methanamine (16-21);
1-{4-[9-phenyl-3-(1,2,3-thiadiazol-4-yl)[1,2,4]triazolo[3,4-f]-1,6-naphthyridin-8-yl]phenyl}methanamine (16-22);
1-[4-(9-phenyl-3-pyrazolo[1,5-a]pyrimidin-3-yl[1,2,4]triazolo[3,4-f]-1,6-naphthyridin-8-yl)phenyl]methanamine (16-23);
{8-[4-(aminomethyl)phenyl]-9-phenyl[1,2,4]triazolo[3,4-f]-1,6-naphthyridin-3-yl}methanamine (16-24);
{8-[4-(aminomethyl)phenyl]-9-phenyl[1,2,4]triazolo[3,4-f]-1,6-naphthyridin-3-yl}methanol (16-25)
1-{4-[9-phenyl-3-(2,2,2-trifluoroethyl)[1,2,4]triazolo[3,4-f]-1,6-naphthyridin-8-yl]phenyl}methanamine (16-26);
1-{4-[9-phenyl-3-(1H-tetrazol-1-ylmethyl)[1,2,4]triazolo[3,4-f]-1,6-naphthyridin-8-yl]phenyl}methanamine (16-27);
8-[4-(aminomethyl)phenyl]-9-phenyl[1,2,4]triazolo[3,4-f]-1,6-naphthyridine-3-carboxamide (16-28);
1-{4-[3-(1H-imidazol-1-ylmethyl)-9-phenyl[1,2,4]triazolo[3,4-f]-1,6-naphthyridin-8-yl]phenyl}methanamine (16-29);
1-(4-{3-[(methylsulfonyl)methyl]-9-phenyl[1,2,4]triazolo[3,4-f]-1,6-naphthyridin-8-yl}phenyl)methanamine (16-30);
{8-[4-(aminomethyl)phenyl]-9-phenyl[1,2,4]triazolo[3,4-f]-1,6-naphthyridin-3-yl}acetonitrile (16-31);
2-{8-[4-(aminomethyl)phenyl]-9-phenyl[1,2,4]triazolo[3,4-f]-1,6-naphthyridin-3-yl}ethanol (16-32);
N-({8-[4-(aminomethyl)phenyl]-9-phenyl[1,2,4]triazolo[3,4-f]-1,6-naphthyridin-3-yl}methyl)acetamide (16-33);
4-[3-(2-methylimidazo[1,2-a]pyridin-3-yl)-9-phenyl[1,2,4]triazolo[3,4-f]-1,6-naphthyridin-8-yl]benzylamine (16-34);
1-[4-(9-phenyl-3-pyrazolo[1,5-a]pyridin-3-yl[1,2,4]triazolo[3,4-f]-1,6-naphthyridin-8-yl)phenyl]methanamine (16-35);
1-[4-(3-imidazo[1,2-a]pyridin-2-yl-9-phenyl[1,2,4]triazolo[3,4-f]-1,6-naphthyridin-8-yl)phenyl]methanamine (16-36);
1-{4-[9-phenyl-3-(4,5,6,7-tetrahydro-1,2-benzisoxazol-3-yl)[1,2,4]triazolo[3,4-f]-1,6-naphthyridin-8-yl]phenyl}methanamine (16-37);
1-[4-(3-imidazo[2,1-b][1,3]thiazol-6-yl-9-phenyl[1,2,4]triazolo[3,4-f]-1,6-naphthyridin-8-yl)phenyl]methanamine (16-38);
1-{4-[3-(1-methyl-1H-imidazol-5-yl)-9-phenyl[1,2,4]triazolo[3,4-f]-1,6-naphthyridin-8-yl]phenyl}methanamine (16-39);
1-{4-[3-(1-methyl-1H-imidazol-4-yl)-9-phenyl[1,2,4]triazolo[3,4-f]-1,6-naphthyridin-8-yl]phenyl}methanamine (16-40);
4-[3-(1-methyl-5-phenyl-1H-pyrazol-4-yl)-9-phenyl[1,2,4]triazolo[3,4-f]-1,6-naphthyridin-8-yl]benzylamine (16-41);
1-{4-[9-phenyl-3-(4,5,6,7-tetrahydro-1-benzothien-3-yl)[1,2,4]triazolo[3,4-f]-1,6-naphthyridin-8-yl]phenyl}methanamine (16-42);
1-{4-[3-(1-isopropyl-1H-pyrazol-4-yl)-9-phenyl[1,2,4]triazolo[3,4-f]-1,6-naphthyridin-8-yl]phenyl}methanamine (16-43);
1-{4-[9-phenyl-3-(1,4,5,6-tetrahydrocyclopenta[c]pyrazol-3-yl)[1,2,4]triazolo[3,4-f]-1,6-naphthyridin-8-yl]phenyl}methanamine (16-44);
1-(4-{9-phenyl-3-[(2S)-pyrrolidin-2-yl][1,2,4]triazolo[3,4-f]-1,6-naphthyridin-8-yl}phenyl)methanamine (16-45);
4-[3-(1-aminoethyl)-9-phenyl[1,2,4]triazolo[3,4-f]-1,6-naphthyridin-8-yl]benzylamine (16-46);
1-{4-[3-(1H-imidazol-2-yl)-9-phenyl[1,2,4]triazolo[3,4-f]-1,6-naphthyridin-8-yl]phenyl}methanamine (16-47);
1-[4-(3-cyclopropyl-9-phenyl[1,2,4]triazolo[3,4-f]-1,6-naphthyridin-8-yl)phenyl]methanamine (16-48);
1-{4-[9-phenyl-3-trifluoromethyl)[1,2,4]triazolo[3,4-f]-1,6-naphthyridin-8-yl]phenyl}methanamine (16-49);
1-{4-[3-(5-methyl-1H-pyrazol-3-yl)-9-phenyl[1,2,4]triazolo[3,4-f]-1,6-naphthyridin-8-yl]phenyl}methanamine (16-50);
1-{4-[3-(1,5-dimethyl-1H-pyrazol-3-yl)-9-phenyl[1,2,4]triazolo[3,4-f]-1,6-naphthyridin-8-yl]phenyl}methanamine (16-51);
4-[3-(1H-indol-2-yl)-9-phenyl[1,2,4]triazolo[3,4-f]-1,6-naphthyridin-8-yl]benzylaminen (16-52);
1-{4-[3-(1-methyl-1H-imidazol-2-yl)-9-phenyl[1,2,4]triazolo[3,4-f]-1,6-naphthyridin-8-yl]phenyl}methanamine (16-53);
1-{4-[3-(3-methyl-2H-3lambda$^5$-imidazol-4-yl)-9-phenyl[1,2,4]triazolo[3,4-f]-1,6-naphthyridin-8-yl]phenyl}methanamine (16-54);

443-(6-chloroimidazo[1,2-a]pyridin-2-yl)-9-phenyl[1,2,4]triazolo[3,4-f]-1,6-naphthyridin-8-ylbenzylamine (16-55);

1-{4-[3-(1H-benzimidazol-2-yl)-9-phenyl[1,2,4]triazolo[3,4-f]-1,6-naphthyridin-8-yl]phenyl}methanamine (16-56);

4-[3-(5-cyclopropyl-4H-pyrazol-3-yl)-9-phenyl[1,2,4]triazolo[3,4-f]-1,6-naphthyridin-8-yl]benzylamine (16-57);

1-{4-[9-phenyl-3-(4,5,6,7-tetrahydro-1H-indazol-3-yl)[1,2,4]triazolo[3,4-f]-1,6-naphthyridin-8-yl]phenyl}methanamine (16-58);

4-[9-phenyl-3-(3-phenyl-1H-pyrazol-5-yl)[1,2,4]triazolo[3,4-f]-1,6-naphthyridin-8-yl]benzylamine (16-59);

1-(4-{9-phenyl-3-[3-(trifluoromethyl)-1H-pyrazol-5-yl][1,2,4]triazolo[3,4-f]-1,6-naphthyridin-8-yl}phenyl)methanamine (16-60);

1-[4-(9-phenyl-3-pyrazolo[1,5-a]pyrimidin-2-yl[1,2,4]triazolo[3,4-f]-1,6-naphthyridin-8-yl)phenyl]methanamine (16-61);

1-{4-[3-(1-benzyl-1H-pyrazol-4-yl)-9-phenyl[1,2,4]triazolo[3,4-f]-1,6-naphthyridin-8-yl]phenyl}methanamine (16-62);

1-[4-(9-phenyl-3-[1,2,4]triazolo[1,5-a]pyrimidin-2-yl[1,2,4]triazolo[3,4-f]-1,6-naphthyridin-8-yl)phenyl]methanamine (16-63);

4-[9-phenyl-3-(1-phenyl-1H-pyrazol-4-yl)[1,2,4]triazolo[3,4-f]-1,6-naphthyridin-8-yl]benzylamine (16-64);

1-{4-[9-phenyl-3-(4,5,6,7-tetrahydro-2-benzothien-1-yl)[1,2,4]triazolo[3,4-f]-1,6-naphthyridin-8-yl]phenyl}methanamine (16-65);

1-{4-[9-phenyl-3-(5,6,7,8-tetrahydroimidazo[1,2-a]pyridin-2-yl)[1,2,4]triazolo[3,4-f]-1,6-naphthyridin-8-yl]phenyl}methanamine (16-66);

2-{8-[4-(aminomethyl)phenyl]-9-phenyl[1,2,4]triazolo[3,4-f]-1,6-naphthyridin-3-yl}propan-2-amine (16-67);

1-{8-[4-(aminomethyl)phenyl]-9-phenyl[1,2,4]triazolo[3,4-f]-1,6-naphthyridin-3-yl}ethane-1,2-diol (16-68);

4-{8-[4-(aminomethyl)phenyl]-9-phenyl[1,2,4]triazolo[3,4-f]-1,6-naphthyridin-3-yl}imidazolidin-2-one (16-69);

(2R)-2-amino-2-{8-[4-(aminomethyl)phenyl]-9-phenyl[1,2,4]triazolo[3,4-f]-1,6-naphthyridin-3-yl}ethanol (16-70);

(2R)-2-{8-[4-(aminomethyl)phenyl]-9-phenyl[1,2,4]triazolo[3,4-f]-1,6-naphthyridin-3-yl}-2-(methylamino)ethanol (16-71); 1-{4-[3-(5-ethylisoxazol-3-yl)-9-phenyl[1,2,4]triazolo[3,4-f]-1,6-naphthyridin-8-yl]phenyl}methanamine (16-72);

5-{8-[4-(aminomethyl)phenyl]-9-phenyl[1,2,4]triazolo[3,4-f]-1,6-naphthyridin-3-yl}-2,4-dihydro-3H-1,2,4-triazol-3-one (16-73);

6-{8-[4-(aminomethyl)phenyl]-9-phenyl[1,2,4]triazolo[3,4-f]-1,6-naphthyridin-3-yl}-4,5-dihydropyridazin-3(2H)-one (16-74);

6-{8-[4-(aminomethyl)phenyl]-9-phenyl[1,2,4]triazolo[3,4-f]-1,6-naphthyridin-3-yl}pyridazin-3(2H)-one (16-75);

N-(4-{8-[4-(aminomethyl)phenyl]-9-phenyl[1,2,4]triazolo[3,4-f]-1,6-naphthyridin-3-yl}phenyl)acetamide (16-76);

1-{4-[3-(4-phenoxyphenyl)-9-phenyl[1,2,4]triazolo[3,4-f]-1,6-naphthyridin-8-yl]phenyl}methanamine (16-77);

1-{4-[3-(1H-benzimidazol-5-yl)-9-phenyl[1,2,4]triazolo[3,4-f]-1,6-naphthyridin-8-yl]phenyl}methanamine (16-78);

(4-{8-[4-(aminomethyl)phenyl]-9-phenyl[1,2,4]triazolo[3,4-f]-1,6-naphthyridin-3-yl}phenyl)methanol (16-79);

4-[3-(4-cyclohexylphenyl)-9-phenyl[1,2,4]triazolo[3,4-f]-1,6-naphthyridin-8-yl]benzylamine (16-80);

4-{8-[4-(aminomethyl)phenyl]-9-phenyl[1,2,4]triazolo[3,4-f]-1,6-naphthyridin-3-yl}-1,3-dihydro-2H-imidazol-2-one (16-81);

1-{4-[3-(4-methyl-1H-imidazol-5-yl)-9-phenyl[1,2,4]triazolo[3,4-f]-1,6-naphthyridin-8-yl]phenyl}methanamine (16-82);

4-[9-phenyl-3-(1-propyl-1H-imidazol-4-yl)[1,2,4]triazolo[3,4-f]-1,6-naphthyridin-8-yl]benzylamine (16-83);

1-{4-[3-(1-isopropyl-1H-imidazol-4-yl)-9-phenyl[1,2,4]triazolo[3,4-f]-1,6-naphthyridin-8-yl]phenyl}methanamine (16-84);

1-{4-[3-(1-butyl-1H-imidazol-4-yl)-9-phenyl[1,2,4]triazolo[3,4-f]-1,6-naphthyridin-8-yl]phenyl}methanamine (16-85);

1-[4-(3-imidazo[1,2-a]pyrimidin-2-yl-9-phenyl[1,2,4]triazolo[3,4-f]-1,6-naphthyridin-8-yl)phenyl]methanamine (16-86);

5-({[4-(3-methyl-9-phenyl[1,2,4]triazolo[3,4-f]-1,6-naphthyridin-8-yl)benzyl]amino}methyl)pyridin-2-ol (17-3);

1-(6-methoxypyridin-3-yl)-N-[4-(3-methyl-9-phenyl[1,2,4]triazolo[3,4-f]-1,6-naphthyridin-8-yl)benzyl]methanamine (17-4);

N-[(2-methoxypyrimidin-5-yl)methyl]-N-[4-(3-methyl-9-phenyl[1,2,4]triazolo[3,4-f]-1,6-naphthyridin-8-yl)benzyl]amine (17-5);

1-[4-(3-ethyl-9-phenyl[1,2,4]triazolo[3,4-f]-1,6-naphthyridin-8-yl)phenyl]methanamine (17-6);

1-[4-(9-phenyl-3-propyl[1,2,4]triazolo[3,4-f]-1,6-naphthyridin-8-yl)phenyl]methanamine (17-7);

N-[4-(9-phenyl[1,2,4]triazolo[3,4-f]-1,6-naphthyridin-8-yl)benzyl]acetamide (18-1);

4-({[4-(9-phenyl[1,2,4]triazolo[3,4-f]-1,6-naphthyridin-8-yl)benzyl]amino}methyl)phenol (19-1);

1-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanamine (20-1);

9-phenyl-3-(1H-1,2,3-triazol-4-yl)-8-(4-{[4-(4H-1,2,4-triazol-3-yl)piperidin-1-yl]methyl}phenyl) [1,2,4]triazolo[3,4-f]-1,6-naphthyridine (21-4);

1-{4-[3-(1H-Imidazol-4-yl)-9-phenyl[1,2,4]triazolo[3,4-f]-1,6-naphthyridin-8-yl]phenyl}methanamine (22-3);

1-{4-[9-phenyl-3-(3H-1lambda$^4$,3-thiazol-5-yl)[1,2,4]triazolo[3,4-f]-1,6-naphthyridin-8-yl]phenyl}methanamine (22-4);

1-{4-[9-phenyl-3-(1H-pyrazol-3-yl)-2H-4lambda$^5$-[1,2,4]triazolo[3,4-f]-1,6-naphthyridin-8-yl]phenyl}methanamine (22-5);

1-{4-[9-phenyl-3-(1,3-thiazol-4-yl)[1,2,4]triazolo[3,4-f]-1,6-naphthyridin-8-yl]phenyl}methanamine (22-6);

4-[9-Phenyl-3-(pyrrolidin-1-ylmethyl)[1,2,4]triazolo[3,4-f]-1,6-naphthyridin-8-yl]benzylamine (26-2);

1-{4-[3-(azetidin-1-ylmethyl)-9-phenyl[1,2,4]triazolo[3,4-f]-1,6-naphthyridin-8-yl]phenyl}methanamine (26-3);

1-({8-[4-(aminomethyl)phenyl]-9-phenyl[1,2,4]triazolo[3,4-f]-1,6-naphthyridin-3-yl}methyl)piperidine-4-carboxamide (26-4);

1-{4-[3-(morpholin-4-ylmethyl)-9-phenyl[1,2,4]triazolo[3,4-f]-1,6-naphthyridin-8-yl]phenyl}methanamine (26-5);

2-[({8-[4-(aminomethyl)phenyl]-9-phenyl[1,2,4]triazolo[3,4-f]-1,6-naphthyridin-3-yl}methyl)amino]ethanol (26-6);

1-(4-{3-[(4-methyl piperazin-1-yl)methyl]-9-phenyl[1,2,4]triazolo[3,4-f]-1,6-naphthyridin-8-yl}phenyl)methanamine (26-7);

4-[9-phenyl-3-(piperazin-1-ylmethyl)[1,2,4]triazolo[3,4-f]-1,6-naphthyridin-8-yl]benzylamine (26-8);

N-({8-[4-(aminomethyl)phenyl]-9-phenyl[1,2,4]triazolo[3,4-f]-1,6-naphthyridin-3-yl}methyl)-N-methylamine (26-9);

N-({8-[4-(aminomethyl)phenyl]-9-phenyl[1,2,4]triazolo[3,4-f]-1,6-naphthyridin-3-yl}methyl)-N,N-dimethylamine (26-10);

[4-(3-Methyl-9-phenyl[1,2,4]triazolo[3,4-f]-1,6-naphthyridin-8-yl)phenyl]methanol (28-1);

{4-[3-(1-Methyl-1H-imidazol-4-yl)-9-phenyl[1,2,4]triazolo[3,4-f]-1,6-naphthyridin-8-yl]phenyl}methanol (28-2);

1-[4-(9-Phenyl-3-[1,2,4]triazolo[1,5-a]pyrimidin-2-yl[1,2,4]triazolo[3,4-f]-1,6-naphthyridin-8-yl)phenyl]ethanol (29-2);

9-phenyl-8-(4-{[4-(4H-1,2,4-triazol-3-yl)piperidin-1-yl]methyl}phenyl)[1,2,4]triazolo[3,4-f]-1,6-naphthyridine (30-1);

3-methyl-9-phenyl-8-(4-{[4-(4H-1,2,4-triazol-3-yl)piperidin-1-yl]methyl}phenyl)[1,2,4]triazolo[3,4-f]-1,6-naphthyridine (31-1);

9-phenyl-8-(4-{[4-(4H-1,2,4-triazol-3-yl)piperidin-1-yl]methyl}phenyl)[1,2,4]triazolo[3,4-f]-1,6-naphthyridin-3-ol (32-1);

1-[4-(3-Methyl-9-phenyl[1,2,4]triazolo[3,4-f]-1,6-naphthyridin-8-yl)phenyl]cyclopropanamine (33-5);

1-{4-[3-(1-methyl-1H-imidazol-4-yl)-9-phenyl[1,2,4]triazolo[3,4-f]-1,6-naphthyridin-8-yl]phenyl}cyclo propanamine (33-6);

1-[4-(9-phenyl-3-[1,2,4]triazolo[1,5-a]pyrimidin-2-yl[1,2,4]triazolo[3,4-f]-1,6-naphthyridin-8-yl)phenyl]cyclopropanamine (33-7);

1-{4-[9-phenyl-3-(5,6,7,8-tetrahydro imidazo[1,2-a]pyridin-2-yl)[1,2,4]triazolo[3,4-f]-1,6-naphthyridin-8-yl]phenyl}cyclopropanamine (33-8);

1-[4-(9-phenyl-3-pyrimidin-2-yl[1,2,4]triazolo[3,4-f]-1,6-naphthyridin-8-yl)phenyl]cyclopropanamine (33-9);

1-{4-[3-(1,5-dimethyl-1H-pyrazol-3-yl)-9-phenyl[1,2,4]triazolo[3,4-f]-1,6-naphthyridin-8-yl]phenyl}cyclopropanamine (33-10);

(1R)-1-[4-(3-Methyl-9-phenyl[1,2,4]triazolo[3,4-f]-1,6-naphthyridin-8-yl)phenyl]ethanamine (34-5);

(1R)-1-[4-(9-phenyl[1,2,4]triazolo[3,4-f]-1,6-naphthyridin-8-yl)phenyl]ethanamine (34-6);

(1R)-1-{4-[9-Phenyl-3-(5-pyridin-2-yl-1H-pyrazol-3-yl)[1,2,4]triazolo[3,4-f]-1,6-naphthyridin-8-yl]phenyl}ethanamine (35-1);

(1R)-1-{4-[3-(hydroxymethyl)-9-phenyl[1,2,4]triazolo[3,4-f]-1,6-naphthyridin-8-yl]phenyl}ethanamine (35-2);

(1R)-1-{4-[3-(1-methyl-1H-imidazol-4-yl)-9-phenyl[1,2,4]triazolo[3,4-f]-1,6-naphthyridin-8-yl]phenyl}ethanamine (35-3);

(1R)-1-[4-(9-phenyl-3-[1,2,4]triazolo[1,5-a]pyrimidin-2-yl[1,2,4]triazolo[3,4-f]-1,6-naphthyridin-8-yl)phenyl]ethanamine (35-4);

(1R)-1-[4-(3-imidazo[2,1-b][1,3]thiazol-6-yl-9-phenyl[1,2,4]triazolo[3,4-f]-1,6-naphthyridin-8-yl)phenyl]ethanamine (35-5);

(1R)-1-[4-(9-phenyl-3-pyrimidin-2-yl[1,2,4]triazolo[3,4-f]-1,6-naphthyridin-8-yl)phenyl]ethanamine (35-6);

(1R)-1-[4-(9-Phenyl[1,2,4]triazolo[3,4-f]-1,6-naphthyridin-8-yl)phenyl]propan-1-amine (36-1);

2-[4-(3-methyl-9-phenyl[1,2,4]triazolo[3,4-f]-1,6-naphthyridin-8-yl)phenyl]propan-2-amine (37-4)

2-[4-(9-phenyl[1,2,4]triazolo[3,4-f]-1,6-naphthyridin-8-yl)phenyl]propan-2-amine (38-1);

3-(2-{[4-(3-methyl-9-phenyl[1,2,4]triazolo[3,4-f]-1,6-naphthyridin-8-yl)benzyl}amino)-2-oxoethyl)pyridine (39-1);

N-[4-(3-methyl-9-phenyl[1,2,4]triazolo[3,4-f]-1,6-naphthyridin-8-yl)benzyl]-5-pyridin-4-yl-2-furamide (39-2);

N-[4-(3-methyl-9-phenyl[1,2,4]triazolo[3,4-f]-1,6-naphthyridin-8-yl)benzyl]-5-pyridin-3-yl-2-furamide (39-3);

N-[4-(3-methyl-9-phenyl[1,2,4]triazolo[3,4-f]-1,6-naphthyridin-8-yl)benzyl]-5-pyridin-3-yl-1H-pyrrole-3-carboxamide (39-4);

2-hydroxy-N-[4-(3-methyl-9-phenyl[1,2,4]triazolo[3,4-f]-1,6-naphthyridin-8-yl)benzyl]acetamide (39-5);

tert-butyl (2-{[4-(3-methyl-9-phenyl[1,2,4]triazolo[3,4-f]-1,6-naphthyridin-8-yl)benzyl]amino}-2-oxoethyl)carbamate (39-6);

4-(2-{[4-(3-methyl-9-phenyl[1,2,4]triazolo[3,4-f]-1,6-naphthyridin-8-yl)benzyl]amino}-2-oxoethyl)morpholine (39-7);

2-{[4-(3-methyl-9-phenyl[1,2,4]triazolo[3,4-f]-1,6-naphthyridin-8-yl)benzyl]amino}-2-oxoethanamine (39-8);

4-(2-{[4-(3-methyl-9-phenyl[1,2,4]triazolo[3,4-f]-1,6-naphthyridin-8-yl)benzyl]amino}-2-oxoethyl)pyridine (39-9);

2,4-dihydroxy-6-(2-{[4-(3-methyl-9-phenyl[1,2,4]triazolo[3,4-f]-1,6-naphthyridin-8-yl)benzyl]amino}-2-oxoethyl)pyrimidine (39-10);

2-(2-{[4-(3-methyl-9-phenyl[1,2,4]triazolo[3,4-f]-1,6-naphthyridin-8-yl)benzyl]amino}-2-oxoethyl)pyridine (39-11);

3-(2-{[4-(3-methyl-9-phenyl[1,2,4]triazolo[3,4-f]-1,6-naphthyridin-8-yl)benzyl]amino}-2-oxoethyl)pyridine (39-12);

N-[4-(3-methyl-9-phenyl[1,2,4]triazolo[3,4-f]-1,6-naphthyridin-8-yl)benzyl]-2-pyrazin-2-ylacetamide (39-13);

3-methyl-9-phenyl-8-[4-({[(pyridin-3-ylamino) carbonyl]amino}methyl)phenyl][1,2,4]triazolo[3,4-f]-1,6-naphthyridine (39-14);

2-(2-hydroxyphenyl)-N-[4-(3-methyl-9-phenyl[1,2,4]triazolo[3,4-f]-1,6-naphthyridin-8-yl) benzyl]acetamide (39-15);

2-(3-hydroxyphenyl)-N-[4-(3-methyl-9-phenyl[1,2,4]triazolo[3,4-f]-1,6-naphthyridin-8-yl)benzyl]acetamide (39-16);

2-(4-hydroxyphenyl)-N-[4-(3-methyl-9-phenyl[1,2,4]triazolo[3,4-f]-1,6-naphthyridin-8-yl) benzyl]acetamide (39-17);

2-(3,4-dihydroxyphenyl)-N-[4-(3-methyl-9-phenyl[1,2,4]triazolo[3,4-f]-1,6-naphthyridin-8-yl)benzyl]acetamide (39-18);

N-[4-(3-methyl-9-phenyl[1,2,4]triazolo[3,4-f]-1,6-naphthyridin-8-yl)benzyl]-2-phenylacetamide (39-19);

3-methyl-9-phenyl-8-(4-{[(pyridin-3-ylcarbonyl)amino]methyl}phenyl)[1,2,4]triazolo[3,4-f]-1,6-naphthyridine (39-20);

2-hydroxy-N-[4-(3-methyl-9-phenyl[1,2,4]triazolo[3,4-f]-1,6-naphthyridin-8-yl)benzyl]benzamide (39-21);

2-(4-hydroxyphenyl)-2-methyl-N-[4-(3-methyl-9-phenyl[1,2,4]triazolo[3,4-f]-1,6-naphthyridin-8-yl)benzyl]propanamide (39-22);

methyl 4-{[4-(3-methyl-9-phenyl[1,2,4]triazolo[3,4-f]-1,6-naphthyridin-8-yl)benzyl]amino}-4-oxobutanoate (39-23);

2-hydroxy-N-(2-{[4-(3-methyl-9-phenyl[1,2,4]triazolo[3,4-f]-1,6-naphthyridin-8-yl)benzyl]amino}-2-oxoethyl)benzamide (39-24);

N-[4-(3-methyl-9-phenyl[1,2,4]triazolo[3,4-f]-1,6-naphthyridin-8-yl)benzyl]-2-(5-phenyl-4H-1,2,4-triazol-3-yl)acetamide (39-25);

3-methyl-9-phenyl-8-(4-{[(quinolin-3-ylcarbonyl)amino]methyl}phenyl)[1,2,4]triazolo[3,4-f]-1,6-naphthyridine (39-26);

N-[4-(3-methyl-9-phenyl[1,2,4]triazolo[3,4-f]-1,6-naphthyridin-8-yl)benzyl]-2-(4-oxoquinazolin-3(4H)-yl)acetamide (39-27);

N-[4-(3-methyl-9-phenyl[1,2,4]triazolo[3,4-f]-1,6-naphthy-ridin-8-yl)benzyl]-2-(2-oxo-1,3-benzoxazol-3(2H)-yl)acetamide (39-28);

8-(4-{[(1H-benzimidazol-1-ylacetyl)amino]methyl}phenyl)-3-methyl-9-phenyl[1,2,4]triazolo[3,4-f]-1,6-naphthyridine (39-29);

8-(4-{[(1H-benzimidazol-2-ylacetyl)amino]methyl}phenyl)-3-methyl-9-phenyl[1,2,4]triazolo[3,4-f]-1,6-naphthyridine (39-30);

2-(4-methyl-1,2,5-oxadiazol-3-yl)-N-[4-(3-methyl-9-phenyl[1,2,4]triazolo[3,4-f]-1,6-naphthyridin-8-yl)benzyl]acetamide (39-31);

2-(1H-indazol-1-yl)-N-[4-(3-methyl-9-phenyl[1,2,4]triazolo[3,4-f]-1,6-naphthyridin-8-yl)benzyl]acetamide (39-32);

2-(5,6-dimethyl-4-oxothieno[2,3-d]pyrimidin-3(4H)-yl)-N-[4-(3-methyl-9-phenyl[1,2,4]triazolo[3,4-f]-1,6-naphthyridin-8-yl)benzyl]acetamide (39-33);

3-methyl-8-[4-({[(6-morpholin-4-ylpyridin-3-yl)carbonyl]amino}methyl)phenyl]-9-phenyl[1,2,4]triazolo[3,4-f]-1,6-naphthyridine (39-34);

2-(6-chloropyridin-3-yl)-N-[4-(3-methyl-9-phenyl[1,2,4]triazolo[3,4-f]-1,6-naphthyridin-8-yl)benzyl]acetamide (39-35);

3-cyano-N-[4-(3-methyl-9-phenyl[1,2,4]triazolo[3,4-f]-1,6-naphthyridin-8-yl)benzyl]propanamide (39-36);

3-methyl-9-phenyl-8-(4-{[(3-pyridin-3-yl propanoyl)amino]methyl}phenyl)[1,2,4]triazolo[3,4-f]-1,6-naphthyridine (39-37);

3-(1-methyl-1H-imidazol-4-yl)-9-phenyl-8-(4-{[(pyridin-3-ylacetyl)amino]methyl}phenyl)[1,2,4]triazolo[3,4-f]-1,6-naphthyridine (39-38);

9-phenyl-3-pyrazolo[1,5-a]pyrimidin-3-yl-8-(4-{[(pyridin-3-ylacetyl)amino]methyl}phenyl)[1,2,4]triazolo[3,4-f]-1,6-naphthyridine (39-39);

N-(3-hydroxy-2,2-dimethylpropyl)-N-[4-(3-methyl-9-phenyl[1,2,4]triazolo[3,4-f]-1,6-naphthyridin-8-yl)benzyl]acetamide (39-40);

N-(3-hydroxy-2,2-dimethylpropyl)-N-{4-[3-(1-methyl-1H-imidazol-4-yl)-9-phenyl[1,2,4]triazolo[3,4-f]-1,6-naphthyridin-8-yl]benzyl}-2-(4-oxoquinazolin-3(4H)-yl)acetamide (39-41);

tert-butyl {2-[[4-(3-{[(tert-butoxycarbonyl)amino]methyl}-9-phenyl[1,2,4]triazolo[3,4-f]-1,6-naphthyridin-8-yl)benzyl](3-hydroxy-2,2-dimethylpropyl)amino]-2-oxoethyl}carbamate (39-42);

3-methyl-9-phenyl-8-(4-{1-[(pyridin-3-ylacetyl)amino]cyclopropyl}phenyl)[1,2,4]triazolo[3,4-f]-1,6-naphthyridine (39-43);

3-methyl-9-phenyl-8-(4-{1-[(quinolin-3-yl carbonyl)amino]cyclopropyl}phenyl)[1,2,4]triazolo[3,4-f]-1,6-naphthyridine (39-44);

N-{1-[4-(3-methyl-9-phenyl[1,2,4]triazolo[3,4-f]-1,6-naphthyridin-8-yl)phenyl]cyclopropyl}-2-(4-oxoquinazolin-3(4H)-yl)acetamide (39-45);

3-(1-methyl-1H-imidazol-4-yl)-9-phenyl-8-(4-{1-[(pyridin-3-ylacetyl)amino]cyclopropyl}phenyl)[1,2,4]triazolo[3,4-f]-1,6-naphthyridine (39-46);

N-{(1R)-1-[4-(3-methyl-9-phenyl[1,2,4]triazolo[3,4-f]-1,6-naphthyridin-8-yl)phenyl]ethyl}-2-pyridin-3-ylacetamide (39-47);

N-[(1R)-1-[4-(3-methyl-9-phenyl[1,2,4]triazolo[3,4-f]-1,6-naphthyridin-8-yl)phenyl]ethyl]acetamide (39-48);

N-((1R)-1-{-4-[3-(hydroxymethyl)-9-phenyl[1,2,4]triazolo[3,4-f]-1,6-naphthyridin-8-yl]phenyl}ethyl)-2-pyridin-3-ylacetamide (39-49);

N-{1-methyl-1-[4-(9-phenyl[1,2,4]triazolo[3,4-f]-1,6-naphthyridin-8-yl)phenyl]ethyl}acetamide (39-50); and N-{1-methyl-1-[4-(3-methyl-9-phenyl[1,2,4]triazolo[3,4-f]-1,6-naphthyridin-8-yl)phenyl]ethyl}acetamide (39-51);

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

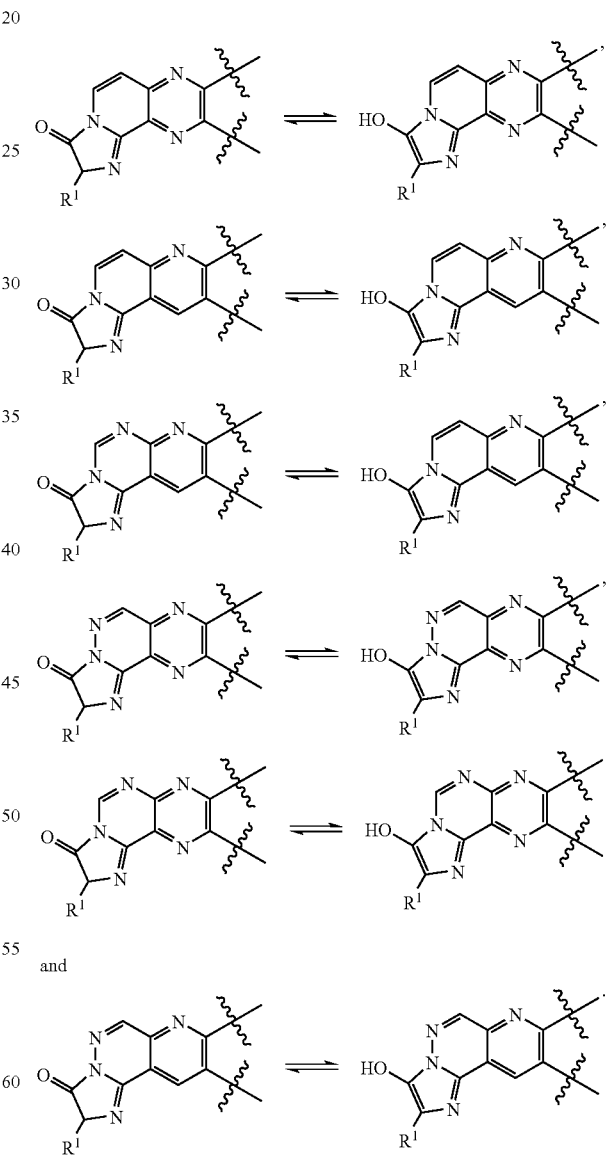

and

Tetrazoles exist as a mixture of 1H/2H tautomers. The tautomeric forms of the tetrazol moiety are also within the scope of the instant invention.

When any variable (e.g. $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, propyl, n-butyl, t-butyl, i-butyl, pentyl, hexyl, heptyl, octyl, nonyl, decyl, and so on.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "($C_2$-$C_{10}$)alkenyl" means an alkenyl radical having from 2 to 10 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "($C_2$-$C_{10}$)alkynyl" means an alkynyl radical having from 2 to 10 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

In an embodiment of Formula A, B, C or D, the moiety illustrated by the formula:

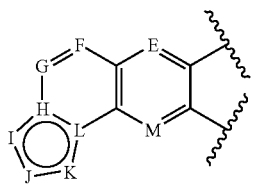

includes the following structures, which are meant to be merely illustrative and not limiting:

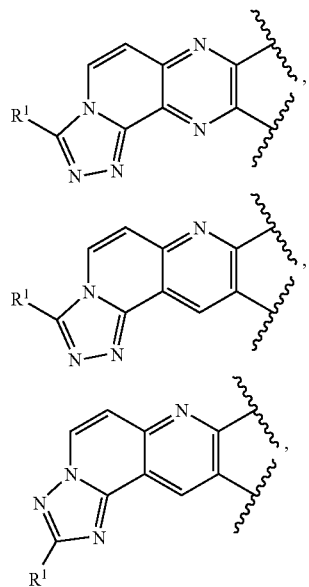

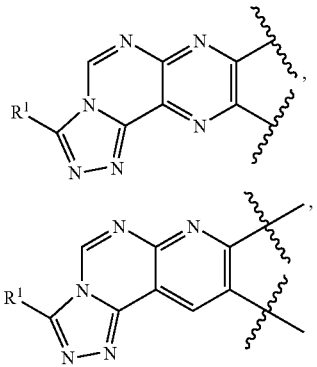

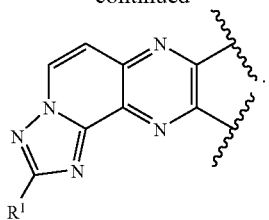

In another embodiment of Formula A, B, C or D, the moiety illustrated by the formula:

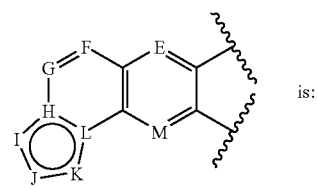

is:

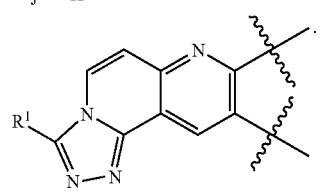

In an embodiment, ring Z is selected from: phenyl and heterocyclyl.

In another embodiment, ring Z is selected from:

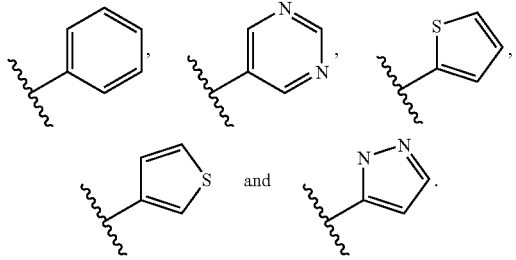

In yet another embodiment, ring Z is phenyl.
In an embodiment, p is independently 0, 1, 2 or 3.
In a further embodiment, p is independently 0, 1 or 2.
In another embodiment, p is independently 1.
In an embodiment, r is 0, 1, 2 or 3.
In a further embodiment, r is 0, 1 or 2.
In another embodiment, r is 1.
In an embodiment, Q is selected from: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, optionally substituted with one to three substituents selected from $R^{6a}$. Attachment of a heterocyclyl substituent can occur via a carbon atom or via a heteroatom.

In a further embodiment, Q is selected from: 2-azepinone, benzimidazolyl, benzimidazolonyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrazolyl, tetrahydrofuryl, tetrahydroisoquinolinyl, and thienyl, optionally substituted with one to three substituents selected from $R^{6a}$. Attachment of a heterocyclyl substituent can occur via a carbon atom or via a heteroatom.

In still a further embodiment, when Q is heterocyclyl, Q is selected from:

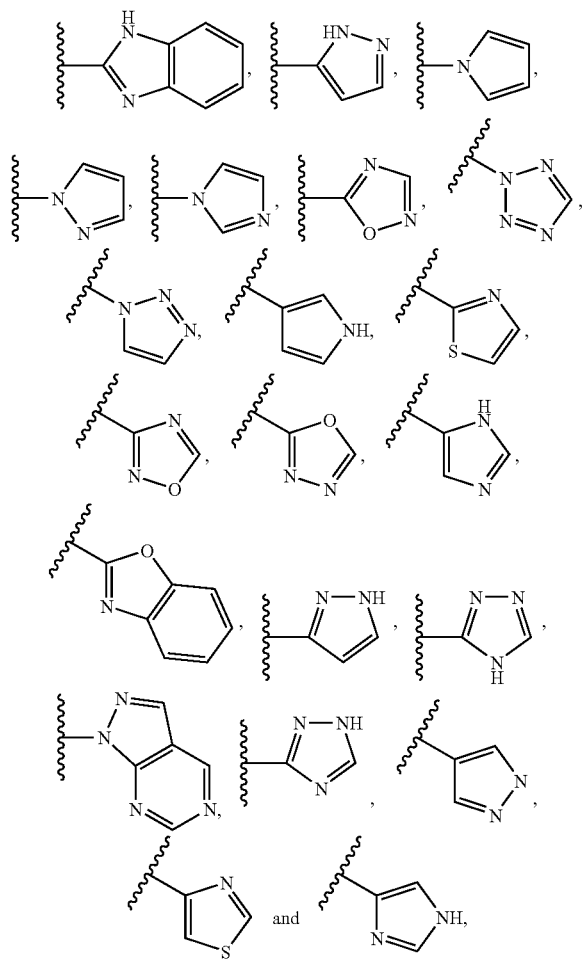

which are optionally substituted with one to three substituents selected from $R^{6a}$.

In yet a further embodiment, when Q is heterocyclyl, Q is selected from:

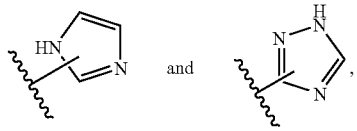

which is optionally substituted with one substituent selected from $R^{6a}$.

In an embodiment, $R^1$ is selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b$ $(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_2NR^7R^8$, SH, $S(O)_2-(C_1-C_{10})$alkyl and $(C=O)_aO_b$-heterocyclyl, said alkyl, aryl, alkenyl, alkynyl, cycloalkyl, and heterocyclyl is optionally substituted with $R^{6a}$.

In another embodiment, $R^1$ is selected from: oxo, $(C=O)_a$ $O_b(C_1-C_{10})$alkyl, $CO_2H$, halo, OH, CN, $(C_1-C_6)$alkoxy, $S(O)_2 NR^7R^8$, SH, $S(O)_2-(C_1-C_{10})$alkyl, $O(C=O)(C_1-C_6)$alkyl and $N(R^b)_2$, said alkyl is optionally substituted with $R^{6a}$.

In another embodiment, $R^1$ is selected from: oxo, $NH_2$, OH, SH, $O_a(C_1-C_6)$alkyl, said alkyl is optionally substituted with $R^{6a}$.

In an embodiment, $R^1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b$ $(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_2NR^7R^8$, SH, $S(O)_2-(C_1-C_{10})$alkyl and $(C=O)_aO_b$-heterocyclyl, said alkyl, aryl, alkenyl, alkynyl, cycloalkyl, and heterocyclyl is optionally substituted with $R^{6a}$.

In another embodiment, $R^1$ is selected from: H, oxo, $(C=O)_aO_b(C_1-C_{10})$alkyl, $CO_2H$, halo, OH, CN, $(C_1-C_6)$alkoxy, $S(O)_2NR^7R^8$, SH, $S(O)_2-(C_1-C_{10})$alkyl, $O(C=O)(C_1-C_6)$alkyl and $N(R^b)_2$, said alkyl is optionally substituted with $R^{6a}$.

In another embodiment, $R^1$ is selected from: H, oxo, $NH_2$, OH, SH, $O_a(C_1-C_6)$alkyl, said alkyl is optionally substituted with $R^{6a}$.

In an embodiment, $R^2$ is selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_2NR^7R^8$, $S(O)_2-(C_1-C_{10})$alkyl and $(C=O)_a$ $O_b$-heterocyclyl, said alkyl, aryl, alkenyl, alkynyl, cycloalkyl, and heterocyclyl is optionally substituted with $R^b$, OH, $(C_1-C_6)$alkoxy, halogen, $CO_2H$, CN, $O(C=O)(C_1-C_6)$alkyl, oxo, and $N(R^b)_2$.

In another embodiment, $R^2$ is selected from: oxo, $(C=O)_a$ $O_b(C_1-C_{10})$alkyl, $CO_2H$, halo, OH, CN, $(C_1-C_6)$alkoxy, $O(C=O)(C_1-C_6)$alkyl, $(C_2-C_{10})$alkenyl and $N(R^b)_2$, said alkyl is optionally substituted with $R^b$, OH, $(C_1-C_6)$alkoxy, halogen, $CO_2H$, CN, $O(C=O)(C_1-C_6)$alkyl, oxo, and N $(R^b)_2$.

In an embodiment, $R^3$ is selected from: H, oxo, $O_b(C_1-C_{10})$alkyl, $O_b$-aryl, $O_b(C_2-C_{10})$alkenyl, $O_b(C_2-C_{10})$alkynyl, halo, OH, $O_b(C_1-C_6)$perfluoroalkyl, $(C=O)_aNR^7R^8$, CN, $(C=O)_a$ $O_b(C_3-C_8)$cycloalkyl, $S(O)_mNR^7R^8$, SH, $S(O)_m-(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one or more substituents selected from $R^6$.

In another embodiment, $R^3$ is selected from: $(C_1-C_{10})$alkyl, aryl, $(C_2-C_{10})$alkenyl, $(C_2-C_{10})$alkynyl, halo, $NR^7R^8$, CN, $(C_3-C_8)$cycloalkyl, $S(O)_mNR^7R^8$, SH, $S(O)_m-(C_1-C_{10})$ alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one or more substituents selected from $R^6$.

In another embodiment, $R^3$ is selected from: $(C_1-C_{10})$alkyl, said alkyl is optionally substituted with one to three substituents selected from $NH_2$, OH, oxo and halo.

In another embodiment, $R^4$ and $R^5$ are H.

In an embodiment, when Q is substituted with $R^{6a}$, said $R^{6a}$ is heterocyclyl optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$.

In another embodiment, when Q is substituted with $R^{6a}$, said $R^{6a}$ is selected from:

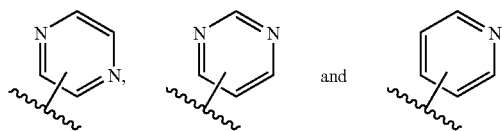

optionally substituted with 1 to 3 substituents selected from oxo, OH, $N(R^b)_2$, halogen and $O_a(C_1-C_6)$alkyl.

In an embodiment $R^b$ is independently selected from H and $(C_1-C_6)$alkyl.

In an embodiment of Formula J, $R^4$ and $R^5$ are independently: H and $CH_3$, or $R^4$ and $R^5$ may be joined to form cyclopropyl.

Included in the instant invention is the free form of compounds of Formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

UTILITY

The compounds of the instant invention are inhibitors of the activity of Akt and are thus useful in the treatment of cancer, in particular cancers associated with irregularities in the activity of Akt and downstream cellular targets of Akt. Such cancers include, but are not limited to, ovarian, pancreatic, breast and prostate cancer, as well as cancers (including glioblastoma) where the tumor suppressor PTEN is mutated (Cheng et al., *Proc. Natl. Acad. Sci.* (1992) 89:9267-9271; Cheng et al., *Proc. Natl. Acad. Sci.* (1996) 93:3636-3641; Bellacosa et al., *Int. J. Cancer* (1995) 64:280-285; Nakatani et al., *J. Biol. Chem.* (1999) 274:21528-21532; Graff, *Expert. Opin. Ther. Targets* (2002) 6(1):103-113; and Yamada and Araki, *J. Cell Science.* (2001) 114:2375-2382; Mischel and Cloughesy, *Brain Pathol.* (2003) 13(1):52-61).

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal:

esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung.

Cancers that may be treated by the compounds, compositions and methods of the invention include: breast, colon, (colorectal) and lung.

Cancers that may be treated by the compounds, compositions and methods of the invention include: lymphoma and leukemia.

Akt signaling regulates multiple critical steps in angiogenesis. Shiojima and Walsh, *Circ. Res.* (2002) 90:1243-1250. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5): 871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther.* (2002) 2(8):953-966). Thus, the Akt inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research*, 61: 3206-3211 (2001)). The Akt inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hyperinsulinism.

The compounds of the invention are also useful in preparing a medicament that is useful in treating the diseases described above, in particular cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins lacking the PH domain.

In a further embodiment, the instant compound is selected from the group of a selective inhibitor of Akt1, a selective inhibitor of Akt2 and a selective inhibitor of both Akt1 and Akt2.

In another embodiment, the instant compound is selected from the group of a selective inhibitor of Akt1, a selective inhibitor of Akt2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

The present invention is further directed to a method of inhibiting Akt activity which comprises administering to a mammal in need thereof a pharmaceutically effective amount of the instant compound.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos.

6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v \beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-43-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9- methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/β agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia.

Such a neutropenia treatment agent is, for example, a hematopoietic growth factor which regulates the production and function of neutrophils such as a human granulocyte colony stimulating factor, (G-CSF). Examples of a G-CSF include filgrastim A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Abbreviations used in the description of the chemistry and in the Examples that follow are: AEBSF (p-aminoethylbenzenesulfonyl fluoride); BSA (bovine serum albumin); BuLi (n-Butyl lithium); CDCl₃ (chloroform-d); CuI (copper iodide); CuSO$_4$ (copper sulfate); DCE (dichloroethane); DCM (dichloromethane); DEAD (diethyl azodicarboxylate); DMF (N,N-dimethylformamide); DMSO (dimethyl sulfoxide); DTT (dithiothreitol); EDTA (ethylene-diamine-tetraacetic acid); EGTA (ethylene-glycol-tetra-acetic acid); EtOAc (ethyl acetate); EtOH (ethanol); HOAc (acetic acid); HPLC (high-performance liquid chromatography); HRMS (high resolution mass spectrum); LCMS (liquid chromatograph-mass spectrometer); LHMDS (lithium bis(trimethylsilyl)amide); LRMS (low resolution mass spectrum); MeOH (methanol); MP-B(CN)H$_3$ (Macroporous cyanoborohydride); NaHCO$_3$ (sodium bicarbonate); Na$_2$SO$_4$ (sodium sulfate); Na(OAc)$_3$BH (sodium triacetoxyborohydride); NH$_4$OAc (ammonium acetate); NBS (N-bromosuccinamide); NMR (nuclear magnetic resonance); PBS (phosphate buffered saline); PCR (polymerase chain reaction); Pd(dppf) ([1,1'-bis(diphenylphosphino)ferrocene]palladium); Pd(Ph3)$_4$ (palladium(0) tetrakis-triphenylphosphine); POCl$_3$ (phosphorous oxychloride); PS-DIEA (polystyrene diisopropylethylamine); PS-PPh$_3$ (polystyrene-triphenyl phosphine); TBAF (tetrabutylammonium fluoride); THF (tetrahydrofuran); TFA (trifluoroacteic acid); TMSCH$_2$N2 (trimethylsilyldiazomethane) and Ac (acetyl); BOC (t-butoxycarbonyl); Bu (butyl); Cal (calculated); Calc'd (calculated); DIEA (diisopropylethylamine); DMAP (4-dimethylaminopyridine); EDC(N-ethyl-N'-(3-dimethylaminopropyl)carbodiimide); Eq (equivalents); Et (ethyl); HOBT (hydroxybenzotriazole); IPA (isopropanol); LC/MS (liquid chromatograph-mass spectrometer); Me (methyl); MeCN (acetonitrile); NMP(N-methylpyrrolidinone); Pr (propyl); Pyr (pyridine); Sat (saturated) and Tosic (p-toluenesulfonic acid).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes does not necessarily correlate to that used in the claims and often, for clarity, a single substituent is shown attached to the compound where multiple substituents are allowed under the definitions of Formula A hereinabove.

Initial synthesis of the instant compounds are shown in Reactions Schemes I-IX. Final reactions that may be used to generate the compounds of this invention are shown in Reaction Schemes X-XIV.

Synopsis of Reaction Schemes

The following Reaction Schemes, Reaction Schemes I-IX, provide useful details for preparing the bicyclic moieties of the instant compounds.

The requisite intermediates are in some cases commercially available, or can be prepared according to literature procedures. As illustrated in Reaction Scheme I, a suitably substituted phenylacetylide may be reacted with copper iodide to form the corresponding copper acetylide I-1 (see for example, Sonogashira, K.; Toda, Y.; Hagihara, N. *Tetrahedron Lett.* 1975, 4467). Intermediate I-1 may then react with a suitably substituted electrophilic moiety to provide the asymetrically substituted I-2. Reaction with NBS followed by hydrolysis provides I-3 (see for example, Yusybov, M. S.; Filimonov, V. D.; *Synthesis* 1991, 2, 131). A variety of substituted and unsubstituted aryls and heterocyclyls may also be obtained commercially.

Reaction Scheme II illustrates the preparation of the compounds, starting with a suitably substituted II-1. This intermediate can be reacted with a suitably substituted amine to provide intermediate II-2, which can be reacted with a suitable aryl or heteroaryl diamine to provide a regioisomeric mixture of the instant compounds, which can usually be separated chromatographically.

Reaction Scheme III illustrates the synthesis of another bicyclic heterocyclyl.

Reaction Scheme IV illustrates the preparation of compounds, starting with a suitably substituted 4-amino-3-nitrobenzonitrile IV-I. This intermediate can then subjected to a microwave promoted [3+2] cycloaddition reaction to afford tetrazole IV-II. Alkylation of the acidic tetrazole with an electrophile, such as methyl iodide, delivers a 2-methyl(IV-III)/1-methyl(IV-IV) mixture of alkylated tetrazoles which are separable by column chromatography. Ra—Ni hydrogenation of IV-III delivers the diamine IV-V. Further synthesis is as described in the Reaction Schemes above.

Reaction Scheme V is illustrative for the synthesis of compounds. Friedlander cyclocondensation of a suitably substituted aryl or heteroaryl aminoaldehyde with a suitably substituted ketone gives intermediates of formula V-1. Conversion of the carboxylic acid functionality to an aldehyde functionality gives intermediate V-2 and is accomplished by methods well known to someone skilled in the art. Reductive alkylation with a suitably substituted amine provides compounds of formula V-3.

Reaction Scheme VI illustrates an alternate synthesis of intermediate V-2.

Reaction Scheme VII illustrates the synthesis of the compounds, starting with ketone VII-I which is prepared according to literature (Renault, O.; Dallemagne, P.; and Rault, S. *Org. Prep. Proced. Int.,* 1999, 31, 324). Condensation of VII-1 with N,N-dimethylformamide dimethylacetal gives keto-enamine VII-2, which cyclizes with 2-cyanoacetamide to afford pyridone VII-3. Treatment of VII-3 with phosphorus oxychloride produces chloropyridin VII-4. Radical bromination followed by displacement with suitably substituted amines generates amines VII-5. Subsequent reaction of chloronicotinonitriles VII-5 with various bisnucleophiles provides the cyclized structures VII-6.

Reaction Scheme VIII illustrates the preparation of the 1,6-naphthyridin-6(5H)-one compounds. Synthesis starts with a commercially available carboxylic acid (VIII-1), which is converted to Weinreb amide (VIII-2). Reaction of amide with an aryl lithium reagent, generated through lithium-halogen exchange reaction of an aryl bromide with n-butyl lithium, provides the ketone (VIII-3) Condensation of this substituted ketone with 4-aminonicotinaldehyde in the presence of a base, for example, sodium hydroxide or sodium methoxide, gives the 1,6-naphthyridine (VIII-4). The R substituent on the phenyl can be a functional group, such as, a (silyl)protected hydroxymethyl, the masked aldehyde (i.e. acetal), or a carboxylic acid. This material can be converted to the requisite aldehyde VIII-4. When the R group is hydroxymethyl, oxidation with a reagent such as activated manganese dioxide gives the aldehyde VIII-4. When R is an acetal, mild acid hydrolysis gives the aldehyde. Reduction of the carboxylic acid group via reduction of a mixed anhydride with a borohydride also gives the aldehyde VIII-4. This aldehyde can then undergo reductive amination with a diverse array of amines, for example, a 4-substituted piperidine, and a borohydride to provide 1,6-naphthyridin-5(H)-ones (VIII-5). Treatment of (VIII-5) with pyridinium hydrochloride at 150° C. furnishes the final product (VIII-6).

Reaction Scheme IX illustrates an alternate strategy of introducing heterocycles at the C3-position. It starts with commercially available dichloro benzopyrazine, which can be coupled to an aryl boronic acid in the presence of a palladium catalyst (Suzuki reaction). Then a repeat of this reaction with another heterocyclic boronic acid provides the final product, under the same reaction conditions.

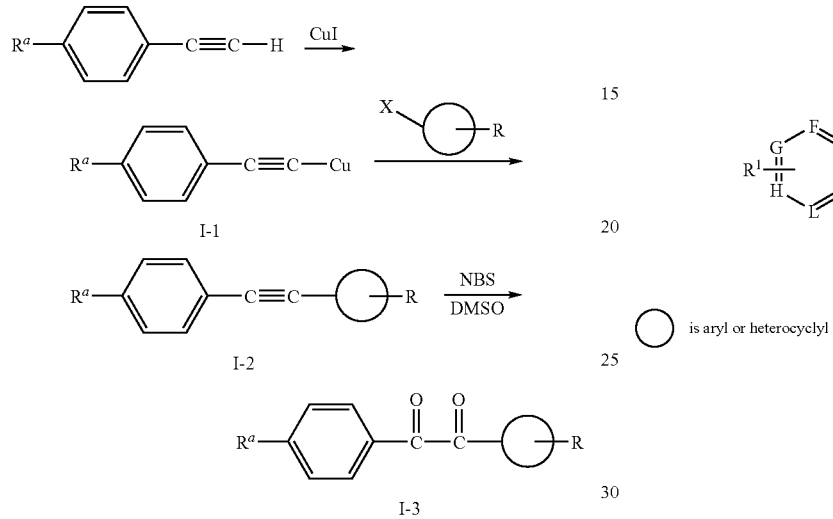

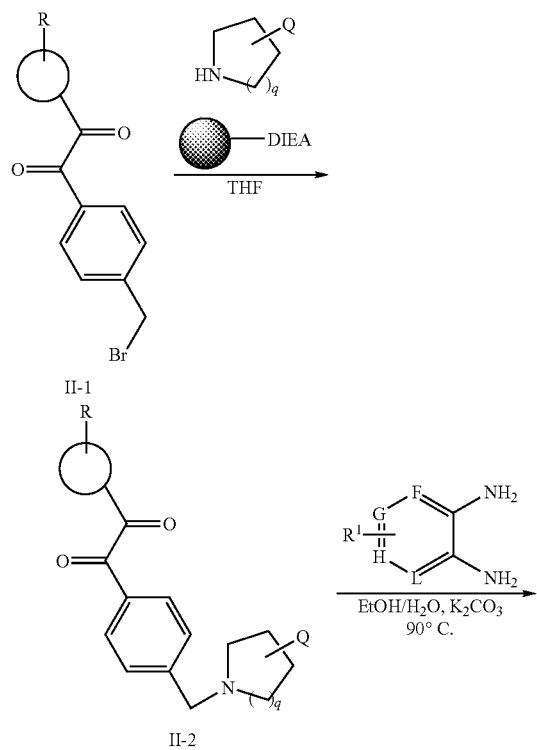

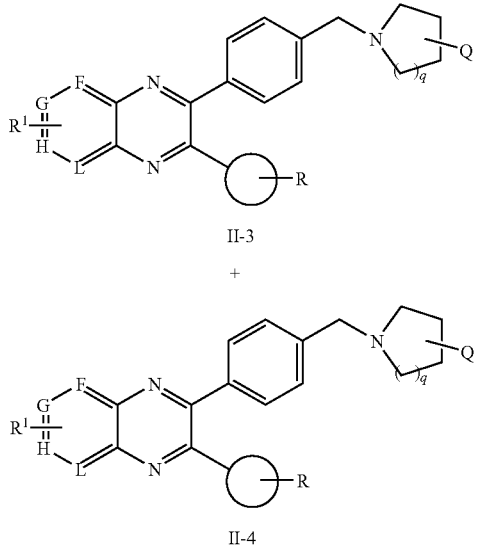

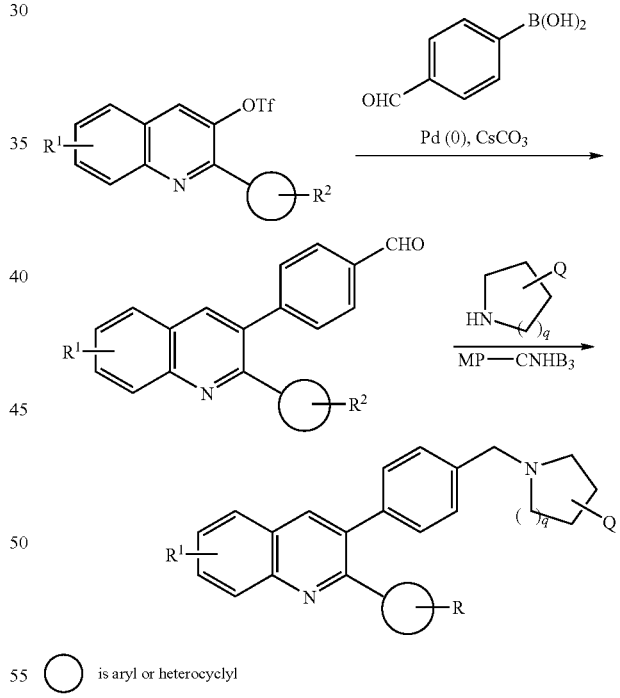

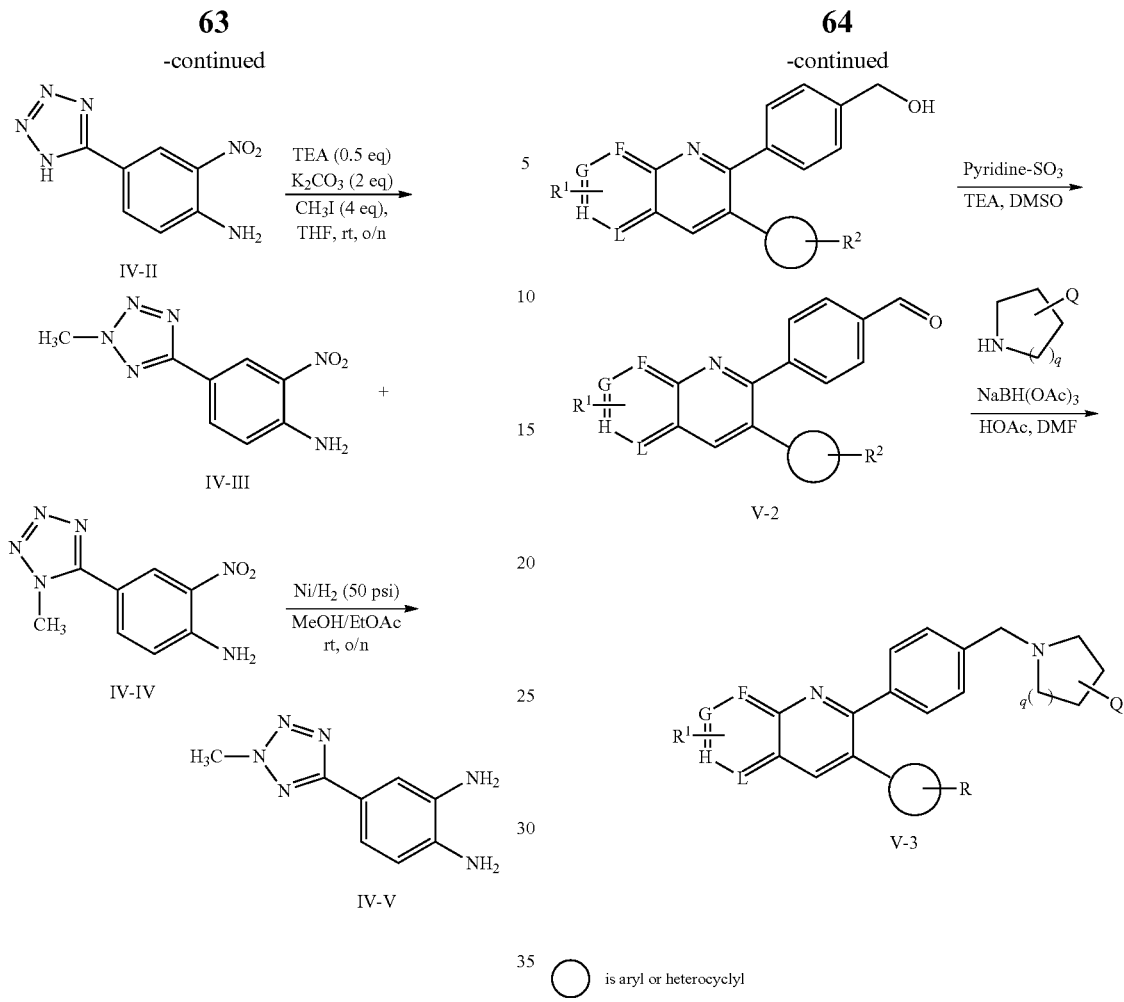
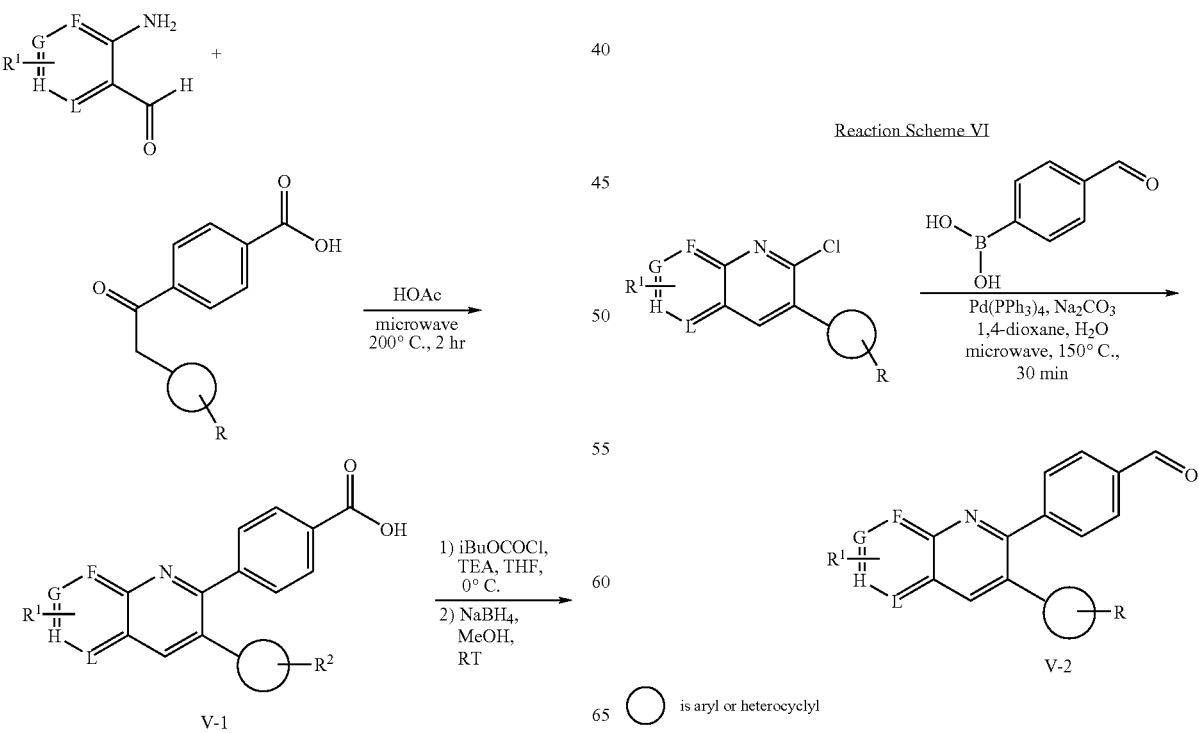

Reaction Scheme VII
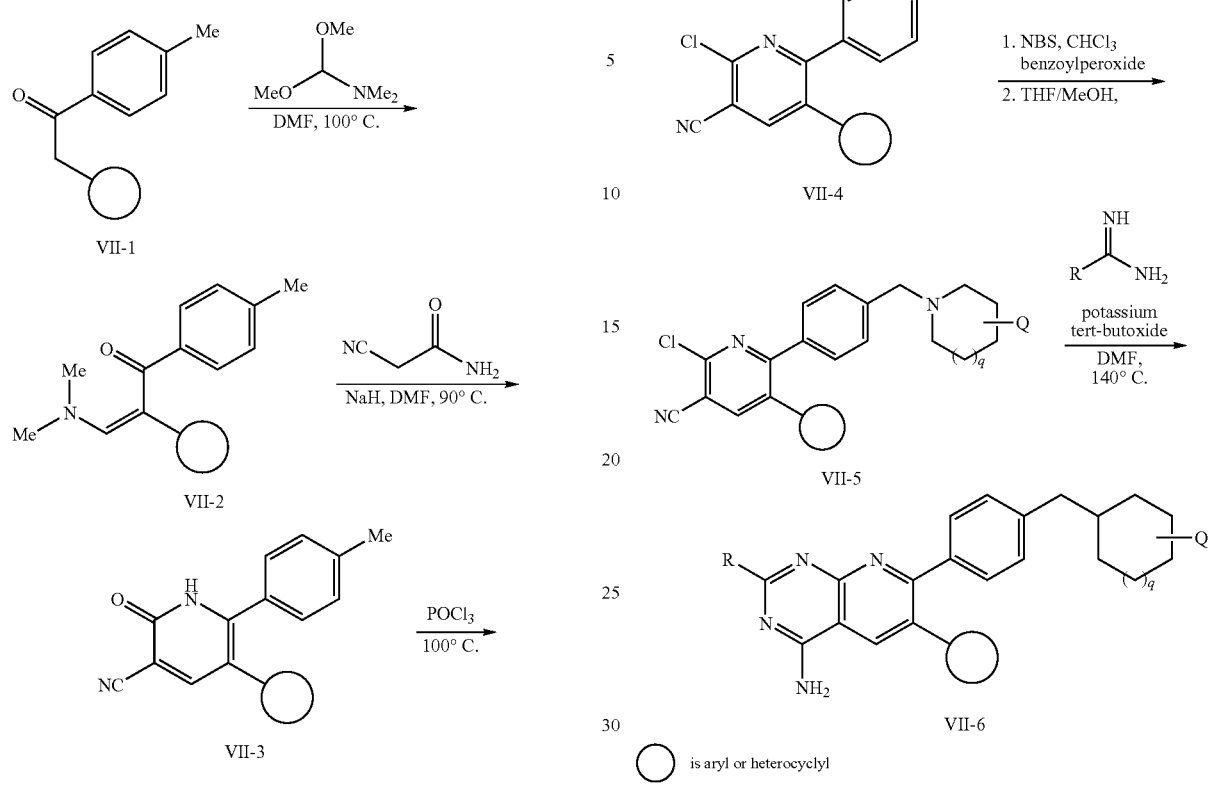
is aryl or heterocyclyl
Reaction Scheme VIII
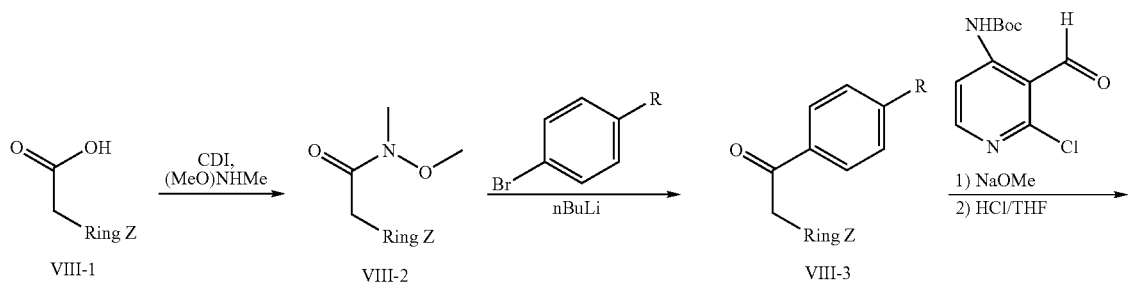
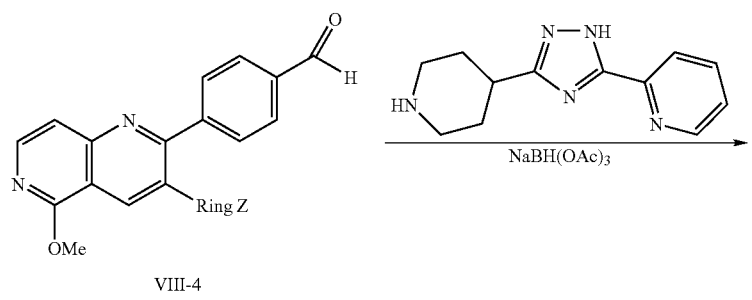

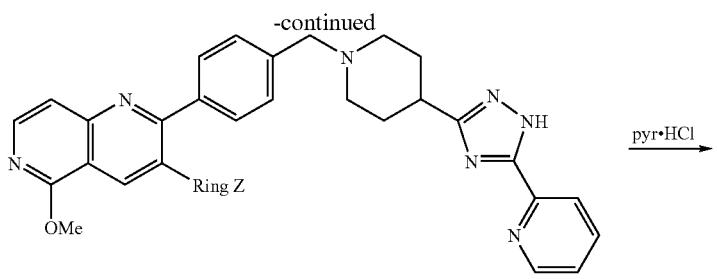

VIII-5

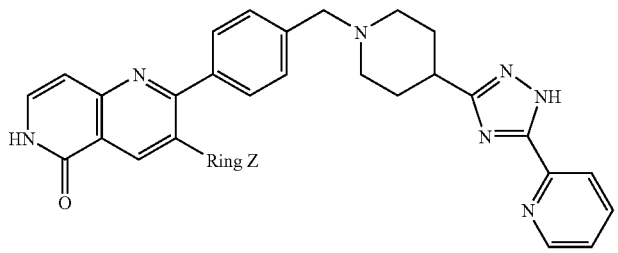

VIII-6

Reaction Scheme IX

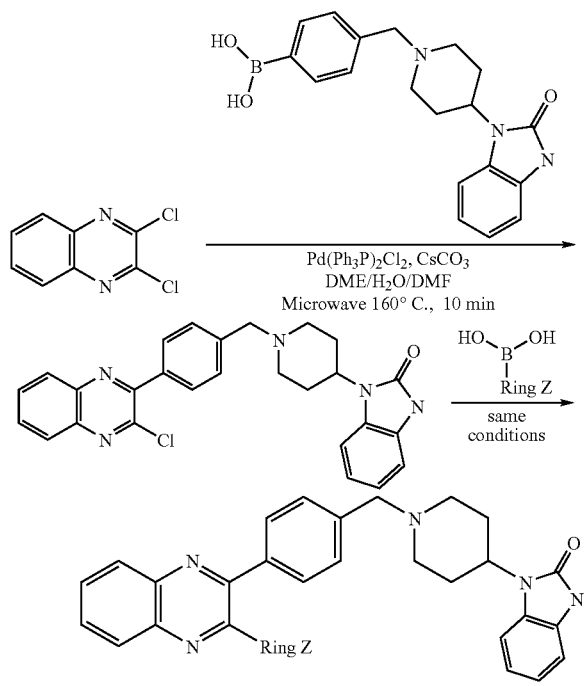

Final Synopsis of Reaction Schemes

The following Reaction Schemes, Reaction Schemes X-XIV, provide useful details for preparing the tricyclic moieties of the instant compounds.

The requisite intermediates are in some cases commercially available, or can be prepared according to literature procedures. Treatment of a suitably substituted aryl or heteroaryl intermediate X-1 with $POCl_3$ gives intermediates of formula X-2. Conversion of the chloride functionality to a hydrazide functionality gives intermediate X-3 and is accomplished by methods well known to someone skilled in the art. Cyclization with a suitably diimidazole precusor provides compounds of formula X-4.

Reaction Scheme XI illustrates an alternate synthesis of compounds of formula X-4.

Reaction Scheme XII illustrates synthesis of compounds of formula XII-2. Condensation of X-3 with appropriate trimethoxychloroacetate gives chloromethyl intermediate XII-1, which, via a nucleophilic displacement, affords structure XII-2.

Reaction Scheme XIII illustrates the preparation of the triazolonaphthyridine compounds. Synthesis starts with literature/patent known naphthyridone (XIII-1), which is converted to naphthyridine chloride (XIII-2) after treatment of $POCl_3$ under reflux condition. Reaction of the latter compound with neat hydrazine, and under reflux condition, provides the hydrazide (XIII-3) which serves as a key intermediate for the synthesis of triazolonaphthyridine compounds. Conversion of this hydrazide (XIII-4) to the requisite triazolonaphthyridine compounds under indicated conditions complete the planned synthesis. The R substituent on the triazolo moiety can be a functional group, such as, an amino group, an oxo group or a thiol group.

Reaction Scheme XIV illustrates an alternate strategy of introducing the triazolo moiety at the left-hand portion of the molecule. It starts with previously synthesized intermediate hydrazide (XIII-3) which can be treated with a trimethoxy orthoacetate to furnish the desired final product, thiazolonaphthridine compounds (XIV-1). The R substituent on the triazolo moiety can be a functional group, such as, a proton, a simple alkyl group, a chloromethyl group or a functionalized alkyl group.

Reaction Scheme XV illustrates the synthesis of compounds of formula XV-1 using three different reductive amination methods to introduce a primary amine at the benzylic position. The methods are also applicable to other aldehydes such as compounds of formula XVII-1.

Reaction Scheme XVI illustrates the synthesis of compounds of formula XVI-2 using a variant of the conditions for the cyclocondensation shown in reaction Scheme VIII. Use of an aprotic solvent and a base gives access to chloronaphthyridines of structure XVI-2.

Reaction Scheme XVII illustrates the synthesis of compounds of formula XVII-4. In this case a methyl substituent is introduced at the benzylic position via sulfinamide XVII-2. Other substituents can be introduced using organometallic reagents such as Grignard reagents. The t-butylsulfinimide can be cleaved using an acid such as HCl to give the amine.

Reaction Scheme XVIII illustrates the synthesis of compounds of formula XVIII-2 as a variant of the triazole synthesis described in Reaction Scheme XI. In this case the hydrazine XVIII-1 is coupled to a carboxylic acid and the intermediate acylhydrazine is cyclized to the fused triazole under acid catalysis.

Reaction Scheme XIX illustrates the synthesis of compounds of formula XIX-2 in which the cyclopropylamine is synthesized from the nitrile XIX-1.

Reaction Scheme XX illustrates the synthesis of compounds of formula XX-2 from amines of formula XX-1 under standard reductive amination conditions.

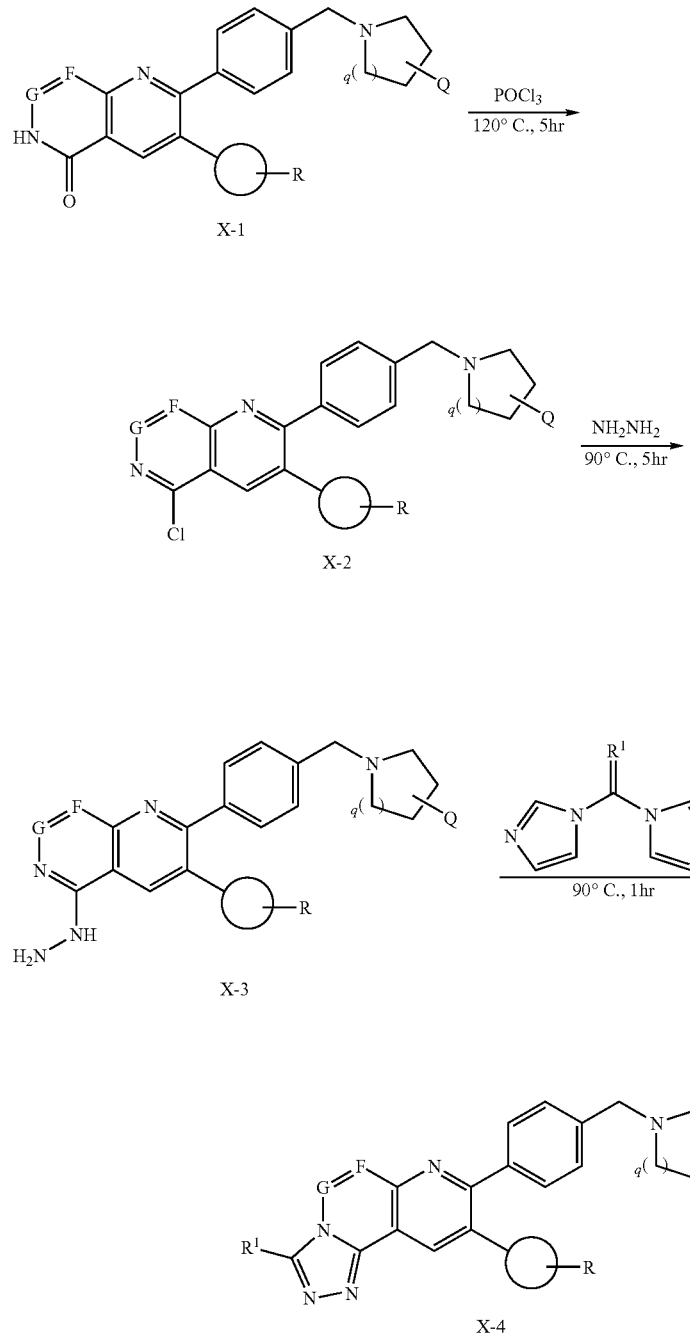

Reaction Scheme XI
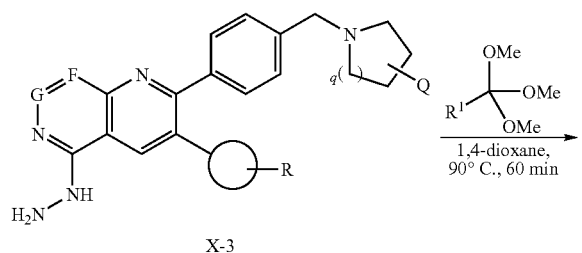
Reaction Scheme XII
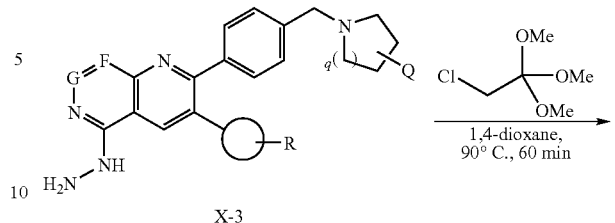
Reaction Scheme XIII
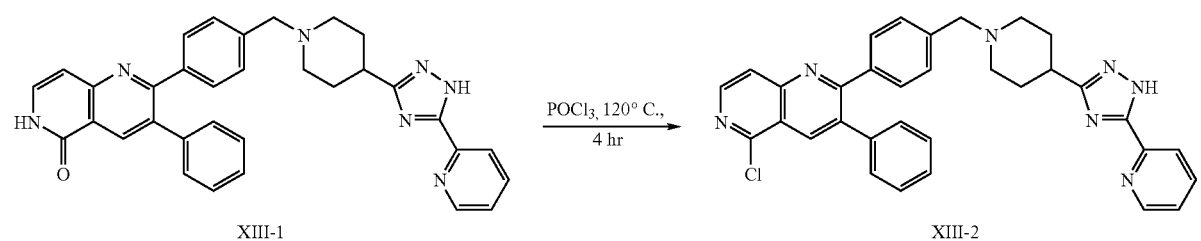
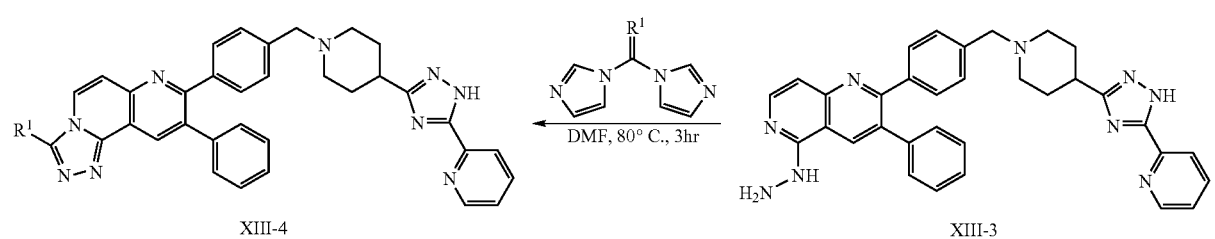

Reaction Scheme XIV
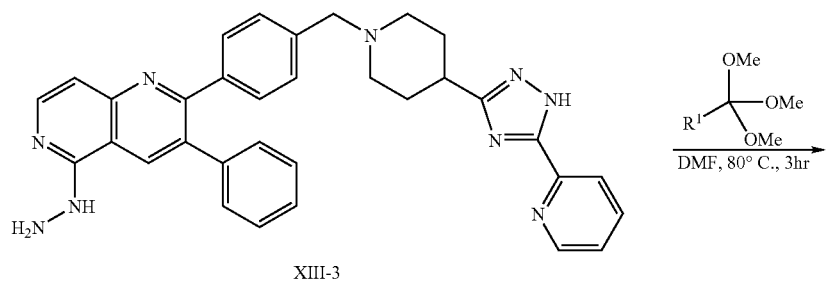
Reaction Scheme XV
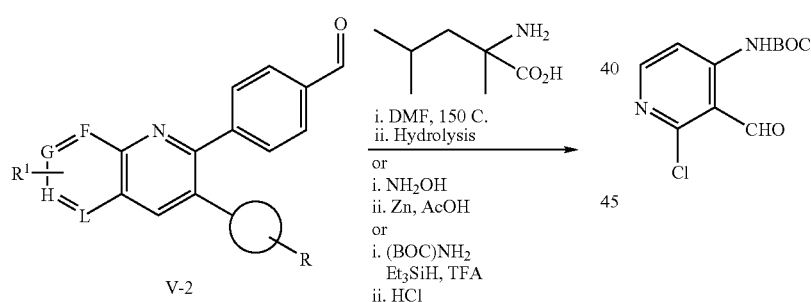
Reaction Scheme XVI
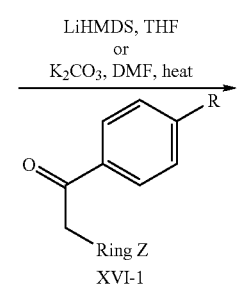
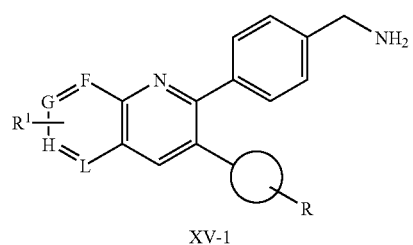
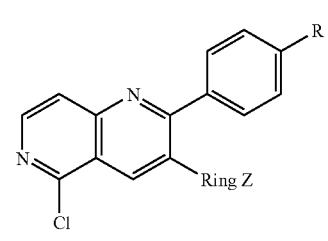

Reaction Scheme XVII
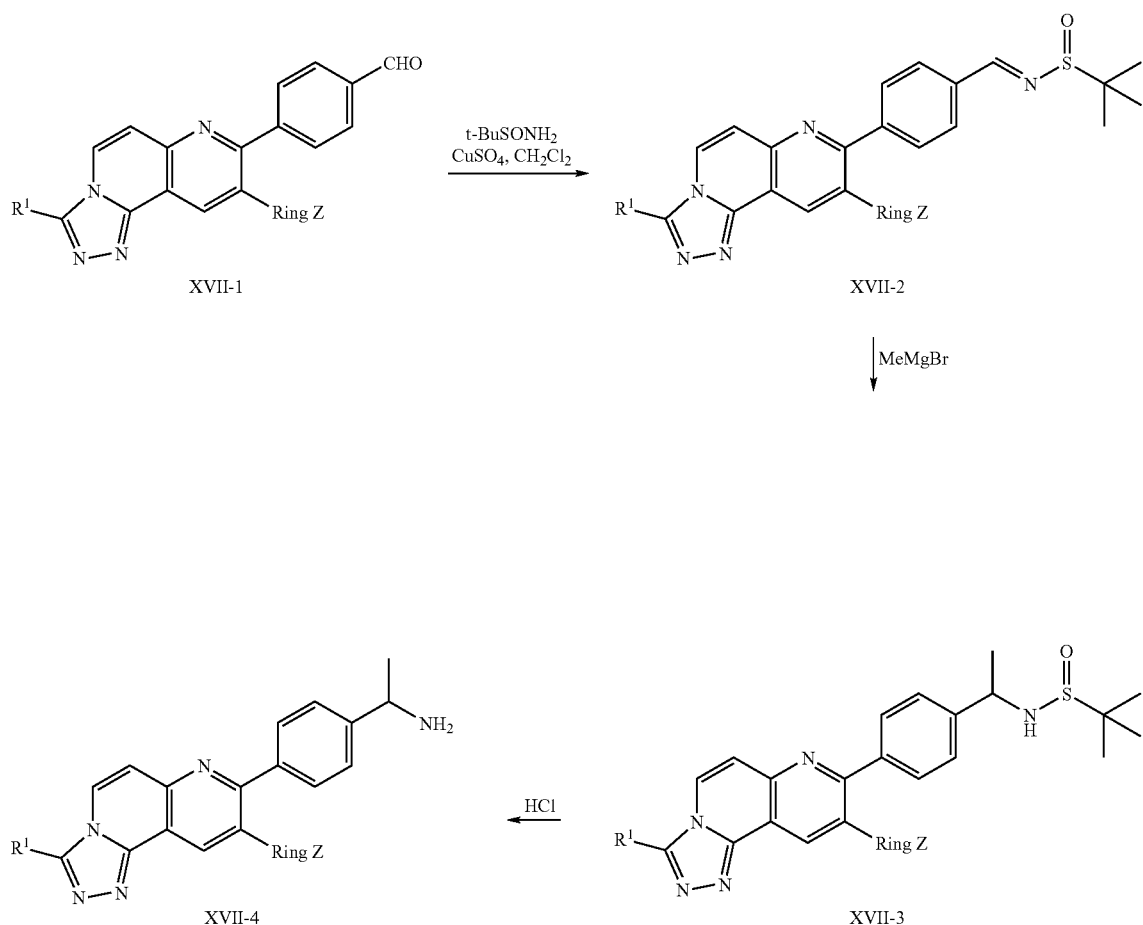
Reaction Scheme XVIII
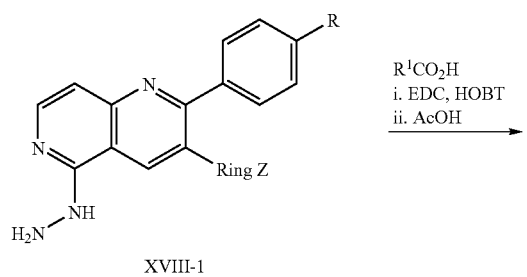
Reaction Scheme XIX
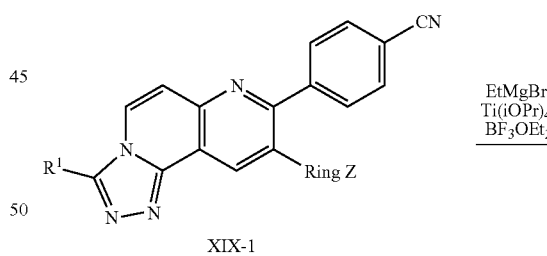
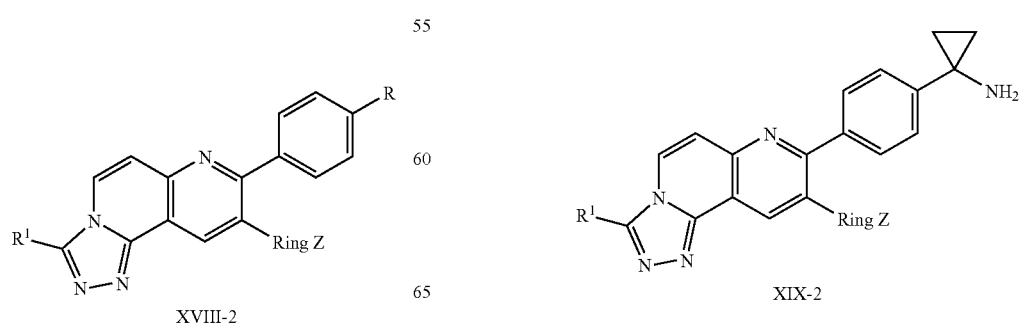

Reaction Scheme XX

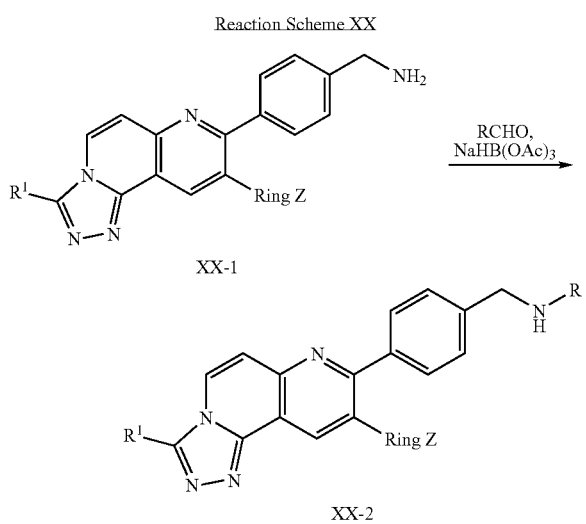

EXAMPLES

Examples and schemes provided are intended to assist in a further understanding of the invention. Particular materials employed, species and conditions are intended to be further illustrative of the invention and do not limit the reasonable scope thereof.

eridin-1-yl]methyl}phenyl)-1,6-naphthyridin-5(6H)-one (0.86 g, 1.6 mmol), followed by anhydrous $POCl_3$ (8 mL). The mixture was heated to 120° C. and stirred under reflux for 4 hours. After the reaction was cooled to room temperature, the reaction mixture was carefully added to a mixture of cold saturated $NaHCO_3$ aqueous solution (20 mL) and EtOAc (20 mL). The PH of the aqueous layer was maintained at around PH 8-9 throughout the quenching process. The aqueous solution was further extracted twice with EtOAc (15 mL) and the residue was washed with MeOH (20 mL). The organic phases were combined and concentrated in vacuo to give 5-chloro-3-phenyl-2-(4-{[4-(5-pyridin-2-yl-1H-1,2,4-triazol-3-yl)piperidin-1-yl]methyl}phenyl)-1,6-naphthylridine (1-2) (900 mg). The crude material was used directly in the next step without further purifications.

5-hydrazino-3-phenyl-2-(4-{[4-(5-pyridin-2-yl-1H-1,2,4-triazol-3-yl)piperidin-1-yl]methyl}phenyl)-1,6-naphthyridine (1-3)

A 25 ml RB flask with a stirring bar was charged with 5-chloro-3-phenyl-2-(4-{[4-(5-pyridin-2-yl-1H-1,2,4-triazol-3-yl)piperidin-1-yl]methyl}phenyl)-1,6-naphthylridine (1-2) (900 mg, 1.6 mmol), followed by anhydrous $NH_2NH_2$ (8 mL). The suspension was heated to 110° C. and stirred under reflux for 5 hours. After the reaction was cooled to room temperature, the reaction mixture was concentrated in vacuo to give a yellowish powder (900 mg). The crude product was taken to the next step without further purification.

SCHEME 1

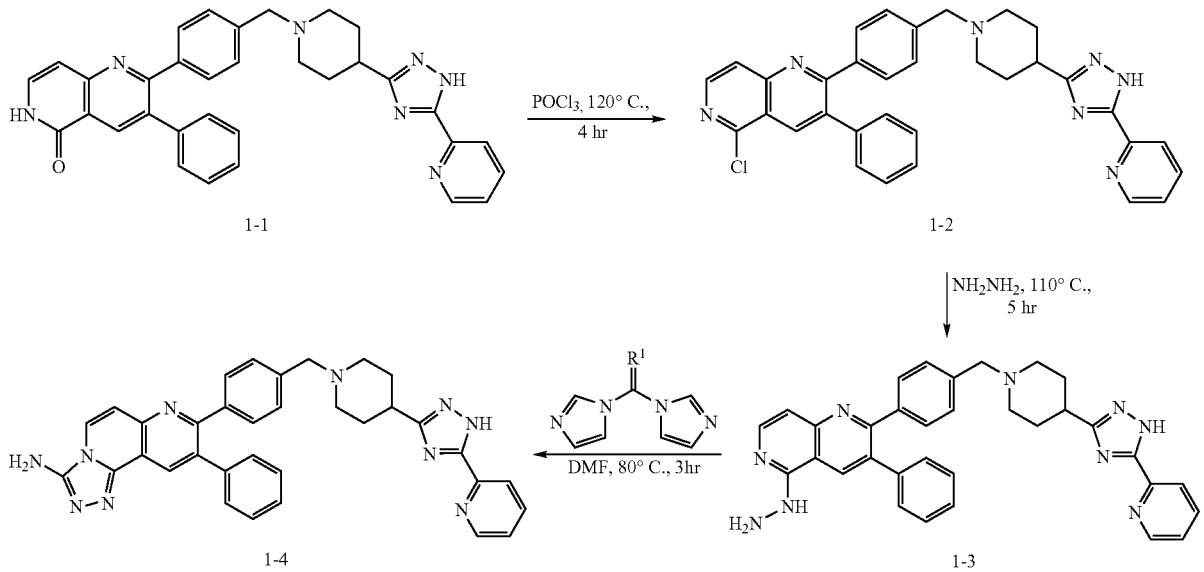

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-amine (1-4)

5-chloro-3-phenyl-2-(4-{[4-(5-pyridin-2-yl-1H-1,2,4-triazol-3-yl)piperidin-1-yl]methyl}phenyl)-1,6-naphthylridine (1-2)

A 25 mL RB flask with a stirring bar was charged with 3-phenyl-2-(4-{[4-(5-pyridin-2-yl-1H-1,2,4-triazo-3-yl)pip- 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-amine (1-4)

To 5-hydrazino-3-phenyl-2-(4-{[4-(5-pyridin-2-yl-1H-1,2,4-triazol-3-yl)piperidin-1-yl]methyl}phenyl)-1,6-naphthyridine (1-3) (70 mg, 0.126 mmol) in DMF (1.5 mL) was added literature known 1,1-di-1H-imidazol-1-ylmethanimine (102 mg, 0.633 mmol). The reaction mixture was stirred at 85° C. for 4 hours, concentrated in vacuo, and chromatographed to furnish the desired 9-phenyl-8-(4-{[40 (5-pyridin-2-yl-1H-1,2,4-triazol-3-yl)piperidin-1-yl] methyl}phenyl}[1,2,4]triazolo[3,4-f]-1,6-naphthyridin-3-amine (1-4) (46 mg) as its trifluoroacetic acid salt. $^1$H NMR: (500 MHz, CDCl$_3$) δ 8.76 (s, 1H), 8.74 (d, J=4.3 Hz, 1H), 8.29-8.27 (m, 2H), 8.19 (m, 1H), 7.67 (m, 1H), 7.54-7.53 (m, 2H), 7.48-7.46 (m, 2H), 7.47 (d, J=7.7 Hz, 1H), 7.34-7.26 (m, 5H), 4.43 (s, 2H), 3.65 (br d, J=10.9 Hz, 2H), 3.46 (br s, 1H), 3.27-3.19 (m, 2H), 2.50-2.42 (m, 2H), 2.10-2.06 (m, 2H).

The following compounds in Table 1 were prepared in a similar manner as shown in Scheme 1 and as shown in the Reaction Schemes.

TABLE 1

| Cmp | Structure | Name | HRMS m/z (M + H) |
|---|---|---|---|
| 1-5 | 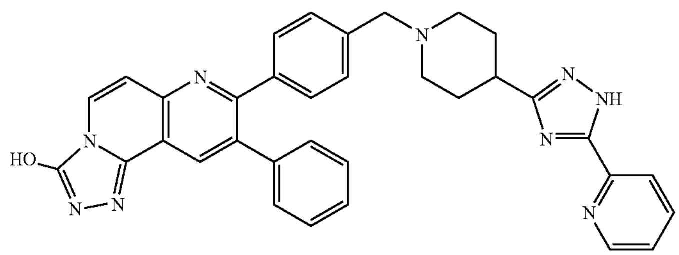 | 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol | 579.3 |
| 1-6 | 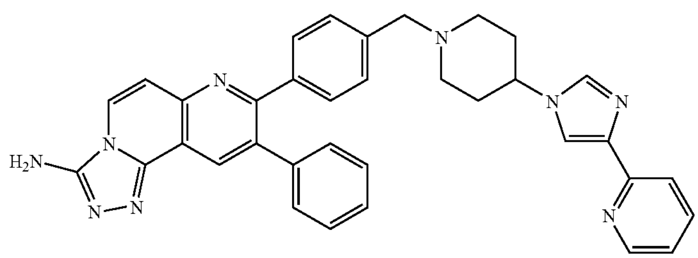 | 9-phenyl-8-(4-{[4-(4-pyridin-2-yl-1H-imidazol-1-yl)piperidin-1-yl]methyl}phenyl)[1,2,4]triazolo[3,4-f]-1,6-naphthyridin-3-amine | 577.3 |
| 1-7 | 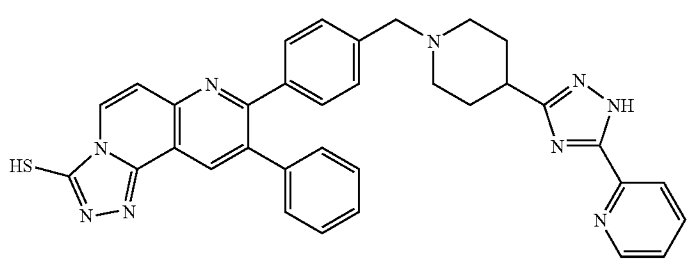 | 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol | 595.2 |

SCHEME 2

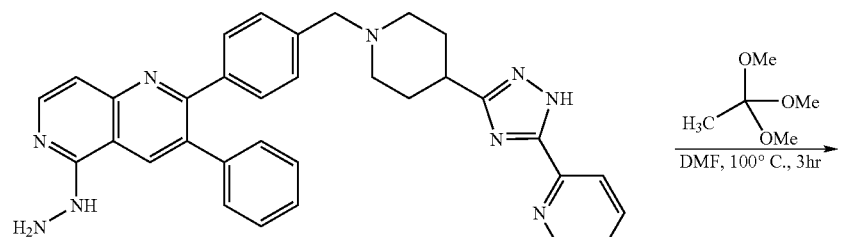

2-1

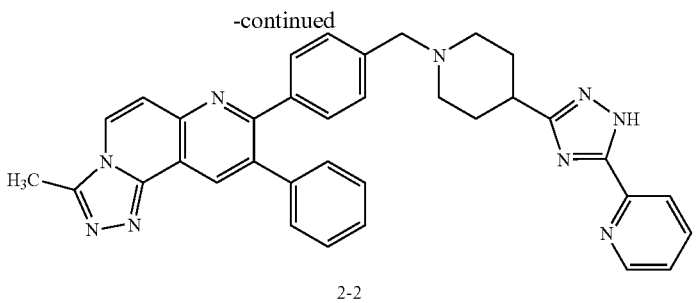

2-2

3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine (2-2)

To 5-hydrazino-3-phenyl-2-(4-{[4-(5-pyridin-2-yl-1H-1,2,4-triazol-3-yl)piperidin-1-yl]methyl}phenyl)-1,6-naphthyridine (2-1) (55 mg, 0.101 mmol) in DMF (1.0 mL) was added trimethyl orthoacetate (0.63 mL, 5.04 mmol). The reaction mixture was stirred at 100° C. for 3 hours, and then concentrated in vacuo, and chromatographed to furnish the desired 3-methyl-9-phenyl-8-(4-{[4-(5-pyridin-2-yl-1,2,4-triazol-3-yl)piperidin-1-yl]methyl}phenyl)[1,2,4]triazolo[3,4-f]-1,6-naphthyridine (2-2) (28 mg) as its trifluoroacetic acid salt. $^1$H NMR: (500 MHz, CDCl$_3$) δ 8.87 (s, 1H), 8.65 (d, J=6.4 Hz, 1H), 8.33 (d, J=7.5 Hz, 1H), 8.11 (d, J=7.8 Hz, 1H), 7.92 (t, J=7.8 Hz, 1H), 7.49-7.41 (m, 3H), 7.36-7.30 (m, 8H), 3.61 (s, 2H), 3.02-3.00 (m, 2H), 3.00-2.84 (m, 1H), 2.25-2.21 (m, 2H), 2.10-1.83 (m, 4H), 1.97 (s, 3H).

The following compounds in Table 1 were prepared in a similar manner as shown in Scheme 2 and as shown in the Reaction Schemes:

TABLE 2

| Cmp | Structure | Name | HRMS m/z (M + H) |
|---|---|---|---|
| 2-3 | 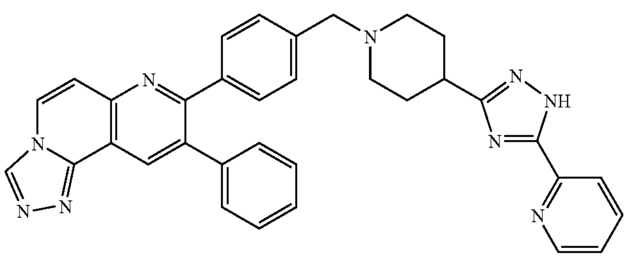 | 9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine | 563.3 |
| 2-4 | 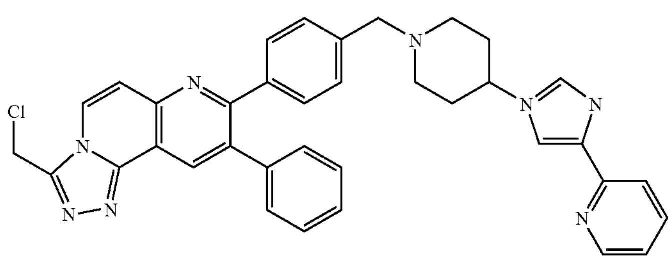 | 3-(chloromethyl)-9-phenyl-8-(4-{[4-(4-pyridin-2-yl-1H-imidazol-1-yl)piperidin-1-yl]methyl}phenyl)[1,2,4]triazolo[3,4-f]-1,6-naphthyridine | 610.2 |
| 2-5 | 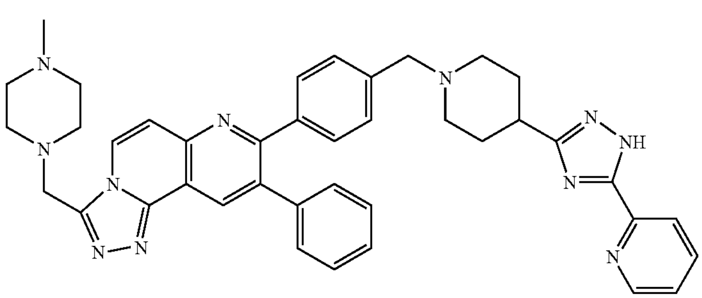 | 3-[(4-methylpiperazin-1-yl)methyl]-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine | 675.4 |

TABLE 2-continued

| Cmp | Structure | Name | HRMS m/z (M + H) |
|---|---|---|---|
| 2-6 | 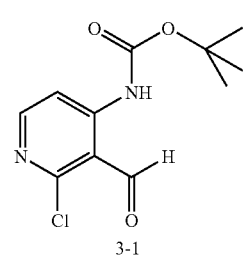 | 2-({[9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-yl]methyl}amino)ethanol | 636.3 |

SCHEME 3

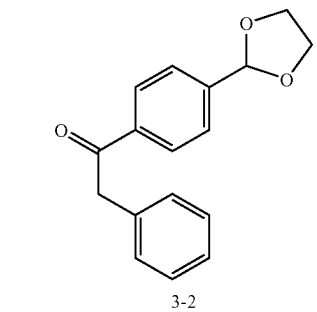

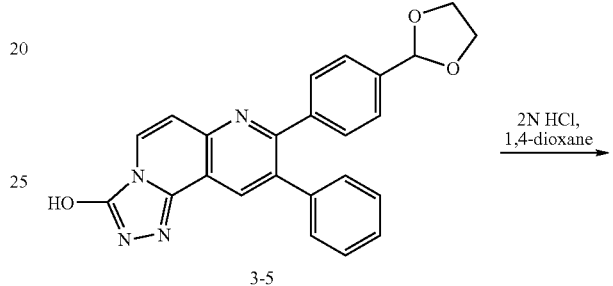

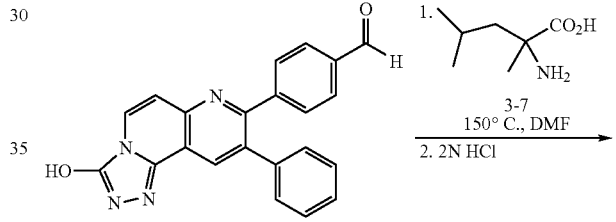

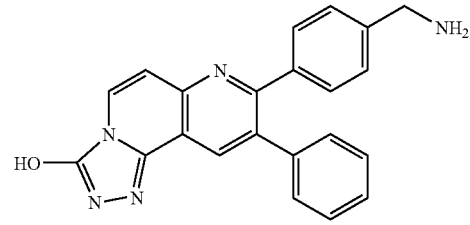

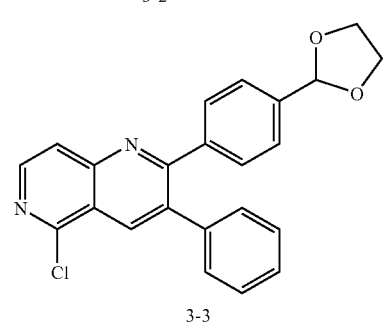

8-(4-Aminomethyl-phenyl)-9-phenyl-[1,2,4]triazolo[3,4-f][1,6]naphthyridin-3-ol (3-8)

STEP A: tert-Butyl (2-chloro-3-formylpyridin-4-yl)carbamate (3-1)

A solution of 4-amino-2-chloropyridine (1.28 gm, 10 mmol) and di-tert-butyl dicarbonate (2.21 gm, 10.1 mmol) in THF (20 mL) was cooled to 0° C. and a solution of 1M lithium bis(trimethylsilyl)amide in THF (20 mL, 20 mmol) was added slowly maintaining the temperature below 0° C. The reaction was allowed to warm to room temperature over one hour and then quenched by the addition of 1.5 N aqueous ammonium chloride (15 mL). After stirring for several hours the reaction was extracted into ethyl acetate, washed with brine, the organic layer dried (Na₂SO₄), filtered and evaporated. The residue was triturated with diethyl ether give pure tert-butyl (2-chloropyridin-4-yl)carbamate. The mother liquors were chromatographed on silica gel eluting with 25-45% ethyl acetate/hexane to afford more product.

A solution of tert-butyl (2-chloropyridin-4-yl)carbamate (1.14 gm, 5 mmol) in dry THF (20 mL) was cooled to −70° C. under an inert atmosphere and 1.7 M t-butyl lithium/pentane (8 mL, 13.5 mmol) was slowly added. The reaction was stirred for two hours and then dry DMF (1.2 mL, 15.5 mmol) was added. The reaction was allowed to slowly warm to room temperature over a three hour period. The reaction mixture was quenched with 3 N HCl (12 mL) and diluted with diethyl ether. The ether layer was washed with aqueous $NaHCO_3$, dried (over $Na_2SO_4$), filtered and evaporated. The residue was triturated with cold diethyl ether to give pure t-butyl (2-chloro-3-formylpyridin-4-yl)carbamate. The mother liquors were chromatographed on silica gel eluting with 15-20% ethyl acetate/hexane to give additional product. $^1$H-NMR (500 MHz, $CDCl_3$): δ11.0 (1H, br s), 10.52 (1H, s), 8.38 (1H, d, J=6 Hz), 8.31 (1H, d, J=6 Hz), 1.54 (9H, s); m/e (m+1): 257.2.

STEP B: 1-[4-(1,3-Dioxolan-2-yl)phenyl]-2-phenylethanone (3-2)

To a solution of 4-cyanobenzaldehyde (20.0 g, 152.5 mmol) and ethylene glycol (25.5 mL, 457.5 mmol) in toluene (250 mL) was added p-toluenesulfonic acid (300 mg). The flask was equipped with a Dean-Stark trap and the mixture heated to reflux. After 5 hr the mixture was concentrated. The residue was taken up in ethyl acetate and washed with saturated $NaHCO_3$, water (2×), and brine. The organic layer was dried ($MgSO_4$), filtered, and concentrated to give 4-(1,3-dioxolan-2-yl)benzonitrile as a clear oil which solidified under vacuum: $^1$H-NMR (500 MHz, $CDCl_3$): δ7.67 (2H, d, J=8.06 Hz), 7.59 (2H, d, J=8.30 Hz), 5.85 (1H, s), 4.13-4.05 (4H, m).

To a solution of 4-(1,3-dioxolan-2-yl)benzonitrile (5.0 g, 28.54 mmol) in anhydrous THF (100 mL) was added benzyl magnesium chloride (36 mL, 20% wt solution in THF, 43 mmol) slowly at 0° C. After one hour the mixture was warmed to room temperature. After four hours the mixture was cooled to 0° C. and quenched with saturated $NH_4Cl$. The mixture was warmed to room temperature and extracted with ethyl acetate (3×). The combined organic layers were dried ($MgSO_4$), filtered, and concentrated. Flash column chromatography (10% ethyl acetate/hexanes) gave 1-[4-(1,3-dioxolan-2-yl)phenyl]-2-phenylethanone as a pale yellow solid: $^1$H-NMR (500 MHz, $CDCl_3$): δ8.02 (2H, d, J=8.30 Hz,), 7.57 (2H, d, J=8.30 Hz,), 7.38-7.24 (% H, m), 5.86 (1H, s), 4.29 (2H, s), 4.28-4.09 (4H, m).

STEP C: 5-Chloro-2-(4-[1,3]dioxolan-2-yl-phenyl)-3-phenyl-[1,6]naphthyridine (3-3)

To a solution of tert-butyl (2-chloro-3-formylpyridin-4-yl) carbamate (3-1, 30.5 g, 118.9 mmol) and 1-[4-(1,3-dioxolan-2-yl)phenyl]-2-phenylethanone (3-2, 29.0 g, 108.1 mmol) in anhydrous THF (300 mL) at room temperature was added LHMDS (1M in THF, 248 mL) in a stream. The reaction mixture was stirred at room temperature overnight and then it was refluxed for 24 hr. It was cooled and concentrated to a syrup and treated with $NaHCO_3$ (saturated, 50 mL) and water (300 mL) to form a solid which was collected via filtration. The solid was dried, washed with ether and further dried with toluene azeotropically to give the title compound. LRMS m/z (M+1) Calcd: 389.1. Found 389.1.

STEP D: [2-(4-[1,3]Dioxolan-2-yl-phenyl)-3-phenyl-[1,6]naphthyridin-5-yl]-hydrazine (3-4)

A suspension of 5-chloro-2-(4-[1,3]dioxolan-2-yl-phenyl)-3-phenyl-[1,6]naphthyridine (3-3, 5.2 g, 13.4 mmol) and anhydrous hydrazine (5 mL) in anhydrous 1,4-dioxane (15 mL) was heated at 100° C. in a microwave reactor for 5 min. The reaction mixture was cooled, concentrated and dried with toluene azotropically to give the title compound as a solid. LRMS m/z (M+1) Calcd: 385.2. Found 385.3.

STEP E: 8-(4-[1,3]Dioxolan-2-yl-phenyl)-9-phenyl-[1,2,4]triazolo[3,4-f][1,6]napthyridin-3-ol (3-5)

To a solution of [2-(4-[1,3]dioxolan-2-yl-phenyl)-3-phenyl-[1,6]naphthyridin-5-yl]-hydrazine (3-4, 5.3 g, 13.8 mmol) in $CH_2Cl_2$ (anhydrous, 40 mL) at 0° C. was added triethylamine (9.7 mL, 68.9 mmol) followed by a rapid addition of phosgene in toluene (2M, 7.6 mL). After stirring for 10 min at room temperature, the mixture was concentrated and water (30 mL) was added. The solid was collected and dried with toluene azeotropically to give the title compound which was used for the next step without further purification. LRMS m/z (M+1) Calcd: 411.1. Found 411.2.

STEP F: 4-(3-Hydroxy-9-phenyl-[1,2,4]triazolo[3,4-f][1,6]naphthyridin-8-yl)-benzaldehyde (3-6)

A suspension of 8-(4-[1,3]dioxolan-2-yl-phenyl)-9-phenyl-[1,2,4]triazolo[3,4-f][1,6]naphthyridin-3-ol (3-5, 2.7 g, 6.6 mmol) in dioxane (20 mL) and 2N HCl (20 mL) was stirred at room temperature for 20 min. It was concentrated to remove most dioxane at 25° C. The residue was poured into ice cold water to give a brown solid which was collected via filtration and dried with toluene azeotropically to give the title compound. LRMS m/z (M+1) Calcd: 367.1. Found 367.1.

STEP G: 8-(4-Aminomethyl-phenyl)-9-phenyl-[1,2,4]triazolo[3,4-f][1,6]naphthyridin-3-ol (3-8)

A suspension of 4-(3-hydroxy-9-phenyl-[1,2,4]triazolo[3,4-f][1,6]naphthyridin-8-yl)-benzaldehyde (3-6, 2.4 g, 6.6 mmol) and 2-amino-2,4-dimethylpentanoic acid (3-7, 1.9 g, 13.1 mmol) in DMF (25 mL) was heated at 150° C. for 20 min. The reaction mixture was cooled, diluted with dioxane (50 mL) and 2N HCl (50 mL) and heated at 100° C. for 30 min. The mixture was cooled and purified via reverse phase HPLC (0-60% acetonitrile/water) to give, upon evaporation of the solvent, the title compound as a yellow solid. HRMS m/z (M+1) Calcd: 368.1506. Found 368.1504.

$^1$H-NMR ($CD_3OD$) δ 8.72 (s, 1H), 7.98 (d, 1H), 7.52 (d, 2H), 7.46 (d, 2H), 7.24-7.38 (m, 5H), 7.12 (d, 1H), 4.14 (s, 2H).

SCHEME 4

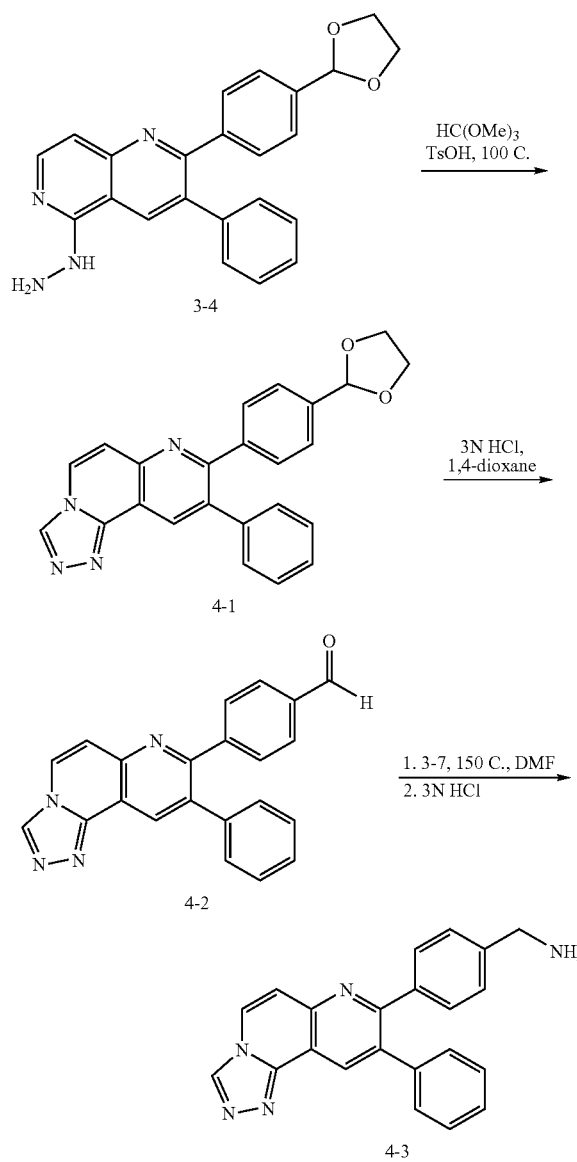

1-[4-(9-Phenyl[1,2,4]triazolo[3,4-f]-1,6-naphthyridin-8-yl)phenyl]methanamine (4-3)

STEP A: 8-[4-(1,3-Dioxolan-2-yl)phenyl]9-phenyl[1,2,4]triazolo[3,4-f]-1,6-naphthyridine (4-1)

To a solution of [2-(4-[1,3]dioxolan-2-yl-phenyl)-3-phenyl-[1,6]naphthyridin-5-yl]-hydrazine (3-4, 1.6 g, 4.2 mmol) and toluenesulfonic acid monohydrate (79 mg, 0.4 mmol) in 3:1 toluene:MeOH (16 mL) was added trimethyl orthoformate (0.58 mL, 12.5 mmol). The mixture was heated to 100° C. in a microwave reactor for 1 hr. The reaction mixture was then concentrated in vacuo. The solid was collected and dried with toluene azeotropically to give the title compound which was used for next step without further purification. LRMS m/z (M+1) Calcd: 395.1. Found 395.2.

STEP B: 4-(9-Phenyl[1,2,4]triazolo[3,4-f]-1,6-naphthyridin-8-yl)benzaldehyde (4-2)

A suspension of 8-[4-(1,3-dioxolan-2-yl)phenyl]-9-phenyl[1,2,4]triazolo[3,4-f]-1,6-naphthyridine (4-1, 0.80 g, 2.0 mmol) in dioxane (10 mL) and 3N HCl (10 mL) was stirred at room temperature for 15 min. The mixture was concentrated at 25° C. to remove most of the dioxane. The residue was poured into ice cold water to give a brown solid which was collected via filtration and dried with toluene (×2) azeotropically the give the title compound. LRMS m/z (M+1) Calcd: 351.1. Found 351.2

STEP C: 1-[4-(9-Phenyl[1,2,4]triazolo[3,4-f]-1,6-naphthyridin-8-yl)phenyl]methanamine (4-3)

A suspension of 4-(9-phenyl[1,2,4]triazolo[3,4-f]-1,6-naphthyridin-8-yl)benzaldehyde (4-2, 0.80 g, 2.3 mmol) and 2-amino-2,4-dimethylpentanoic acid (3-7, 0.340 g, 2.3 mmol) in DMF (10 mL) was heated at 150° C. for 30 min. The reaction mixture cooled and the solvent was removed in vacuo. The crude residue was dissolved in 3N HCl (8 mL) and was heated at 100° C. for 30 min. The mixture was cooled and purified via reverse phase HPLC (5-65% acetonitrile/water over 15 min) to give, upon evaporation of the solvents, the title compound as a yellow solid. $^1$H-NMR (CD$_3$OD) δ 9.60 (s, 1H), 8.98 (s, 1H), 8.73 (d, 1H), 7.75 (d, 1H), 7.60 (d, 2H), 7.46 (d, 2H), 7.39-7.36 (m, 5H), 4.15 (s, 2H).

SCHEME 5

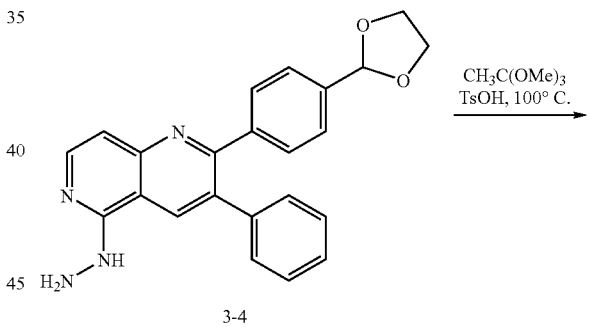

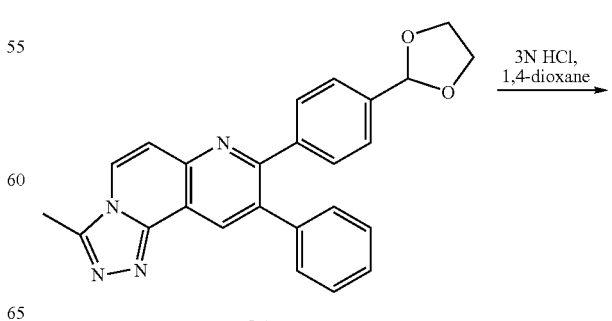

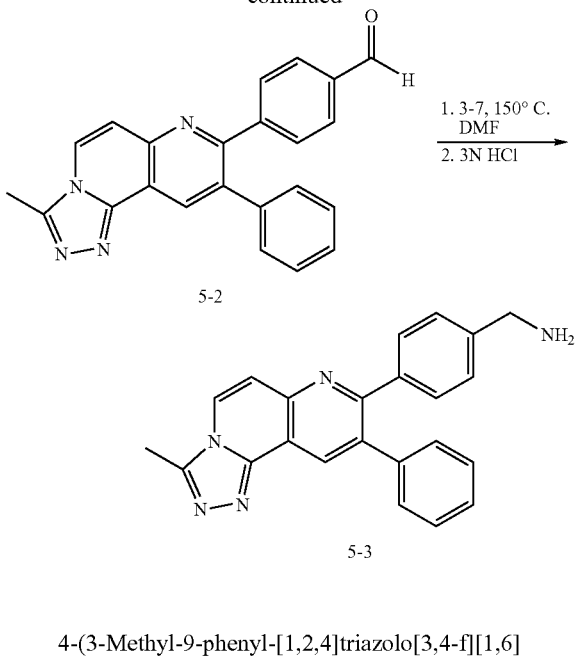

4-(3-Methyl-9-phenyl-[1,2,4]triazolo[3,4-f][1,6]naphthyridin-8-yl)-benzylamine (5-3)

STEP A: 8-[4-(1,3-Dioxolan-2-yl)phenyl]-3-methyl-9-phenyl[1,2,4]triazolo[3,4-f]-1,6-naphthyridine (5-1)

To a solution of [2-(4-[1,3]dioxolan-2-yl-phenyl)-3-phenyl-[1,6]naphthyridin-5-yl]-hydrazine (3-4, 0.35 g, 0.91 mmol) and toluenesulfonic acid monohydrate (17 mg, 0.09 mmol) in 3:1 toluene:MeOH (4 mL) was added trimethyl orthoacetate (0.157 mL, 1.23 mmol). The mixture was heated to 100° C. in a microwave reactor for 75 min. The reaction mixture was then concentrated in vacuo. The solid was collected and dried with toluene azeotropically to give the title compound which was used for next step without further purification. LRMS m/z (M+1) Calcd: 409.2. Found 409.2.

STEP B: 4-(3-Methyl-9-phenyl[1,2,4]triazolo[3,4-f]-1,6-naphthyridin-8-yl) Benzaldehyde (5-2)

A suspension of 8-[4-(1,3-dioxolan-2-yl)phenyl]-3-methyl-9-phenyl[1,2,4]triazolo[3,4-f]-1,6-naphthyridine (5-1, 0.30 g, 0.73 mmol) in dioxane (5 mL) and 3N HCl (5 mL) was stirred at room temperature for 15 min. The mixture was concentrated at 25° C. to remove most of the dioxane. The residue was poured into ice cold water to give a brown solid which was collected via filtration and dried with toluene (×2) azeotropically the give the title compound. LRMS m/z (M+1) Calcd: 365.1. Found 365.2.

STEP C: 4-(3-Methyl-9-phenyl-[1,2,4]triazolo[3,4-f][1,6]naphthyridin-8-yl)-benzylamine (5-3)

A suspension of 4-(3-methyl-9-phenyl[1,2,4]triazolo[3,4-f]-1,6-naphthyridin-8-yl)benzaldehyde (13, 0.25 g, 0.69 mmol) and 2-amino-2,4-dimethylpentanoic acid (3-7, 0.101 g, 0.69 mmol) in DMF (3 mL) was heated at 150° C. for 30 min. The reaction mixture cooled and the solvent was removed in vacuo. The crude residue was dissolved in 3N HCl (2.5 mL) and was heated at 100° C. for 30 min. The mixture was cooled and purified via reverse phase HPLC (5-65% acetonitrile/water over 15 min) to give, upon evaporation of the solvents, the title compound as a yellow solid. HRMS m/z (M+1) Calcd: 366.1713. Found 366.1715.

SCHEME 5 (ALTERNATE SYNTHESIS)

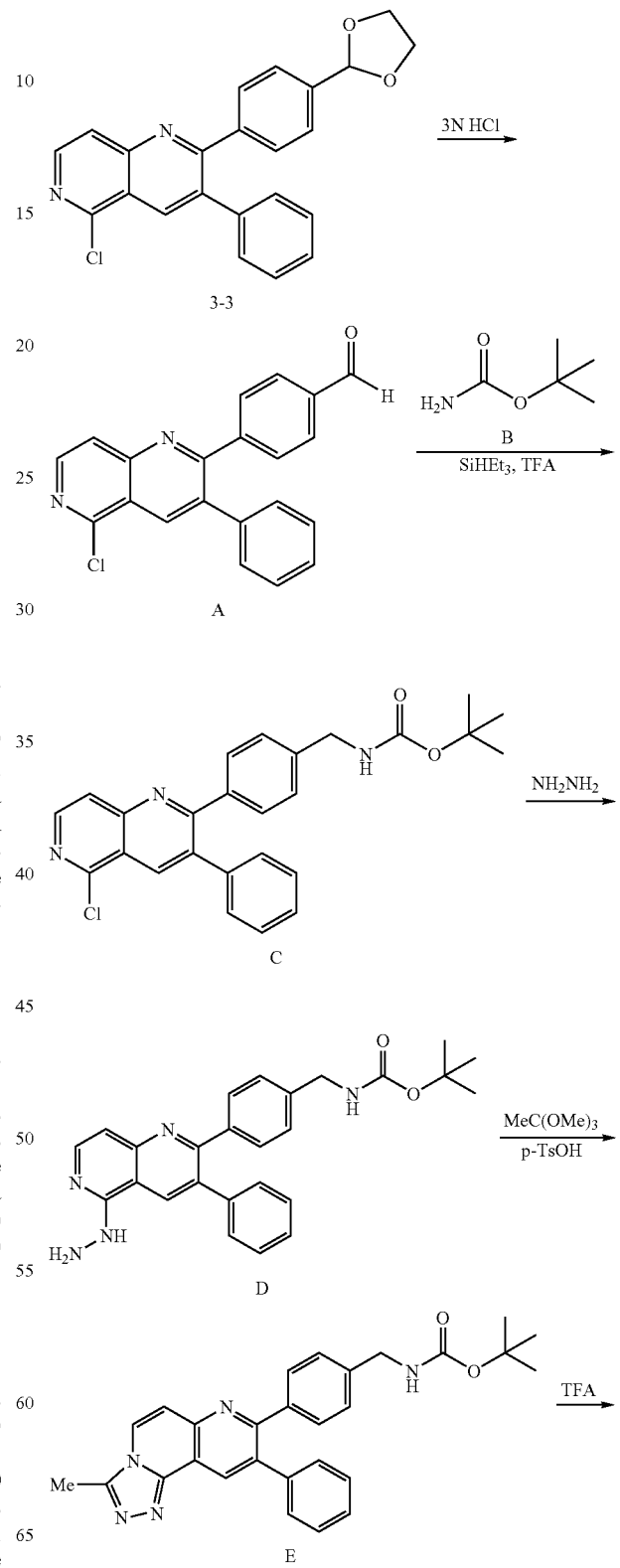

91

-continued

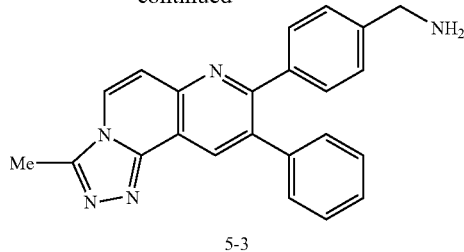

5-3

4-(3-Methyl-9-phenyl-[1,2,4]triazolo[3,4-f][1,6]naphthyridin-8-yl)-benzyl amine (5-3)

STEP A: 4-(5-Chloro-3-phenyl-[1,6]naphthyridin-2-yl)-benzaldehyde (A)

To a solution of 3-3 (5.0 g, 12.9 mmol) in 1,4-dioxane (30 mL) at 0° C. was added 8.5 mL of 3NHCl (25.7 mmol). The mixture was allowed to warm up to room temperature and stirred for 1.3 hr. The reaction was quenched by NaHCO$_3$ (sat) until pF=7-8. The mixture was extracted by EtOAc (×3). The combined organic layers was washed with brine and dried over MgSO$_4$ and concentrated to afford a yellow solid as the desired product A. LC/MS found: M+1=345.1

STEP B: [4-(5-Chloro-3-phenyl-[1,6]naphthyridin-2-yl)-benzyl]carbamic acid tert-butyl ester (C)

To a solution of A (2.8 g, 8.1 mmol) and B (1.1 g, 8.9 mmol) in 15 mL anhydrous MeCN was added triethylsilane (8.5 g, 73 mmol) followed by trifluoroacetic acid (3.7 g, 32.5 mmol). The mixture was stirred at room temperature for 3 hrs. The mixture was then poured into aqueous sodium bicarbonate solution (30 mL) and extracted by EtOAc (×3). The combined organic layers were washed by brine and dried over MgSO$_4$. Upon removal of the solvent, the residue was purified via flash column chromatograph to afford the desired product C. LC/MS found: M+1=446.1

STEP C: [4-(5-Hydrazino-3-phenyl-[1,6]naphthyridin-2-yl)-benzyl]-carbamic acid tert-butyl ester (D)

To a solution of C (3.7 g, 8.3 mmol) in 22 mL 1,4-dioxane was added hydrazine (6.1 g, 189.1 mmol) dropwise. The mixture was heated at 100° C. in a microwave reactor for 5 mins. Upon removal of the solvent, the residue was taken up in EtOAc and washed with saturated NaHCO$_3$ solution. The organic layer was washed by brine and dried over MgSO$_4$ and concentrated to afford the desired product D, which was used in the next step without further purification. LC/MS found: M+1=442.2

STEP D: [4-(3-Methyl-9-phenyl-[1,2,4]triazolo[3,4-f][1,6]naphthyridin-8-yl)-benzyl]-carbamic acid tert-butyl ester (E)

To a solution of D (3.8 g, 8.6 mmol) and p-toluenesulfonic acid monohydrate (0.08 g, 0.4 mmol) in 20 mL toluene/methanol (3:1) was added trimethyl orthoacetate (1.4 g, 11.6 mmol). The solution was heated in microwave reactor at 100° C. for 35 mins. The reaction was quenched by NaHCO$_3$ (0.5 g) solid. The organic layer was concentrated and purified on flash column chromatograph (100% EtOAc to 10% MeOH/90% EtOAc over 35 mins) to afford the desired product E. LC/MS found: M+1=466.2

92

STEP E: 4-(3-Methyl-9-phenyl-[1,2,4]triazolo[3,4-f][1,6]naphthyridin-8-yl)-benzylamine (5-3)

To a solution of E (4.1 g, 8.7 mmol) in 80 mL CH$_2$Cl$_2$ was added 40 mL TFA dropwise. The mixture was stirred at room temperature for 15 min. The solvent was removed. The residue was treated with NaHCO$_3$ (sat) until pH=9. The mixture was extracted with EtOAc (×6). The combined organic layers was concentrated and dried over MgSO$_4$. Upon removal of the solvent, the desired product 5-6 was obtained a yellow solid. LC/MS found: M+1=366.1

$^1$H-NMR (CD$_3$OD) δ 8.95 (s, 1H), 8.66 (d, 1H), 7.82 (d, 1H), 7.60 (d, 2H), 7.45 (d, 2H), 7.42-7.34 (m, 5H), 4.15 (s, 2H), 3.00 (s, 3H).

SCHEME 6

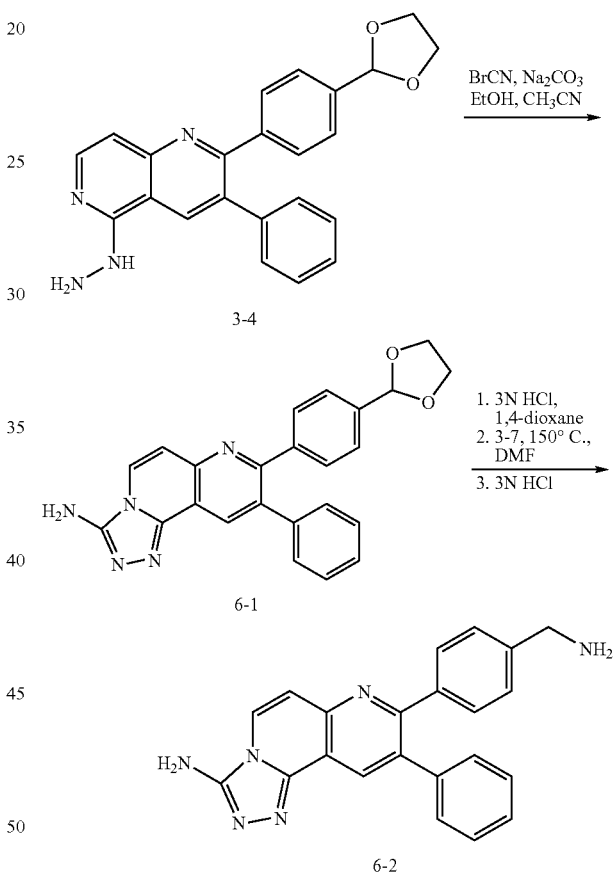

8-[4-(Aminomethyl)phenyl]-9-phenyl[1,2,4]triazolo[3,4-f]-1,6-naphthyridin-3-amine (6-2)

STEP A: 8-[4-(1,3-Dioxolan-2-yl)phenyl]-9-phenyl[1,2,4]triazolo[3,4-f]-1,6-naphthyridin-3-amine (6-1)

To dry EtOH (1 mL) was added cyanogen bromide (0.104 mL, 0.52 mmol, 5M in MeCN) followed by sodium carbonate (96 mg, 0.91 mmol). [2-(4-[1,3]Dioxolan-2-yl-phenyl)-3-phenyl-[1,6]naphthyridin-5-yl]-hydrazine (3-4, 100 mg, 0.26 mmol) was added and the mixture was stirred for 3 h. The reaction mixture was concentrated in vacuo and the resulting solid was used without further purification. LRMS m/z (M+1) Calcd: 410.2. Found 410.1.

STEP B: 8-[4-(Aminomethyl)phenyl]-9-phenyl[1,2,4]triazolo[3,4-f]-1,6-naphthyridin-3-amine (6-2)

The title compound was prepared from 8-[4-(1,3-dioxolan-2-yl)phenyl]-9-phenyl[1,2,4]triazolo[3,4-f]-1,6-naphthyridin-3-amine (6-1) using the procedures described in Scheme 5 (5-1 to 5-3). LRMS m/z (M+1) Calcd: 367.2. Found 367.1.

SCHEME 7

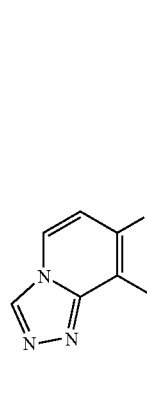

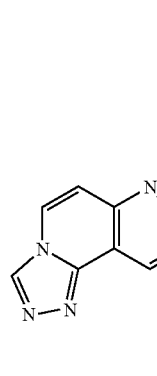

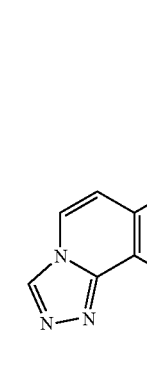

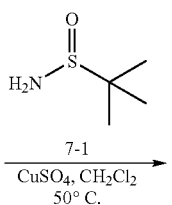

1-[4-(9-Phenyl[1,2,4]triazolo[3,4-f]-1,6-naphthyridin-8-yl)phenyl]ethanamine (7-4)

STEP A: 2-Methyl-N-{(1E)-[4-(9-phenyl[1,2,4]triazolo[3,4-f]-1,6-naphthyridin-8-yl)phenyl]methylidene}propane-2-sulfinamide (7-2)

Racemic 2-methyl-2-propane-sulfinamide (7-1, 647 mg, 5.3 mmol), cupric sulfate (1.70 g, 7.30 mmol), and aldehyde 4-2 (511 mg, 1.45 mmol) were stirred in methylene chloride (10 mL) for 5 d at 50° C. After cooling to rt, the mixture was filtered through celite, concentrated to a minimum volume and purified via automated silica gel chromatography (0-10% MeOH in $CH_2Cl_2$ over 30 min) to give the title compound as a brown foam. LRMS m/z (M+1) Calcd: 454.2. Found 454.2

STEP B: 2-Methyl-N-{1-[4-(9-phenyl[1,2,4]triazolo[3,4-f]-1,6-naphthyridin-8-yl)phenyl]ethyl}propane-2-sulfinamide (7-3)

Methylmagnesium bromide solution (13.5 mL of 1.4 M solution in 3:1 toluene/THF, 19 mmol) was added to a stirred solution of 2-methyl-N-{(1E)-[4-(9-phenyl[1,2,4]triazolo[3,4-f]-1,6-naphthyridin-8-yl)phenyl]methylidene}propane-2-sulfinamide (7-2, 298 mg, 0.66 mmol) in methylene chloride (5 mL) at −78° C. and the solution was warmed to rt. After 18 h, the reaction was quenched with saturated ammonium chloride solution and extracted with ethyl acetate, washed with brine, dried over magnesium sulfate, filtered, and concentrated to give an amber foam, which was purified via silica gel chromatography (0-10% MeOH/$CH_2Cl_2$ over 30 min) to give the title compound as a yellow foam.

LRMS m/z (M+1) Calcd: 470.2. Found 470.3

STEP C: 1-[4-(9-Phenyl[1,2,4]triazolo[3,4-f]-1,6-naphthyridin-8-yl)phenyl]ethanamine (7-4)

To a stirred solution of 2-methyl-N-{1-[4-(9-phenyl[1,2,4]triazolo[3,4-f]-1,6-naphthyridin-8-yl)phenyl]ethyl}propane-2-sulfinamide (7-3, 180 mg, 0.38 mmol) in methanol (6 mL) was added conc. HCl (1.5 mL). After 1 h, water was added and the mixture was washed with methylene chloride. The aqueous portion was basified with saturated sodium carbonate solution and extracted with methylene chloride. 2N HCl (5 mL) was added to the organic layer and the mixture was concentrated to a minimum volume. The crude product was purified using reverse phase preparative HPLC to give the title compound as a pale yellow solid. LRMS m/z (M+1) Calcd: 366.2. Found 366.3.

SCHEME 8

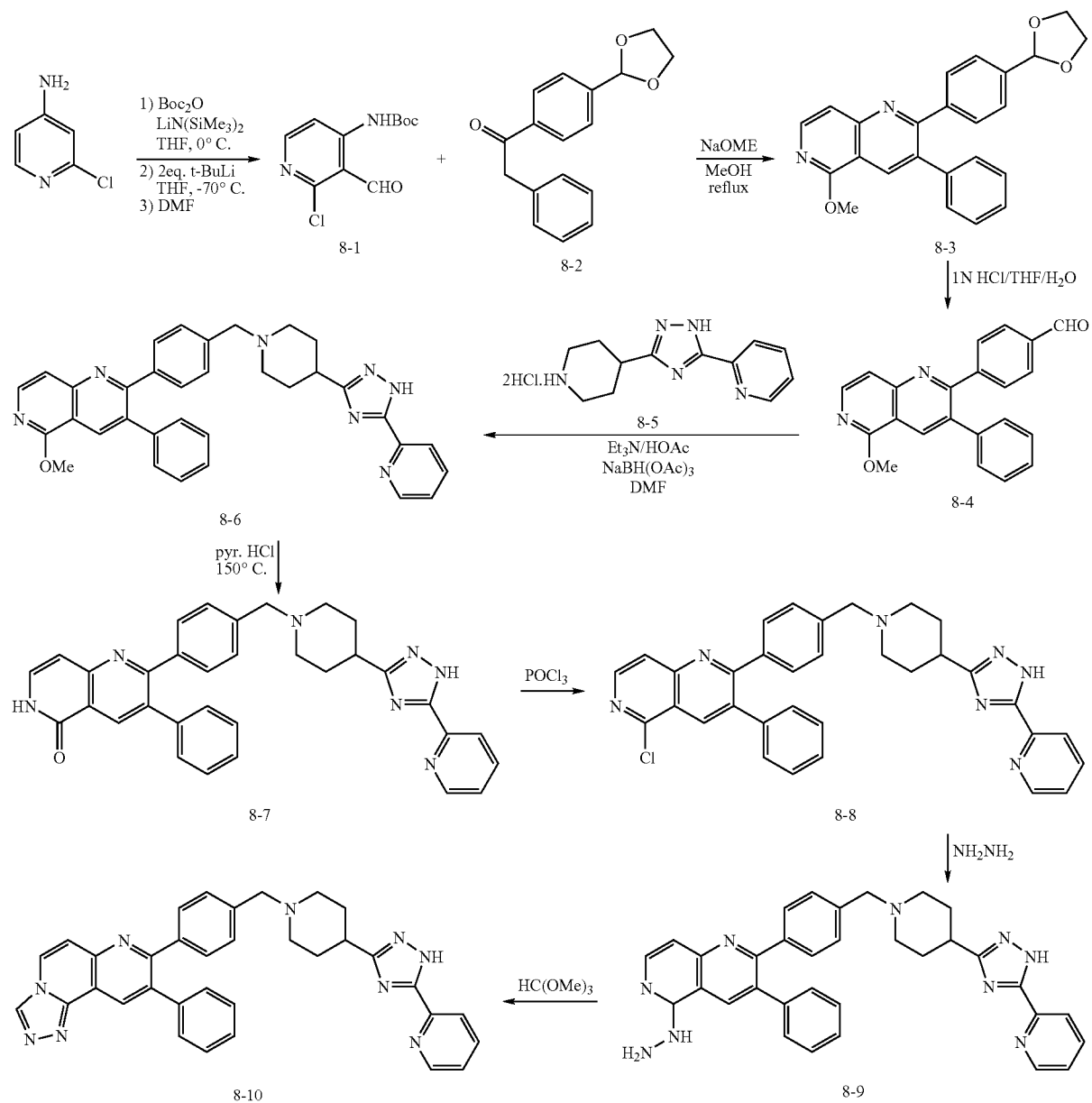

9-Phenyl-8-{4-[4-(5-pyridin-2-yl-4H-[1,2,4]triazol-3-yl)-piperidin-1-ylmethyl]-phenyl}-[1,2,4]triazolo[3,4-f][1,6]naphthyridine (8-10)

tert-Butyl (2-chloro-3-formylpyridin-4-yl)carbamate (8-1)

A solution of 4-amino-2-chloropyridine (1.28 g, 10 mmol) and di-tert-butyl dicarbonate (2.21 g, 10.1 mmol) in THF (20 mL) was cooled to 0° C. and a solution of 1M lithium bis(trimethylsilyl)amide in THF (20 mL, 20 mmol) was added slowly maintaining the temperature below 0° C. The reaction was allowed to warm to room temperature over one hour and then quenched by the addition of 1.5 N aqueous ammonium chloride (15 mL). The mixture was extracted into ethyl acetate, washed with brine and the organic layer was dried ($Na_2SO_4$), filtered and evaporated. The residue was triturated with diethyl ether give pure tert-butyl (2-chloropyridin-4-yl) carbamate. The mother liquors were chromatographed on silica gel eluting with 25-45% ethyl acetate/hexane to afford more product.

A solution of tert-butyl (2-chloropyridin-4-yl)carbamate (1.14 g, 5 mmol) in dry THF (20 mL) was cooled to −70° C. under an inert atmosphere and 1.7 M t-butyl lithium/pentane (8 mL, 13.5 mmol) was slowly added. The reaction was stirred for two hours and then dry DMF (1.2 mL, 15.5 mmol) was added. The reaction was allowed to slowly warm to room temperature over a three hour period. The reaction mixture was quenched with 3 N HCl (12 mL) and diluted with diethyl ether. The ether layer was washed with aqueous $NaHCO_3$, dried (over $Na_2SO_4$), filtered and evaporated. The residue was triturated with cold diethyl ether to give pure t-butyl (2-chloro-3-formylpyridin-4-yl)carbamate. The mother liquors were chromatographed on silica gel eluting with 15-20% ethyl acetate/hexane to give additional product. ¹H-NMR (500 MHz, CDCl₃): δ 11.0 (1H, br s), 10.52 (1H, s), 8.38 (1H, d, J. 6 Hz), 8.31 (1H, d, J. 6 Hz), 1.54 (9H, s); m/e (m+1): 257.2.

1-[4-(1,3-Dioxolan-2-yl)phenyl]-2-phenylethanone (8-2)

To a solution of 4-cyanobenzaldehyde (20.0 g, 152.5 mmol) and ethylene glycol (25.5 mL, 457.5 mmol) in toluene (250 mL) was added p-toluenesulfonic acid (300 mg). The flask was equipped with a Dean-Stark trap and the mixture heated to reflux. After 5 hr the mixture was concentrated. The residue was taken up in ethyl acetate and washed with saturated NaHCO₃, water (2×), and brine. The organic layer was dried (MgSO₄), filtered, and concentrated to give 4-(1,3-dioxolan-2-yl)benzonitrile as a clear oil which solidified under vacuum: ¹H-NMR (500 MHz, CDCl₃): δ 7.67 (2H, d, J=8.06 Hz), 7.59 (2H, d, J=8.30 Hz), 5.85 (1H, s), 4.13-4.05 (4H, m).

To a solution of 4-(1,3-dioxolan-2-yl)benzonitrile (5.0 g, 28.54 mmol) in anhydrous THF (100 mL) was added benzyl magnesium chloride (36 mL, 20% wt solution in THF, 43 mmol) slowly at 0° C. After one hour the mixture was warmed to room temperature. After four hours the mixture was cooled to 0° C. and quenched with saturated NH₄Cl. The mixture was warmed to room temperature and extracted with ethyl acetate (3×). The combined organic layers were dried (MgSO₄), filtered, and concentrated. Flash column chromatography (10% ethyl acetate/hexanes) gave 1-[4-(1,3-dioxolan-2-yl)phenyl]-2-phenylethanone as a pale yellow solid: ¹H-NMR (500 MHz, CDCl₃): δ 8.02 (2H, d, J=8.30 Hz,), 7.57 (2H, d, J=8.30 Hz,), 7.38-7.24 (5H, m), 5.86 (1H, s), 4.29 (2H, s), 4.28-4.09 (4H, m).

2-[4-(1,3-Dioxolan-2-yl)phenyl]-5-methoxy-3-phenyl-1,6-naphthyridine (8-3)

To a partial solution of 1-[4-(1,3-dioxolan-2-yl)phenyl]-2-phenylethanone (997 mg, 3.72 mmol) and tert-butyl (2-chloro-3-formylpyridin-4-yl)carbamate (924 mg, 3.6 mmol) in dry methanol (14 mL) was added 25 wt % sodium methoxide/methanol (2.5 mL, 11.4 mmol). The reaction mixture was warmed at 65° C. for four hours. The cooled reaction was concentrated to remove the methanol and the residue was partitioned between water and ethyl acetate. The organic layer was dried (Na₂SO₄), filtered and evaporated. The residue was triturated with cold ether to give pure 2-[4-(1,3-dioxolan-2-yl)phenyl]-5-methoxy-3-phenyl-1,6-naphthyridine. The mother liquors were purified by chromatography on silica gel and elution with 20-40% ethyl acetate/hexane gave additional product. ¹H-NMR (500 MHz, CDCl₃): δ 8.54 (1H, s), 8.23 (1H, d, J=5.9 Hz), 7.55 (1H, d, J=5.9 Hz), 7.48 (2H, d, J=8 Hz), 7.40 (2H, d, J=8 Hz), 7.29-7.30 (3H, m), 7.22-7.25 (2H, m), 4.16 (3H, s), 4.02-411 (4H, 2 m). m/e (m+1): 385.1.

4-(5-Methoxy-3-phenyl-1,6-naphthyridin-2-yl)benzaldehyde (8-4)

To a solution of 2-[4-(1,3-dioxolan-2-yl)phenyl]-5-methoxy-3-phenyl-1,6-naphthyridine (760 mg, 1.98 mmol) in THF (8 mL) was added 1 N HCl (6 mL) and the solution was stirred for three hours. Ethyl acetate was added and the mixture was made basic with aqueous Na₂CO₃. The organic layer was dried (Na₂SO₄) and the solvent evaporated. The residue was triturated with diethyl ether to give pure product. The mother liquors were purified by column chromatography on silica gel and elution with 10-30% ethyl acetate/hexane gave additional product. ¹H-NMR (500 MHz, CDCl₃): 10.10 (1H, s), 8.60 (1H, s), 8.26 (1H, d, J=6 Hz), 7.81 (2H, d, J=8.3 Hz), 7.62 (2H, d, J=8.3 Hz), 7.56 (1H, d, J=6.1 Hz), 7.30-7.32 (3H, m), 7.21-7.23 (2H, m), 4.17 (3H, s). m/e (m+1): 341.1.

2-(3-Piperidin-4-yl-1H-1,2,4-triazol-5-yl)pyridine Dihydrochloride (8-5)

Carbonyl diimidazole (3.57 g, 22 mmol) was added to a solution of 1-(tert-butoxycarbonyl)-piperidine-4-carboxylic acid (4.59 g, 20 mmol) in methylene chloride (50 mL) and stirred for two hours until gas evolution ceased. Then hydrazine (0.8 mL, ~26 mmol) was added to the reaction and the reaction was stirred at room temperature for another two hours. The reaction was diluted with more methylene chloride and washed with sat'd aqueous NaHCO₃. The organic layer was dried over anhydrous Na₂SO₄, filtered and the solvent evaporated to give a viscous residue. Trituration with diethyl ether afforded tert-butyl 4-(hydrazinocarbonyl)-piperidine-1-carboxylate as an off-white solid. ¹H NMR (500 MHz, CDCl₃): δ 6.77 (1H, br s), 4.15 (2H, br s), 3.90 (2H, v br s), 2.75 (2H, b s), 2.22 (1H, m), 1.78 (2H, br d, J=11.9 Hz), 1.66 (2H, br q, J=12.2 Hz, J=27.5 Hz), 1.47 (9H, s).

This material (2.43 g, 10 mmol) was dissolved in anhydrous 2-ethoxyethanol (20 mL) and 2-cyanopyridine (1.14 g, 11 mmol) was added to the solution. After 25 wt. % sodium methoxide/methanol (1.1 mL, ~5 mmol) was added the mixture was heated to 130° C. for 16 hours. The cooled reaction was neutralized with acetic acid and partitioned between ethyl acetate and aq. NaHCO₃. The organic layer was dried over Na₂SO₄, the salts removed by filtration and the solvent evaporated under vacuum. This residue was triturated with diethyl ether to give tert-butyl 4-(5-pyridin-2-yl-1H-1,2,4-triazol-3-yl)piperidine-1-carboxylate as a white solid. 1H NMR (500 MHz, CDCl₃): δ 8.70 (1H, d, J=3.9 Hz), 8.19 (1H, d, J=7.9 Hz), 7.87 (1H, d t, J=1.7 Hz, J=8 Hz), 7.40 (1H, m), 4.20 (2H, br s), 3.03 (1H, m), 2.95 (2H, br s), 2.09 (2H, br d, J=12 Hz), 1.86 (2H, br q, J=4.2 Hz), 1.49 (9H, s); m/e (m+1): 330.2

This material (2.68 g, 8.14 mmol) was suspended in 4 N HCl/dioxane. The stoppered reaction mixture was stirred at room temperature for 16 hours and then diluted with diethyl ether. The solids were isolated by filtration and the hygroscopic solid was digested in acetonitrile. This solid was isolated by filtration and partially dissolved in hot methanol. Upon cooling and addition of some ethyl ether to the solution 2-(3-piperidin-4-yl-1H-1,2,4-triazol-5-yl)pyridine slowly precipitated as the dihydrochloride salt. ¹H NMR (500 MHz, DMSO-d₆): δ 9.10 (1H, br s), 8.92 (1H, br s), 8.73 (1H, d, J=4.9 Hz), 8.10-8.20 (2H, m), 7.64 (1H, t, J=5.7 Hz), 3.33 (2H, br d, J=12.7 Hz), 3.16 (1H, m), 3.05 (2H, br q, J=11.9 Hz, J=21.8 Hz), 2.18 (2H, br d, J=11.5 Hz), 1.99 (2H, br q, j=11.0 Hz, J=22.2 Hz): m/e (m+1): 230.3.

5-Methoxy-3-phenyl-2-(4-{[4-(5-pyridin-2-yl-1H-1,2,4-triazol-3-yl)piperidin-1-yl]methyl}phenyl-1,6-naphthyridine (8-6)

To a solution of 2-(3-piperidin-4-yl-1H-1,2,4-triazol-5-yl) pyridine dihydrochloride (542 mg, 1.80 mmol) and 4-(5-methoxy-3-phenyl-1,6-naphthyridin-2-yl)benzaldehyde (560 mg, 1.65 mmol) in dry DMF (6 mL) was added triethylamine (0.83 mL, 6 mmol). After stirring for 10 minutes, acetic acid (1.03 mL, 18 mmol) was added and the mixture was stirred at room temperature over night. Then sodium triacetoxy borohydride (367 mg, 1.73 mmol) was added in one portion and stirred for six hours. After monitoring by LC/MS determined the reaction was not complete, additional portions of sodium triacetoxy borohydride (2×90 mg) were added over the next several hours at which time the reaction was complete. The mixture was diluted with ethyl acetate and aqueous $Na_2CO_3$ was added. The organic layer was separated and washed twice with water, dried ($Na_2SO_4$) and the solvent evaporated. The residue was digested with acetonitrile and upon cooling the solid product was isolated by filtration. This solid was suspended in hot ethyl acetate and methanol was slowly added until there was complete dissolution. The solvents were then boiled down to a small volume and allowed to cool as the pure product crystallized out. The mother liquors were purified by column chromatography on silica gel and elution with 1-7% methanol/ethyl acetate gave additional product. 1H NMR (500 MHz, $CDCl_3$): δ 8.66 (1H, d, J=4.7 Hz), 8.54 (1H, s), 8.23 (1H, d, J=6 Hz), 8.16 (1H, d, J=7.8 Hz), 7.83 (1H, dt, J=1.7 Hz, J=7.8 Hz), 7.56 (1H, d, J=6 Hz), 7.40 (2H, d, J=8 Hz), 7.36 (1H, dd), 7.28-7.30 (3H, m), 7.23-7.25 (2H, m), 4.16 (3H, s), 3.54 (2H, s), 2.96 (2H, br d, J=11.5 Hz), 2.85 (1H, t, J=3.7 Hz), 2.06-2.17 (4H, m), 1.92-2.01 (2H, m). m/e (m+1): 554.3, 277.9 [(m+2)/2].

3-phenyl-2-(4-{[4-(5-pyridin-2-yl-1H-1,2,4-triazol-3-yl)piperidin-1-yl]methyl}phenyl)-1,6-naphthyridin-5(6H)-one (8-7)

A mixture of 5-methoxy-3-phenyl-2-(4-{[4-(5-pyridin-2-yl-1H-1,2,4-triazol-3-yl)piperidin-1-yl]methyl}phenyl)-1,6-naphthyridine (725 mg, 1.31 mmol) and pyridine hydrochloride (6.9 gm, ~60 mmol) was heated at 150° C. for ten minutes. The cooled residue was dissolved in the minimum amount of water and neutralized with aqueous $NaHCO_3$. The precipitated solid was collected by filtration and purified by column chromatography on silica gel eluting with 1-14% methanol/ethyl acetate (sat'd $NH_4OH$). The isolated product was digested in methanol/acetonitrile to give pure product. $^1$H NMR (500 MHz, DMSO-d6): δ 11.58 (1H, d, J=4.8 Hz), 8.68 (1H, br s), 8.39 (1H, s), 8.03 (1H, d, J=7.3 Hz), 7.50 (2H, t, J=6.5 Hz), 7.31-7.33 (5H, m), 7.24-7.25 (4H, m), 6.79 (2H, d, J=7.3 Hz), 3.50 (2H, s), 2.84 (2H, br d, J=10.5 Hz), 2.72 (1H, m), 2.08 (2H, br t, J=11 Hz), 1.95 (2H, br d, J=11.6 Hz), 1.77 (2H, m). m/e (m+1): 540.3, 270.9 [(m+2)/2].

5-Chloro-3-phenyl-2-{4-[4-(5-pyridin-2-yl-4H-[1,2,4]triazol-3-yl)-piperidin-1-ylmethyl]-phenyl}-[1,6]naphthyridine (8-8)

A mixture of 8-7 (5.5 g, 10.2 mmol) and $POCl_3$ (50.0 g, 326.1 mmol) and DMF (0.3 g, 4.1 mmol) was heated to reflux at 130° C. for 3 hr. The reaction mixture was cooled and concentrated to remove $POCl_3$. 40 mL Toluene was added and concentrated to obtain a solid. To the solid was added 50 mL $H_2O$ and 40 mL $NaHCO_3$ (saturated) and 20 mL 1NNaOH to pH=9. The mixture was stirred to precipitate a solid which was collected via filtration as the desired product 8-8. It was washed by water and $CH_3CN$ and dried under vacuum.
LC/MS: M+1=559.09

(3-Phenyl-2-{4-[4-(5-pyridin-2-yl-4H-[1,2,4]triazol-3-yl)-piperidin-1-ylmethyl]-phenyl}-[1,6]naphthyridin-5-yl)-hydrazine (8-9)

A suspension of 8-8 (4.3 g, 7.7 mmol) in 30 mL 1,4-dioxane and hydrazine (7.4 g, 231.1 mmol) was heated in a microwave reactor at 100° C. for 5 mins. The mixture was cooled and concentrated to remove solvents. Toluene 40 mL (×3) was added and removed under vacuum to remove the residual hydrazine. The desired product 8-9 was obtained as a solid.
LC/MS: M+1=554.4

9-Phenyl-8-{4-[4-(5-pyridin-2-yl-4H-[1,2,4]triazol-3-yl)-piperidin-1-ylmethyl]phenyl}-[1,2,4]triazolo-[3,4-f][1,6]naphthyridine (8-10)

To a solution of 8-9 (4.5 g, 8.1 mmol) in 20 mL methanol and 60 mL toluene was added trimethoxy orthoformate (3.5 g, 32.5 mmol) and toluenesulfonic acid (0.1 g, 0.8 mmol). The mixture was refluxed for 10 hrs. Upon removal of the solvent, the residue was purified by flash column chromatography (100% $CHCl_3$ to 50% $CHCl_3$ and 50% methanol) to afford the desired product 8-10.
HRMS: M+1 (cal)=564.2619. Found=564.2589
1H NMR (500 MHz, $CD_3OD$): δ 9.35 (1H, s), 8.96 (1H, s), 8.72 (1H, d), 8.59 (1H, d), 8.28-8.10 (2H, m), 7.68-7.48 (6H, m), 7.40-7.30 (5H, m), 4.40 (2H, s), 3.68-3.20 (5H, m), 2.50-2.10 (4H, m).

SCHEME 9

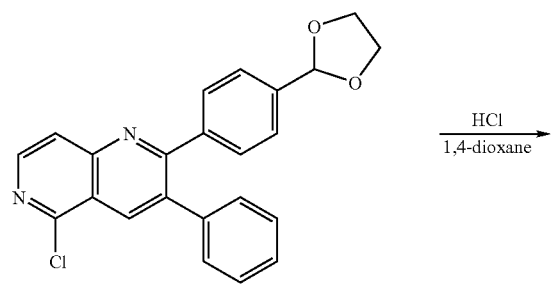

3-3

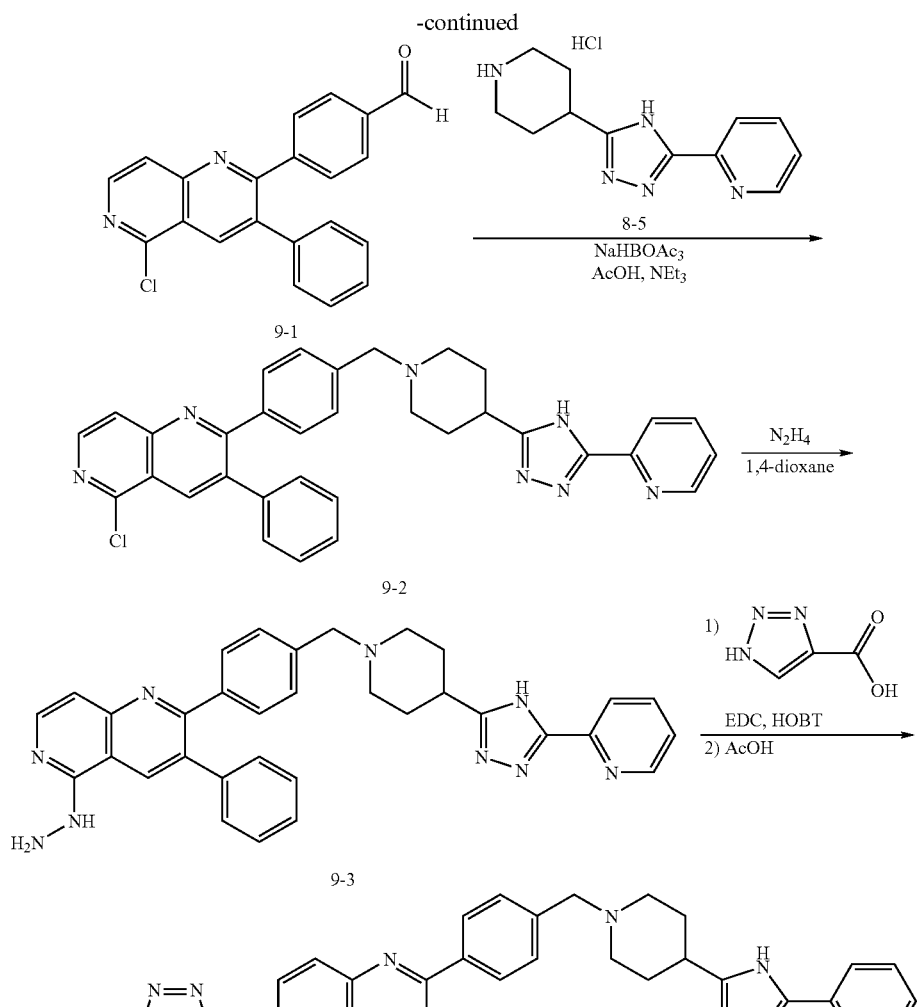

9-phenyl-8-(4-{[4-(5-pyridin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine (9-4)

4-(5-chloro-3-phenyl-1,6-naphthyridin-2-yl)benzaldehyde (9-1)

To a stirred solution of 3-3 (16 g, 41.1 mMol) in anhydrous 1,4-dioxane (75 mL) at 0° C. was added 3N HCl (27 mL). The reaction was then allowed to reach room temperature and was stirred for around 3 hours. Upon completion, the reaction was quenched with saturated NaHCO₃ solution to reach a pH of >7. The product was extracted into ethyl acetate (3×150 mL). The combined organic layers were washed with brine, dried with Na₂SO₄ and MgSO₄, filtered and concentrated in vacuo to yield 4-(5-chloro-3-phenyl-1,6-naphthyridin-2-yl)benzaldehyde 9-1 as a tan solid. LC/MS (M+1) calculated: 345.8; observed: 345.0

5-chloro-3-phenyl-2-(4-{[4-(5-pyridin-2-yl-4H-1,2,4-triazol-3-yl)piperidin-1-yl]methyl}phenyl)-1,6-naphthyridine (9-2)

To a stirred solution of 9-1 (4.9 g, 14.2 mMol) and 8-5 (4.2 g, 15.6 mMol) in NMP (50 mL) was added triethylamine (6 mL, 42.6 mMol) followed by acetic acid (1.6 mL, 28.4 mMol). After stirring at ambient temperature overnight, sodium triacetoxyborohydride (3.6 g, 17 mMol) was added in portions. Upon completion, the reaction was diluted with ethyl acetate and washed with saturated NaHCO₃, followed by water, then brine. The organic layer was dried with Na₂SO₄ and MgSO₄, filtered and concentrated in vacuo. The crude residue purified using flash chromatography on silica (gradient: 0% to 10% MeOH in CHCl₃ over 25 min) to yield 9-2 as an orange solid. LC/MS (M+1) calculated: 559.1; observed: 559.2

5-hydrazino-3-phenyl-2-(4-{[4-(5-pyridin-2-yl-4H-1,2,4-triazol-3-yl)piperidin-1-yl]methyl}phenyl)-1,6-naphthyridine (9-3)

To a stirred solution of 9-2 (5 g, 8.9 mMol) in anhydrous 1,4-dioxane (20 mL) was added hydrazine (5.9 mL, 188.1 mMol). The solution was heated to 100° C. in a microwave reactor for 5 minutes. The solvent was removed in vacuo and was dried azeotropically with toluene three times. The crude solid was triturated with a saturated NaHCO₃ solution for 20 minutes. The suspension was filtered and washed with copious amounts of water. The solid was dried azeotropically with toluene three times to yield 9-3 as a tan solid. LC/MS (M+1) calculated: 554.6; observed: 554.2

9-phenyl-8-(4-{[4-(5-pyridin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine (9-4)

To a stirred solution of 9-3 (2.0 g, 3.6 mMol), HOBT (0.5 g, 3.9 mMol), and 1H-1,2,3-triazole-4-carboxylic acid (0.4 g, 3.9 mMol) in anhydrous DMF (20 mL) was added DIEA (1.2 mL, 7.2 mMol) followed by EDC (0.76 g, 3.9 mMol). The solution was stirred at ambient temperature overnight. The solution was then treated with 2 mL of acetic acid and was heated to 80° C. for 3 hrs. Upon cooling to room temperature, the solution was filtered through a syringe filter and purified on a C18 reverse phase HPLC to give 9-4 as a solid. Mass (M+1) calculated: 631.2789 observed: 631.2778

The following table (Table 3) contains compounds made using the procedures of Scheme 9, substituting the appropriate amine for 8-9 and the appropriate carboxylic acid for 1H-1,2,3-triazole-4-carboxylic acid. Compounds 9-5-9-8 and 9-13-9-25 were isolated as HCl salts. Compounds 9-9-9-12 were isolated as TFA salts.

TABLE 3

| Cmp | Structure | Name | LRMS m/z (M + H) |
| --- | --- | --- | --- |
| 9-5 | 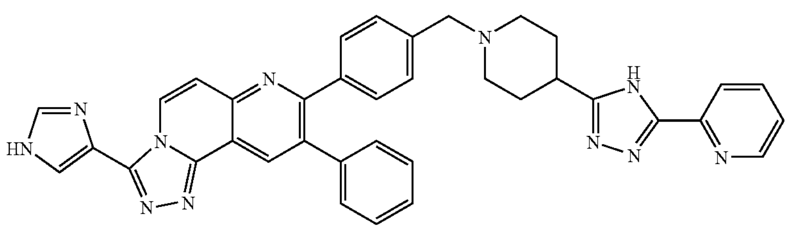 | 3-(1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 630.2831 |
| 9-6 | 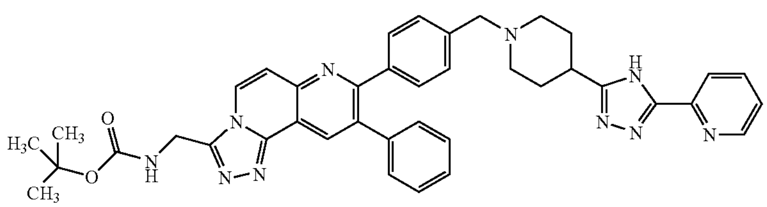 | tert-butyl [9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]methylcarbamate | 693.3394 |
| 9-7 | 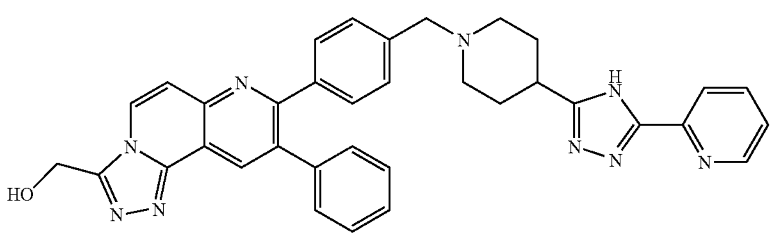 | [9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanol | 594.2703 |
| 9-8 | 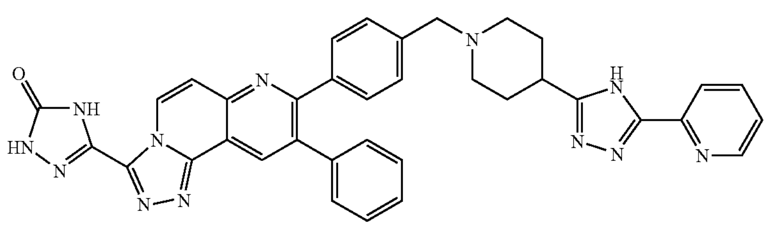 | 5-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]-2,4-dihydro-3H-1,2,4-triazol-3-one | 647.2729 |

TABLE 3-continued

| Cmp | Structure | Name | LRMS m/z (M + H) |
|---|---|---|---|
| 9-9 | 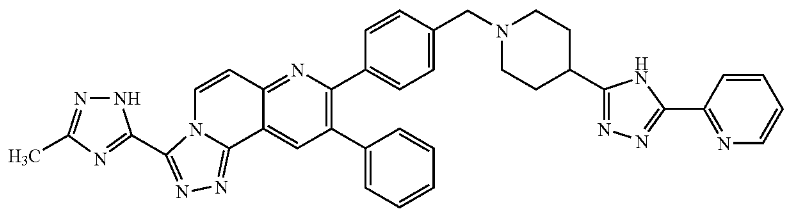 | 3-(3-methyl-1H-1,2,4-triazol-5-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 645.2948 |
| 9-10 | 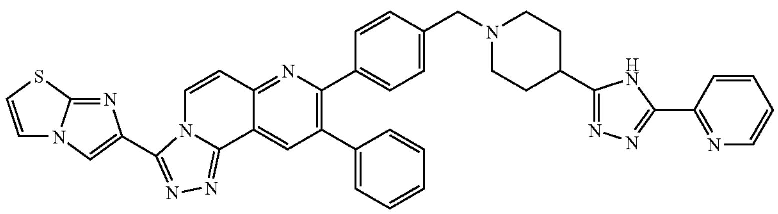 | 3-imidazo[2,1-b][1,3]thiazol-6-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 686.2547 |
| 9-11 | 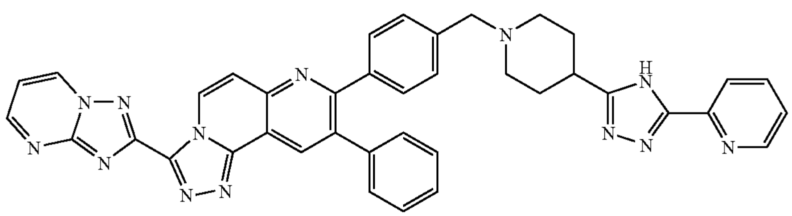 | 9-phenyl-8-(4-{[4-(5-pyridin-2-yl-4H-1,2,4-triazol-3-yl)piperidin-1-yl]methyl}phenyl)-3-[1,2,4]triazolo[1,5-a]pyrimidin-2-yl[1,2,4]triazolo[3,4-f]-1,6-naphthyridine | 682.2902 |
| 9-12 | 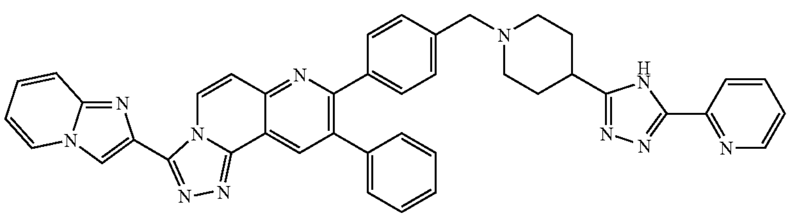 | 3-imidazo[1,2-a]pyridin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | LRMS (M + 1) = 680.3 |
| 9-13 | 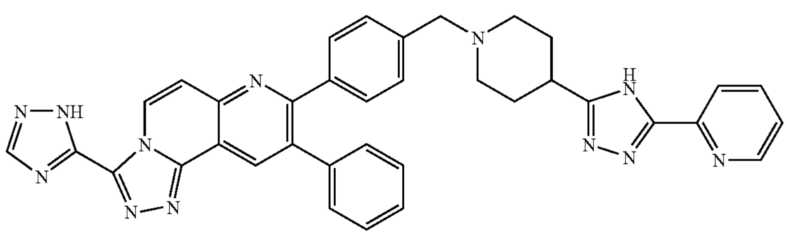 | 9-phenyl-8-(4-{[4-(5-pyridin-2-yl-4H-1,2,4-triazol-3-yl)piperidin-1-yl]methyl}phenyl)-3-(1H-1,2,4-triazol-5-yl)[1,2,4]triazolo[3,4-f]-1,6-naphthyridine | 631.2792 |
| 9-14 | 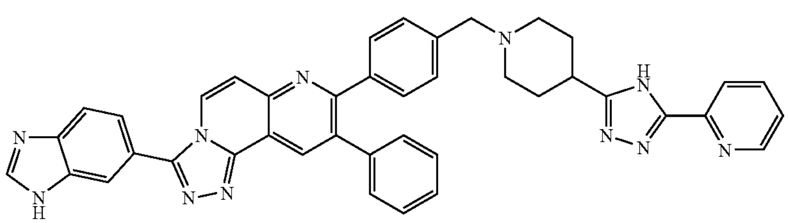 | 3-(1H-benzimidazol-6-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 680.2988 |
| 9-15 | 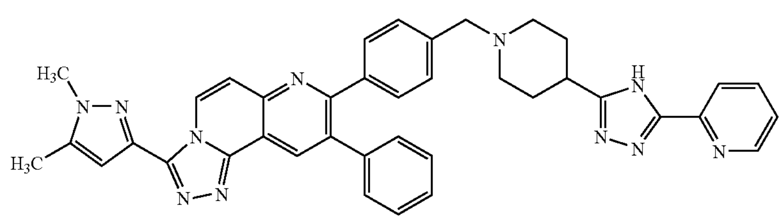 | 3-(1,5-dimethyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 658.3145 |

TABLE 3-continued

| Cmp | Structure | Name | LRMS m/z (M + H) |
|---|---|---|---|
| 9-16 | 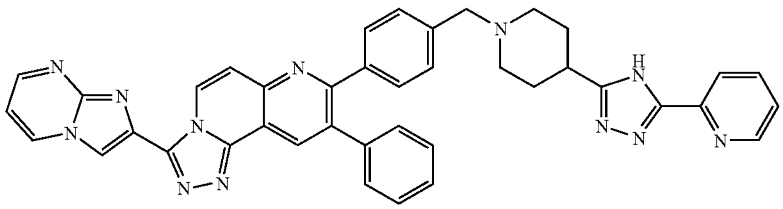 | 3-imidazo[1,2-a]pyrimidin-2-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 681.2949 |
| 9-17 | 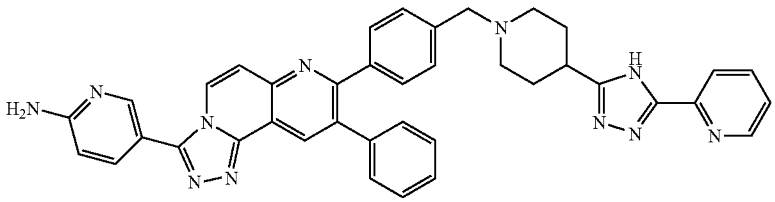 | 5-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]pyridin-2-amine | 656.2988 |
| 9-18 | 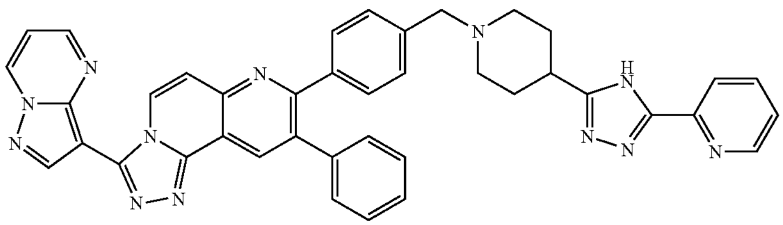 | 9-phenyl-3-pyrazolo[1,5-a]pyrimidin-3-yl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 681.2951 |
| 9-19 | 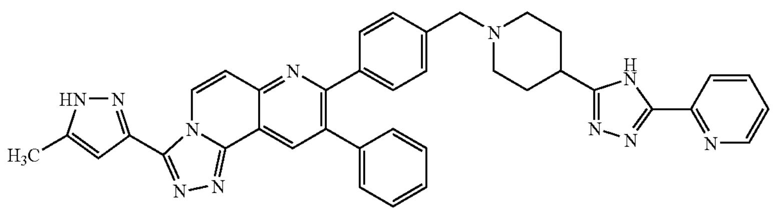 | 3-(5-methyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine | 644.2998 |
| 9-20 | 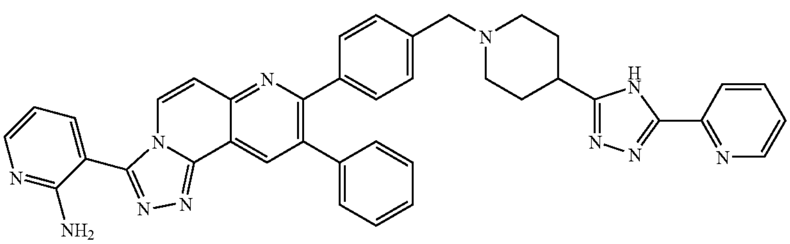 | 3-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]pyridin-2-amine | 656.298 |
| 9-21 | 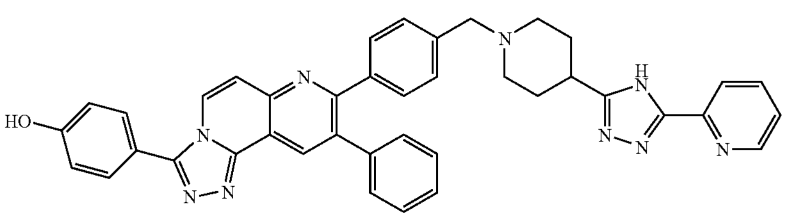 | 4-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]phenol | 656.288 |
| 9-22 | 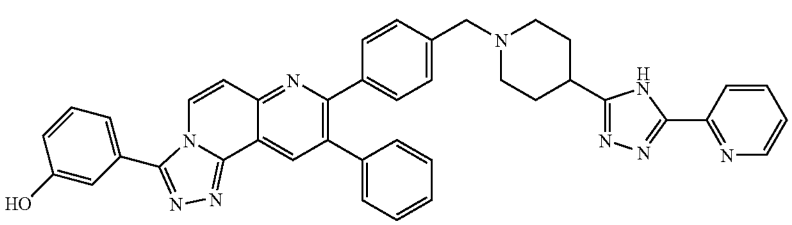 | 3-[9-phenyl-9-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]phenol | 656.288 |

TABLE 3-continued
| Cmp | Structure | Name | LRMS m/z (M + H) |
|---|---|---|---|
| 9-23 | 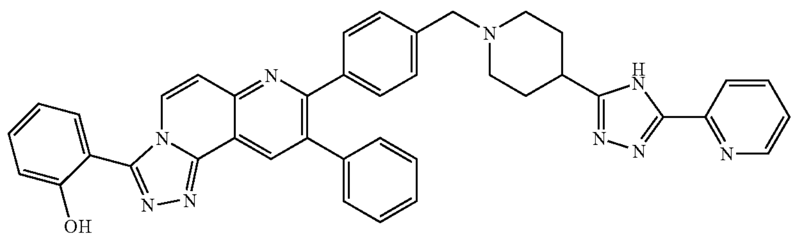 | 2-[9-phenyl-8-(4-{[4-(5-pyridin-2-yl-4H-1,2,4-triazol-3-yl)piperidin-1-yl]methyl}phenyl)[1,2,,4]triazolo[3,4-f]-1,6-naphthyridin-3-yl]phenol | 656.2894 |
| 9-24 | 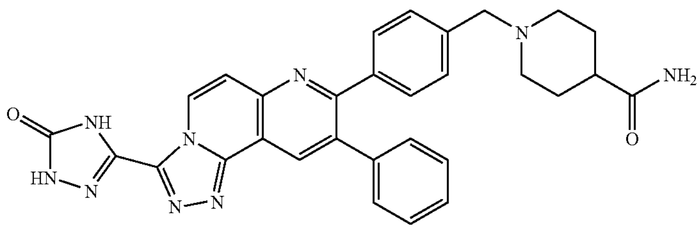 | 1-{4-[3-(5-oxo-4,5-dihydro-1H-1,2,4-triazolo-3-yl)-9-phenyl[1,2,4]triazol[3,4-f]-1,6-naphthyridin-8-yl]benzyl}piperidine-4-carboxamide | 546.2344 |
| 9-25 | 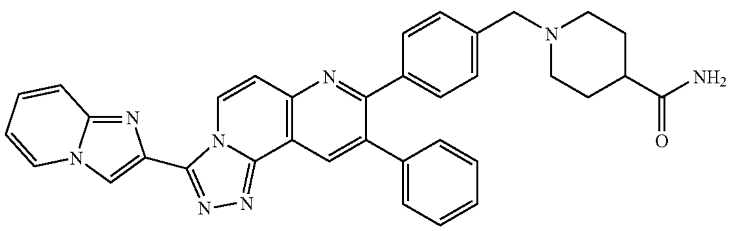 | 1-[4-(3-imidazo[1,2-a]pyridin-2-yl-9-phenyl[1,2,4]triazolo[3,4-f]-1,6-naphthyridin-8-yl)benzyl]piperidine-4-carboxamide | 579.2598 |
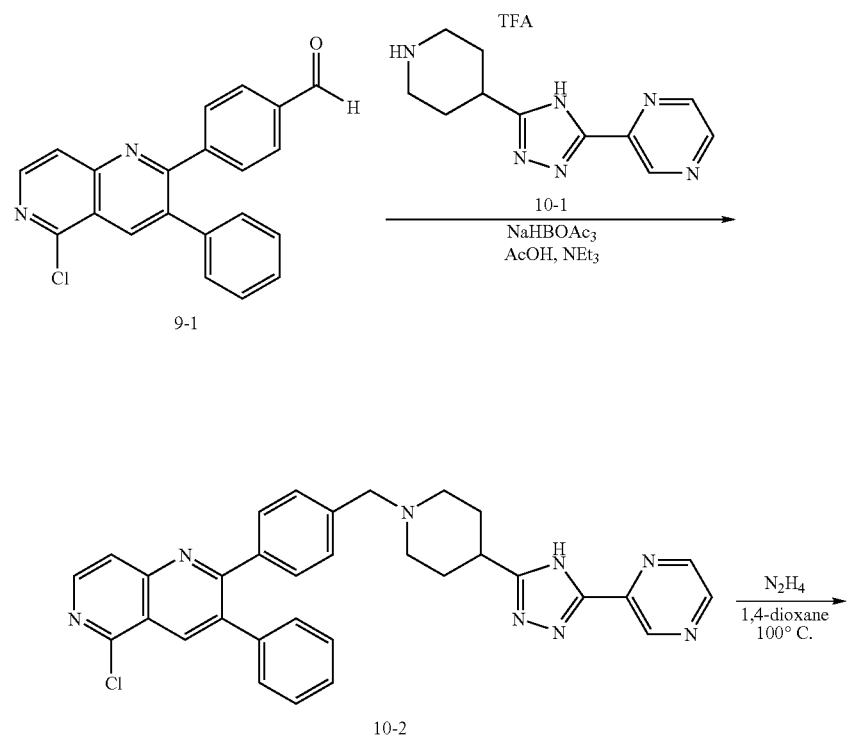
SCHEME 10

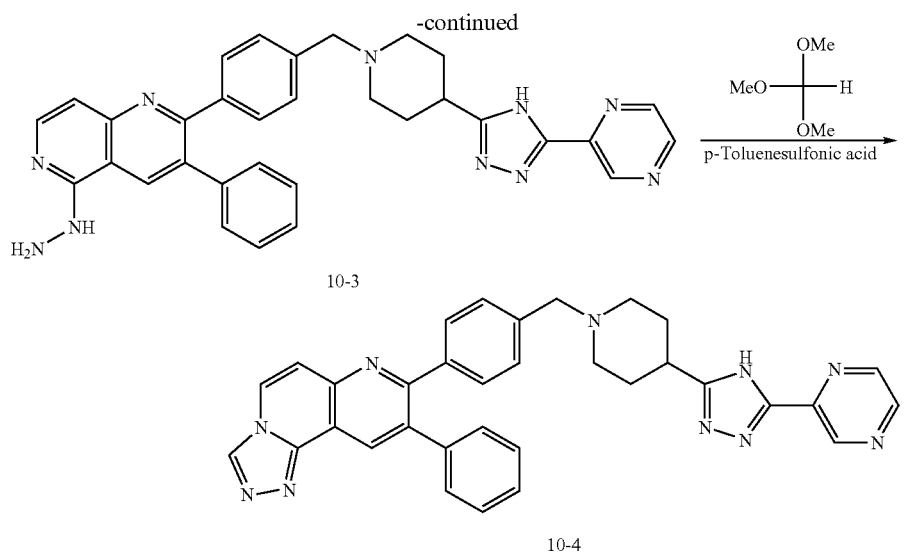

9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (10-4)

2-(3-piperidin-4-yl-1H-1,24-triazol-5-yl)pyrazine (10-1)

To a solution of 1-(tert-butoxycarbonyl)piperidine-4-carboxylic acid (120 g, 520 mmol) in DCM (250 mL) was added carbonyldiimidazole (96 g, 590 mmol) in portions at room temperature. After 30 minutes, the reaction mixture was added to a freshly prepared solution of hydrazine (27 g, 840 mmol) in DCM (100 mL). After 30 minutes, the reaction was washed with a saturated solution of sodium carbonate, brine, dried over sodium sulfate, filtered and concentrated. The resulting solid was suspended in ether and filtered to give tert-butyl 4-(hydrazinocarbonyl)piperidine-1-carboxylate as a white solid. $^1$H NMR (400 MHz, DMSO-d$_6$): δ 9.00 (s, 1H), 4.15-4.10 (s, 2H), 3.95-3.90 (m, 2H), 2.80-2.60 (m, 2H), 2.25-2.20 (m, 1H), 1.62-1.55 (m, 2H), 1.40 (s, 9H).

A solution of pyrazinecarbonitrile (2.0 g, 19 mmol) in methanol (20 mL) was treated with sodium methoxide in methanol (25 wt %, 1.3 mL, 5.7 mmol) at room temperature. After 30 minutes, a solution of tert-butyl 4-(hydrazinocarbonyl)piperidine-1-carboxylate (4.6 g, 19 mmol) in methanol (20 mL) was added and the reaction was heated to reflux for 19 hours. The reaction mixture was concentrated, dissolved in ethoxyethanol (50 mL) and heated to reflux for 22 hours. The reaction was cooled to room temperature, quenched with acetic acid (0.38 mL, 6.6 mmol) and concentrated. The residue was suspended in ether and filtered to give tert-butyl 4-(5-pyrazin-2-yl-1H-1,2,4-triazol-3-yl)piperidine-1-carboxylate as a solid. HRMS (M+H$^+$): observed=331.1876, calculated=331.1877; $^1$H NMR (400 MHz, CD$_3$OD): δ 9.29 (d, J=1.6 Hz, 1H), 8.70 (dd, J=2.4, 1.6 Hz, 1H), 8.64 (d, J=2.4 Hz, 2H), 4.19-4.15 (m, 2H), 3.15-3.09 (m, 1H), 2.97 (m, 2H), 2.07-2.03 (m, 2H), 1.84-1.75 (m, 2H), 1.48 (s, 9H).

A solution of tert-butyl 4-(5-pyrazin-2-yl-1H-1,2,4-triazol-3-yl)piperidine-1-carboxylate (6.0 g, 18 mmol) in trifluoroacetic acid (25 mL) was stirred at room temperature. After 1 hour, the reaction was concentrated. The resulting solid was suspended in ethyl acetate and methanol and filtered to give 10-1 as the TFA salt. The salt was dissolved in 1:1 acetonitrile:water, loaded onto an SCX ion exchange resin, rinsed with acetonitrile, and eluted with 10% NH3 in ethanol to give 10-1 as a solid. $^1$H NMR (400 MHz, CDCl$_3$): δ 9.28-9.26 (m, 1H), 8.70-8.68 (m, 1H), 8.60-8.58 (m, 1H), 3.35-3.22 (m, 2H), 3.15-3.05 (m, 1H), 2.90-2.85 (m, 2H), 2.15-2.08 (m, 2H), 1.95-1.90 (m, 2H).

5-chloro-3-phenyl-2-(4-{[4-(5-pyrazin-2-yl-4H-1,2,4-triazol-3-yl)piperidin-1-yl]methyl}phenyl)-1,6-naphthyridine (10-2)

To a stirred solution of 9-1 (1 g, 2.9 mMol) and 10-1 (1.09 g, 3.2 mMol) in NMP (10 mL) was added triethylamine (0.8 mL, 5.8 mMol) followed by acetic acid (0.3 mL, 5.8 mMol). After stirring at ambient temperature overnight, sodium triacetoxyborohydride (0.6 g, 2.9 mMol) was added in portions. Upon completion, the reaction was diluted with ethyl acetate and washed with saturated NaHCO$_3$, followed by water, then brine. The organic layer was dried with Na$_2$SO$_4$ and MgSO$_4$, filtered and concentrated in vacuo. The crude residue was purified using flash chromatography on silica (gradient: 0% to 10% MeOH in CHCl$_3$ over 25 min) to yield 10-2 as a solid. LC/MS (M+1) calculated: 560.1; observed: 560.2

5-hydrazino-3-phenyl-2-(4-{[4-(5-pyrazin-2-yl-4H-1,2,4-triazol-3-yl)piperidin-1-yl]methyl}phenyl)-1,6-napthyridine (10-3)

To a stirred solution of 10-2 (0.5 g, 0.9 mMol) in anhydrous 1,4-dioxane (5 mL) was added hydrazine (0.56 mL, 17.8 mMol). The solution was heated to 100° C. in a microwave reactor for 20 minutes. The solvent was removed in vacuo and was dried azeotropically with toluene three times. The crude solid was triturated with a saturated NaHCO$_3$ solution for 20 minutes. The suspension was filtered and washed with copious amounts of water. The solid was dried azeotropically with toluene three times to yield 10-3 as a brown solid. LC/MS (M+1) calculated: 555.6; observed: 555.2

9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (10-4)

To a stirred solution of 10-3 (0.5 g, 0.9 mMol) in 16 mL of 3:1 toluene:methanol was added trimethyl orthoformate (0.3 g, 2.7 mMol) and p-toluenesulfonic acid monohydrate (0.017 g, 0.09 mMol). The reaction was heated to 100° C. in a microwave reactor for 1 hour. After cooling to room temperature, the solvent was removed under reduced pressure. The product was purified on a C18 reverse phase HPLC to give 10-4 as a solid. Mass (M+1) calculated: 565.2571 observed: 565.2523

(4.36 g, 41.5 mmol) in 1-butanol (20 mL) was heated to reflux for 48 hours. The mixture was concentrated, suspended in ether, and filtered to give tert-butyl 4-(5-pyrimidin-2-yl-1H-1,2,4-triazol-3-yl)piperidine-1-carboxylate as a solid. MS (M+H⁺): 331.2 observed; $^1$H-NMR (400 MHz, CD$_3$OD): δ 8.92 (d, J=4.0 Hz, 2H), 7.52 (t, J=4.0 Hz, 1H), 4.18-4.15 (m,

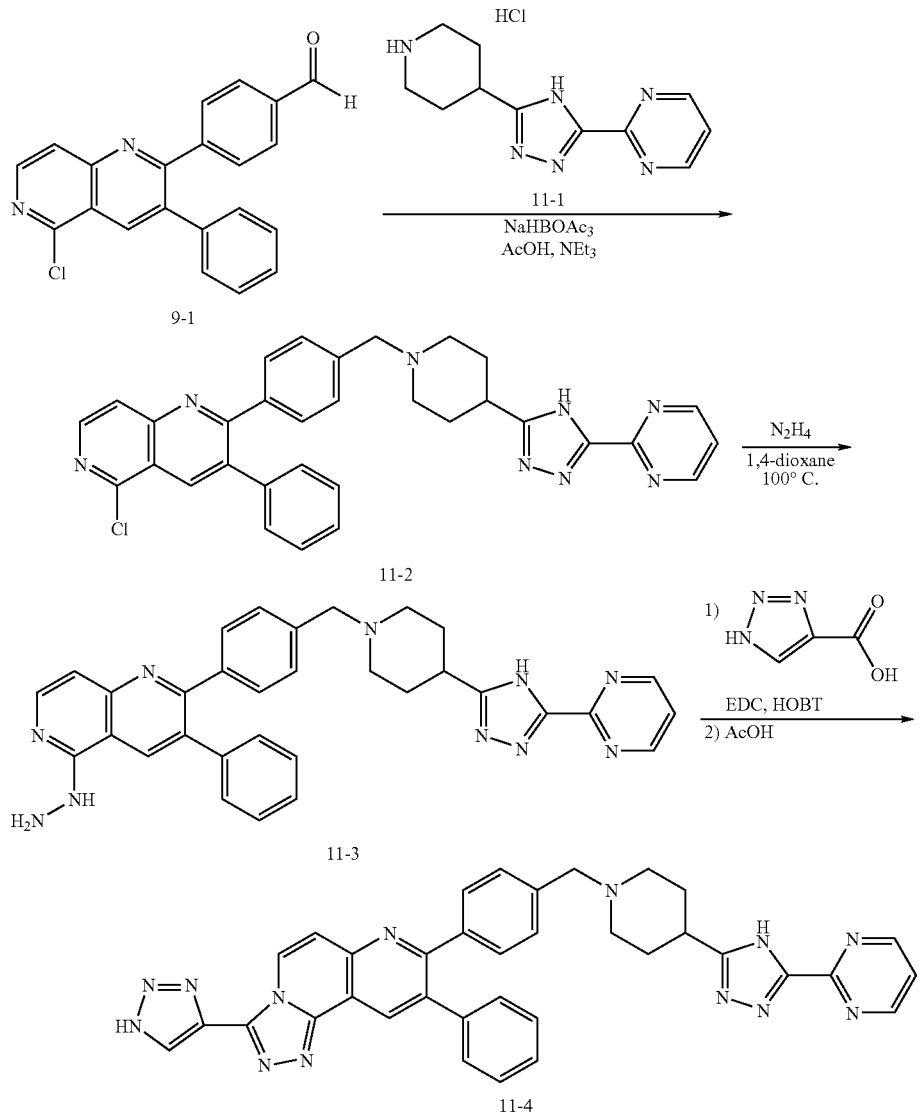

9-phenyl-8-(4-{[4-(5-pyrimidin-2-yl-4H-1,2,4-triazol-3-yl)piperidin-1-yl]methyl}phenyl)-3-(1H-1,23-triazol-4-yl)[1,2,4]triazolo[3,4-f]-1,6-naphthyridine (11-4)

2-(3-piperidin-4-yl-1H-1,2,4-triazol-5-yl)pyrimidine (11-1)

A mixture of tert-butyl 4-(hydrazinocarbonyl)piperidine-1-carboxylate (10.1 g, 41.5 mmol) and 2-cyanopyrimidine 2H), 3.14-3.08 (m, 1H), 2.98 (br.s, 2H), 2.07-2.01 (m, 2H), 1.85-1.77 (m, 2H), 1.48 (s, 9H).

To a solution of tert-butyl 4-(5-pyrimidin-2-yl-1H-1,2,4-triazol-3-yl)piperidine-1-carboxylate (13.6 g, 41.1 mmol) in methanol (30 mL) and DCM (15 mL) was added a saturated solution of anhydrous HCl in ethyl acetate (60 mL). After 2 hours, the reaction was concentrated. The resulting solid was suspended in ethyl acetate and methanol and filtered to give 11-1 as the HCl salt. The salt was dissolved in 1:1 acetonitrile: water, loaded onto an SCX ion exchange resin, rinsed with acetonitrile, and eluted with 10% NH$_3$ in ethanol to give 11-1 as a solid. MS (M+H⁺): 231.2

5-chloro-3-phenyl-2-(4-{[4-(5-pyrimidin-2-yl-4H-1,2,4-triazol-3-yl)piperidin-1-yl]methyl}phenyl)-1,6-naphthyridine (11-2)

To a stirred solution of 9-1 (0.25 g, 0.73 mMol) and 11-1 (0.23 g, 0.87 mMol) in NMP (5 mL) was added triethylamine (0.3 mL, 2.2 mMol) followed by acetic acid (0.082 mL, 1.5 mMol). After stirring at ambient temperature overnight, sodium triacetoxyborohydride (0.18 g, 0.87 mMol) was added. Upon completion, the reaction was diluted with ethyl acetate and washed with saturated NaHCO$_3$, followed by water, then brine. The organic layer was dried with Na$_2$SO$_4$ and MgSO$_4$, filtered and concentrated in vacuo to yield 11-2. LC/MS calculated: 559.1; observed: 559.3

5-hydrazino-3-phenyl-2-(4-{[4-(5-pyrimidin-2-yl-4H-1,2,4-triazol-3-yl)piperidin-1-yl]methyl}phenyl)-1,6-naphthyridine (11-3)

To a stirred solution of 11-2 (0.4 g, 0.7 mMol) in anhydrous 1,4-dioxane (3 mL) was added hydrazine (0.45 mL, 14.5 mMol). The solution was heated to 100° C. in a microwave reactor for 5 minutes. The solvent was removed in vacuo and was dried azeotropically with toluene three times to yield 11-3.

LC/MS (M+1) calculated: 555.6; observed: 555.4

9-phenyl-8-(4-{[4-(5-pyrimidin-2-yl-4H-1,2,4-triazol-3-yl)piperidin-1-yl]methyl}phenyl)-3-(1-H-1,2,3-triazol-4-yl)[1,2,4]triazolo[3,4-f]-1,6-naphthyridine (11-4)

To a stirred solution of 11-3 (0.2 g, 0.36 mMol), HOBT (0.05 g, 0.4 mMol), and 1H-1,2,3-triazole-4-carboxylic acid (0.05 g, 0.4 mMol) in anhydrous DMF (2 mL) was added DIEA (0.18 mL, 1.1 mMol) followed by EDC (0.08 g, 0.4 mMol). The solution was heated in the microwave reactor for 30 minutes at 80° C. Solution was then treated with 0.5 mL of acetic acid and was heated to 80° C. in the microwave reactor for 10 min. Upon cooling to room temperature, the solution was passed through a syringe filter and purified on a C18 reverse phase HPLC to give 11-4 as a solid. Mass (M+1) calculated: 632.2742 observed: 632.274

SCHEME 12

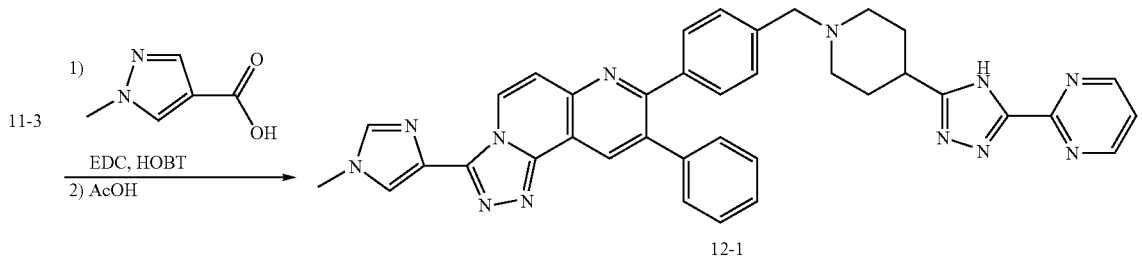

3-(1-methyl-1H-imidazol-4-yl)-9-phenyl-8-(4-{[4-(5-pyrimidin-2-yl-4H-1,2,4-triazol-3-yl)piperidin-1-yl]methyl}phenyl)[1,2,4]triazolo[3,4-f]-1,6-naphthyridine (12-1)

To a stirred solution of 11-3 (0.23 g, 0.4 mMol), HOBT (0.06 g, 0.45 mMol), and 1-methyl-1H-imidazole-4-carboxylic acid (0.06 g, 0.45 mMol) in anhydrous DMF (2 mL) was added DIEA (0.13 mL, 0.8 mMol) followed by EDC (0.09 g, 0.5 mMol). The solution was heated in the microwave reactor for 15 minutes at 80° C. Solution was then treated with 0.2 mL of acetic acid and was heated to 80° C. in the microwave reactor for 20 minutes. Upon cooling to room temperature, the solution was passed through a syringe filter and purified on a C18 reverse phase HPLC to give 12-1 as a solid. Mass (M+1) calculated: 632.2742 observed: 632.274

SCHEME 13

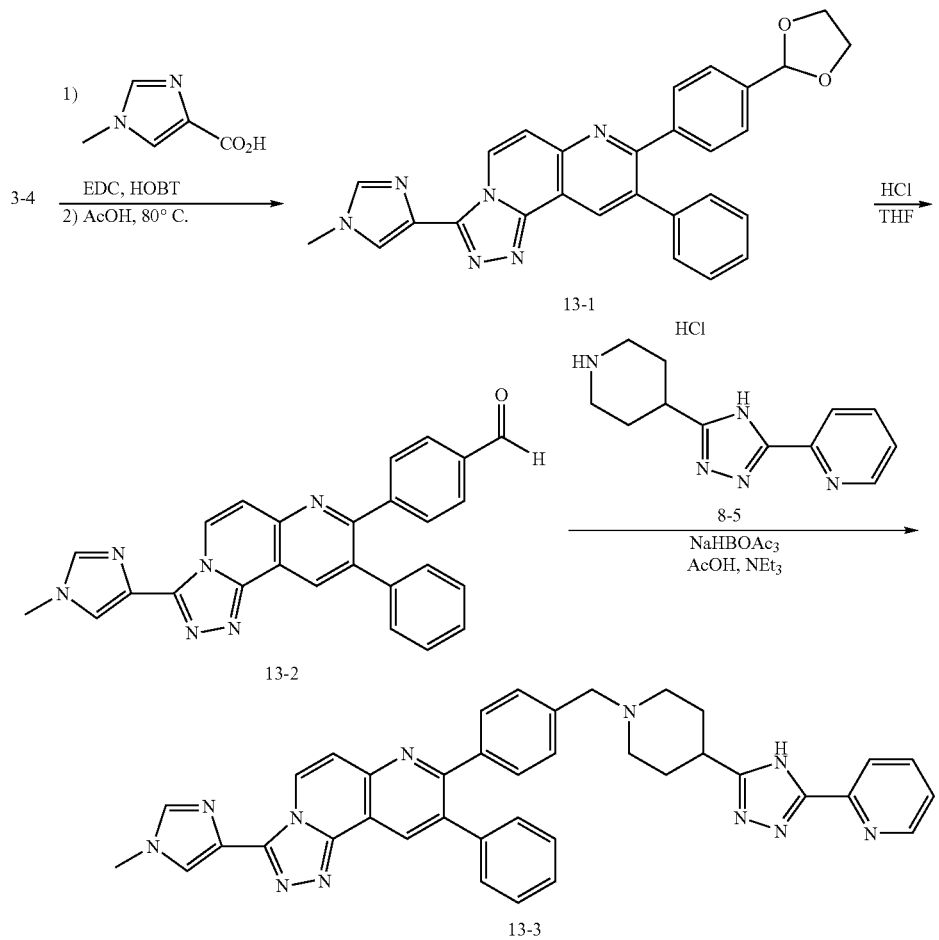

3-(1-methyl-1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine (13-3)

8-[4-(1,3-dioxolan-2-yl)phenyl]-3-(1-methyl-1H-imidazol-4-yl)-9-phenyl[1,2,4]triazolo[3,4-f]-1,6-naphthyridine (13-1)

To a stirred solution of 3-4 (5 g, 13 mMol), HOBT (1.9 g, 14.3 mMol), and 1-methyl-1H-imidazole-4-carboxylic acid (2 g, 15.6 mMol) in anhydrous DMF (100 mL) was added EDC (2.7 g, 14.3 mMol). The solution was stirred overnight at ambient temperature. The solution was then treated with 24 mL of acetic acid and was heated to 80° C. in an oil bath for 5 hours. Upon cooling to room temperature, an equal volume of water was added and the resulting suspension was filtered and washed with copious amounts of water. The collected solid was dried azeotropically with toluene three times to yield 13-1 as a tan solid. Mass (M+1) calculated: 475.1877 observed: 475.1871

4-[3-(1-methyl-1H-imidazol-4-yl)-9-phenyl[1,2,4]triazolo[3,4-f]-1,6-naphthyridin-8-yl]benzaldehyde (13-2)

To a stirred solution of 13-1 (2 g, 4.2 mMol) in THF (32 mL) was added 1N HCl (32 mL). A suspension developed as the reaction stirred at room temperature for 1 hour. The reaction was then quenched with 100 mL of a saturated $NaHCO_3$ solution. The suspension was filtered and washed with water. The collected solid was dried azeotropically with toluene three times to yield 13-2 as a tan solid. Mass (M+1) calculated: 431.1615 observed: 431.1616

3-(1-methyl-1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-napthyridine (13-3)

To a stirred solution of 13-2 (0.5 g, 1.2 mMol) and 8-5 (0.34 g, 1.3 mMol) in NMP (10 mL) was added triethylamine (0.33 mL, 2.3 mMol) followed by acetic acid (0.13 mL, 2.3 mMol). After stirring overnight at room temperature, sodium triacetoxyborohydride (0.3 g, 1.3 mMol) was added in portions. After stirring for 6 hours, the solution was filtered through a syringe filter and purified on a C18 reverse phase HPLC to give 13-3 as a solid. Mass (M+1) calculated: 644.2993 observed: 644.2988

The following table (Table 4) contains compounds made using the procedures of Scheme 13, substituting the appropriate amine for 8-5. Compounds 13-4-13-7, 13-10-13-19 and 13-21 were isolated as the HCl salt. Compounds 13-8 and 13-9 were isolated as TFA salts.

TABLE 4

| Cmp | Structure | Name | HRMS m/z (M + H) |
|---|---|---|---|
| 13-4 | 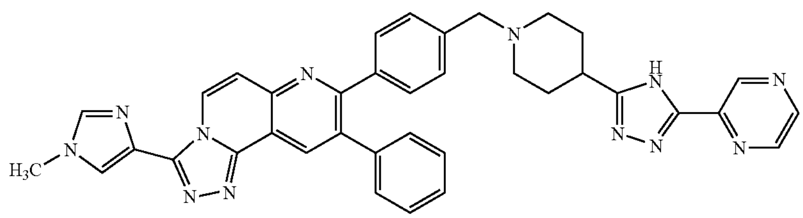 | 3-(1-methyl-1H-imidazol-4-yl)-9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine | 645.2946 |
| 13-5 | 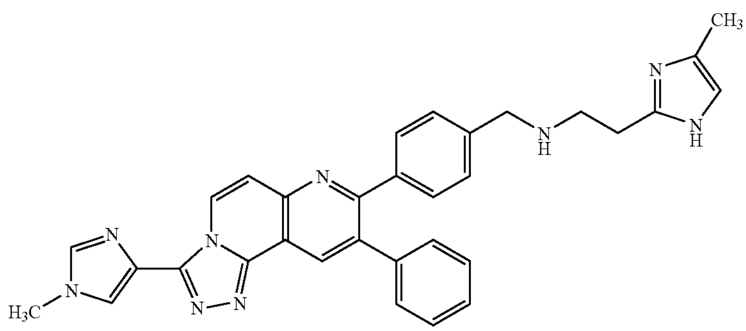 | N-[2-(4-methyl-1H-imidazol-2-yl)ethyl]-N-{4-[3-(1-methyl-1H-imidazol-4-yl)-9-phenyl[1,2,4]triazolo[3,4-f]-1,6-naphthyridin-8-yl]benzyl}amine | 540.2609 |
| 13-6 | 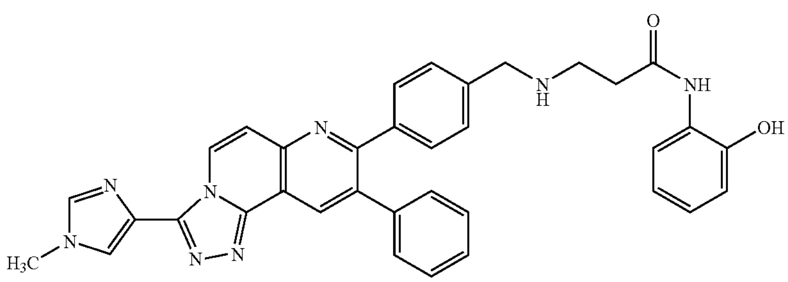 | $N^1$-(2-hydroxyphenyl)-$N^3$-{4-[3-(1-methyl-1H-imdiazol-4-yl)-9-phenyl[1,2,4]triazolo[3,4-f]-1,6-naphthyridin-8-yl]benzyl}-beta-alaninamide | 595.2564 |
| 13-7 | 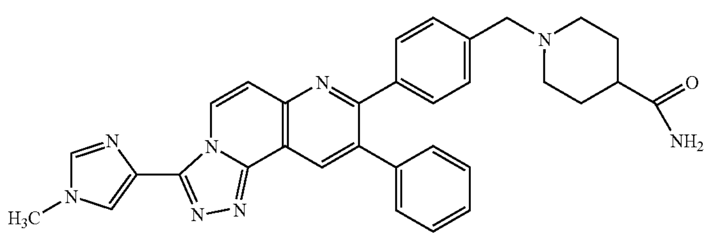 | 1-{4-[3-(1-methyl-1H-imidazol-4-yl)-9-phenyl[1,2,4]triazolo[3,4-f]-1,6-naphthyridin-8-yl]benzyl}piperidine-4-carboxamide | 543.2611 |
| 13-8 | 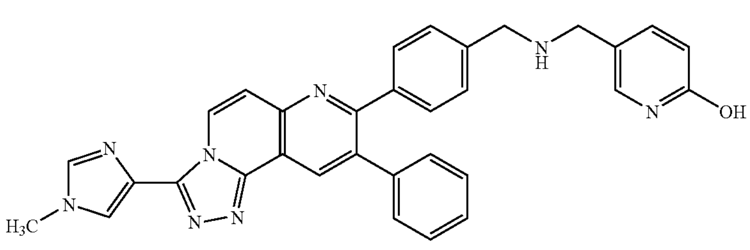 | 5-[({4-[3-(1-methyl-1H-imidazol-4-yl)-9-phenyl[1,2,4]triazolo[3,4-f]-1,6-naphthyridin-8-yl]benzyl}amino)methyl]pyridin-2-ol | 539.2302 |
| 13-9 | 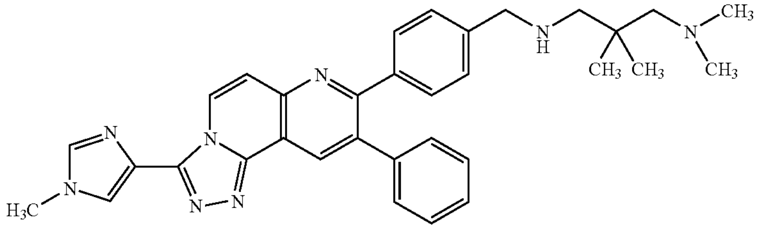 | $N^1,N^1$,2,2-tetramethyl-$N^3$-{4-[3-(1-methyl-1H-imidazol-4-yl)-9-phenyl[1,2,4]triazolo[3,4-f]1,6-naphthyridin-8-yl]benzyl}propane-1,3-diamine | 545.3125 |

TABLE 4-continued

| Cmp | Structure | Name | HRMS m/z (M + H) |
|---|---|---|---|
| 13-10 | 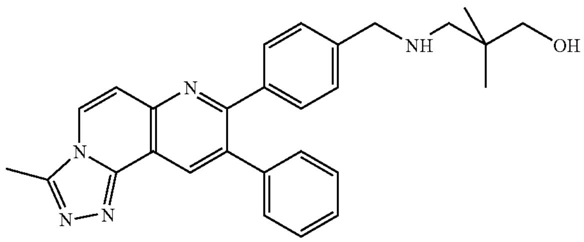 | 3-hydroxy-2,2-dimethyl-N-[4-(3-methyl-9-phenyl[1,2,4]triazolo[3,4-f]-1,6-naphthyridin-8-yl)benzyl]propan-1-amine | Calc'd: 452.2659 Observed: 452.2655 |
| 13-11 | 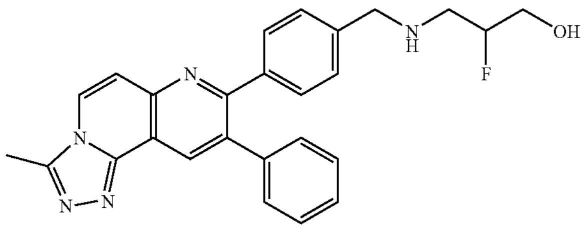 | 2-fluoro-3-hydroxy-N-[4-(3-methyl-9-phenyl[1,2,4]triazolo[3,4-f]-1,6-naphthyridin-8-yl)benzyl]propan-1-amine | Calc'd: 442.2038 Observed: 442.2021 |
| 13-12 | 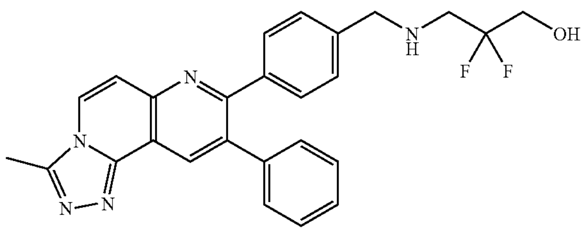 | 2,2-difluoro-3-hydroxy-N-[4-(3-methyl-9-phenyl[1,2,4]triazolo[3,4-f]-1,6-naphthyridin-8-yl)benzyl]propan-1-amine | Calc'd: 460.1944 Observed: 460.1926 |
| 13-13 | 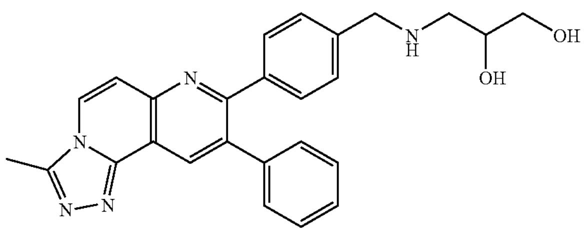 | 2,3-dihydroxy-N-[4-(3-methyl-9-phenyl[1,2,4]triazolo[3,4-f]-1,6-naphthyridin-8-yl)benzyl]propan-1-amine | Calc'd: 440.2081 Observed: 440.2076 |
| 13-14 | 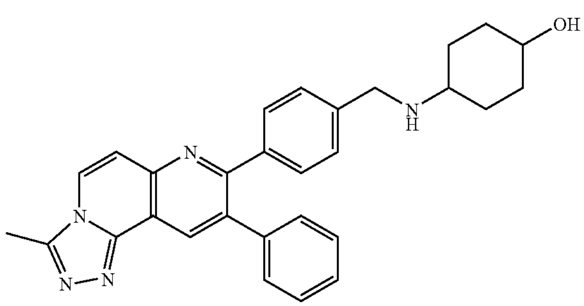 | 4-hydroxy-N-[4-(3-methyl-9-phenyl[1,2,4]triazolo[3,4-f]-1,6-naphthyridin-8-yl)benzyl]cyclohexanamine | Calc'd: 464.2445 Observed: 464.2448 |
| 13-15 | 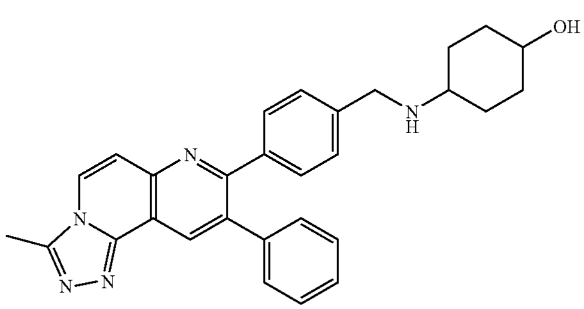 | 4-hydroxy-N-[4-(3-methyl-9-phenyl[1,2,4]triazolo[3,4-f]-1,6-naphthyridin-8-yl)benzyl]cyclohexanamine | Calc'd: 464.2445 Observed: 454.2438 |

TABLE 4-continued

| Cmp | Structure | Name | HRMS m/z (M + H) |
|---|---|---|---|
| 13-16 | 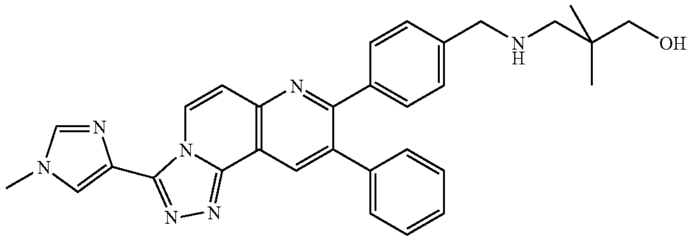 | 3-hydroxy-2,2-dimethyl-N-{4-[3-(1-methyl-1H-imidazol-4-yl)-9-phenyl[1,2,4]triazol[3,4-f]-1,6-naphthyridin-8-yl]benzyl}propan-1-amine | Calc'd: 518.2663 Observed: 518.2663 |
| 13-17 | 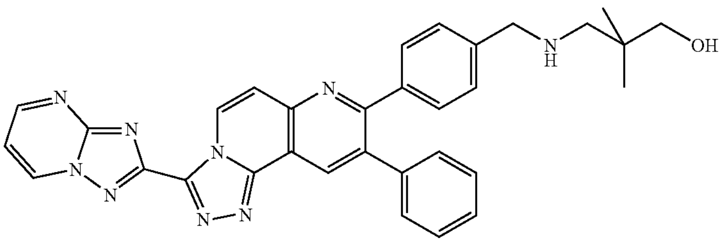 | 3-hydroxy-2,2-dimethyl-N-[4-(9-phenyl-3-[1,2,4]triazolo[1,5-a]pyrimidin-2-yl[1,2,4]triazolo[3,4-f]-1,6-naphthyridin-8-yl)benzyl]propan-1-amine | Calc'd: 556.2568 Observed: 556.2570 |
| 13-18 | 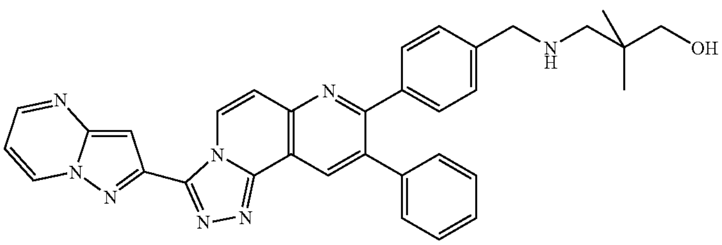 | 3-hydroxy-2,2-dimethyl-N-[4-(9-phenyl-3-pyrazolo[1,5-a]pyrimidin-2-yl[1,2,4]triazolo[3,4-f]-1,6-naphthyridin-8-yl)benzyl]propan-1-amine | Calc'd: 555.2616 Observed: 555.2575 |
| 13-19 | 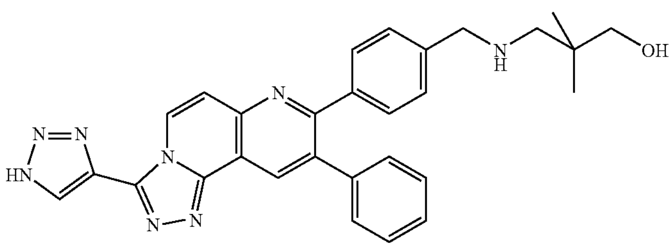 | 3-hydroxy-2,2-dimethyl-N-{4-[9-phenyl-3-(1H-1,2,3-triazol-4-yl) [1,2,4]triazolo[3,4-f]-1,6-naphthyridin-8-yl]benzyl}propan-1-amine | Calc'd: 505.2459 Observed: 505.2453 |
| 13-20 | 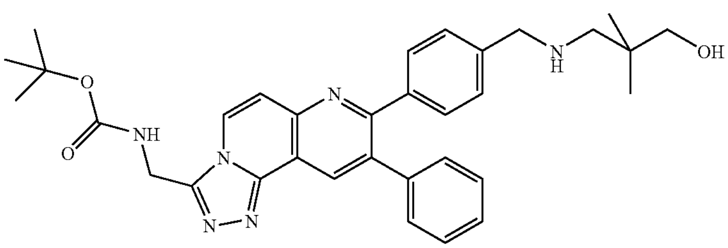 | tert-butyl {[8-(4-{[(3-hydroxy-2,2-dimethylpropyl)amino]methyl}phenyl)-9-phenyl[1,2,4]triazolo[3,4-f]-1,6-naphthyridin-3-yl]methyl}carbamate | Calc'd: 567.3018 Observed: 567.3015 |
| 13-21 | 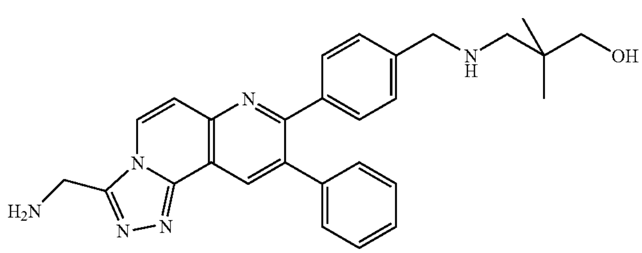 | N-{4-[3-(ammoniomethyl)-9-phenyl[1,2,4]triazolo[3,4-f]-1,6-naphthyridin-8-yl]benzyl}-3-hydroxy-2,2-dimethylpropan-1-amine | Calc'd: 467.2554 Observed: 467.2553 |

Compound 13-4

3-(1-methyl-1H-imidazol-4-yl)-9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridine (13-4)

To a stirred solution of 13-2 (1.5 g, 3.5 mMol) and 10-1 (1.4 g, 4.0 mMol) in NMP (30 mL) was added triethylamine (1 mL, 7 mMol) followed by acetic acid (0.4 mL, 7 mMol). After stirring overnight at room temperature, sodium triacetoxyborohydride (0.9 g, 4.2 mMol) was added in portions. After stirring for 6 hours, saturated NaHCO$_3$ solution was added until the pH was above 7. The resulting suspension was filtered and washed with water. The solid was dried azeotropically with toluene three times and was purified using normal phase flash chromatography (gradient: 100% CHCl$_3$ to 10% MeOH in CHCl$_3$ over 40 min.) to yield 13-4 as a white solid. Mass (M+1) calculated: 645.2946 observed: 645.2946

[9-phenyl-8-(4-{[4-(5-pyrazin-2-yl-4H-1,2,4-triazol-3-yl)piperidin-1-yl]methyl}phenyl)[1,2,4]triazolo[3,4-f]-1,6-naphthyridin-3-yl]methanol (14-3)

{8-[4-(1,3-dioxolan-2-yl)phenyl]-9-phenyl[1,2,4]triazolo[3,4-f]-1,6-naphthyridin-3-yl}methanol (14-1)

To a stirred solution of 3-4 (5 g, 13 mMol), HOBT (1.9 g, 14.3 mMol), and glycolic acid (1.2 g, 15.6 mMol) in anhydrous DMF (100 mL) was added EDC (2.7 g, 14.3 mMol). The solution was stirred overnight at ambient temperature. The solution was then treated with 5 mL of glacial acetic acid and was heated to 80° C. in an oil bath for 2 hours. Upon cooling to room temperature, the reaction was diluted with ethyl acetate and washed with NaHCO$_3$ $_{(aq)}$, water, and brine. The organic layer was dried with MgSO$_4$, filtered and concentrated in vacuo to yield 14-1 as a red solid. LC/MS (M+1) calculated: 425.5; observed: 425.6

SCHEME 14

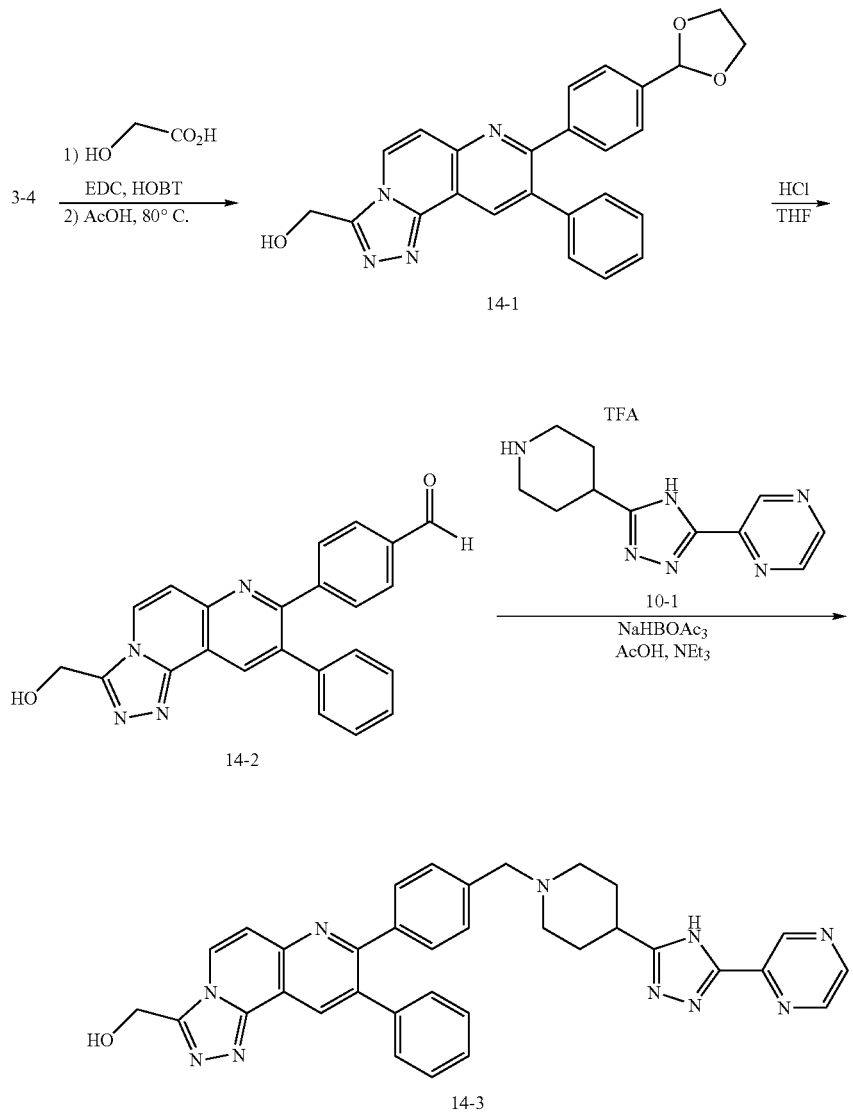

4-[3-(hydroxymethyl)-9-phenyl[1,2,4]triazolo[3,4-f]-1,6-naphthyridin-8-yl]benzaldehyde (14-2)

To a suspension of 14-1 (2.1 g, 4.9 mMol) in THF (50 mL) was added 1N HCl (50 mL). After stirring at room temperature for 30 minutes, the reaction was diluted with ethyl acetate and washed twice with water, followed by brine. The organic layer was dried with $MgSO_4$ and $Na_2SO_4$, filtered and concentrated in vacuo to yield 14-2 as a red solid. Mass (M+1) calculated: 381.1346 observed: 381.1346.

[9-phenyl-8-(4-{[4-(5-pyrazin-2-yl-4H-1,2,4-triazol-3-yl)piperidin-1-yl]-methyl}phenyl)[1,2,4]triazolo[3,4-f]-1,6-naphthyridin-3-yl]methanol (14-3)

To a stirred solution of 14-2 (0.05 g, 0.1 mMol) and 10-1 (0.05 g, 0.15 mMol) in NMP (1 mL) was added triethylamine (0.04 mL, 0.26 mMol) followed by acetic acid (0.01 mL, 0.26 mMol). After stirring overnight at room temperature, sodium triacetoxyborohydride (0.03 g, 0.2 mMol) was added. After stirring for 6 hours, the solution was filtered through a syringe filter and purified on a C18 reverse phase HPLC to give 14-3 as a solid. Mass (M+1) calculated: 595.2677 observed: 595.2679

The following table (Table 5) contains compounds made using the procedures of Scheme 14, substituting the appropriate amine for 10-1. Compounds 14-4, 14-5, 14-7 and 14-8 were isolated as HCl salts. Compound 14-6 was isolated as a TFA salt.

TABLE 5

| Cmp | Structure | Name | HRMS m/z (M + H) |
|---|---|---|---|
| 14-4 | 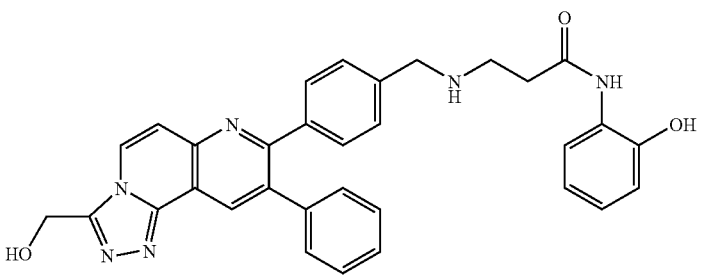 | $N^3$-{4-[3-(hydroxymethyl)-9-phenyl[1,2,4]triazolo[3,4-f]-1,6-naphthyridin-8-yl]benzyl}-$N^1$-(2-hydroxyphenyl)-beta-alaninamide | 545.2293 |
| 14-5 | 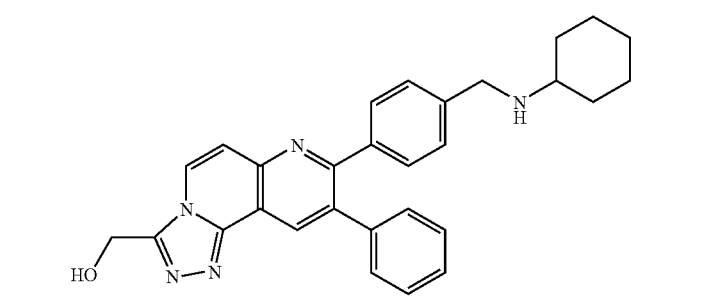 | (8-{4-[(cyclohexylamino)methyl]phenyl}-9-phenyl[1,2,4]triazolo[3,4-f]-1,6-naphthyridin-3-yl)methanol | 464.2435 |
| 14-6 | 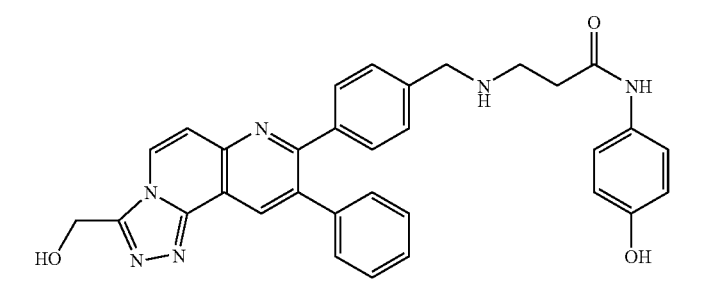 | $N^3$-{4-[3-(hydroxymethyl)-9-phenyl[1,2,4]triazolo[3,4-f]-1,6-naphthyridin-8-yl]benzyl}-$N^1$-(4-hydroxyphenyl)-beta-alaninamide | 545.2296 |
| 14-7 | 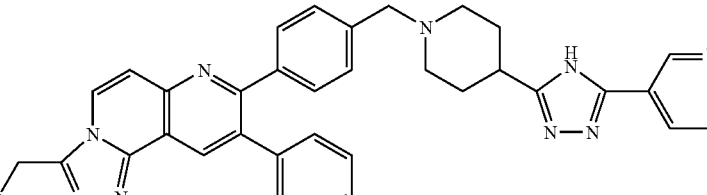 | [9-phenyl-8-(4-{[4-(5-pyridin-3-yl-4H-1,2,4-triazol-3-yl)piperidin-1-yl]methyl}phenyl)[1,2,4]triazolo[3,4-f]-1,6-naphthyridin-3-yl]methanol | LRMS (M + 1) = 594.2 |

TABLE 5-continued

| Cmp | Structure | Name | HRMS m/z (M + H) |
|---|---|---|---|
| 14-8 | 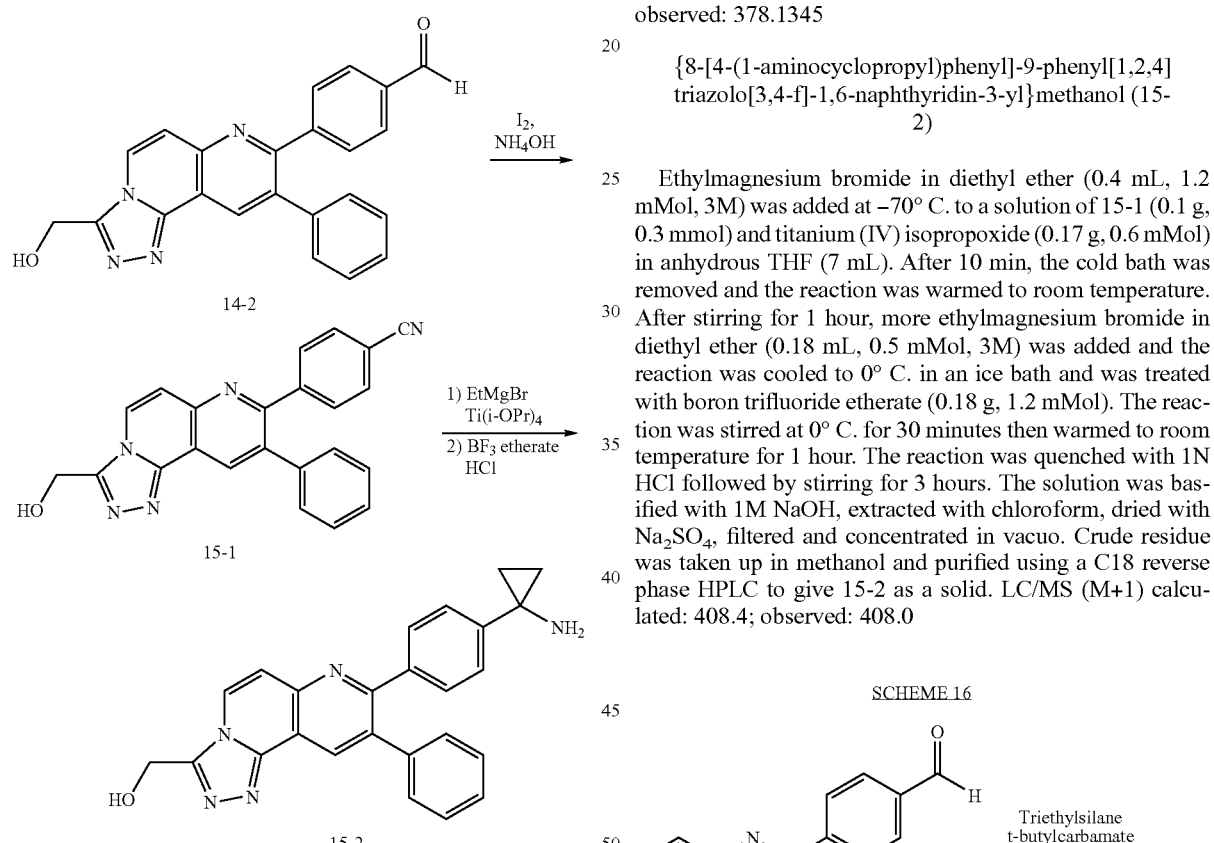 | 1-{4-[3-(hydroxymethyl)-9-phenyl[1,2,4]triazolo[3,4-f]-1,6-naphthyridin-8-yl]benzyl}piperidine-4-carboxamide | 493.2344 | dried with $Na_2SO_4$, filtered and concentrated in vacuo to yield 15-1 as a tan solid. Mass (M+1) calculated: 378.135 observed: 378.1345

{8-[4-(1-aminocyclopropyl)phenyl]-9-phenyl[1,2,4]triazolo[3,4-f]-1,6-naphthyridin-3-yl}methanol (15-2)

Ethylmagnesium bromide in diethyl ether (0.4 mL, 1.2 mMol, 3M) was added at −70° C. to a solution of 15-1 (0.1 g, 0.3 mmol) and titanium (IV) isopropoxide (0.17 g, 0.6 mMol) in anhydrous THF (7 mL). After 10 min, the cold bath was removed and the reaction was warmed to room temperature. After stirring for 1 hour, more ethylmagnesium bromide in diethyl ether (0.18 mL, 0.5 mMol, 3M) was added and the reaction was cooled to 0° C. in an ice bath and was treated with boron trifluoride etherate (0.18 g, 1.2 mMol). The reaction was stirred at 0° C. for 30 minutes then warmed to room temperature for 1 hour. The reaction was quenched with 1N HCl followed by stirring for 3 hours. The solution was basified with 1M NaOH, extracted with chloroform, dried with $Na_2SO_4$, filtered and concentrated in vacuo. Crude residue was taken up in methanol and purified using a C18 reverse phase HPLC to give 15-2 as a solid. LC/MS (M+1) calculated: 408.4; observed: 408.0

{8-[4-(1-aminocyclopropyl)phenyl]-9-phenyl[1,2,4]triazolo[3,4-f]-1,6-naphthyridin-3-yl}methanol (15-2)

4-[3-(hydroxymethyl)-9-phenyl[1,2,4]triazolo[3,4-f]-1,6-naphthyridin-8-yl]benzonitrile (15-1)

To a stirred suspension of 14-2 (0.4 g, 1.1 mMol) in anhydrous THF (15 mL) was added 3 mL of concentrated $NH_4OH$. The solution was then treated with iodine (0.4 g, 1.6 mMol) followed by stirring at room temperature overnight. The reaction was quenched with saturated sodium thiosulfate solution (20 mL) and the product was extracted into ethyl acetate three times. The combined organic layers were washed with brine,

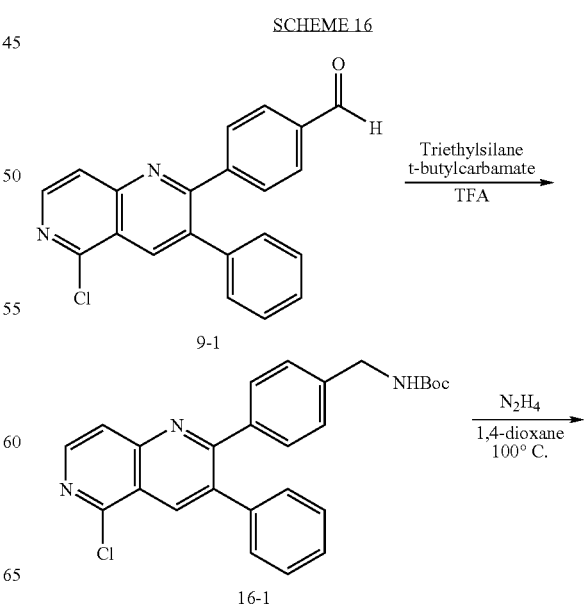

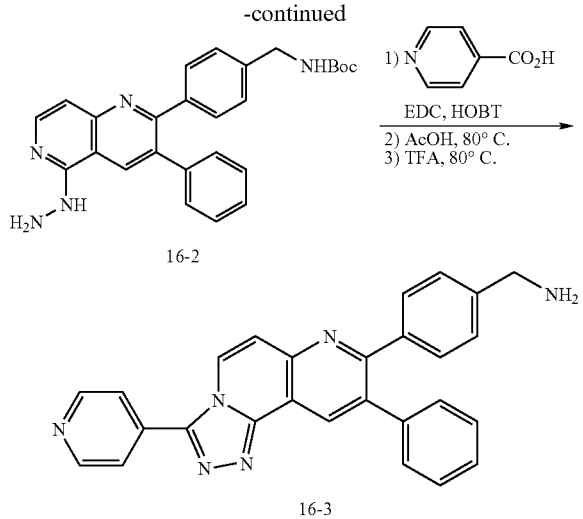

1-[4-(9-phenyl-3-pyridin-4-yl[1,2,4]triazolo[3,4-f]-1,6-naphthyridin-8-yl]methanamine (16-3)

tert-butyl 4-(5-chloro-3-phenyl-1,6-naphthyridin-2-yl)benzylcarbamate (16-1)

To a stirred solution of 9-1 (7 g, 20.2 mMol) and t-butylcarbamate (2.6 g, 22.3 mMol) in dry acetonitrile (35 mL) was added triethylsilane (29.1 mL, 182 mMol) followed by trifluoroacetic acid (6 mL, 81 mMol). After stirring for 3 hours, the solution was poured into aqueous NaHCO₃ and was extracted into ethyl acetate three times. The combined organic layers were washed with water followed by brine. The organic layer was then dried with Na₂SO₄, filtered, and concentrated in vacuo and purified using flash chromatography on silica. LC/MS (M+1) calculated: 446.9; observed: 446.1 tert-butyl 4-(5-hydrazino-3-phenyl-1,6-naphthyridin-2-yl)benzylcarbamate (16-2)

To a stirred solution of 16-1 (6.8 g, 15.2 mMol) in anhydrous 1,4-dioxane (20 mL) was added hydrazine (10.8 mL, 343 mMol). The solution was heated to 100° C. in a microwave reactor for 5 minutes. The solvent was removed in vacuo and the crude residue was taken up in ethyl acetate and washed with aqueous NaHCO₃ solution followed by brine. The organic layer was dried with MgSO₄, filtered and concentrated in vacuo to yield 16-2 as an orange solid. LC/MS (M+1) calculated: 442.5; observed: 442.2

1-[4-(9-phenyl-3-pyridin-4-yl[1,2,4]triazolo[3,4-f]-1,6-naphthyridin-8-yl)phenyl]methanamine (16-3)

To a stirred solution of 16-2 (0.08 g, 0.2 mMol), HOBT (0.03 g, 0.2 mMol), and isonicotinic acid (0.02 g, 0.2 mMol) in anhydrous DMF (1 mL) was added DIEA (0.08 mL, 0.5 mMol) followed by EDC (0.04 g, 0.2 mMol). The solution was heated in a microwave reactor at 80° C. for 12 min. The solution was then treated with 0.5 mL of acetic acid and was heated in a microwave reactor at 80° C. for 30 minutes. Upon cooling to room temperature, the volatiles were evaporated in vacuo and the solution was filtered through a syringe filter and purified on a C18 reverse phase HPLC to give 16-3 as a solid. Mass (M+1) calculated: 429.1822 observed: 429.1811

The following table (Table 6) contains compounds made using the procedures to of Scheme 16, substituting the appropriate carboxylic acid for isonicotinic acid:

TABLE 6

| Cmp | Structure | Name | HRMS m/z (M + H) |
|---|---|---|---|
| 16-4 | 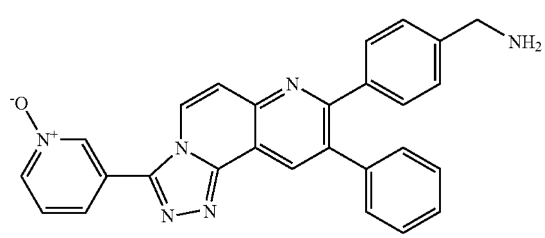 | 1-{4-[3-(1-oxidopyridin-3-yl)-9-phenyl[1,2,4]triazolo[3,4-f]-1,6-naphthyridin-8-yl]phenyl}methanamine; isolated as the HCl salt | 445.1772 |
| 16-5 | 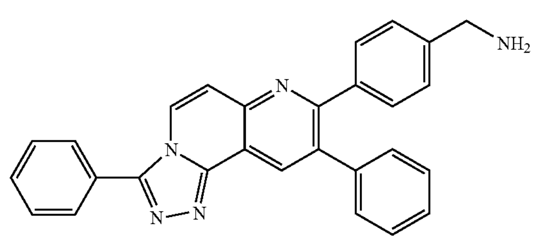 | 1-[4-(3,9-diphenyl[1,2,4]triazolo[3,4-f]-1,6-naphthyridin-8-yl)phenyl]methanamine; isolated as the HCl salt | 428.1865 |

TABLE 6-continued

| Cmp | Structure | Name | HRMS m/z (M + H) |
|---|---|---|---|
| 16-6 | 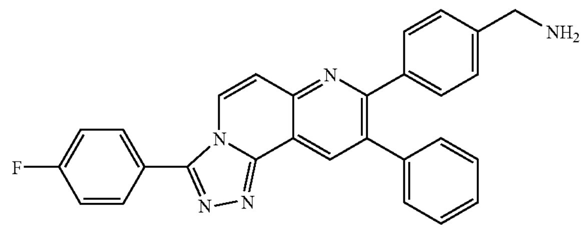 | 1-{4-[3-(4-fluorophenyl)-9-phenyl[1,2,4]triazolo[3,4-f]-1,6-naphthyridin-8-yl]phenyl}methanamine; isolated as the HCl salt | 446.177 |
| 16-7 | 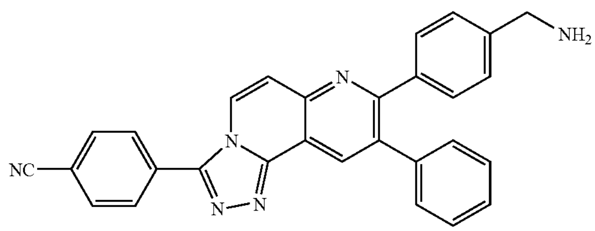 | 4-{8-[4-(aminomethyl)phenyl]-9-1,6-naphthyridin-3-yl}benzonitrile; isolated as the HCl salt | 453.182 |
| 16-8 | 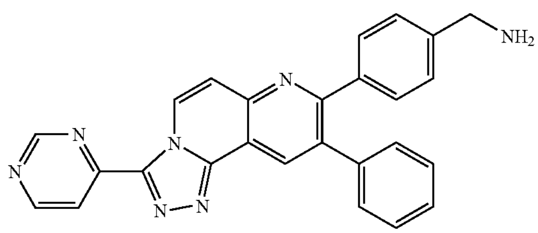 | 4-(9-phenyl-3-pyrimidin-4-yl[1,2,4]triazolo[3,4-f]-1,6-naphthyridin-8-yl)benzylamine; isolated as the HCl salt | 430.1774 |
| 16-9 | 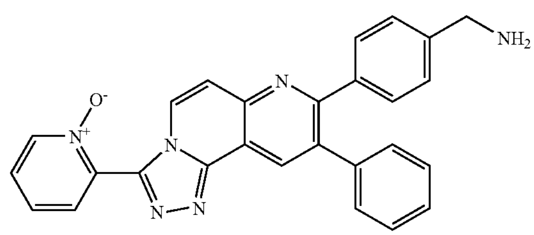 | 1-{4-[3-(1-oxidopyridin-2-yl)-9-phenyl[1,2,4]triazolo[3,4-f]-1,6-naphthyridin-8-yl]phenyl}methanamine; isolated as the HCl salt | 445.174 |
| 16-10 | 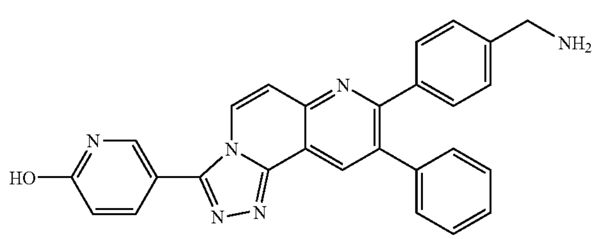 | 5-{8-[4-(aminomethyl)phenyl]-9-phenyl[1,2,4]triazolo[3,4-f]-1,6-naphthyridin-3-yl}yridine-2-ol; isolated as the HCl salt | 445.1771 |
| 16-11 | 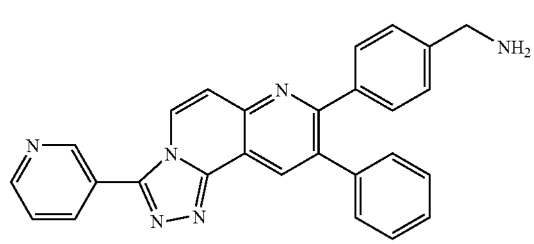 | 1-[4-(9-phenyl-3-pyridin-3-yl[1,2,4]triazolo[3,4-f]-1,6-naphthyridin-8-yl)phenyl]methanamine; isolated as the HCl salt | 429.1846 |

TABLE 6-continued

| Cmp | Structure | Name | HRMS m/z (M + H) |
|---|---|---|---|
| 16-12 | 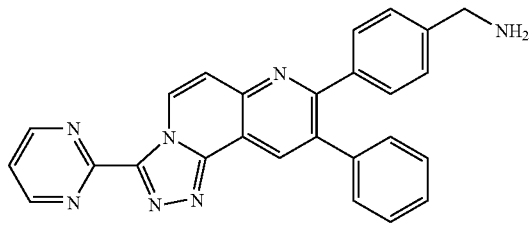 | 4-(9-phenyl-3-pyrimidin-2-yl[1,2,4]triazolo[3,4-f]-1,6-naphthyridin-8-yl)benzylamine; isolated as the HCl salt | 430.177 |
| 16-13 | 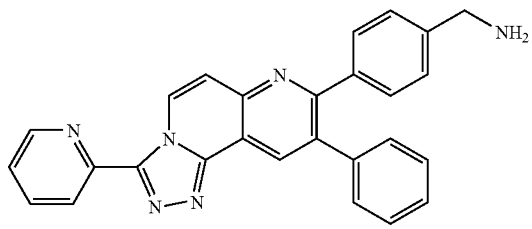 | 1-[4-(9-phenyl-3-pyridin-2-yl[1,2,4]triazolo[3,4-f]-1,6-naphthyridin-8-yl)phenyl]methanamine; isolated as the TFA salt | LRMS (M + 1) = 429.1 |
| 16-14 | 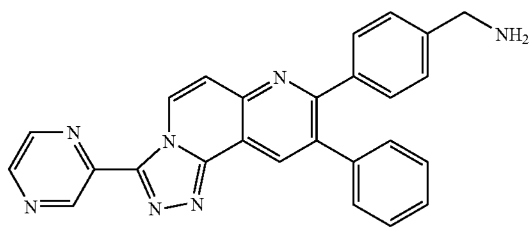 | 1-[4-(9-phenyl-3-pyrazin-2-yl[1,2,4]triazolo[3,4-f]-1,6-naphthyridin-8-yl)phenyl]methanamine; isolated as the HCl salt | 430.1775 |
| 16-15 | 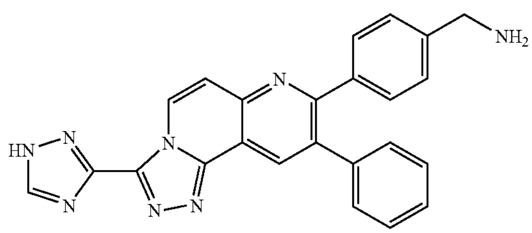 | 1-{4-[9-phenyl-3-(1H-1,2,4-triazol-3-yl)[1,2,4]triazolo[3,4-f]-1,6-naphthyridin-8-yl]phenyl}methanamine; isolated as the HCl salt | 419.1727 |
| 16-16 | 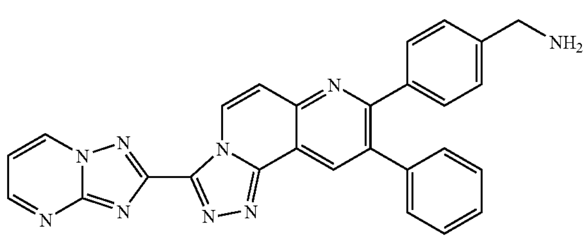 | 1-{4-[9-phenyl-3-(1,3-thiazol-4-yl)[1,2,4]triazolo[3,4-f]-1,6-naphthyridin-8-yl]phenyl}methanamine; isolated as the HCl salt | 470.1824 |
| 16-17 | 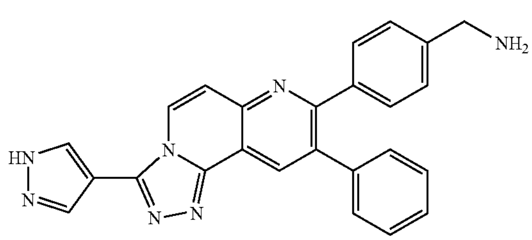 | 1-{4-[9-phenyl-3-(1H-pyrazol-4-yl)[1,2,4]triazolo[3,4-f]-1,6-naphthyridin-8-yl]phenyl}methanamine; isolated as the HCl salt | 418.1764 |

TABLE 6-continued

| Cmp | Structure | Name | HRMS m/z (M + H) |
|---|---|---|---|
| 16-18 | 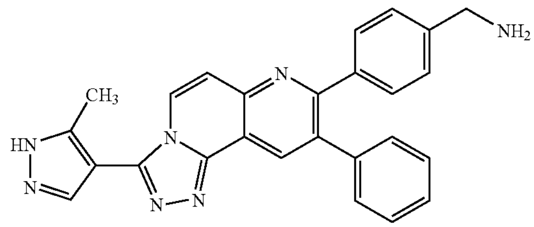 | 1-{4-[3-(3-methyl-1H-pyrazol-4-yl)-9-phenyl[1,2,4]triazolo[3,4-f]-1,6-naphthyridin-8-yl]phenyl}methanamine; isolated as the HCl salt | 432.193 |
| 16-19 | 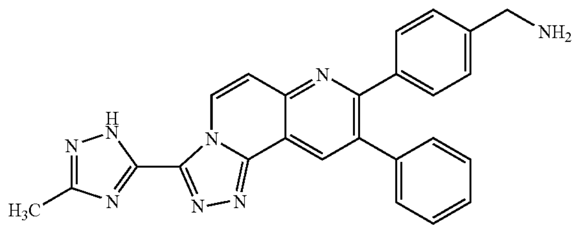 | 1-{4-[3-(3-methyl-1H-1,2,4-triazol-5-yl)-9-phenyl[1,2,4]triazolo[3,4-f]-1,6-naphthyridin-8-yl]phenyl}methanamine; isolated as the HCl salt | 433.182 |
| 16-20 | 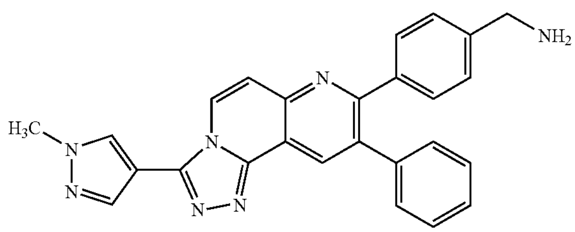 | 1-{4-[3-(1-methyl-1H-pyrazol-4-yl)-9-phenyl[1,2,4]triazolo[3,4-f]-1,6-naphthyridin-8-yl]phenyl}methanamine; isolated as the HCl salt | 432.193 |
| 16-21 | 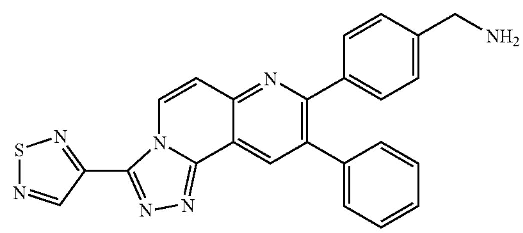 | 1-{4-[9-phenyl-3-(1,2,5-thiadiazol-3-yl)[1,2,4]triazolo[3,4-f]-1,6-naphthyridin-8-yl]phenyl}methanamine; isolated as the HCl salt | 436.1341 |
| 16-22 | 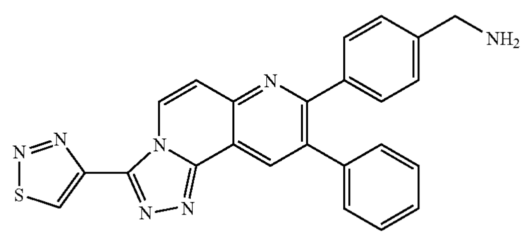 | 1-{4-[9-phenyl-3-(1,2,3-thiadiazol-4-yl)[1,2,4]triazolo[3,4-f]-1,6-naphthyridin-8-yl]phenyl}methanamine; isolated as the HCl salt | 436.1333 |
| 16-23 | 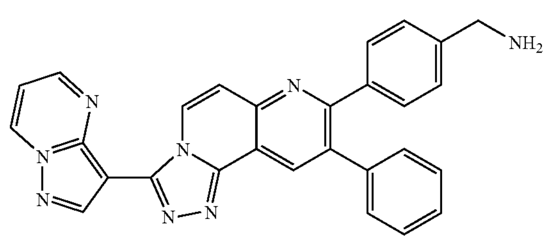 | 1-[4-(9-phenyl-3-pyrazolo[1,5-a]pyrimidin-3-yl[1,2,4]triazolo[3,4-f]-1,6-naphthyridin-8-yl]phenyl]methanamine; isolated as the HCl salt | 469.1882 |

TABLE 6-continued

| Cmp | Structure | Name | HRMS m/z (M + H) |
|---|---|---|---|
| 16-24 | 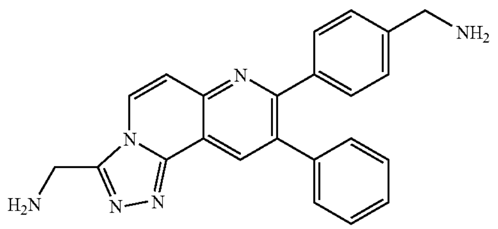 | {8-[4-(aminomethyl)phenyl]-9-phenyl[1,2,4]triazolo[3,4-f]-1,6-naphthyridin-3-yl}mehanamine; isolated as the HCl salt | 381.1817 |
| 16-25 | 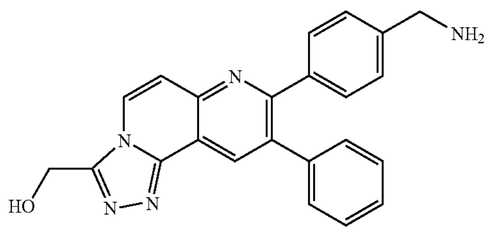 | {8-[4-(aminomethyl)phenyl]-9-phenyl[1,2,4]triazolo[3,4-f]-1,6-naphthyridin-3-yl}methanol; isolated as the HCl salt | 382.1657 |
| 16-26 | 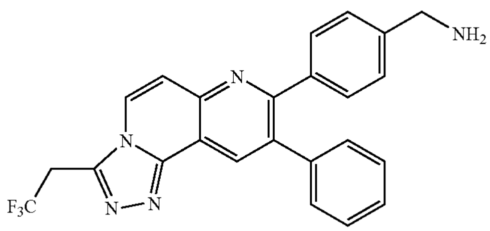 | 1-{4-[9-phenyl-3-(2,2,2-trifluoroethyl)[1,2,4]triazolo[3,4-f]-1,6-naphthyridin-8-yl]phenyl}methanamine; isolated as the HCl salt | 434.1584 |
| 16-27 | 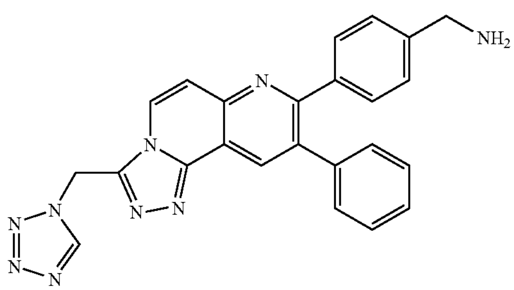 | 1-{4-[9-phenyl-3-(1H-tetraazol-1-ylmethyl)[1,2,4]triazolo[3,4-f]-1,6-naphthyridin-8-yl]phenyl}methanamine; isolated as the HCl salt | 434.1831 |
| 16-28 | 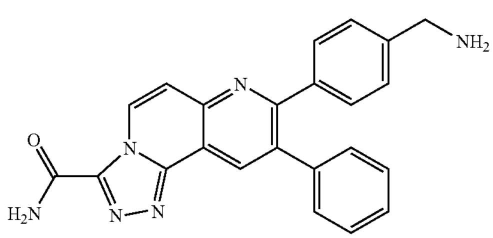 | 8-[4-(aminomethyl)phenyl]-9-phenyl[1,2,4]triazolo[3,4-f]-1,6-naphthyridine-3-carboxamide; isolated as the HCl salt | LRMS (M + 1) = 395.2 |
| 16-29 | 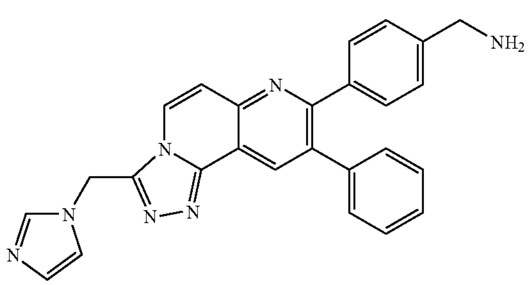 | 1-{4-[3-(1H-imidazol-1-ylmethyl)-9-phenyl[1,2,4]triazolo[3,4-f]-1,6-naphthyridin-8-yl]phenyl}methanamine; isolated as the HCl salt | 432.1931 |

TABLE 6-continued

| Cmp | Structure | Name | HRMS m/z (M + H) |
|---|---|---|---|
| 16-30 | 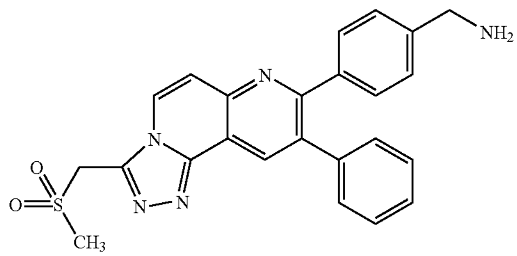 | 1-(4-{3-[(methylsulfonyl)methyl]-9-phenyl[1,2,4]triazolo[3,4-f]-1,6-naphthyridin-8-yl}phenyl) methanamine; isolated as the HCl salt | 444.1488 |
| 16-31 | 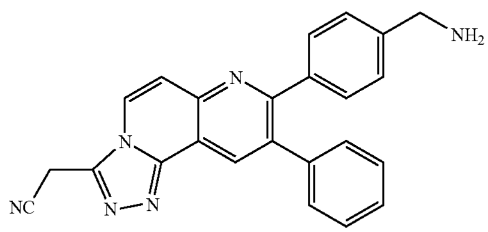 | {8-[4-(aminomethyl)phenyl]-9-phenyl[1,2,4]triazolo[3,4-f]-1,6-naphthyridin-3-yl}acetonitrile; isolated as the HCl salt | 391.166 |
| 16-32 | 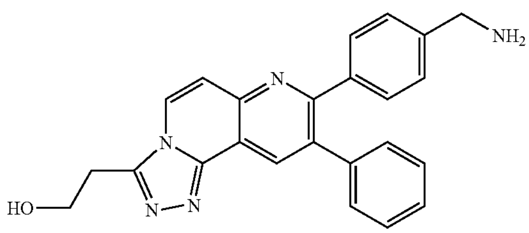 | 2-{8-[4-(aminomethyl)phenyl]-9-phenyl[1,2,4]triazolo[3,4-f]-1,6-naphthyridin-3-yl}ethanol; isolated as the HCl salt | 396.1819 |
| 16-33 | 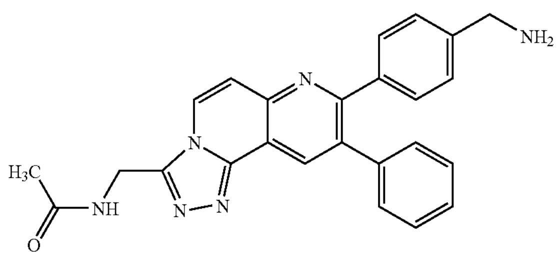 | N-({8-[4-(aminomethyl)phenyl]-9-phenyl[1,2,4]triazolo[3,4-f]-1,6-naphthyridin-3-yl}methyl)acetamide; isolated as the HCl salt | 423.1925 |
| 16-34 | 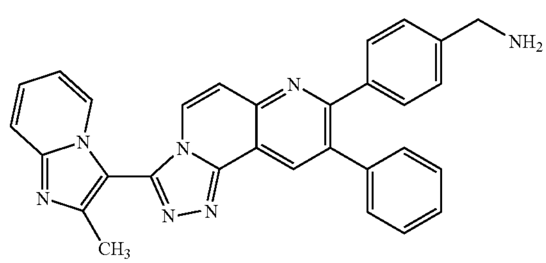 | 4-[3-(2-methylimidazo[1,2-a]pyridin-3-yl)-9-phenyl[1,2,4]triazolo[3,4-f]-1,6-naphthyridin-8-yl]benzylamine | LRMS (M + 1) = 482.2 |
| 16-35 | 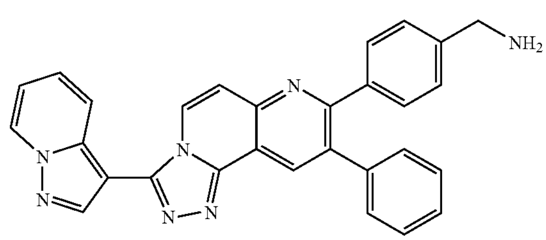 | 1-[4-(9-phenyl-3-pyrazolo[1,5-a]pyridin-3-yl[1,2,4]triazolo[3,4-f]-1,6-naphthyridin-8-yl)phenyl]methanamine | LRMS (M + 1) = 468.1 |

TABLE 6-continued

| Cmp | Structure | Name | HRMS m/z (M + H) |
|---|---|---|---|
| 16-36 | 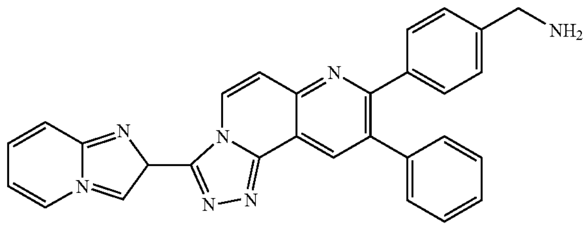 | 1-[4-(3-imidazo[1,2-a]pyridin-2-yl-9-phenyl[1,2,4]triazolo[3,4-f]-1,6-naphthyridin-8-yl)phenyl]methanamine; isolated as the free base and the HCl salt | 468.1923 |
| 16-37 | 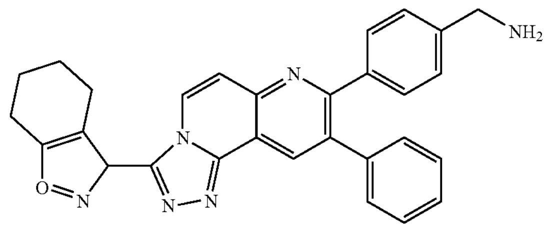 | 1-{4-[9-phenyl-3-(4,5,6,7-tetrahydro-1,2-benzisoxazol-3-yl)[1,2,4]triazolo[3,4-f]-1,6-naphthyridin-8-yl]phenyl}methanamine | LRMS (M + 1) = 456.2 [M − NH2] |
| 16-38 | 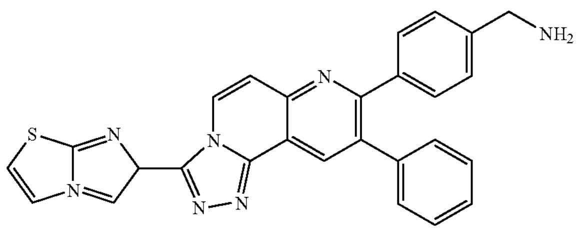 | 1-[4-(3-imidazo[2,1-b][1,3]thiazol-6-yl-9-phenyl[1,2,4]triazolo[3,4-f]-1,6-naphthyridin-8-yl)phenyl]methanamine; isolated as the free base and the HCl salt | 474.1474 |
| 16-39 | 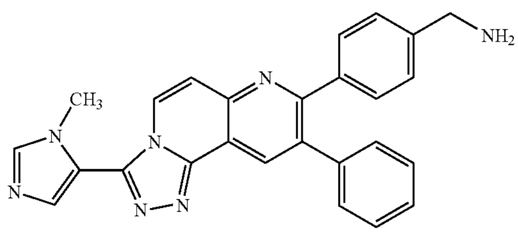 | 1-{4-[3-(1-methyl-1H-imidazol-5-yl)-9-phenyl[1,2,4]triazolo[3,4-f]-1,6-naphthyridin-8-yl]phenyl}methanamine | LRMS (M + 1) = 415.1 [M − NH2] |
| 16-40 | 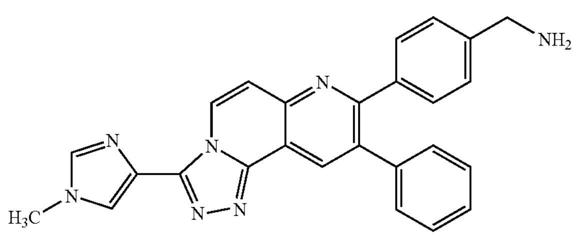 | 1-{4-[3-(1-methyl-1H-imidazol-4-yl)-9-phenyl[1,2,4]triazolo[3,4-f]-1,6-naphthyridin-8-yl]phenyl}methanamine; isolated as the free base and the HCl salt | LRMS (M + 1) = 432.1 |
| 16-41 | 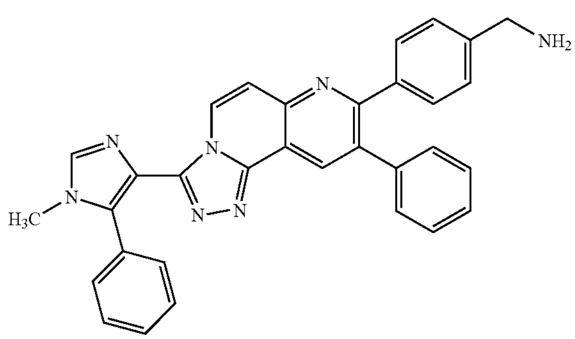 | 4-[3-(1-methyl-5-phenyl-1H-pyrazol-4-yl)-9-phenyl[1,2,4]triazolo[3,4-f]-1,6-naphthyridin-8-yl]benzylamine; isolated as the TFA salt | 508.2232 |

TABLE 6-continued

| Cmp | Structure | Name | HRMS m/z (M + H) |
|---|---|---|---|
| 16-42 | 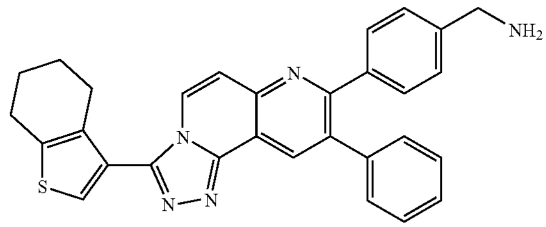 | 1-{4-[9-phenyl-3-(4,5,6,7-tetrahydro-1-benzothien-3-yl)[1,2,4]triazolo[3,4-f]-1,6-naphthyridin-8-yl]phenyl}methanamine; isolated as the TFA salt | 488.189 |
| 16-43 | 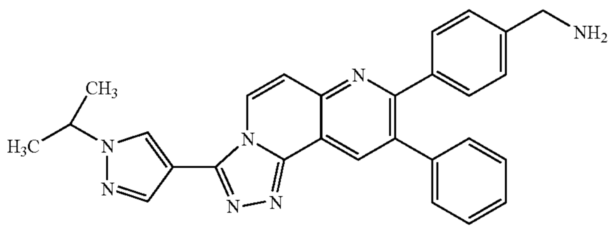 | 1-{4-[3-(1-isopropyl-1H-pyrazol-4-yl)-9-phenyl[1,2,4]triazolo[3,4-f]-1,6-naphthyridin-8-yl]phenyl}methanamine; isolated as the TFA salt | 460.2245 |
| 16-44 | 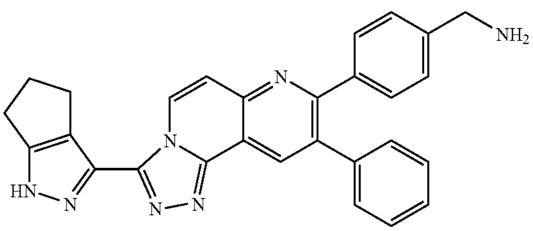 | 1-{4-[9-phenyl-3-(1,4,5,6-tetrahydrocyclopenta[c]pyrazol-3-yl)[1,2,4]triazolo[3,4-f]-1,6-naphthyridin-8-yl]phenyl}methanamine; isolated as the TFA salt | 458.2067 |
| 16-45 | 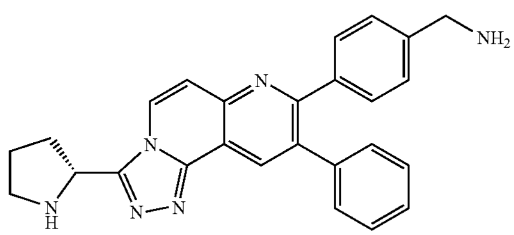 | 1-(4-{9-phenyl-3-[(2S)-pyrrolidin-2-yl][1,2,4]triazolo[3,4-f]-1,6-naphthyridin-8-yl}phenyl)methanamine; isolated as the HCl salt | 421.2137 |
| 16-46 | 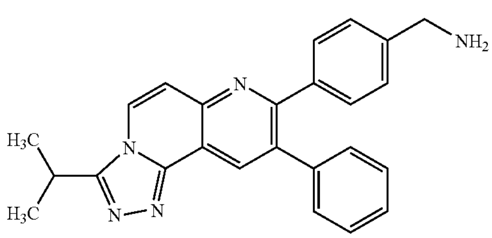 | 4-[3-(1-aminoethyl)-9-phenyl[1,2,4]triazolo[3,4-f]-1,6-naphthyridin-8-yl]benzylamine; isolated as the HCl salt | 395.1962 |
| 16-47 | 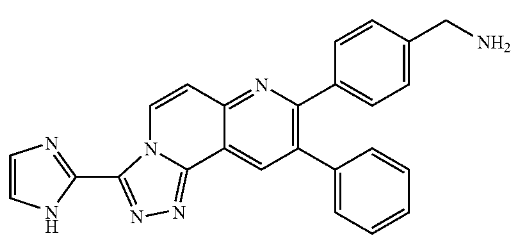 | 1-{4-[3-(1H-imidazol-2-yl)-9-phenyl[1,2,4]triazolo[3,4-f]-1,6-naphthyridin-8-yl]phenyl}methanamine; isolated as the HCl salt | 418.1774 |

TABLE 6-continued

| Cmp | Structure | Name | HRMS m/z (M + H) |
|---|---|---|---|
| 16-48 | 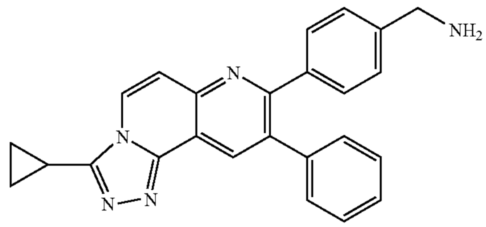 | 1-[4-(3-cyclopropyl-9-phenyl[1,2,4]triazolo[3,4-f]-1,6-naphthyridin-8-yl)phenyl]methanamine; isolated as the TFA salt | 392.1866 |
| 16-49 | 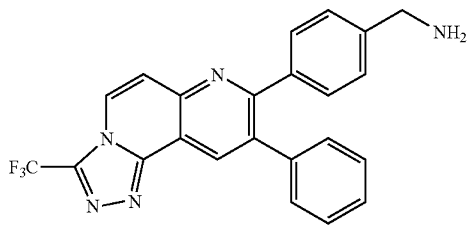 | 1-{4-[9-phenyl-3-(trifluoromethyl)[1,2,4]triazolo[3,4-f]-1,6-naphthyridin-8-yl]phenyl}methanamine; isolated as the TFA salt | 420.1423 |
| 16-50 | 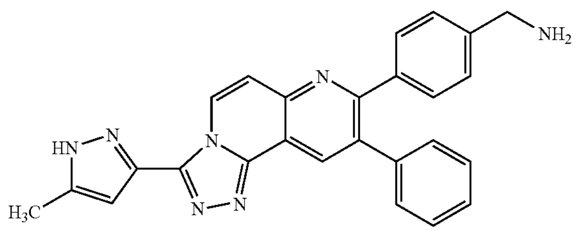 | 1-{4-[3-(5-methyl-1H-pyrazol-3-yl)-9-phenyl[1,2,4]triazolo[3,4-f]-1,6-naphthyridin-8-yl]phenyl}methanamine; isolated as the TFA salt | 432.1924 |
| 16-51 | 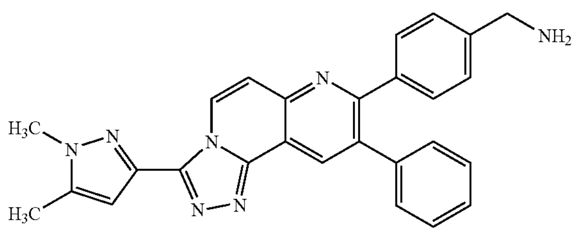 | 1-{4-[3-(1,5-dimethyl-1H-pyrazol-3-yl)-9-phenyl[1,2,4]triazolo[3,4-f]-1,6-naphthyridin-8-yl]phenyl}methanamine; isolated as the TFA salt | 446.2077 |
| 16-52 | 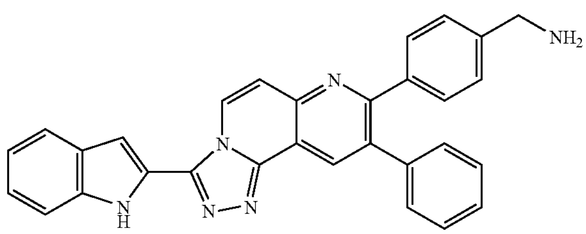 | 4-[3-(1H-indol-2-yl)-9-phenyl[1,2,4]triazolo[3,4-f]-1,6-naphthyridin-8-yl]benzylamine; isolated as the TFA salt | 467.1968 |
| 16-53 | 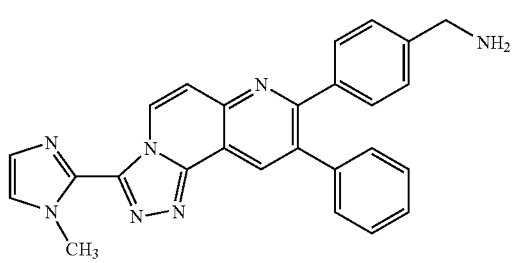 | 1-{4-[3-(1-methyl-1H-imidazol-2-yl)-9-phenyl[1,2,4]triazolo[3,4-f]-1,6-naphthyridin-8-yl]phenyl}methanamine; isolated as the TFA salt | 432.1921 |

TABLE 6-continued

| Cmp | Name | HRMS m/z (M + H) |
|---|---|---|
| 16-54 | 1-{4-[3-(3-methyl-2H-3lambda⁵-imidazol-4-yl)-9-phenyl[1,2,4]triazolo[3,4-f]-1,6-naphthyridin-8-yl]phenyl}methanamine; isolated as the TFA salt | LRMS (M + 1) = 432.1 |
| 16-55 | 4-[3-(6-chloroimidazo[1,2-a]pyridin-2-yl)-9-phenyl[1,2,4]triazolo[3,4-f]-1,6-naphthyridin-8-yl]benzylamine; isolated as the TFA salt | LRMS (M + 1) = 502.1 |
| 16-56 | 1-{4-[3-(1H-benzimidazol-2-yl)-9-phenyl[1,2,4]triazolo[3,4-f]-1,6-naphthyridin-8-yl]phenyl}methanamine; isolated as the TFA salt | 468.1921 |
| 16-57 | 4-[3-(5-cyclopropyl-4H-pyrazol-3-yl)-9-phenyl[1,2,4]triazolo[3,4-f]-1,6-naphthyridin-8-yl]benzylamine; isolated as the TFA salt | 458.2087 |
| 16-58 | 1-{4-[9-phenyl-3-(4,5,6,7-tetrahydro-1H-indazol-3-yl)[1,2,4]triazolo[3,4-f]-1,6-naphthyridin-8-yl]phenyl}methanamine; isolated as the TFA salt | 472.2244 |
| 16-59 | 4-[9-phenyl-3-(3-phenyl-1H-pyrazol-5-yl)[1,2,4]triazolo[3,4-f]-1,6-naphthyridin-8-yl]benzylamine; isolated as the TFA salt | 494.2085 |

TABLE 6-continued

| Cmp | Structure | Name | HRMS m/z (M + H) |
|---|---|---|---|
| 16-60 | 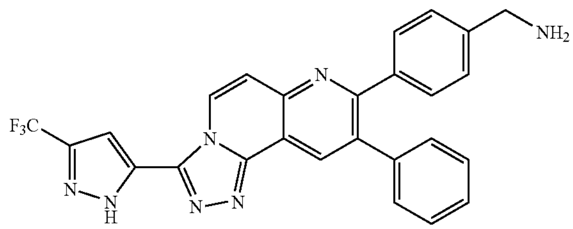 | 1-(4-{9-phenyl-3-[3-(trifluoromethyl)-1H-pyrazol-5-yl][1,2,4]triazolo[3,4-f]-1,6-naphthyridin-8-yl}phenyl)methanamine; isolated as the TFA salt | 486.1643 |
| 16-61 | 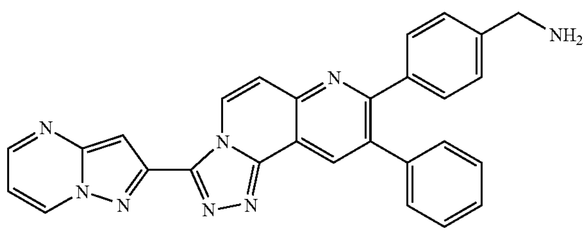 | 1-[4-(9-phenyl-3-pyrazolo[1,5-a]pyrimidin-2-yl[1,2,4]triazolo[3,4-f]-1,6-naphthyridin-8-yl)phenyl]methanamine; isolated as the TFA salt | 469.1881 |
| 16-62 | 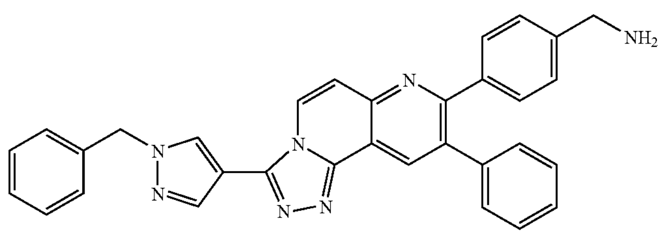 | 1-{4-[3-(1-benzyl-1H-pyrazol-4-yl)-9-phenyl[1,2,4]triazolo[3,4-f]-1,6-naphthyridin-8-yl]phenyl}methanamine; isolated as the TFA salt | 508.2235 |
| 16-63 | 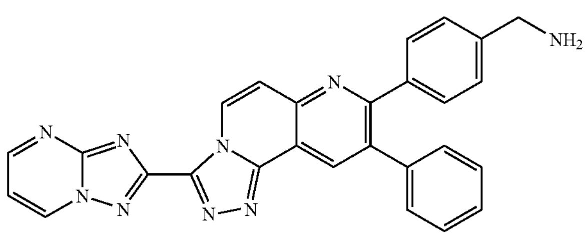 | 1-[4-(9-phenyl-3-[1,2,4]triazolo[1,5-a]pyrimidin-2-yl[1,2,4]triazolo[3,4-f]-1,6-naphthyridin-8-yl)phenyl]methanamine; isolated as the TFA salt | 470.1834 |
| 16-64 | 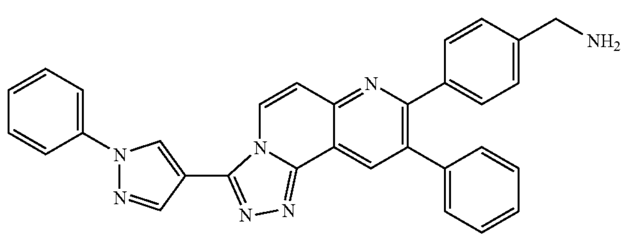 | 4-[9-phenyl-3-(1-phenyl-1H-pyrazol-4-yl)[1,2,4]triazolo[3,4-f]-1,6-naphthyridin-8-yl]benzylamine; isolated as the TFA salt | 494.2085 |
| 16-65 | 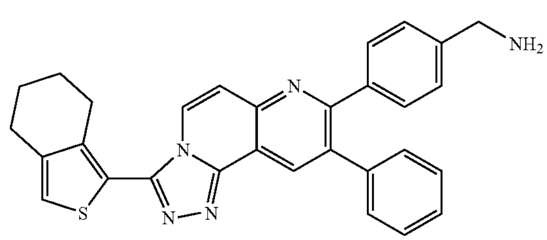 | 1-{4-[9-phenyl-3-(4,5,6,7-tetrahydro-2-benzothien-1-yl)[1,2,4]triazolo[3,4-f]-1,6-naphthyridin-8-yl]phenyl}methanamine; isolated as the TFA salt | 488.1901 |

TABLE 6-continued

| Cmp | Structure | Name | HRMS m/z (M + H) |
|---|---|---|---|
| 16-66 | 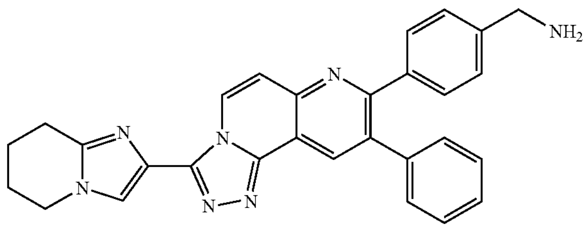 | 1-{4-[9-phenyl-3-(5,6,7,8-tetrahydroimidazo[1,2-a]pyridin-2-yl)[1,2,4]triazolo[3,4-f]-1,6-naphthyridin-8-yl]phenyl}methanamine; isolated as the HCl salt | 472.2231 |
| 16-67 | 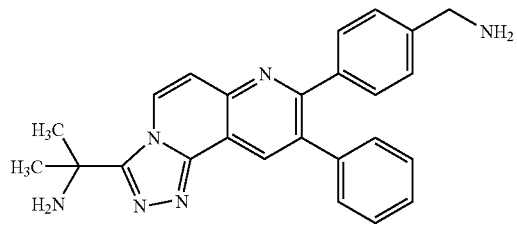 | 2-{8-[4-(aminomethyl)phenyl]-9-phenyl[1,2,4]triazolo[3,4-f]-1,6-naphthyridin-3-yl}propan-2-amine; isolated as the HCl salt | 409.2126 |
| 16-68 | 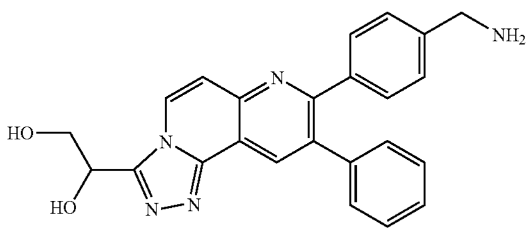 | 1-{8-[4-(aminomethyl)phenyl]-9-phenyl[1,2,4]triazolo[3,4-f]-1,6-naphthyridin-3-yl}ethane-1,2-diol; isolated as the TFA salt | 412.1761 |
| 16-69 | 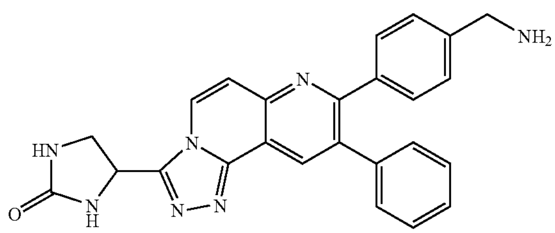 | 4-{8-[4-(aminomethyl)phenyl]-9-phenyl[1,2,4]triazolo[3,4-f]-1,6-naphthyridin-3-yl}imidazolidin-2-one; isolated as the TFA salt | 436.1873 |
| 16-70 | 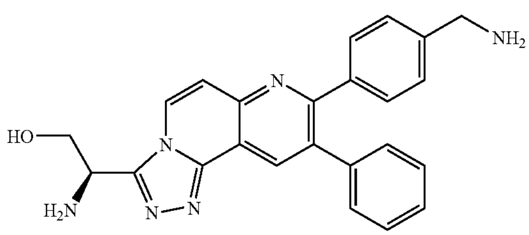 | (2R)-2-amino-2-{8-[4-(aminomethyl)phenyl]-9-phenyl[1,2,4]triazolo[3,4-f]-1,6-naphthyridin-3-yl}ethanol; isolated as the TFA salt | 411.1921 |
| 16-71 | 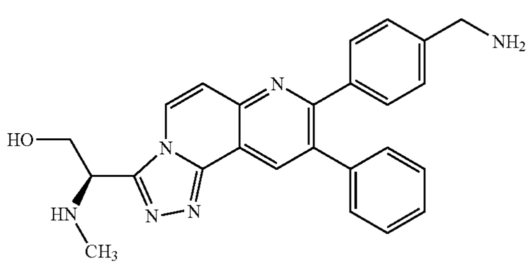 | (2R)-2-{8-[4-(aminomethyl)phenyl]-9-phenyl[1,2,4]triazolo[3,4-f]-1,6-naphthyridin-3-yl}-2-(methylamino)ethanol; isolated as the TFA salt | 425.2077 |

TABLE 6-continued

| Cmp | Structure | Name | HRMS m/z (M + H) |
|---|---|---|---|
| 16-72 | 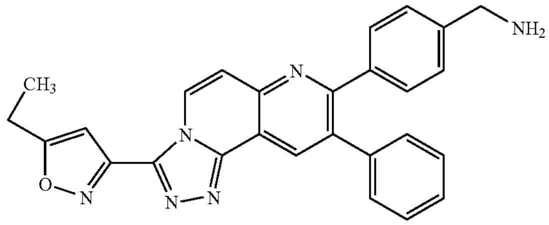 | 1-{4-[3-(5-ethylisoxazol-3-yl)-9-phenyl[1,2,4]triazolo[3,4-f]-1,6-naphthyridin-8-yl]phenyl}methanamine; isolated as the HCl salt | 447.1913 |
| 16-73 | 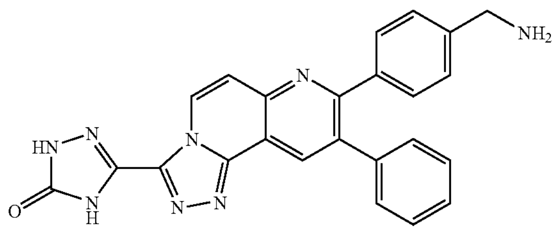 | 5-{8-[4-(aminomethyl)phenyl]-9-phenyl[1,2,4]triazolo[3,4-f]-1,6-naphthyridin-3-yl}-2,4-dihydro-3H-1,2,4-triazol-3-one; isolated as the HCl salt | LRMS (M + 1) = 435.2 |
| 16-74 | 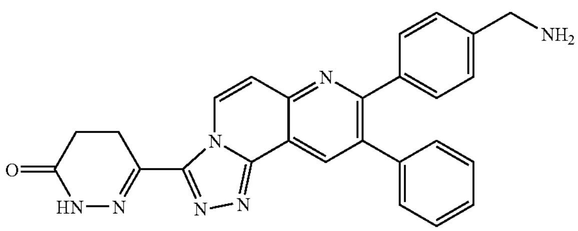 | 6-{8-[4-(aminomethyl)phenyl]-9-phenyl[1,2,4]triazolo[3,4-f]-1,6-naphthyridin-3-yl}-4,5-dihydropyridazin-3(2H)-one; isolated as the HCl salt | LRMS (M + 1) = 431.2 [M − NH2] |
| 16-75 | 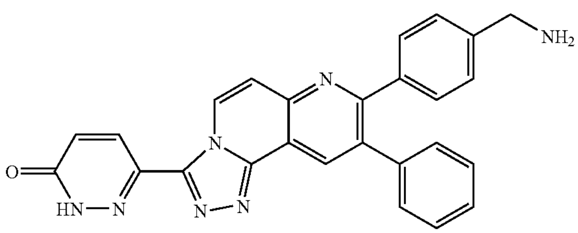 | 6-{8-[4-(aminomethyl)phenyl]-9-phenyl[1,2,4]triazolo[3,4-f]-1,6-naphthyridin-3-yl}pyridazin-3(2H)-one; isolated as the HCl salt | LRMS (M + 1) = 429.1 [M − NH2] |
| 16-76 | 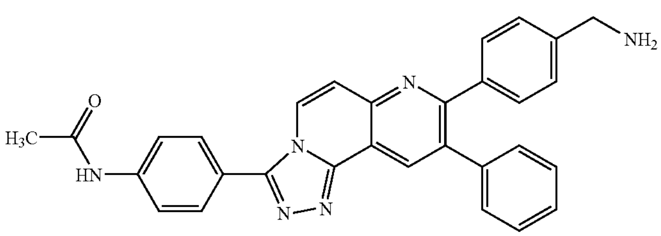 | N-(4-{8-[4-(aminomethyl)phenyl]-9-phenyl[1,2,4]triazolo[3,4-f]-1,6-naphthyridin-3-yl}phenyl)acetamide; isolated as the HCl salt | 485.2074 |
| 16-77 | 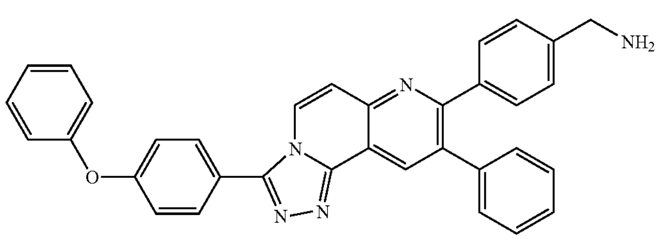 | 1-{4-[3-(4-phenoxyphenyl)-9-phenyl[1,2,4]triazolo[3,4-f]-1,6-naphthyridin-8-yl]phenyl}methanamine; isolated as the HCl salt | 520.2136 |

TABLE 6-continued

| Cmp | Structure | Name | HRMS m/z (M + H) |
|---|---|---|---|
| 16-78 | 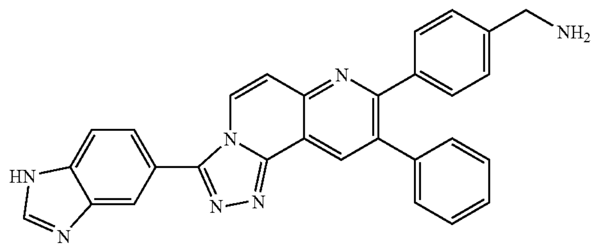 | 1-{4-[3-(1H-benzimidazol-5-yl)-9-phenyl[1,2,4]triazolo[3,4-f]-1,6-naphthyridin-8-yl]phenyl}methanamine; isolated as the HCl salt | 468.1927 |
| 16-79 | 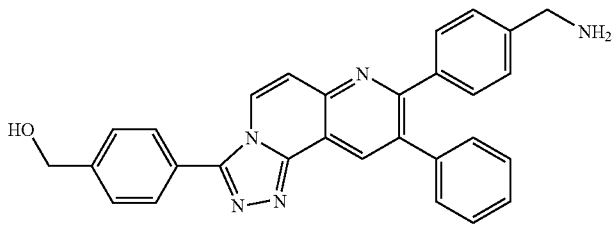 | (4-{8-[4-(aminomethyl)phenyl]-9-phenyl[1,2,4]triazolo[3,4-f]-1,6-naphthyridin-3-yl}phenyl)methanol; isolated as the HCl salt | 458.1963 |
| 16-80 | 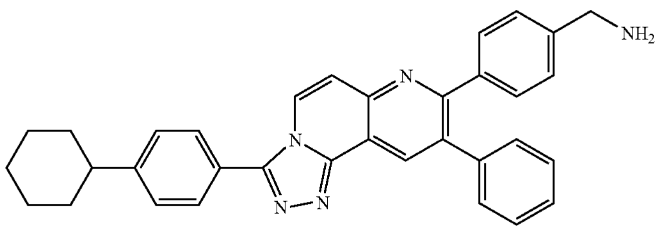 | 4-[3-(4-cyclohexylphenyl)-9-phenyl[1,2,4]triazolo[3,4-f]-1,6-naphthyridin-8-yl]benzylamine; isolated as a HCl salt | 510.2634 |
| 16-81 | 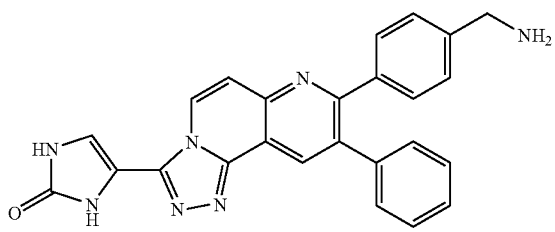 | 4-{8-[4-(aminomethyl)phenyl]-9-phenyl[1,2,4]triazolo[3,4-f]-1,6-naphthyridin-3-yl}-1,3-dihydro-2H-imidazol-2-one; isolated as a HCl salt | 434.1719 |
| 16-82 | 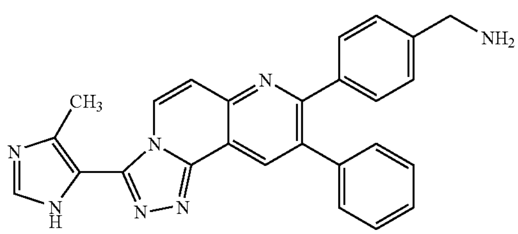 | 1-{4-[3-(4-methyl-1H-imidazol-5-yl)-9-phenyl[1,2,4]triazolo[3,4-f]-1,6-naphthyridin-8-yl]phenyl}methanamine; isolated as the HCl salt | 432.1921 |
| 16-83 | 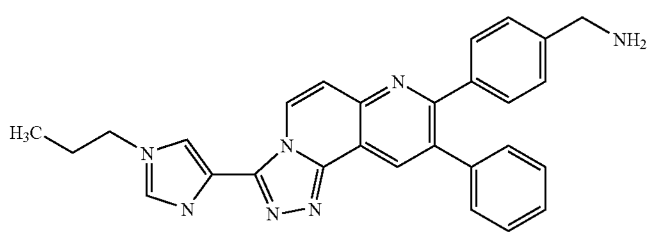 | 4-[9-phenyl-3-(1-propyl-1H-imidazol-4-yl)[1,2,4]triazolo[3,4-f]-1,6-naphthyridin-8-yl]benzylamine; isolated as the HCl salt | 460.2231 |

TABLE 6-continued

| Cmp | Structure | Name | HRMS m/z (M + H) |
|---|---|---|---|
| 16-84 | 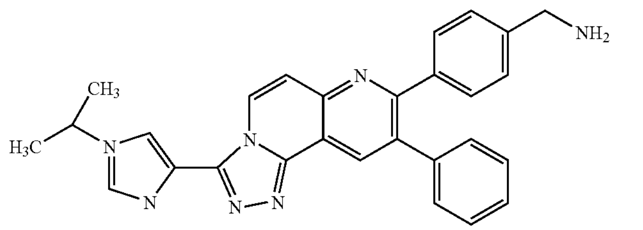 | 1-{4-[3-(1-isopropyl-1H-imidazol-4-yl)-9-phenyl[1,2,4]triazolo[3,4-f]-1,6-naphthyridin-8-yl]phenyl}methanamine; isolated as the HCl salt | 460.2231 |
| 16-85 | 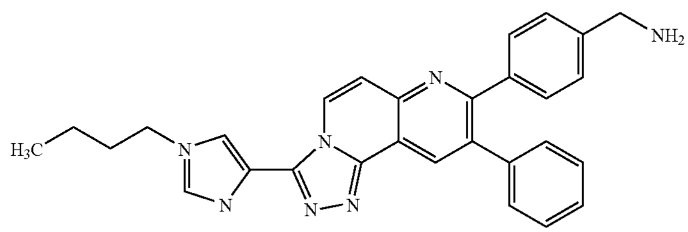 | 1-{4-[3-(1-butyl-1H-imidazol-4-yl)-9-phenyl[1,2,4]triazolo[3,4-f]-1,6-naphthyridin-8-yl]phenyl}methanamine; isolated as the HCl salt | 474.2387 |
| 16-86 | 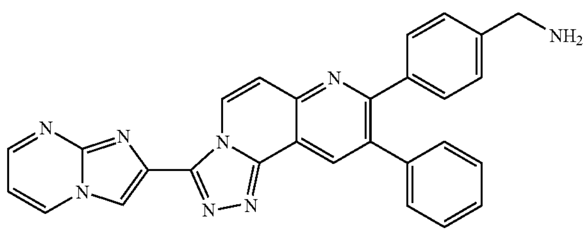 | 1-[4-(3-imidazo[1,2-a]pyrimidin-2-yl-9-phenyl[1,2,4]triazolo[3,4-f]-1,6-naphthyridin-8-yl)phenyl]methanamine; isolated as the HCl salt | 469.1867 |

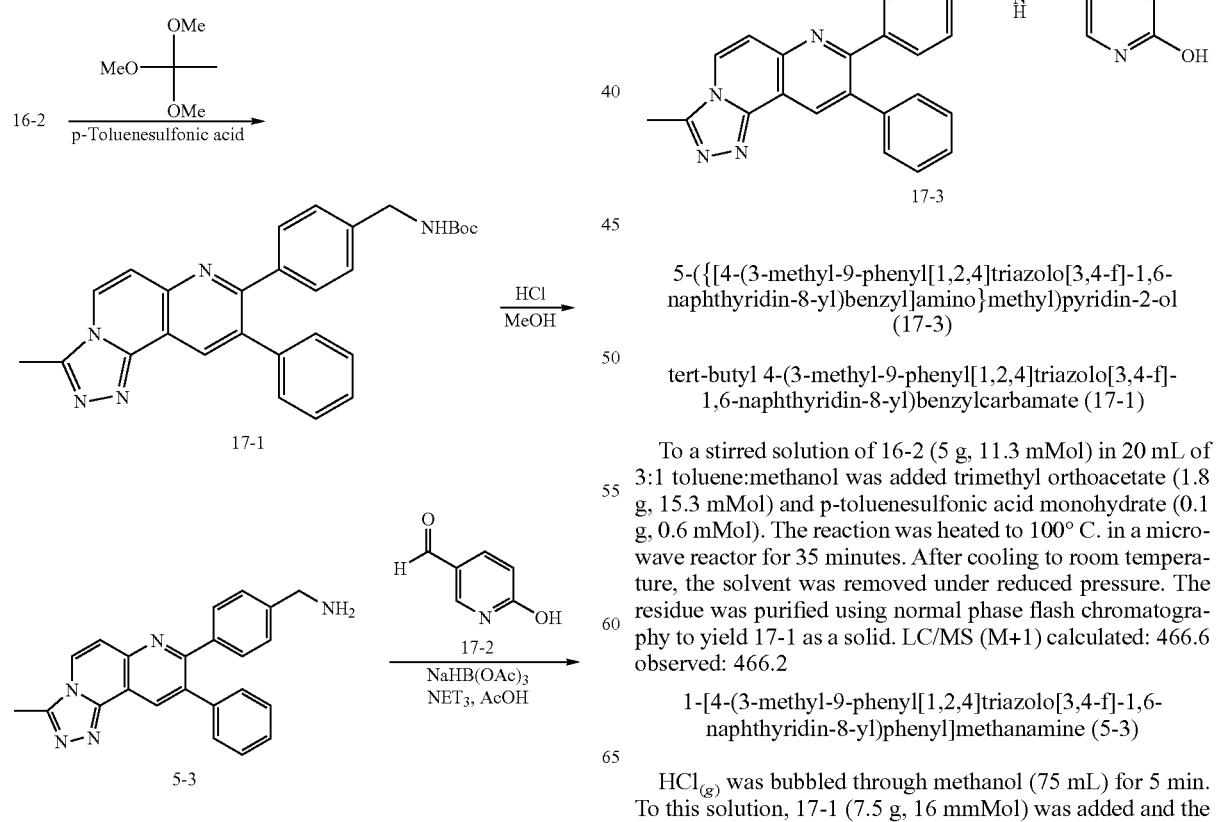

5-({[4-(3-methyl-9-phenyl[1,2,4]triazolo[3,4-f]-1,6-naphthyridin-8-yl)benzyl]amino}methyl)pyridin-2-ol (17-3)

tert-butyl 4-(3-methyl-9-phenyl[1,2,4]triazolo[3,4-f]-1,6-naphthyridin-8-yl)benzylcarbamate (17-1)

To a stirred solution of 16-2 (5 g, 11.3 mMol) in 20 mL of 3:1 toluene:methanol was added trimethyl orthoacetate (1.8 g, 15.3 mMol) and p-toluenesulfonic acid monohydrate (0.1 g, 0.6 mMol). The reaction was heated to 100° C. in a microwave reactor for 35 minutes. After cooling to room temperature, the solvent was removed under reduced pressure. The residue was purified using normal phase flash chromatography to yield 17-1 as a solid. LC/MS (M+1) calculated: 466.6 observed: 466.2

1-[4-(3-methyl-9-phenyl[1,2,4]triazolo[3,4-f]-1,6-naphthyridin-8-yl)phenyl]methanamine (5-3)

HCl(g) was bubbled through methanol (75 mL) for 5 min. To this solution, 17-1 (7.5 g, 16 mmMol) was added and the solution was stirred at room temperature for 6 hours. After removing the solvent in vacuo, the resulting solid was triturated for 30 minutes with a 10:1 solution of ethyl acetate and methanol, respectively. The suspension was filtered and dried to yield 5-3 as the HCl salt. Mass (M+1) calculated: 366.1713 observed: 366.1694

6-hydroxynicotinaldehyde (17-2)

A stirred solution of 6-methoxy-3-pyridinecarboxaldehyde (0.45 g, 3.3 mMol) in 3N HCl (10 mL) was heated to 100° C. for 30 minutes. Upon cooling, needle-like crystals developed. The crystals were collected via filtration to yield 17-2. $^1$H-NMR (CD$_3$OD) δ 9.64 (s, 1H), δ 8.17-8.16 (m, 1H), S 7.96-7.94 (m, 1H), δ 6.58 (d, 1H).

5-({[4-(3-methyl-9-phenyl[1,2,4]triazolo[3,4-f]-1,6-naphthyridin-8-yl)benzyl]amino}methyl)pyridin-2-ol (17-3)

To a stirred solution of 5-3 (0.1 g, 0.3 mMol) and triethylamine (0.08 mL, 0.5 mMol) in NMR (1 mL) was added 17-2 (0.03 g, 0.3 mMol) and acetic acid (0.03 mL, 0.5 mMol), followed by sodium triacetoxyborohydride (0.12 g, 0.5 mMol). After stirring overnight at room temperature, the reaction was filtered through a syringe filter and purified on a C18 reverse phase HPLC to yield 17-3 as the HCl salt. Mass (M+1) calculated: 473.2085 observed: 473.2092.

The following table (Table 7) contains compounds made using the procedures of Scheme 17, substituting the appropriate aldehyde for 17-2. Compounds 17-4 and 17-5 were isolated as HCl salts. Compounds 17-6 and 17-7 were isolated as TFA salts.

TABLE 7

| Cmp | Structure | Name | HRMS m/z (M + H) |
|---|---|---|---|
| 17-4 | 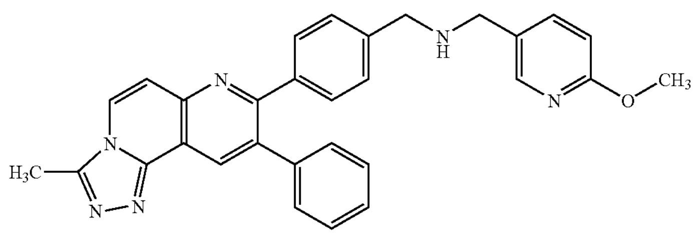 | 1-(6-methoxypyridin-3-yl)-N-[4-(3-methyl-9-phenyl[1,2,4]triazolo[3,4-f]-1,6-naphthyridin-8-yl)benzyl]methanamine | 487.2237 |
| 17-5 | 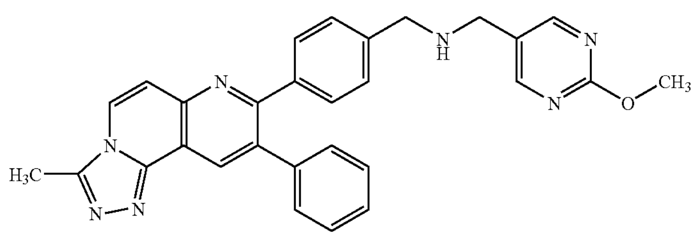 | N-[(2-methoxypyrimidin-5-yl)methyl]-N-[4-(3-methyl-9-phenyl[1,2,4]triazolo[3,4-f]-1,6-naphthyridin-8-yl)benzyl]amine | LRMS (M + 1) = 488.1 |
| 17-6 | 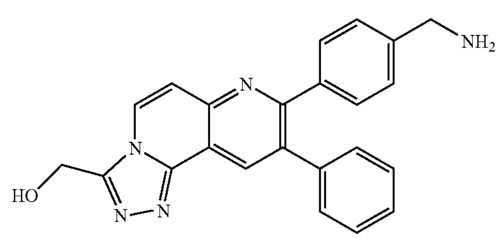 | 1-[4-(3-ethyl-9-phenyl[1,2,4]triazolo[3,4-f]-1,6-naphthyridin-8-yl)phenyl]methanamine | LRMS (M + 1) = 380.2 |
| 17-7 | 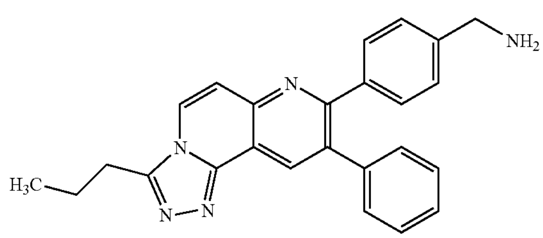 | 1-[4-(9-phenyl-3-propyl[1,2,4]triazolo[3,4-f]-1,6-naphthyridin-8-yl)phenyl]methanamine | 394.2023 |

SCHEME 18

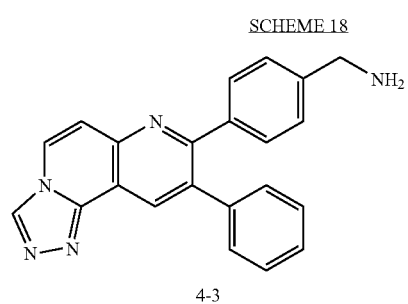

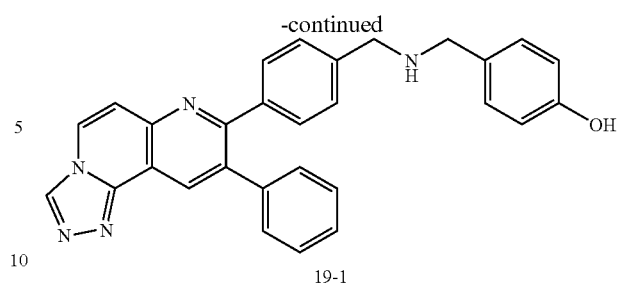

4-({[4-(9-phenyl[1,2,4]triazolo[3,4-f]-1,6-naphthyridin-8-yl)benzyl]amino}methyl)phenol (19-1)

To a stirred solution of 4-2 (0.05 g, 0.14 mMol) and 4-(aminomethyl)phenol (0.04, 0.35 mMol) in DMF (0.5 mL) was added acetic acid (0.04 mL, 0.7 mMol). After stirring for 2 hours at room temperature, sodium triacetoxyborohydride (0.06 g, 0.3 mMol) was added. After stirring overnight, the reaction was filtered through a syringe filter and purified on a C18 reverse phase HPLC to yield 19-1 as a solid. LC/MS (M+1) calculated: 458.5; observed: 458.3.

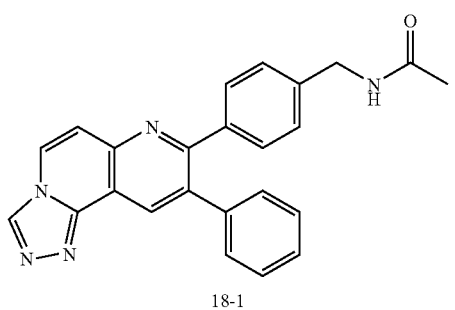

SCHEME 20

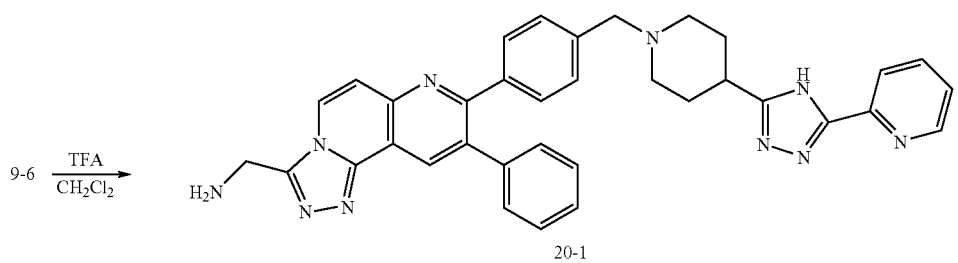

N-[4-(9-phenyl[1,2,4]triazolo[3,4-f]-1,6-naphthyridin-8-yl)benzyl]acetamide (18-1)

To a solution of 4-3 (0.02 g, 0.06 mMol) and triethylamine (0.02 mL, 0.2 mMol) in absolute ethanol (0.5 mL) was added acetic anhydride (0.02 mL, 0.2 mMol). The reaction was complete after 10 minutes and was purified directly on a C18 reverse phase HPLC to give 18-1 as a solid. LC/MS (M+1) calculated: 394.5; observed: 394.2

SCHEME 19

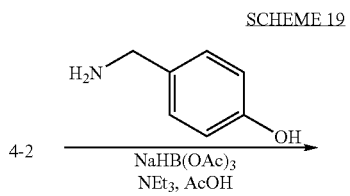

1-[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanamine 20-1

A solution of 9-6 (0.03 g, 0.04 mMol) in 30% TFA in dichloromethane (1 mL, 30% by volume) was stirred at room temperature for 30 minutes. The solvent was removed in vacuo and the crude residue was taken up in methanol and purified on a C18 reverse phase HPLC to give 20-1 as a solid. Mass (M+1) calculated: 593.2884; observed: 593.2867.

SCHEME 21

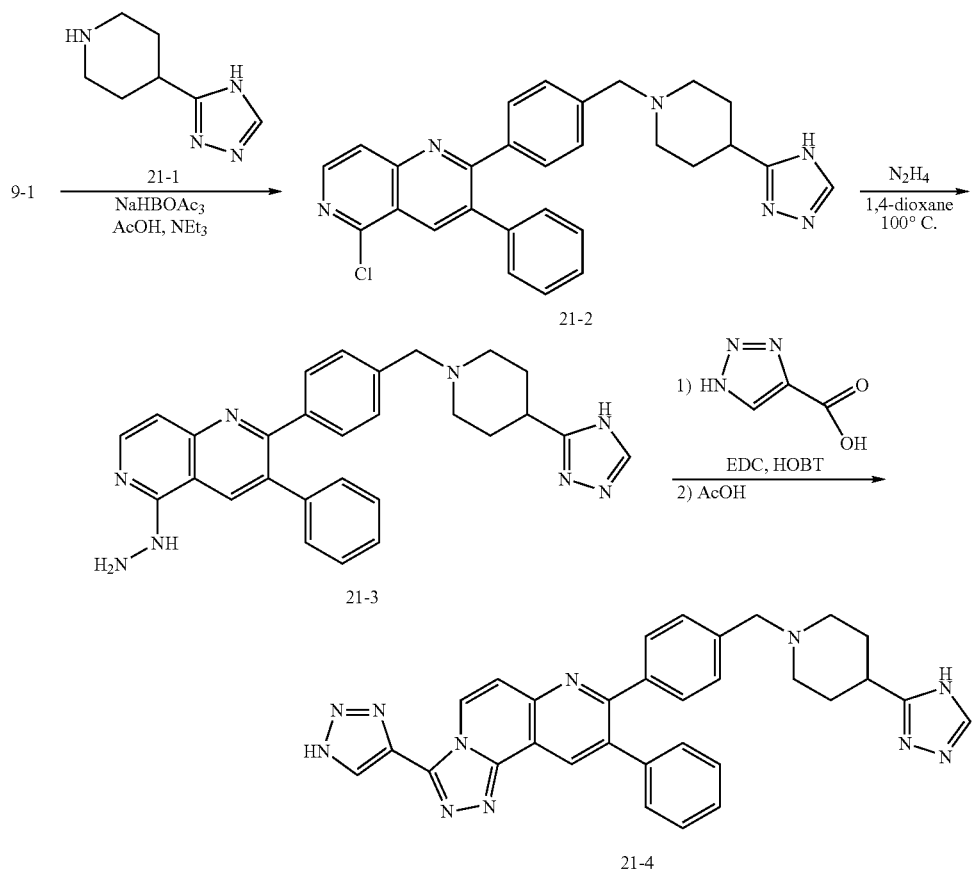

9-phenyl-3-(1H-1,2,3-triazol-4-yl)-8-(4-{[4-(4H-1,2,4-triazol-3-yl)piperidin-1-yl]methyl}phenyl)[1,2,4]triazolo[3,4-f]-1,6-naphthyridine (21-4)

4-(1H-1,2,4-triazol-3-yl)piperidine (21-1)

To a solution of benzyl 4-cyanopiperidine-1-carboxylate (20 g, 82 mmol) in methanol (150 mL) was added a solution of sodium methoxide in methanol (25 wt %, 5.6 mL, 25 mmol) at room temperature. After 30 minutes, a solution of formic hydrazide (4.9 g, 82 mmol) in methanol (20 mL) was added and the reaction was heated to reflux for 24 hours, at which time sodium methoxide in methanol (25 wt %, 5.6 mL, 25 mmol) and formic hydrazide (4.9 g, 82 mmol) was added. After 72 hours, the reaction was cooled to room temperature and quenched with acetic acid (3.0 mL, 49 mmol) and concentrated. The resulting residue was dissolved in ethyl acetate, washed with water, saturated sodium bicarbonate, brine, dried over sodium sulfate, filtered and concentrated. The residue was purified by column chromatography eluting with 1-35% IPA/DCM. The appropriate fractions were combined and the solvent removed in vacuo to give benzyl 4-(1H-1,2,4-triazol-3-yl)piperidine-1-carboxylate as a solid. MS (M+H$^+$): 287.2; $^1$H-NMR (400 MHz, CDCl$_3$): δ 11.13 (s, 1H), 8.06 (s, 1H), 7.36-7.31 (m, 5H), 5.15 (s, 2H), 4.24 (br.s, 2H), 3.06-2.98 (m, 3H), 2.07-2.04 (m, 2H), 1.84-1.78 (m, 2H).

To a solution of benzyl 4-(1H-1,2,4-triazol-3-yl)piperidine-1-carboxylate (7.3 g, 25 mmol) in ethanol (100 mL) was added 10% palladium on carbon (500 mg) and the reaction vessel was purged with hydrogen and stirred over an atmosphere of hydrogen for 3 hours. The reaction was filtered and concentrated to give 21-1 as a solid. MS (M+H$^+$): 153.2; $^1$H-NMR (400 MHz, DMSO-d$_6$): δ 7.99 (s, 1H), 2.98-2.94 (m, 2H), 2.82-2.74 (m, 1H), 2.57-2.50 (m, 2H), 1.82-1.78 (m, 2H), 1.60-1.50 (m, 2H).

5-chloro-3-phenyl-2-(4-{[4-(4H-1,2,4-triazol-3-yl)piperidin-1-yl]methyl}phenyl)-1,6-naphthyridine (21-2)

To a stirred solution of 9-1 (0.25 g, 0.73 mMol) and 21-1 (0.13 g, 0.87 mMol) in NMP (5 mL) was added triethylamine (0.3 mL, 2.2 mMol) followed by acetic acid (0.082 mL, 1.5 mMol). After stirring at ambient temperature overnight, sodium triacetoxyborohydride (0.18 g, 0.87 mMol) was added. Upon completion, the reaction was diluted with ethyl acetate and washed with saturated NaHCO$_3$, followed by water, then brine. The organic layer was dried with Na$_2$SO$_4$ and MgSO$_4$, filtered and concentrated in vacuo to yield 21-2. LC/MS (M+1) calculated: 482.0; observed: 482.2

5-hydrazino-3-phenyl-2-(4-{[4-(4H-1,2,4-triazol-3-yl)piperidin-1-yl]methyl}phenyl)-1,6-naphthyridine (21-3)

To a stirred solution of 21-2 (0.4 g, 0.8 mMol) in anhydrous 1,4-dioxane (3 mL) was added hydrazine (0.45 mL, 14.5 mMol). The solution was heated to 100° C. in a microwave reactor for 5 minutes. The solvent was removed in vacuo and was dried azeotropically with toluene three times to yield 21-3.

LC/MS (M+1) calculated: 477.6; observed: 477.3

9-phenyl-3-(1H-1,2,3-triazol-4-yl)-8-(4-{[4-(4H-1,2,4-triazol-3-yl)piperidin-1-yl]methyl}phenyl)[1,2,4]triazolo[3,4-f]-1,6-naphthyridine (21-4)

To a stirred solution of 21-3 (0.2 g, 0.36 mMol), HOBT (0.05 g, 0.4 mMol), and 1H-1,2,3-triazole-4-carboxylic acid (0.05 g, 0.4 mMol) in anhydrous DMF (2 mL) was added DIEA (0.18 mL, 1.1 mMol) followed by EDC (0.08 g, 0.4 mMol). The solution was heated in the microwave reactor for 12 minutes at 80° C. The solution was then treated with 0.5 mL of acetic acid and was heated to 80° C. in the microwave reactor for and additional 10 minutes. Upon cooling to room temperature, the solution was passed through a syringe filter and purified on a C18 reverse phase HPLC to yield 21-4 as the HCl salt. Mass (M+1) calculated: observed: LC/MS (M+1) calculated: 554.6; observed: 554.3.

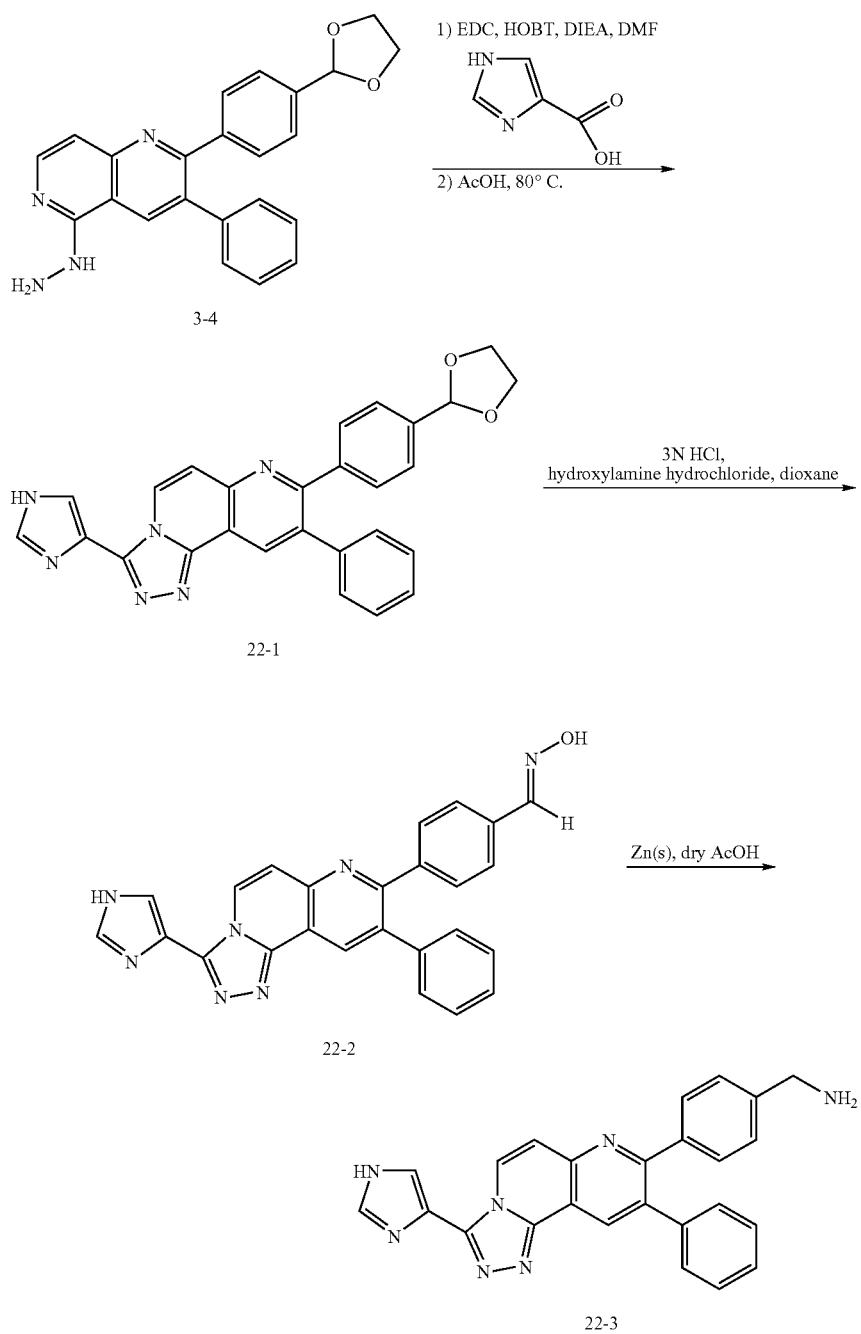

1-{4-[3-(1H-Imidazol-4-yl)-9-phenyl[1,2,4]triazolo[3,4-f]-1,6-naphthyridin-8-yl]phenyl}methanamine (22-3)

8-[4-(1,3-Dioxolan-2-yl)phenyl]-3-(1H-imidazol-4-yl)-9-phenyl[1,2,4]triazolo[3,4-f]-1,6-naphthyridine (22-1)

To a solution of 3-4 (0.2 g, 0.5 mmol), 1H-imidazole-4-carboxylic acid (0.06 g, 0.5 mmol), HOBT (0.06 g, 0.5 mmol), and DIEA (0.2 ml, 1.4 mmol) in DMF (2 ml) was added EDC (0.1 g, 0.6 mmol). The solution was stirred at room temperature for 45 min and was then heated at 80° C. in the microwave for 15 min. The solvent was removed in vacuo. The residue was taken up in DMF (0.5 ml) and was treated with glacial AcOH (2.0 ml). The reaction mixture was heated at 80° C. for 45 min. The reaction was then quenched with water (10 ml) and extracted into EtOAc (3×20 ml). The combined organic layers were concentrated in vacuo to give 22-1 as a brown residue.

MS calculated M+H, 461.5. Found 461.2

4-[3-(1H-Imidazol-4-yl)-9-phenyl[1,2,4]triazolo[3,4-f]-1,6-naphthyridin-8-yl]benzaldehyde oxime (22-2)

To a solution of 22-1 (0.8 g, 1.7 mmol) in 1,4-dioxane (3 ml) was added 3N HCl (1.1 ml, 3.4 mmol) dropwise. After stirring for 10 min the solution was treated with hydroxylamine hydrochloride (0.5 g, 6.9 mmol) in water (0.5 ml). The mixture was stirred for 1 h and was then quenched with NaHCO$_3$(s) until pH=8. Upon solvent removal the residue was taken up in water, filtered, and dried azeotropically with toluene to afford 22-2 as a solid.

MS calculated M+H, 432.5. Found 432.2

1-{4-[3-(1H-Imidazol-4-yl)-9-phenyl[1,2,4]triazolo[3,4-f]-1,6-naphthyridin-8-yl]phenyl}methanamine (22-3)

A solution of 22-2 (0.06, 0.1 mmol) and Zn(s) (0.02 g, 0.3 mmol) in dry glacial AcOH was stirred at room temperature for 30 min. To the solution was added another 4 equivalents of Zn(s) (0.04 g, 0.6 mmol). The reaction mixture was stirred for an additional 1 h. After filtration and solvent removal the residue was taken up in MeOH and was treated with ammonium hydroxide. Upon solvent removal, the residue was purified by reverse phase HPLC to give 22-3 as a solid.

MS calculated M+H, 418.5. Found 401.1 (M—NH$_2$)

The following table (Table 8) contains compounds made using the procedures of Scheme 22 substituting the appropriate acid for the imidazole-4-carboxylic acid. The compounds in Table 8 were isolated as the HCl salt.

TABLE 8

| Cmp | Structure | Name | HRMS m/z (M + H) |
|---|---|---|---|
| 22-4 | 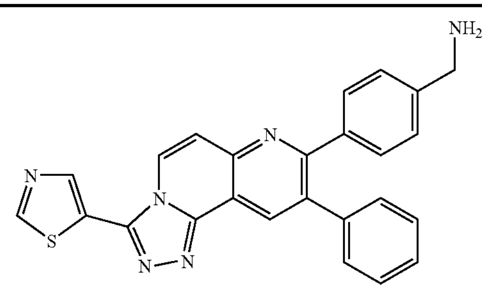 | 1-{4-[9-phenyl-3-(3H-1lambda$^4$,3-thiazol-5-yl)[1,2,4]triazolo[3,4-f]-1,6-naphthyridin-8-yl]phenyl}methanamine | 437.1543 |
| 22-5 | 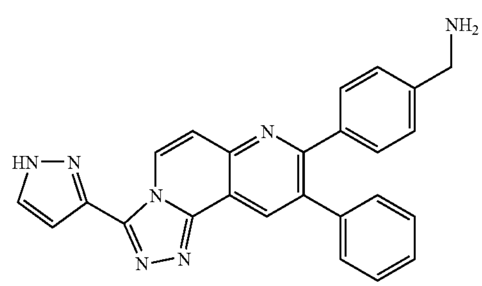 | 1-{4-[9-phenyl-3-(1H-pyrazol-3-yl)-2H-4lambda$^5$-[1,2,4]triazolo[3,4-f]-1,6-naphthyridin-8-yl]phenyl}methanamine | 418.1776 |
| 22-6 | 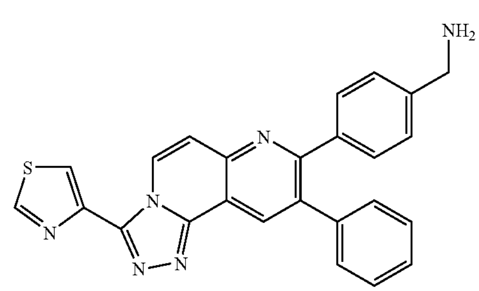 | 1-{4-[9-phenyl-3-(1,3-thiazol-4-yl)[1,2,4]triazolo[3,4-f]-1,6-naphthyridin-8-yl]phenyl}methanamine | 435.1385 |

SCHEME 23

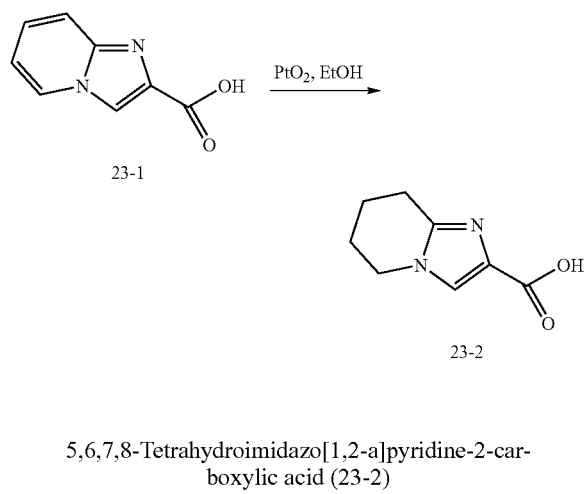

5,6,7,8-Tetrahydroimidazo[1,2-a]pyridine-2-carboxylic acid (23-2)

To a solution of 23-1 (0.1 g, 0.7 mmol) in EtOH (15 ml) in a dried flask was added Pt$_2$O (0.1 g, 0.4 mmol). The reaction mixture was placed under a nitrogen atmosphere and was subsequently evacuated. This was repeated 3 times before placing the reaction mixture under an atmosphere of hydrogen. After 3 h the reaction mixture was filtered through celite. Upon solvent removal the desired product 23-2 was obtained as an off-white powder. MS calculated M+H, 167.2. Found 167.1

SCHEME 24

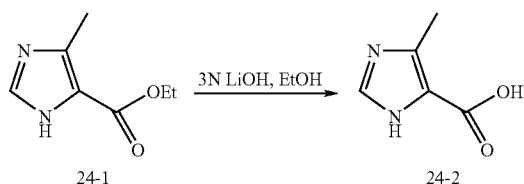

4-Methyl-1H-imidazole-5-carboxylic acid (24-2)

To a solution of 24-1 (0.5 g, 2.4 mmol) in EtOH (2 ml) was added 3N LiOH (2.2 ml, 6.5 mmol). The reaction mixture was heated at 80° C. for 1 h. The heat was reduced to 40° C. and the mixture was stirred overnight. The mixture was then heated at 80° C. for an additional 5.5 h. The reaction was neutralized with 12N HCl and was concentrated in vacuo. The residue was dried azeotropically with toluene to afford the desired product 24-2 as a solid. MS calculated M+H, 127.1. Found 127.1

SCHEME 25

Methyl 1-propyl-1H-imidazole-4-carboxylate (25-2)

To a solution of 25-1 (0.5 g, 4.0 mmol) in anhydrous THF (15 ml) in a dried flask was added NaH (0.1 g, 4.8 mmol) in portions. Once bubbling had subsided iodopropane (0.8 ml, 8.0 mmol) was added and stirred at room temperature overnight. To the reaction mixture was added another 0.5 eq of NaH was added along with 3 eq of iodopropane. After stirring for 50 h another 0.5 eq of NaH was added along with 2 eq of iodopropane. The reaction mixture stirred for another 20 h before being quenched with ethanol (5 ml). Solvent removal afforded the desired product 25-2 as a solid.

MS calculated M+H, 169.2. Found 155.1 (M—CH$_2$).

1-Propyl-1H-imidazole-4-carboxylic acid (25-3)

To a solution of 25-2 (0.6 g, 3.6 mmol) in anhydrous MeOH (2 ml) was added 3N LiOH (2.6 ml, 7.9 mmol). The reaction mixture was heated at 80° C. for 1 h. The heat was reduced and the mixture was stirred at 40° C. overnight. The reaction was then neutralized with 12N HCl and subsequently concentrated in vacuo. The residue was dried azeotropically with toluene to afford the desired product 25-3 as a solid. MS calculated M+H, 155.2. Found 155.1

The following table (Table 9) contains compounds made using the procedures of Scheme 25 substituting the appropriate alkyl halide.

TABLE 9

| Cmp | Structure | Name | HRMS m/z (M + H) |
|---|---|---|---|
| 25-4 | 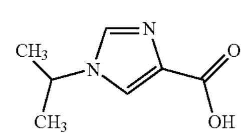 | 1-isopropyl-1H-imidazole-4-carboxylic acid | 155.1 |

TABLE 9-continued

| Cmp | Structure | Name | HRMS m/z (M + H) |
|---|---|---|---|
| 25-5 | 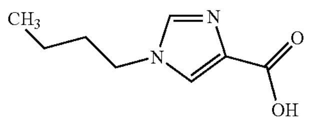 | 1-butyl-1H-imidazole-4-carboxylic acid | 155.1 |

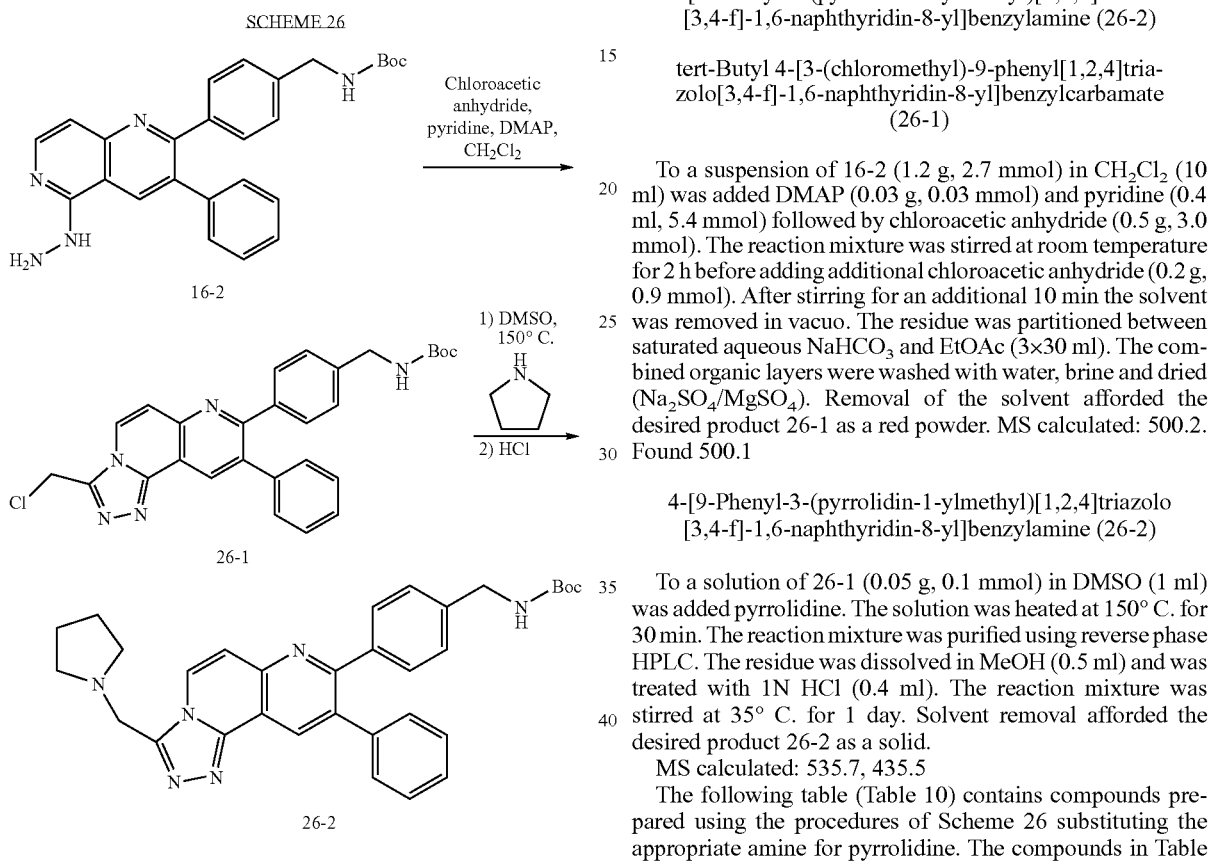

4-[9-Phenyl-3-(pyrrolidin-1-ylmethyl)[1,2,4]triazolo[3,4-f]-1,6-naphthyridin-8-yl]benzylamine (26-2)

tert-Butyl 4-[3-(chloromethyl)-9-phenyl[1,2,4]triazolo[3,4-f]-1,6-naphthyridin-8-yl]benzylcarbamate (26-1)

To a suspension of 16-2 (1.2 g, 2.7 mmol) in $CH_2Cl_2$ (10 ml) was added DMAP (0.03 g, 0.03 mmol) and pyridine (0.4 ml, 5.4 mmol) followed by chloroacetic anhydride (0.5 g, 3.0 mmol). The reaction mixture was stirred at room temperature for 2 h before adding additional chloroacetic anhydride (0.2 g, 0.9 mmol). After stirring for an additional 10 min the solvent was removed in vacuo. The residue was partitioned between saturated aqueous $NaHCO_3$ and EtOAc (3×30 ml). The combined organic layers were washed with water, brine and dried ($Na_2SO_4/MgSO_4$). Removal of the solvent afforded the desired product 26-1 as a red powder. MS calculated: 500.2. Found 500.1

4-[9-Phenyl-3-(pyrrolidin-1-ylmethyl)[1,2,4]triazolo[3,4-f]-1,6-naphthyridin-8-yl]benzylamine (26-2)

To a solution of 26-1 (0.05 g, 0.1 mmol) in DMSO (1 ml) was added pyrrolidine. The solution was heated at 150° C. for 30 min. The reaction mixture was purified using reverse phase HPLC. The residue was dissolved in MeOH (0.5 ml) and was treated with 1N HCl (0.4 ml). The reaction mixture was stirred at 35° C. for 1 day. Solvent removal afforded the desired product 26-2 as a solid.

MS calculated: 535.7, 435.5

The following table (Table 10) contains compounds prepared using the procedures of Scheme 26 substituting the appropriate amine for pyrrolidine. The compounds in Table 10 were isolated as HCl salts.

TABLE 10

| Cmp | Structure | Name | HRMS m/z (M + H) |
|---|---|---|---|
| 26-3 | 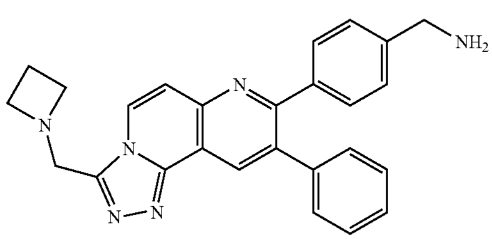 | 1-{4-[3-(azetidin-1-ylmethyl(-9-phenyl[1,2,4]triazolo[3,4-f]-1,6-naphthyridin-8-yl]phenyl}methanamine | 421.2124 |

TABLE 10-continued

| Cmp | Name | HRMS m/z (M + H) |
|---|---|---|
| 26-4 | 1-({8-[4-(aminomethyl) phenyl]-9-phenyl[1,2,4]triazolo[3,4-f]-1,6-naphthyridin-3-yl}methyl)piperidine-4-carboxamide | 492.249 |
| 26-5 | 1-{4-[3-(morpholin-4-ylmethyl)-9-phenyl[1,2,4]triazolo[3,4-f]-1,6-naphthyridin-8-yl]phenyl}methanamine | 451.2228 |
| 26-6 | 2-[({8-[4-(aminomethyl)phenyl]-9-phenyl[1,2,4]triazolo[3,4-f]-1,6-naphthyridin-3-yl}methyl)amino]ethanol | 425.2071 |
| 26-7 | 1-(4-{3-[(4-methylpiperazin-1-yl)methyl]-9-phenyl[1,2,4]triazolo[3,4-f]-1,6-naphthyridin-8-yl}phenyl)methanamine | 462.2543 |
| 26-8 | 4-[9-phenyl-3-(piperazin-1-ylmethyl)[1,2,4]triazolo[3,4-f]-1,6-naphthyridin-8-yl]benzylamine | 450.2386 |
| 26-9 | N-({8-[4-(aminomethyl)phenyl]-9-phenyl[1,2,4]triazolo[3,4-f]-1,6-naphthyridin-3-yl}methyl)-N-methylamine | 395.1969 |

| Cmp | Structure | Name | HRMS m/z (M + H) |
|---|---|---|---|
| 26-10 | 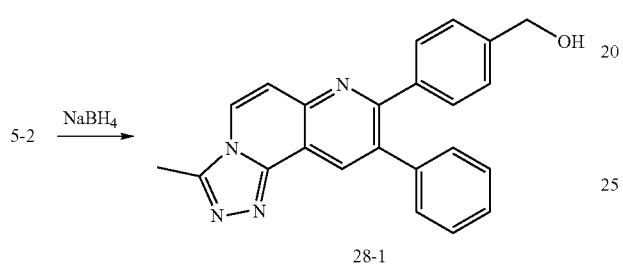 | N-({8-[4-(aminomethyl) phenyl]-9-phenyl[1,2,4] triazolo[3,4-f]-1,6-naphthyridin-3-yl} methyl)-N,N-dimethylamine | 409.2125 |

SCHEME 28

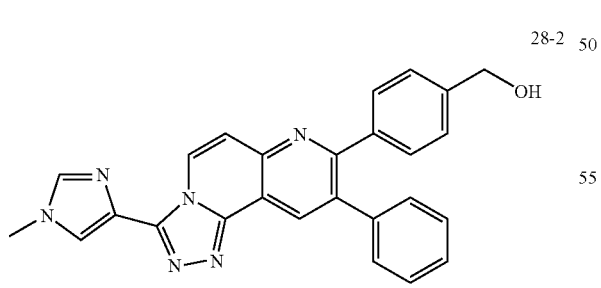

[4-(3-Methyl-9-phenyl[1,2,4]triazolo[3,4-f]-1,6-naphthyridin-8-yl)phenyl]methanol (28-1)

To a solution of 4-(3-methyl-9-phenyl[1,2,4]triazolo[3,4-f]-1,6-naphthyridin-8-yl)benzaldehyde (5-2, 0.317 g, 0.870 mmol) in methanol (5 mL) was added sodium borohydride (0.033 g, 0.870 mmol) at 0° C. After 10 minutes, the reaction mixture was poured into ethyl acetate, and the organic layer was washed with a saturated solution of sodium bicarbonate, water, then brine, dried over sodium sulfate, filtered and concentrated to dryness under reduced pressure. Purification by reverse phase chromatography (Waters Sunfire MSC18, 1% acetonitrile/0.1% trifluoroacetic acid/water→95% acetonitrile/0.1% trifluoroacetic acid/water) gave the title compounds as a solid. HRMS (M+H$^+$): calculated=367.1554, observed=367.1547.

{4-[3-(1-Methyl-1H-imidazol-4-yl)-9-phenyl[1,2,4]triazolo[3,4-f]-1,6-naphthyridin-8-yl]phenyl}methanol (28-2)

The title compound was prepared from 13-2 according to the procedure of Scheme 28;

HRMS (M+H$^+$): calculated=433.1772, observed=433.1761.

SCHEME 29

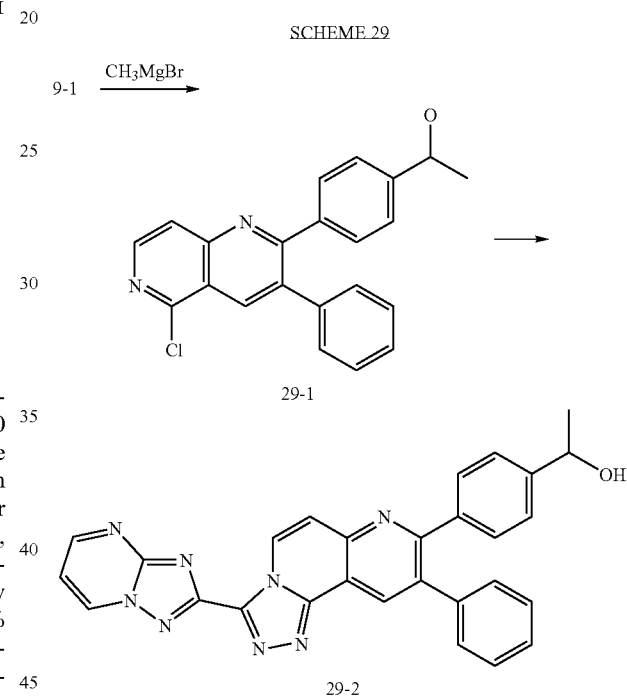

1-[4-(9-Phenyl-3-[1,2,4]triazolo[1,5-a]pyrimidin-2-yl[1,2,4]triazolo[3,4-f]1,6-naphthyridin-8-yl)phenyl]ethanol (29-2)

1-[4-(5-Chloro-3-phenyl-1,6-naphthyridin-2-yl)phenyl]ethanol (29-1)

To a solution of 4-(5-chloro-3-phenyl-1,6-naphthyridin-2-yl)benzaldehyde (9-1, 0.500 g, 1.450 mmol) in anhydrous methylene chloride (10 mL) was added methymagnesium bromide (2.072 mL, 2.9 mmol, 1.4M in toluene/tetrahydrofuran (75:25)) at 0° C. After 15 minutes, the reaction mixture was poured into ethyl acetate, and the organic layer was washed with a saturated solution of sodium bicarbonate, water, then brine, dried over sodium sulfate, filtered and concentrated to dryness under reduced pressure gave the title compound. MS (M+H$^+$): calculated=361.85, observed=361.1.

1-[4-(9-Phenyl-3-[1,2,4]triazolo[1,5-a]pyrimidin-2-yl[1,2,4]triazolo[3,4-f]-1,6-naphthyridin-8-yl)phenyl]ethanol (29-2)

The title compound was prepared according to the procedures of Scheme 9; HRMS (M+H$^+$): calculated=485.1833, observed=485.1812.

The following compounds in Table 11 were prepared according to the procedure of Scheme 13 from piperidine 21-1 and the indicated aldehyde.

TABLE 11

| Cmp | Structure | Name | HRMS m/z (M + H) |
|---|---|---|---|
| 30-1 (from 4-2) | 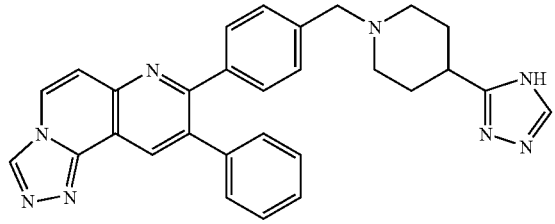 | 9-phenyl-8-(4-{[4-(4H-1,2,4-triazol-3-yl) piperidin-1-yl]methyl} phenyl)[1,2,4]triazolo[3,4-f]-1,6-naphthyridine | Calc'd: 487.2353 Observed: 484.2371 |
| 31-1 (from 5-2) | 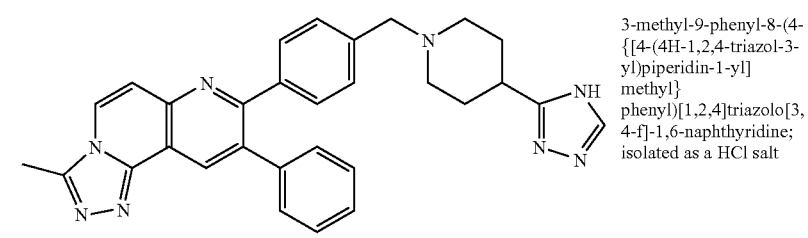 | 3-methyl-9-phenyl-8-(4-{[4-(4H-1,2,4-triazol-3-yl)piperidin-1-yl] methyl} phenyl)[1,2,4]triazolo[3,4-f]-1,6-naphthyridine; isolated as a HCl salt | Calc'd: 501.2510 Observed: 501.2531 |
| 32-1 (from 3-6) | 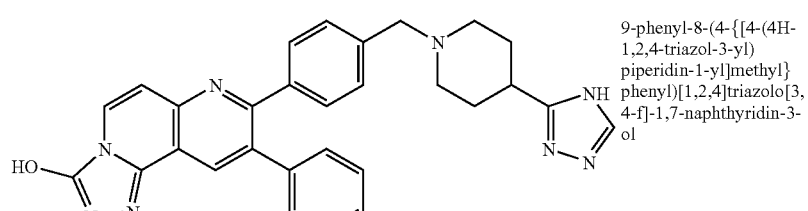 | 9-phenyl-8-(4-{[4-(4H-1,2,4-triazol-3-yl) piperidin-1-yl]methyl} phenyl)[1,2,4]triazolo[3,4-f]-1,7-naphthyridin-3-ol | Calc'd: 503.2303 Observed: 503.2327 |

SCHEME 33

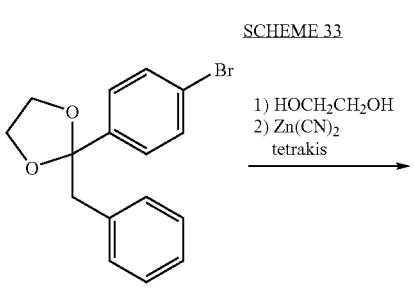

1) HOCH$_2$CH$_2$OH
2) Zn(CN)$_2$ tetrakis

-continued

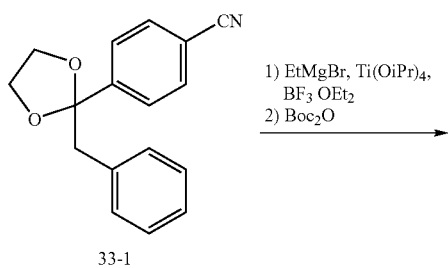

1) EtMgBr, Ti(OiPr)$_4$, BF$_3$·OEt$_2$
2) Boc$_2$O 33-1

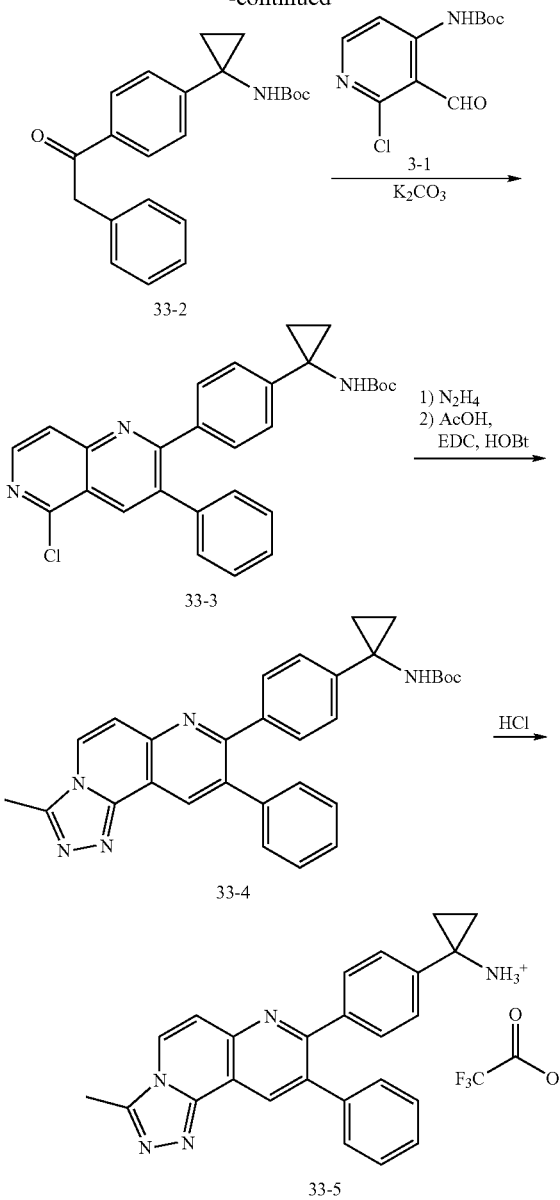

1-[4-(3-Methyl-9-phenyl[1,2,4]triazolo[3,4-f]-1,6-naphthyridin-8-yl)phenyl]cyclopropanaminium trifluoroacetate (33-5)

4-(2-Benzyl-1,3-dioxolan-2-yl)benzonitrile (33-1)

A solution of 1-(4-bromophenyl)-2-phenylethanone (5.0 g, 18 mmol), ethylene glycol (3.0 mL, 54 mmol) and tosic acid (0.04 g, 0.2 mmol) in toluene (30 mL) was heated to reflux with a Dean-Stark trap for 15 hours. The reaction was cooled to room temperature, diluted with ethyl acetate, washed with saturated sodium bicarbonate, brine, dried over sodium sulfate, filtered and concentrated to give crude 2-benzyl-2-(4-bromophenyl)-1,3-dioxolane as a white solid. To the crude material was added zinc cyanide (2.3 g, 20 mmol), tetrakis(triphenylphosphine)palladium (3.3 g, 2.8 mmol), DMF (20 mL) and dioxane (20 mL) and the resulting suspension was purged with nitrogen for 15 minutes prior to being heated 100° C. for 15 hours. The reaction was cooled to room temperature, poured into ether and filtered. The organic filtrate was washed with water, saturated bicarbonate, brine, dried over sodium sulfate, filtered and concentrated. Purification by silica gel chromatography (1% ethyl acetate/hexane→50% ethyl acetate/hexane) gave the title compound as white solid. MS (M+H$^+$): calculated=265.31, observed=266.1.

tert-Butyl {1-[4-(phenylacetyl)phenyl]cyclopropyl}carbamate (33-2)

To a solution of 4-(2-benzyl-1,3-dioxolan-2-yl)benzonitrile (33-1, 1.5 g, 5.6 mmol) in ether (25 mL) was added titanium isopropoxide (1.8 mL, 6.2 mmol) followed by ethyl magnesium bromide (4.2 mL, 12 mmol, 3M in ether) at −78° C. After 10 minutes, the reaction was warmed to room temperature for 60 minutes. The reaction was cooled to 0° C. and boron trifluoride etherate complex (1.4 mL, 11 mmol) was added. After 30 minutes at 0° C., the reaction was warmed to room temperature for 1 hour at which time the reaction was quenched and acidified with 1M HCl. The suspension was stirred for an additional 3 hours at room temperature, at which time the mixture was basified with 1M NaOH and extracted with chloroform. The combined organics were dried over sodium sulfate, filtered and concentrated. To the crude material was immediately added acetonitrile (15 mL) and di-tert-butyl dicarbonate (1.2 g, 5.6 mmol) at room temperature. After 12 hours, the reaction was concentrated to dryness and purified by silica gel chromatography (1% ethyl acetate/hexane→60% ethyl acetate/hexane) to give the title compound as white solid. MS (M+H$^+$): calculated=351.44, observed=352.1.

tert-Butyl {1-[4-(5-chloro-3-phenyl-1,6-naphthyridin-2-yl)phenyl]cyclopropyl}carbamate (33-3)

A solution of 33-2 (0.64 g, 2.5 mmol), 3-1 (0.88 g, 2.5 mmol) and potassium carbonate (2.1 g, 15 mmol) in DMF (14 mL) was heated to 120° C. for 4.5 hours. The reaction was cooled to room temperature, diluted with ethyl acetate, washed with water, brine, dried over sodium sulfate, filtered and concentrated. Purification by silica gel chromatography (1% ethyl acetate/hexane→70% ethyl acetate/hexane) gave the title compound as a foam. MS (M+H$^+$): calculated=471.98, observed=472.1.

tert-Butyl {1-[4-(3-methyl-9-phenyl[1,2,4]triazolo[3,4-f]-1,6-naphthyridin-8-yl)phenyl]cyclopropyl}carbamate (33-4)

The title compound was prepared from 33-3 according to the procedure of Scheme 27; MS (M+H$^+$): calculated=491.58, observed=492.1.

1-[4-(3-Methyl-9-phenyl[1,2,4]triazolo[3,4-f]-1,6-naphthyridin-8-yl)phenyl]cyclopropanaminium trifluoroacetate (33-5)

The title compound was prepared according to the procedure of Scheme 27; HRMS (M+H$^+$): calculated=392.1870, observed=392.1893.

The following compounds in Table 12 were prepared according to the procedure of Scheme 33. Compounds 33-8-33-10 were isolated as HCl salts. Compound 33-6 was isolated as a TFA salt.

TABLE 12

| Cmpd | Structure | Name | HRMS m/z (M + H) |
|---|---|---|---|
| 33-6 | 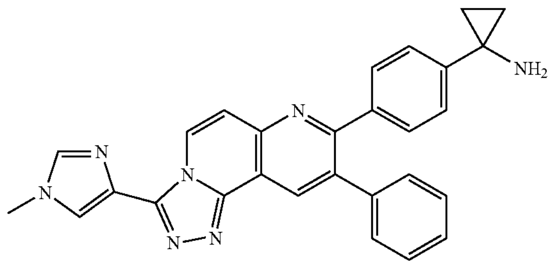 | 1-{4-[3-(1-methyl-1H-imidazol-4-yl)-9-phenyl[1,2,4]triazolo[3,4-f]-1,6-naphthyridin-8-yl]phenyl}cyclopropanamine | Calcd'd: 458.2088<br>Observed: 458.2114 |
| 33-7 | 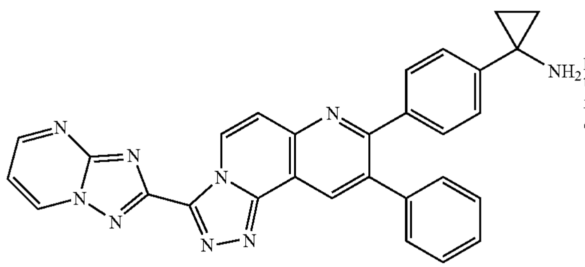 | 1-[4-(9-phenyl-3-[1,2,4]triazolo[1,5-a]pyrimidine-2-yl[1,2,4]triazolo[3,4-f]-1,6-naphthyridin-8-yl)phenyl]cyclopropanamine | Calc'd: 496.1993<br>Observed: 496.1987 |
| 33-8 | 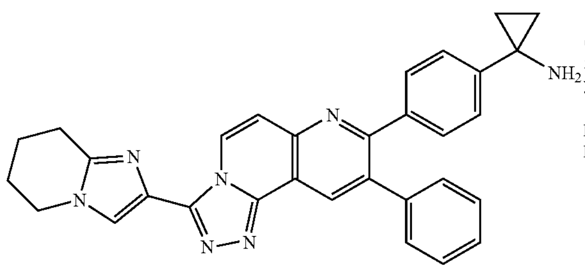 | 1-{4-[9-phenyl-3-(5,6,7,8-tetrahydroimidazo[1,2-a]pyridin-2-yl)[1,2,4]triazolo[3,4-f]-1,6-naphthyridin-8-yl]phenyl}cyclopropanamine | 498.238 |
| 33-9 | 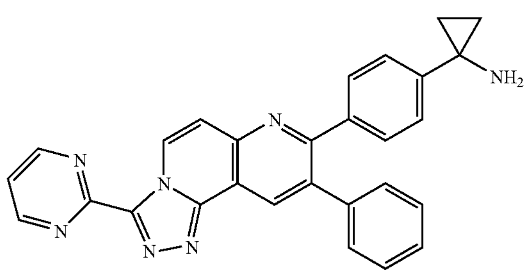 | 1-[4-(9-phenyl-3-pyrimidin-2-yl[1,2,4]triazolo[3,4-f]-1,6-naphthyridin-8-yl)phenyl]cyclopropanamine | 456.1915 |
| 33-10 | 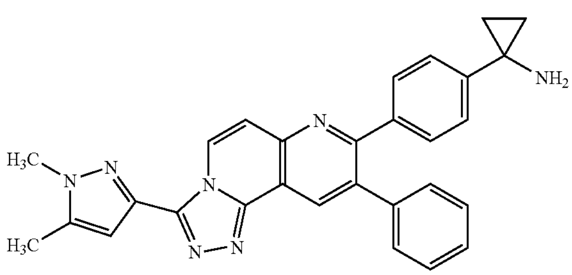 | 1-{4-[3-(1,5-dimethyl-1H-pyrazol-3-yl)-9-phenyl[1,2,4]triazolo[3,4-f]-1,6-naphthyridin-8-yl]phenyl}cyclopropanamine | 472.2227 |

SCHEME 34

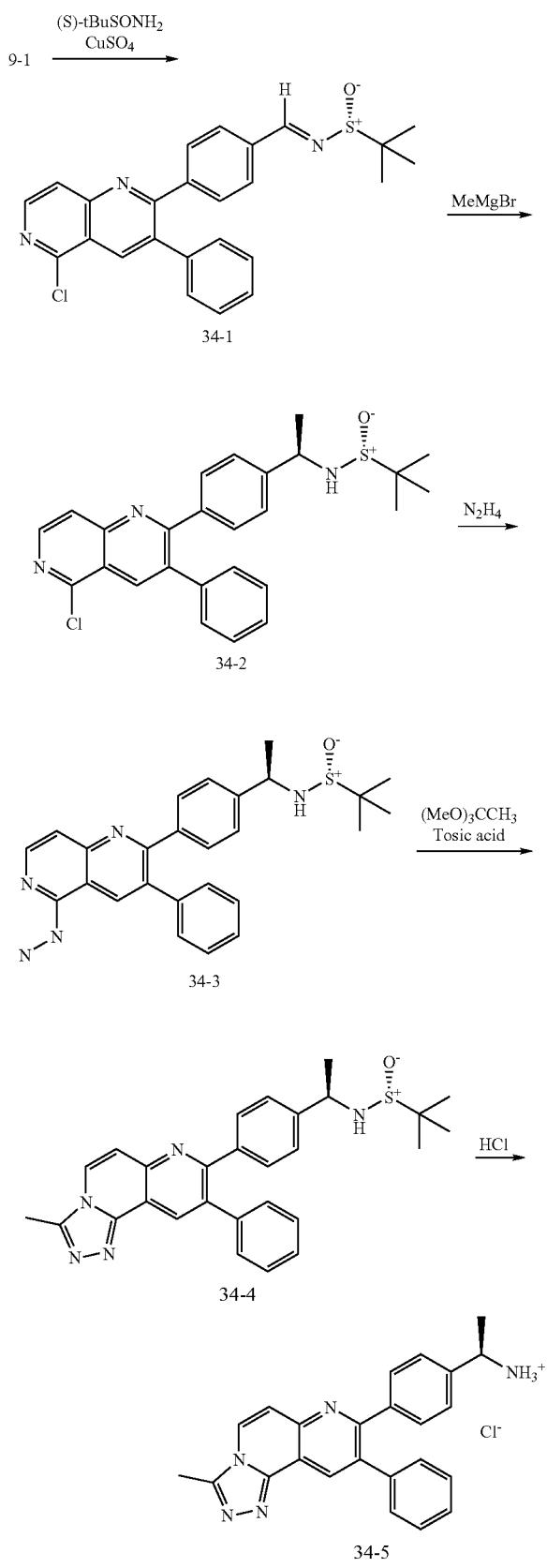

(1R)-1-[4-(3-Methyl-9-phenyl[1,2,4]triazolo[3,4-f]-1,6-naphthyridin-8-yl)phenyl]ethanaminium chloride (34-5)

N-{(1E)-[4-(5-chloro-3-phenyl-1,6-naphthyridin-2-yl)phenyl]methylene}-2-methylpropane-2-sulfinamide (34-1)

A solution of 4-(5-chloro-3-phenyl-1,6-naphthyridin-2-yl)benzaldehyde (9-1, 4.24 g, 12.3 mmol), S-(−)-2-methylpropane-2-sulfinamide (3.43 mL, 28.3 mmol) and cupric sulfate (4.49 g, 28.1 mmol) in methylene chloride (20 mL) was heated to reflux under an atmosphere of nitrogen. After 18 hours, the reaction was washed with saturated sodium bicarbonate, brine, dried over magnesium sulfate, filtered and concentrated. Purification by silica gel chromatography (0% ethyl acetate/hexane→45% ethyl acetate/hexane) gave the title compound as an orange foam. MS (M+H$^+$): calculated=447.99, observed=448.2

N-{(1R)-1-[4-(5-chloro-3-phenyl-1,6-naphthyridin-2-yl)phenyl]ethyl}-2-methylpropane-2-sulfinamide (34-2)

To a solution of N-{(1E)-[4-(5-chloro-3-phenyl-1,6-naphthyridin-2-yl)phenyl]methylene}-2-methylpropane-2-sulfinamide (34-1, 4.53 g, 10.1 mmol) in methylene chloride (100 mL) was added methyl magnesium bromide (30 mL, 42.0 mmol, 1.4M in 75:25 toluene:THF) at −10° C. After 30 minutes, the reaction was quenched by addition of saturated ammonium chloride solution (while maintaining the temperature below 0° C.) and extracted with methylene chloride. The combined organics were washed with water, brine, dried over magnesium sulfate, filtered and concentrated to give the title compound as a pale yellow solid. MS (M+H$^+$): calculated=464.03, observed=464.2 tert-Butyl({(1R)-1-[4-(5-hydrazino-3-phenyl-1,6-naphthyridin-2-yl)phenyl]ethyl}amino)sulfoniumolate (34-3)

To a solution of a N-{(1R)-1-[4-(5-chloro-3-phenyl-1,6-naphthyridin-2-yl)phenyl]ethyl}-2-methylpropane-2-sulfinamide (34-2, 0.707 g, 1.52 mmol) and anhydrous hydrazine (15 ml) was heated at 115° C. for 1 hour. The reaction mixture was poured into ethyl acetate, and the organic layer was washed with a saturated solution of sodium bicarbonate, then water, then brine, dried over magnesium sulfate, filtered and concentrated to dryness under reduced pressure to give the crude hydrazine adduct as an orange solid. MS (M+H$^+$): calculated=459.62, observed=460.4.

tert-Butyl({(1R)-1-[4-(3-methyl-9-phenyl[1,2,4]triazolo[3,4-f]-1,6-naphthyridin-8-yl)phenyl]ethyl}amino)sulfoniumolate (34-4)

To crude tert-butyl({(1R)-1-[4-(5-hydrazino-3-phenyl-1,6-naphthyridin-2-yl)phenyl]ethyl}amino)sulfoniumolate (34-3, 1.06 g, 2.31 mmol), p-toluenesulfonic acid (63 mg, 0.36 mmol), and trimethyl orthoacetate (1.0 mL, 7.7 mmol) was added anhydrous toluene (10 mL) and heated to 110° C. for 48 hours. The reaction mixture was reduced under pressure and purified by silica gel chromatography (0-10% methanol/methylene chloride) to give an orange foam. MS (M+H$^+$): calculated=483.64, observed=484.2.

(1R)-1-[4-(3-Methyl-9-phenyl[1,2,4]triazolo[3,4-f]-1,6-naphthyridin-8-yl)phenyl]ethanaminium chloride (34-5)

tert-Butyl({(1R)-1-[4-(3-methyl-9-phenyl[1,2,4]triazolo[3,4-f]-1,6-naphthyridin-8-yl)phenyl]ethyl}amino)sulfoniumolate (34-4) was treated with 4N HCl in dioxane at room temperature for 15 minutes. The reaction mixture was reduced under pressure and purified by reverse phase chromatography (Waters Sunfire MSC18, 1% acetonitrile/0.1% trifluoroacetic acid/water→95% acetonitrile/0.1% trifluoroacetic acid/water) & conversion to HCl salt (addition of saturated solution of HCl in ethyl acetate (~4N) & concentration) gave the title compound as a solid. MS (M+H$^+$): calculated=379.47, observed=380.2.

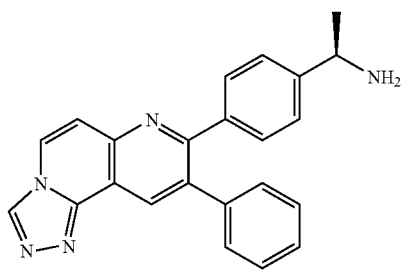

(1R)-1-[4-(9-phenyl[1,2,4]triazolo[3,4-f]-1,6-naphthyridin-8-yl)phenyl]ethanamine (34-6)

The title compound was prepared according the procedures of Scheme 34; MS (M+H$^+$): calculated=365.43, observed=366.2. Compound 34-6 was isolated as an HCl salt.

SCHEME 35

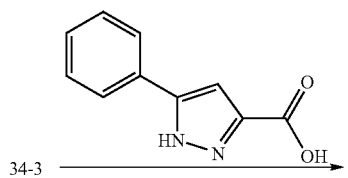

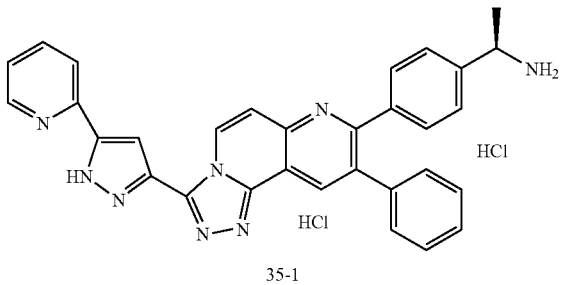

(1R)-1-{4-[9-Phenyl-3-(5-pyridin-2-yl-1H-pyrazol-3-yl)[1,2,4]triazolo[3,4-f]-1,6-naphthyridin-8-yl]phenyl}ethanamine dihydrochloride (35-1)

To tert-butyl({(1R)-1-[4-(5-hydrazino-3-phenyl-1,6-naphthyridin-2-yl)phenyl]ethyl}amino)sulfoniumolate (34-3, 0.20 g, 0.43 mmol), EDC (0.11 g, 0.57 mmol), anhydrous HOBT (0.06 g, 0.39 mmol), DIPEA (0.17 mL, 0.96 mmol), and 5-pyridin-2-yl-1H-pyrazole-3-carboxylic acid (0.08 g, 0.43 mmol) was added anhydrous DMF (2 mL) and stirred at room temperature overnight. HCl/Ether (1 mL, 2N) was added to the reaction mixture and stirred for 20 min at room temperature, then microwaved at 100° C. for 30 min. The solvent was removed under vacuum and purified by reverse phase chromatography (Waters Sunfire MSC18, 1% acetonitrile/0.1% trifluoroacetic acid/water 95% acetonitrile/0.1% trifluoroacetic acid/water) & conversion to HCl salt (addition of saturated solution of HCl in ethyl acetate (~4N) & concentration) gave the title compound as a solid. MS (M+H$^+$): calculated=508.58, observed=509.1.

The following compounds in Table 13 were prepared according to the procedure of Scheme 35. The compounds in Table 13 were isolated as HCl salts.

TABLE 13

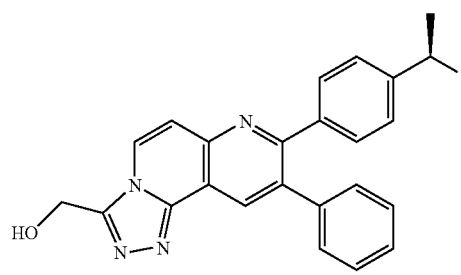

| Cmp | Structure | Name | MS m/z (M + H) |
|---|---|---|---|
| 35-2 | 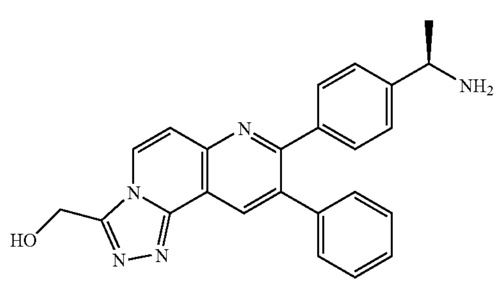 | (1R)-1-{4-[3-(hydroxymethyl)-9-phenyl[1,2,4]triazolo[3,4-f]-1,6-naphthyridin-8-yl]phenyl}ethanamine | Observed: 396.0 |

TABLE 13-continued

| Cmp | Structure | Name | MS m/z (M + H) |
|---|---|---|---|
| 35-3 | 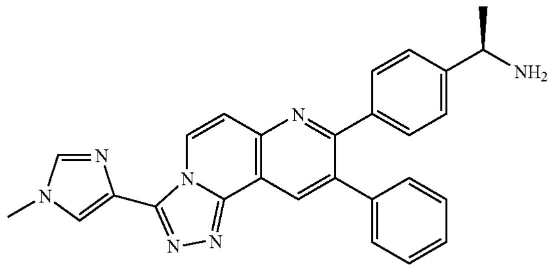 | (1R)-1-{4-[3-(1-methyl-1H-imidazol-4-yl)-9-phenyl[1,2,4]triazolo[3,4-f]-1,6-naphthyridin-8-yl]phenyl}ethanamine | Observed: 445.9 |
| 35-4 | 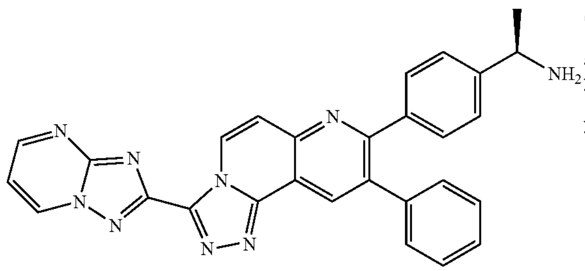 | (1R)-1-[4-(9-phenyl-3-[1,2,4]triazolo[1,5-a]pyrimidin-2-yl[1,2,4]triazolo[3,4-f]-1,6-naphthyridin-8-yl)phenyl]ethanamine | Observed: 484.1 |
| 35-5 | 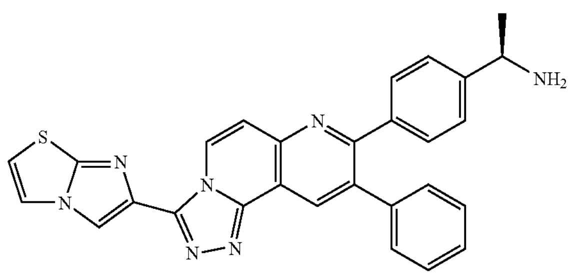 | (1R)-1-[4-(3-imidazo[2,1-b][1,3]thiazol-6-yl-9-phenyl[1,2,4]triazolo[3,4-f]-1,6-naphthyridin-8-yl)phenyl]ethanamine | Observed: 488.0 |
| 35-6 | 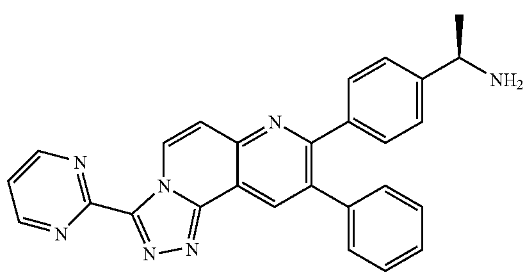 | (1R)-1-[4-(9-phenyl-3-pyrimidin-2-yl[1,2,4]triazolo[3,4-f]-1,6-naphthyridin-8-yl)phenyl]ethanamine | Observed: 444.1 |

(1R)-1-[4-(9-Phenyl[1,2,4]triazolo[3,4-f]-1,6-naphthyridin-8-yl)phenyl]propan-1-amine (36-1)

36-1

The title compound was prepared according the procedures of Scheme 34. MS (M+H⁺): calculated=379.47, observed=380.2 Compound 36-1 was isolated as an HCl salt.

SCHEME 37

PhCH₂COCl
AlCl₃
→

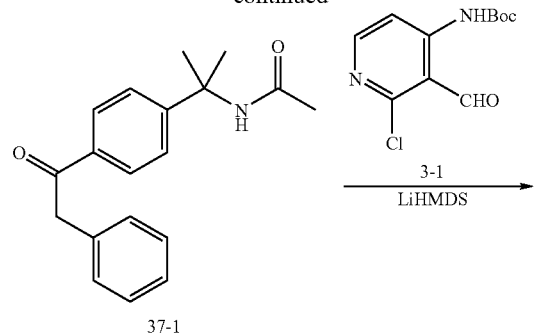

37-1

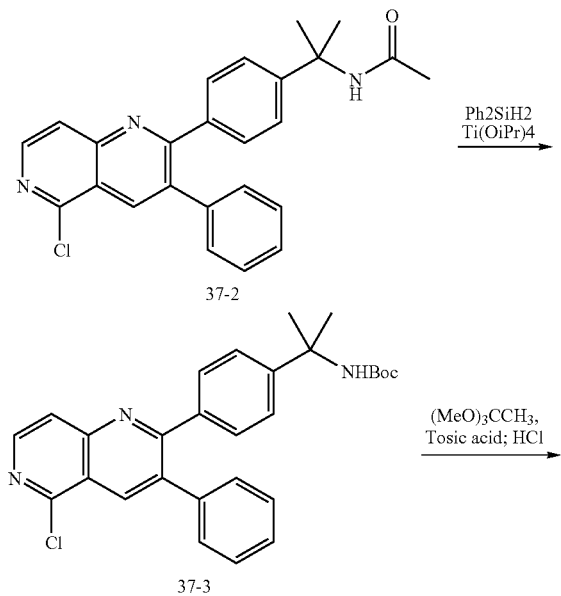

2-[4-(3-methyl-9-phenyl[1,2,4]triazolo[3,4-f]-1,6-naphthyridin-8-yl)phenyl]propan-2-amine (37-4)

N-{1-methyl-1-[4-(phenylacetyl)phenyl]ethyl}acetamide (37-1)

A solution of N-(1-methyl-1-phenylethyl)acetamide (21.3 g, 121 mmol), phenylacetyl chloride (19.5 g, 126 mmol) and aluminum trichloride (19 g, 142 mmol) in methylene chloride (140 mL) was stirred overnight at room temperature under an atmosphere of nitrogen. The reaction was poured onto ice and stirred until the ice melted, then the layers were separated and the organic layer was washed with saturated sodium bicarbonate, brine, dried over magnesium sulfate, filtered and concentrated. Purification by silica gel chromatography gave the title compound. MS (M+H+): calculated=295.38, observed=296.1

N-{1-[4-(5-chloro-3-phenyl-1,6-naphthyridin-2-yl)phenyl]-1-methylethyl}acetamide (37-2)

The title compound was prepared from 37-1 according to the procedure of Scheme 3; MS (M+H+): calculated=415.91, observed=416.1 tert-Butyl {1-[4-(5-chloro-3-phenyl-1,6-naphthyridin-2-yl)phenyl]-1-methylethyl}carbamate (37-3)

To a solution of N-{1-[4-(5-chloro-3-phenyl-1,6-naphthyridin-2-yl)phenyl]-1-methylethyl}acetamide (37-2, 4.73 g, 11.4 mmol) in anhydrous THF (120 mL) was added diphenylsilane (10.5 ml, 56.9 mmol) and titanium isopropoxide (16.6 mL, 56.9 mmol) at 40° C. for 1 hour. The reaction mixture was removed from heat and quenched by addition of saturated bicarbonate solution. Methylene chloride was added and filtered through a pad of celite and magnesium sulfate. Di-tert-butyl dicarbonate (3.08 g, 14.1 mmol) was added to the solution before rotavaping to min volume. Anhydrous methylene chloride (140 mL), di-tert-butyl dicarbonate (4.1 g, 18.8 mmol), and TEA (4.0 mL, 28.7 mmol) were added and stirred overnight at room temperature. The reaction mixture was washed with sodium bicarbonate, brine, dried over magnesium sulfate, filtered, and concentrated. Purified by silica gel chromatography (0-40% EtOAc/hex over 30 min) gave the title compound as a white foam. MS (M+H+): calculated=473.99, observed=474.1

2-[4-(3-methyl-9-phenyl[1,2,4]triazolo[3,4-f]-1,6-naphthyridin-8-yl)phenyl]propan-2-amine hydrochloride (37-4)

The title compound was prepared from 37-3 according to the procedures of Scheme 5; MS (M+H+): calculated=393.48, observed=394.1.

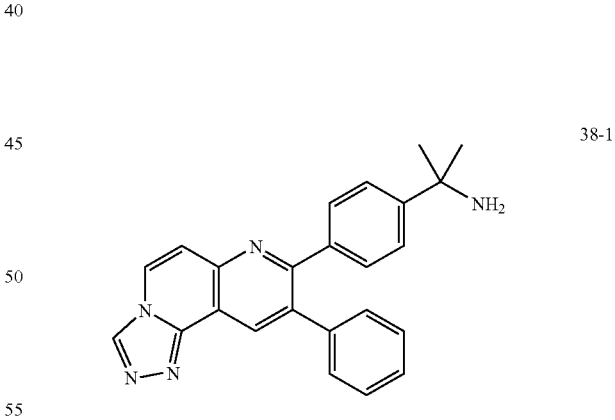

38-1

2-[4-(9-phenyl[1,2,4]triazolo[3,4-f]-1,6-naphthyridin-8-yl)phenyl]propan-2-amine (38-1)

The title compound was prepared according to the procedures of Scheme 37; MS (M+H+): calculated=421.51, observed=422.3. Compound 38-1 was isolated as an HCl salt.

SCHEME 39

5-3 →EDC, HOBt→

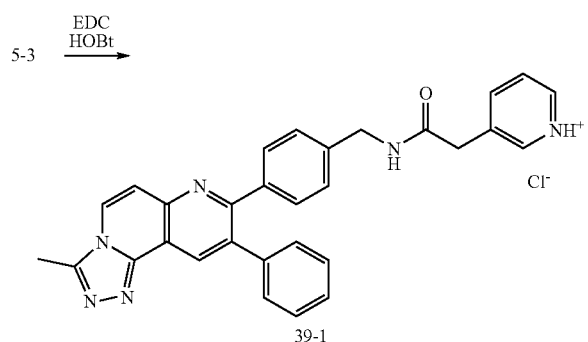

39-1

3-(2-{[4-(3-methyl-9-phenyl[1,2,4]triazolo[3,4-f]-1,6-naphthyridin-8-yl)benzyl]amino}-2-oxoethyl)pyridinium chloride (39-1)

To 1-[4-(3-methyl-9-phenyl[1,2,4]triazolo[3,4-f]-1,6-naphthyridin-8-yl)phenyl]methanamine hydrochloride (5-3, 20 mg, 0.050 mmol)), EDC (12 mg, 0.065 mmol), HOBT (10 mg, 0.0650 mmol), DIPEA (0.033 ml, 0.199 mmol), and pyridin-3-ylacetic acid hydrochloride (11 mg, 0.0650 mmol) was added 0.6 mL anhydrous dimethylformamide. The reaction mixture was then heated under microwave irradiation at 100° C. for 5 minutes. Purification of crude reaction mixture by reverse phase chromatography (Waters Sunfire MSC18, 1% acetonitrile/0.1% trifluoroacetic acid/water→95% acetonitrile/0.1% trifluoroacetic acid/water) & conversion to HCl salt (addition of saturated solution of HCl in ethyl acetate (~4N) & concentration) gave the title compound as yellow solid. HRMS (M+H$^+$): calculated=243.1079, observed=243.1083.

The following compounds in Table 14 were prepared from the indicated amine (see the Cmp column parentheticals) according to the procedure of Scheme 39.

TABLE 14

| Cmp (amine) | Structure | Name | HRMS m/z (M + H) |
|---|---|---|---|
| 39-2 (5-3) | 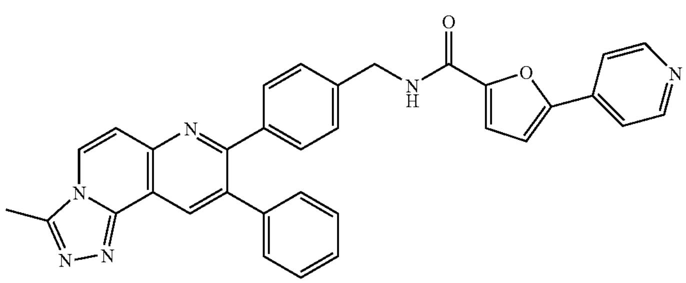 | N-[4-(3-methyl-9-phenyl [1,2,4]triazolo[3,4-f]-1,6-naphthyridin-8-yl) benzyl]-5-pyridin-4-yl-2-furamide; isolated as a TFA salt | Calc'd: 537.2034 Observed: 537.2027 |
| 39-3 (5-3) | 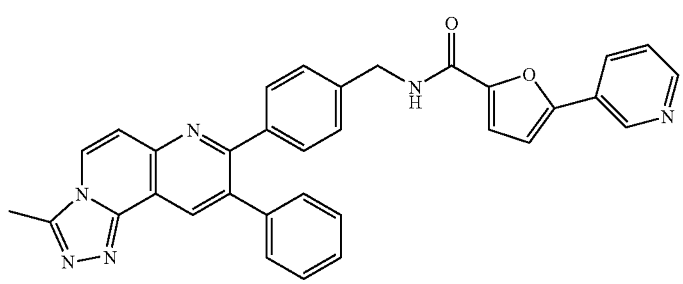 | N-[4-(3-methyl-9-phenyl [1,2,4]triazolo[3,4-f]-1,6-naphthyridin-8-yl) benzyl]-5-pyridin-3-yl-2-furamide; isolated as a HCl salt | Calc'd: 537.2034 Observed: 537.2023 |
| 39-4 (5-3) | 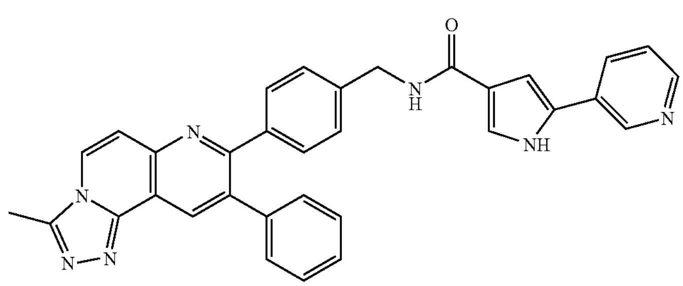 | N-[4-(3-methyl-9-phenyl [1,2,4]triazolo[3,4-f]-1,6-naphthyridin-8-yl) benzyl]-5-pyridin-3-yl-1H-pyrrole-3-carboxamide; isolated as a HCl salt | Calc'd: 536.2194 Observed: 536.2218 |

TABLE 14-continued

| Cmp (amine) | Structure | Name | HRMS m/z (M + H) |
|---|---|---|---|
| 39-5 (5-3) | 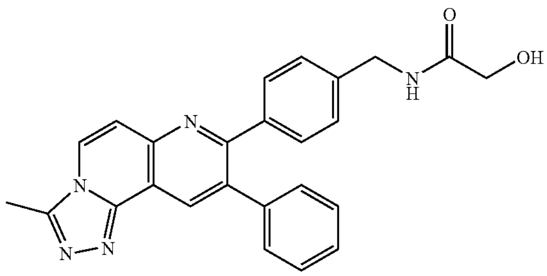 | 2-hydroxy-N-[4-(3-methyl-9-phenyl[1,2,4]triazolo[3,4-f]-1,6-naphthyridin-8-yl)benzyl]acetamide | Calc'd: 424.1768 Observed: 424.1767 |
| 39-6 (5-3) | 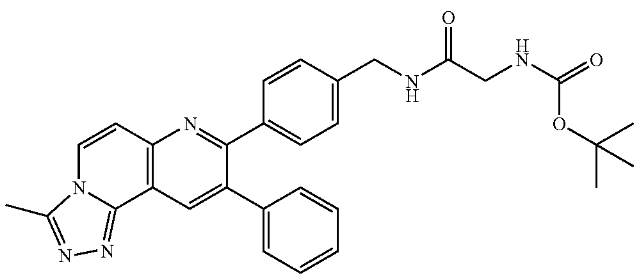 | tert-butyl (2-{[4-(3-methyl-9-phenyl[1,24]triazolo[3,4-f]-1,6-naphthyridin-8-yl)benzyl]amino}-2-oxoethyl)carbamate | Calc'd: 523.2452 Observed: 523.2444 |
| 39-7 (5-3) | 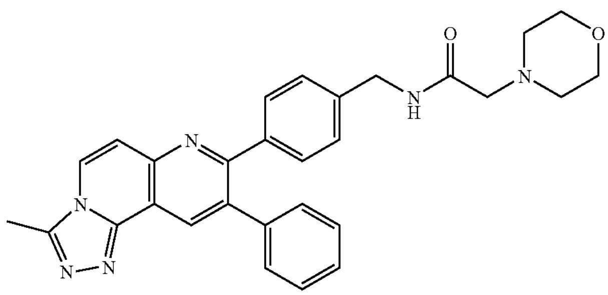 | 4-(2-{[4-(3-methyl-9-phenyl[1,2,4]triazolo[3,4-f]-1,6-naphthyridin-8-yl)benzyl]amino}-2-oxoethyl)morpholine; isolated as an HCl salt | Calc'd: 493.2347 Observed: 493.2358 |
| 39-8 (5-3) | 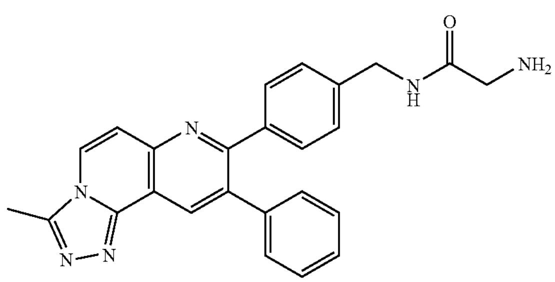 | 2-{[4-(3-methyl-9-phenyl[1,2,4]triazolo[3,4-f]-1,6-naphthyridin-8-yl)benzyl]amino}-2-oxoethanamine; isolated as an HCl salt | Calc'd: 423.1928 Observed: 423.1942 |
| 39-9 (5-3) | 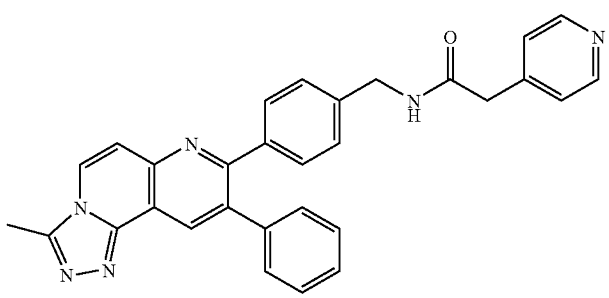 | 4-(2-{[4-(3-methyl-9-phenyl[1,2,4]triazolo[3,4-f]-1,6-naphthyridin-8-yl)benzyl]amino}-2-oxoethyl)pyridine; isolated as an HCl salt | Calc'd: 485.2085 Observed: 485.2120 |

TABLE 14-continued

| Cmp (amine) | Structure | Name | HRMS m/z (M + H) |
|---|---|---|---|
| 39-10 (5-3) | 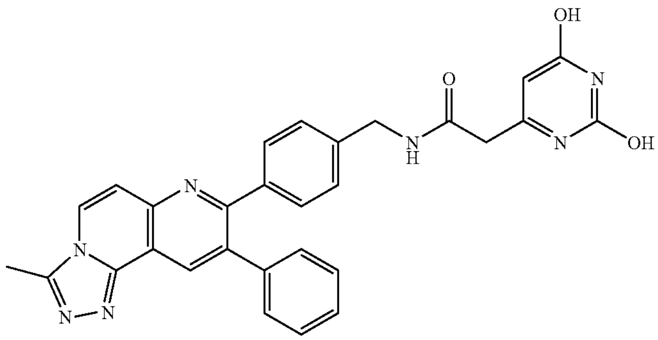 | 2,4-dihydroxy-6-(2-{[4-(3-methyl-9-phenyl[1,2,4]triazolo[3,4-f]-1,6-naphthyridin-8-yl)benzyl]amino}-2-oxoethyl)pyrimidine; isolated as an HCl salt | Calc'd: 518.1935 Observed: 518.1960 |
| 39-11 (5-3) | 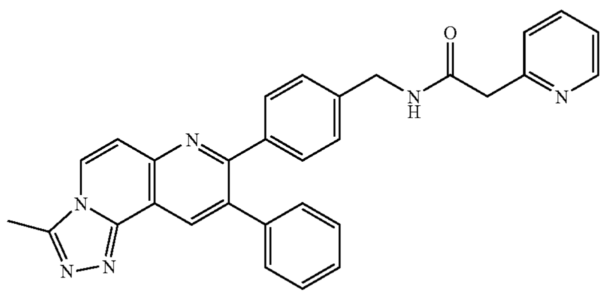 | 2-(2-{[4-(3-methyl-9-phenyl[1,2,4]triazolo[3,4-f]-1,6-naphthyridin-8-yl)benzyl]amino}-2-oxoethyl)pyridine; isolated as an HCl salt | Calc'd: 485.2085 Observed: 485.2118 |
| 39-12 (5-3) | 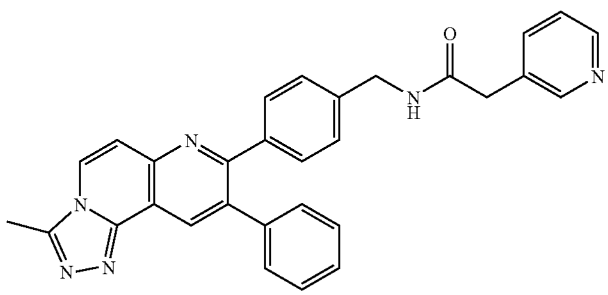 | 3-(2-{[4-(3-methyl-9-phenyl[1,2,4]triazolo[3,4-f]-1,6-naphthyridin-8-yl)benzyl]amino}-2-oxoethyl)pyridinium chloride | Calc'd: 243.1079 Observed: 243.1083 |
| 39-13 (5-3) | 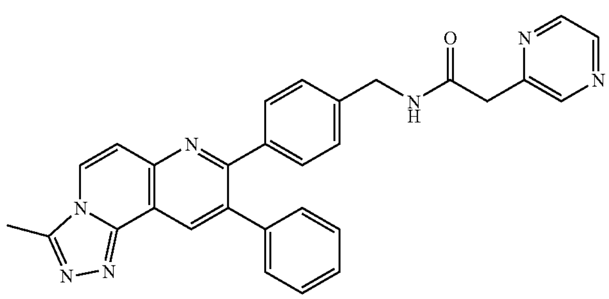 | N-[4-(3-methyl-9-phenyl[1,2,4]triazolo[3,4-f]-1,6-naphthyridin-8-yl)benzyl]-2-pyrazin-2-ylacetamide | Calcd'd: 486.2037 Observed: 486.2044 |
| 39-14 (5-3) | 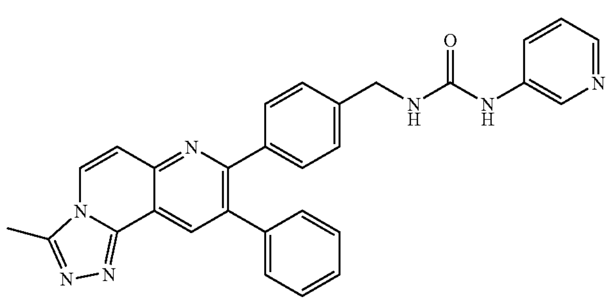 | 3-methyl-9-phenyl-8-[4-({[[(pyridin-3-ylamino)carbonyl]amino}methyl)phenyl][1,2,4]triazolo[3,4-f]-1,6-naphthyridine; isolated as an HCl salt | Calc'd: 486.2037 Observed: 486.2056 |

TABLE 14-continued

| Cmp (amine) | Structure | Name | HRMS m/z (M + H) |
|---|---|---|---|
| 39-15 (5-3) | 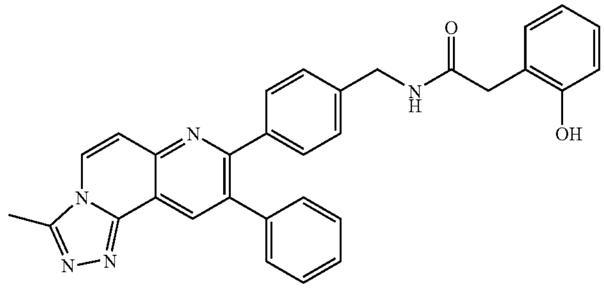 | 2-(2-hydroxyphenyl)-N-[4-(3-methyl-9-phenyl[1,2,4]triazolo[3,4-f]-1,6-naphthyridin-8-yl)benzyl]acetamide | Calc'd: 500.2081<br>Observed: 500.2087 |
| 39-16 (5-3) | 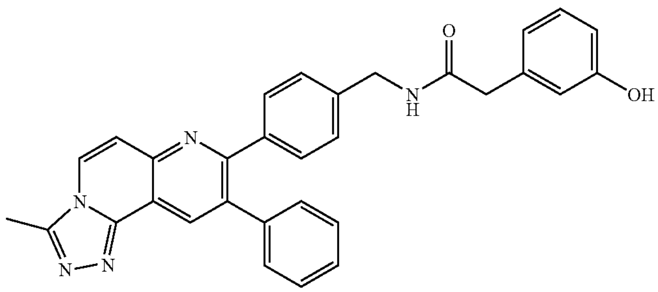 | 2-(3-hydroxyphenyl)-N-[4-(3-methyl-9-phenyl[1,2,4]triazolo[3,4-f]-1,6-naphthyridin-8-yl)benzyl]acetamide | Calc'd: 500.2081<br>Observed: 500.2086 |
| 39-17 (5-3) | 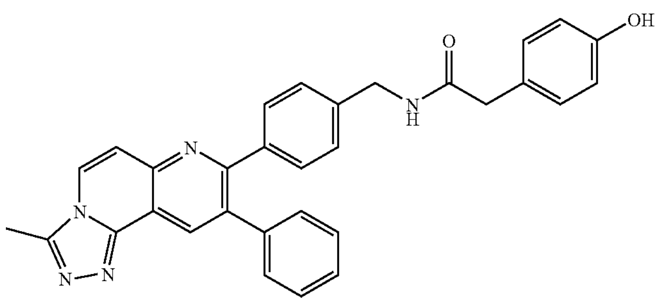 | 2-(4-hydroxyphenyl)-N-[4-(3-methyl-9-phenyl[1,2,4]triazolo[3,4-f]-1,6-naphthyridin-8-yl)benzyl]acetamide | Calc'd: 500.2081<br>Observed: 500.2085 |
| 39-18 (5-3) | 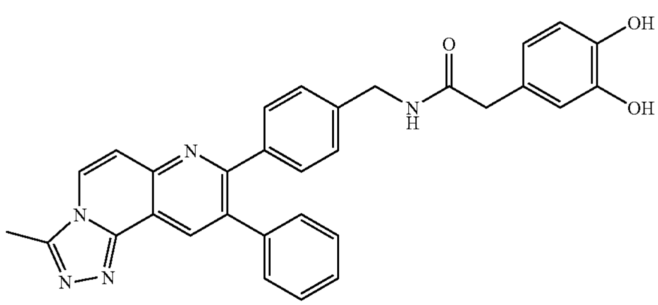 | 2-(3,4-dihydroxyphenyl)-N-[4-(3-methyl-9-phenyl[1,2,4]triazolo[3,4-f]-1,6-naphthyridin-8-yl)benzyl]acetamide | Calc'd: 576.2030<br>Observed: 576.2025 |
| 39-19 (5-3) | 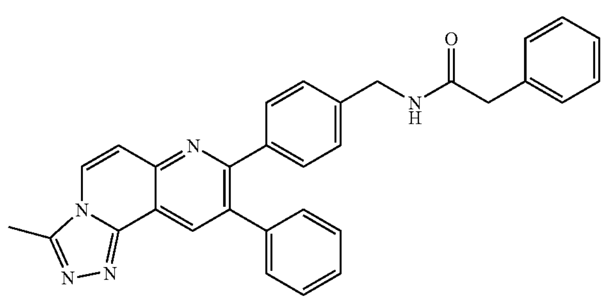 | N-[4-(3-methyl-9-phenyl[1,2,4]triazolo[3,4-f]-1,6-naphthyridin-8-yl)benzyl]-2-phenylacetamide | Calc'd: 484.2132<br>Observed: 484.2161 |

TABLE 14-continued

| Cmp (amine) | Structure | Name | HRMS m/z (M + H) |
|---|---|---|---|
| 39-20 (5-3) | 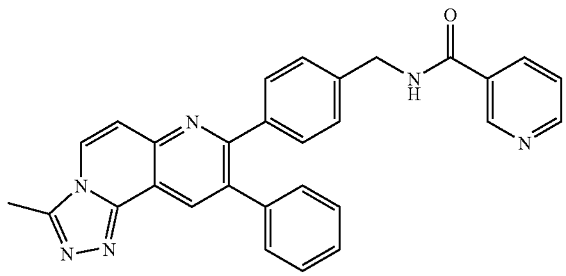 | 3-methyl-9-phenyl-8-(4-{[(pyridin-3-ylcarbonyl)amino]methyl}phenyl)[1,2,4]triazolo[3,4-f]-1,6-naphthyridine; isolated as an HCl salt | Calc'd: 471.1928<br>Observed: 471.1928 |
| 39-21 (5-3) | 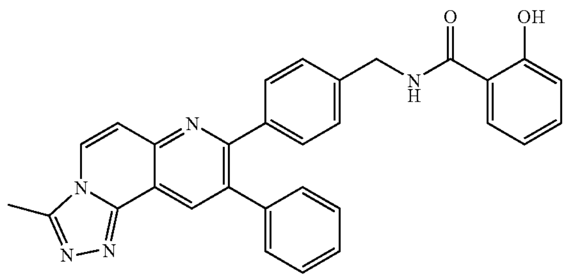 | 2-hydroxy-N-[4-(3-methyl-9-phenyl[1,2,4]triazolo[3,4-f]-1,6-naphthyridin-8-yl)benzyl]benzamide | Calc'd: 486.1925<br>Observed: 486.1919 |
| 39-22 (5-3) | 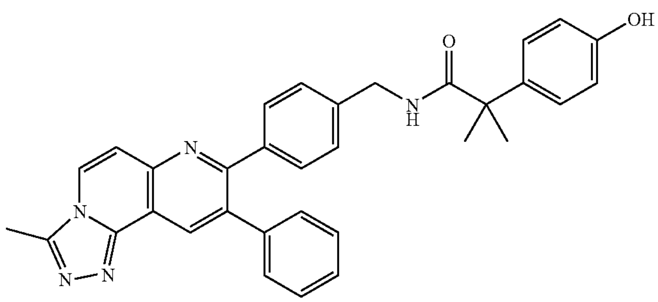 | 2-(4-hydroxyphenyl)-2-methyl-N-[4-(3-methyl-9-phenyl[1,2,4]triazolo[3,4-f]-1,6-naphthyridin-8-yl)benzyl]propanamide | Calc'd: 528.2394<br>Observed: 528.2386 |
| 39-23 (5-3) | 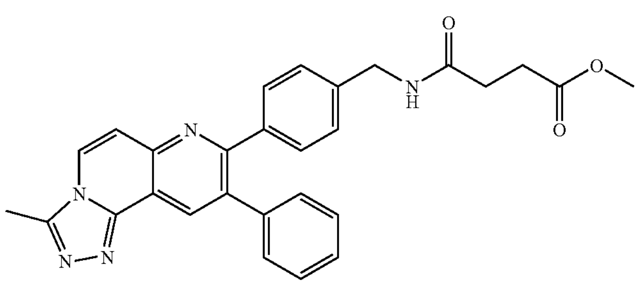 | methyl 4-{[4-(3-methyl-9-phenyl[1,2,4]triazolo[3,4-f]-1,6-naphthyridin-8-yl)benzyl]amino}-4-oxobutanoate | Calc'd: 480.2030<br>Observed: 480.2030 |
| 39-24 (5-3) | 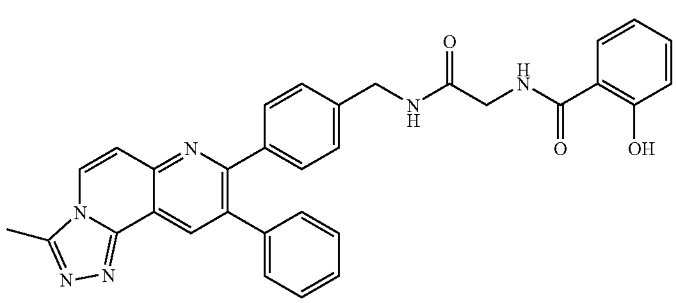 | 2-hydroxy-N-(2-{[4-(3-methyl-9-phenyl[1,2,4]triazolo[3,4-f]-1,6-naphthyridin-8-yl)benzyl]amino}-2-oxoethyl)benzamide | Calc'd: 543.2139<br>Observed: 543.2127 |

TABLE 14-continued

| Cmp (amine) | Structure | Name | HRMS m/z (M + H) |
|---|---|---|---|
| 39-25 (5-3) | 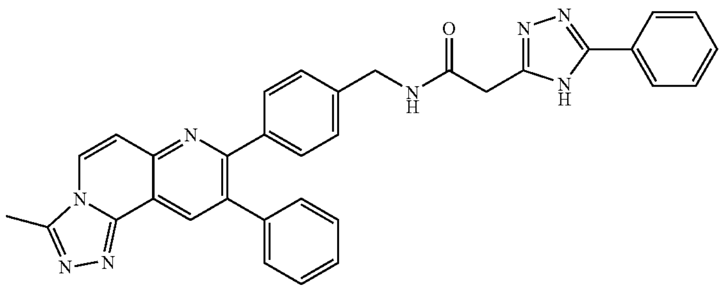 | N-[4-(3-methyl-9-phenyl[1,2,4]triazolo[3,4-f]-1,6-naphthyridin-8-yl)benzyl]-2-(5-phenyl-4H-1,2,4-triaozl-3-yl)acetamide | Calc'd: 551.2303 Observed: 551.2292 |
| 39-26 (5-3) | 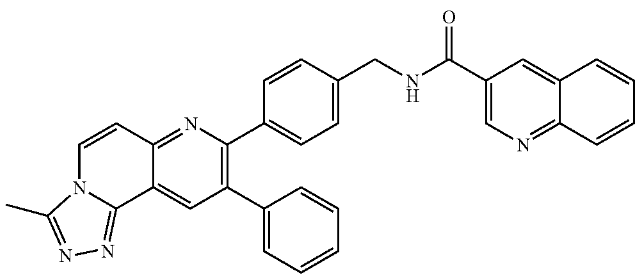 | 3-methyl-9-phenyl-8-(4-{[(quinolin-3-ylcarbonyl)amino]methyl}phenyl)[1,2,4]triazolo[3,4-f]-1,6-naphthyridine; isolated as an HCl salt | Calc'd: 521.2085 Observed: 521.2061 |
| 39-27 (5-3) | 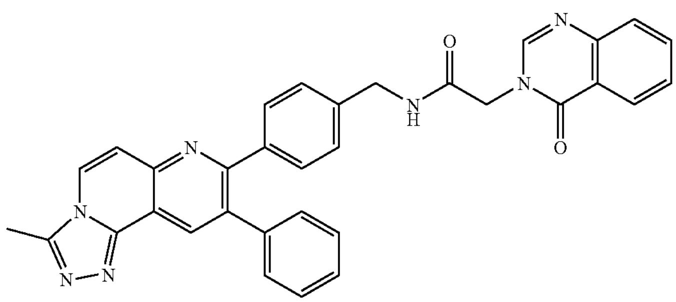 | N-[4-(3-methyl-9-phenyl[1,2,4]triazolo[3,4-f]-1,6-naphthyridin-8-yl)benzyl]-2-(4-oxoquinazolin-3(4H)-yl)acetamide | Calc'd: 552.2143 Observed: 552.2126 |
| 39-28 (5-3) | 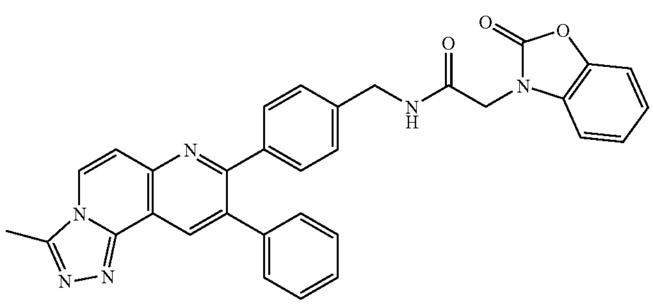 | N-[4-(3-methyl-9-phenyl[1,2,4]triazolo[3,4-f]-1,6-naphthyridin-8-yl)benzyl]-2-(2-oxo-1,3-benzoxazol-3(2H)-yl)acetamide | Calc'd: 541.1983 Observed: 541.1965 |
| 39-29 (5-3) | 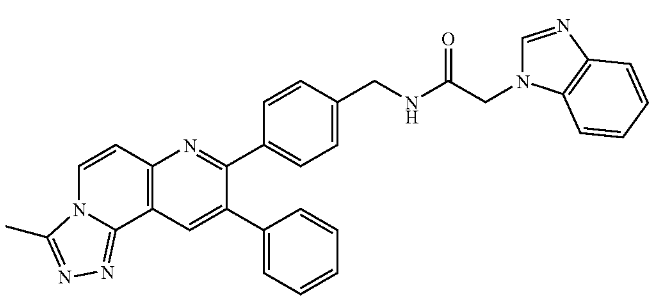 | 8-(4-{[(1H-benzimidazol-1-ylacetyl)amino]methyl}phenyl)-3-methyl-9-phenyl[1,2,4]triazolo[3,4-f]-1,6-naphthyridine; isolated as an HCl salt | Calc'd: 524.2194 Observed: 524.2199 |

TABLE 14-continued

| Cmp (amine) | Structure | Name | HRMS m/z (M + H) |
|---|---|---|---|
| 39-30 (5-3) | 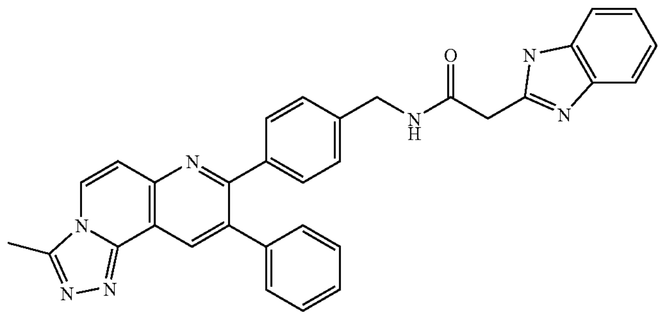 | 8-(4-{[(1H-benzimidazol-2-ylacetyl)amino]methyl} phenyl)-3-methyl-9-phenyl[1,2,4]triazolo[3,4-f]-1,6-naphthyridine; isolated as an HCl salt | Calc'd: 524.2194 Observed: 524.2185 |
| 39-31 (5-3) | 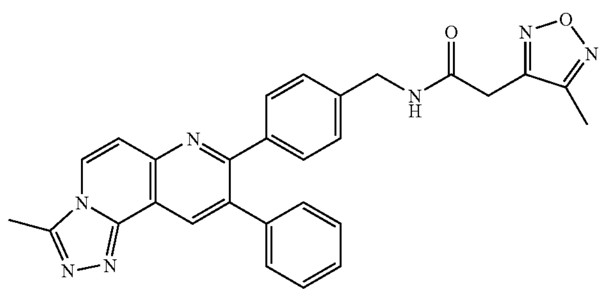 | 2-(4-methyl-1,2,5-oxadiazol-3-yl)-N-[4-(3-methyl-9-phenyl[1,2,4]triazolo[3,4-f]-1,6-naphthyridin-8-yl)benzyl]acetamide | Calc'd: 440.1986 Observed: 490.1976 |
| 39-32 (5-3) | 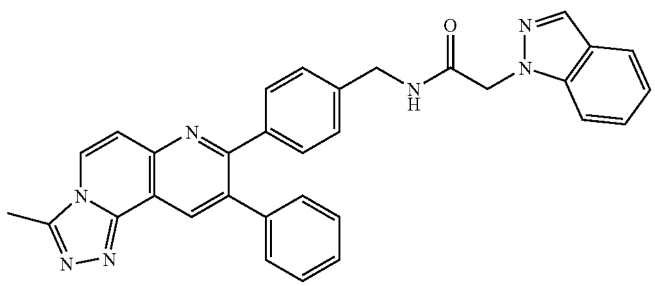 | 2-(1H-indazol-1-yl)-N-[4-(3-methyl-9-phenyl[1,2,4]triazolo[3,4-f]-1,6-naphthyridin-8-yl)benzyl]acetamide | Calc'd: 524.2194 Observed: 524.2171 |
| 39-33 (5-3) | 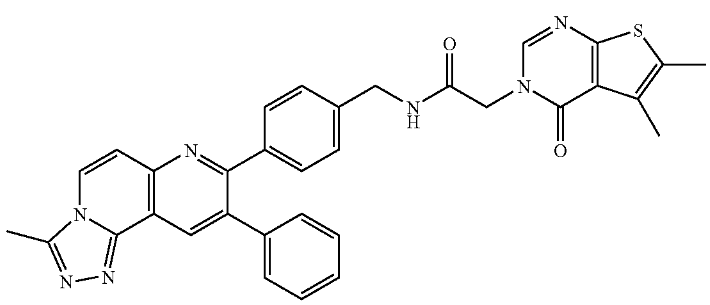 | 2-(5,6-dimethyl-4-oxothieno[2,3-d]pyrimidin-3(4H)-yl)-N-[4-(3-methyl-9-phenyl[1,2,4]triazolo[3,4-f]-1,6-naphthyridin-8-yl)benzyl]acetamide | Calc'd: 586.2020 Observed: 586.1993 |
| 39-34 (5-3) | 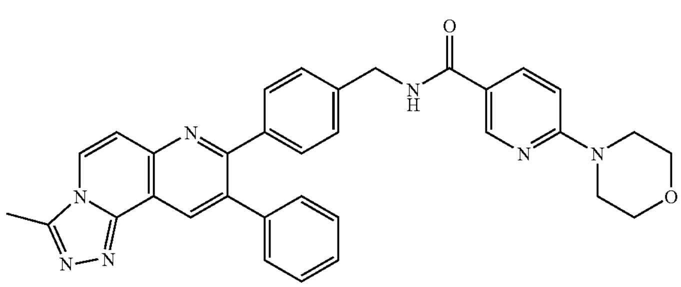 | 3-methyl-8-[4-({[(6-morpholin-4-ylpyridin-3-yl)carbonyl]amino}methyl)phenyl]-9-phenyl[1,2,4]triazolo[3,4-f]-1,6-naphthyridine; isolated as an HCl salt | Calc'd: 556.2456 Observed: 556.2441 |

TABLE 14-continued

| Cmp (amine) | Structure | Name | HRMS m/z (M + H) |
|---|---|---|---|
| 39-35 (5-3) | 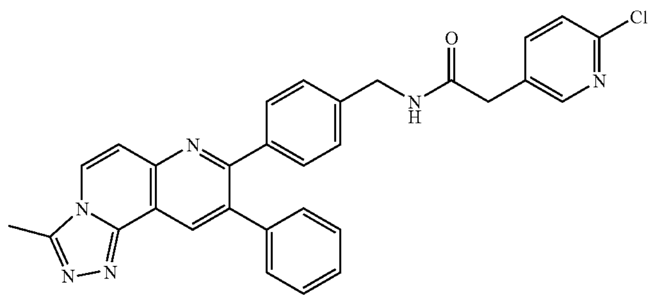 | 2-(6-chloropyridin-3-yl)-N-[4-(3-methyl-9-phenyl[1,2,4]triazolo[3,4-f]-1,6-naphthyridin-8-yl)benzyl]acetamide | Calc'd: 519.1695 Observed: 519.1673 |
| 39-36 (5-3) | 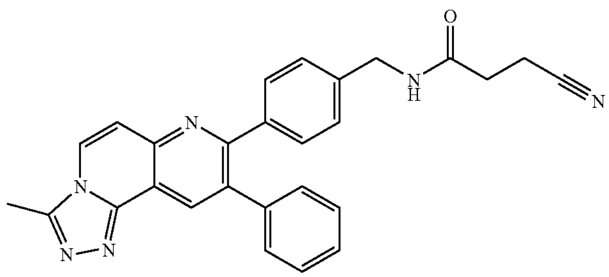 | 3-cyano-N-[4-(3-methyl-9-phenyl[1,2,4]triazolo[3,4-f]-1,6-naphthyridin-8-yl)benzyl]propanamide | Calc'd: 447.1928 Observed: 447.1921 |
| 39-37 (5-3) | 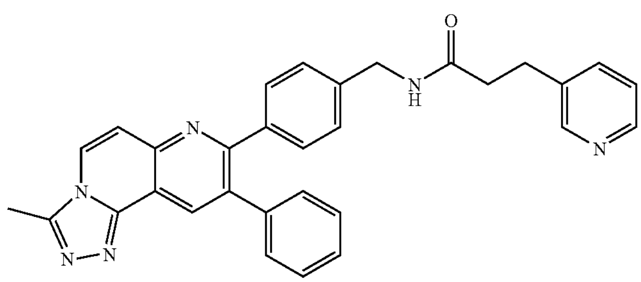 | 3-methyl-9-phenyl-8-(4-{[(3-pyridin-3-yl propanoyl)amino]methyl} phenyl)[1,2,4]triazolo[3,4-f]-1,6-naphthyridine; isolated as an HCl salt | Calc'd: 499.2241 Observed: 499.2244 |
| 39-38 (16-44) | 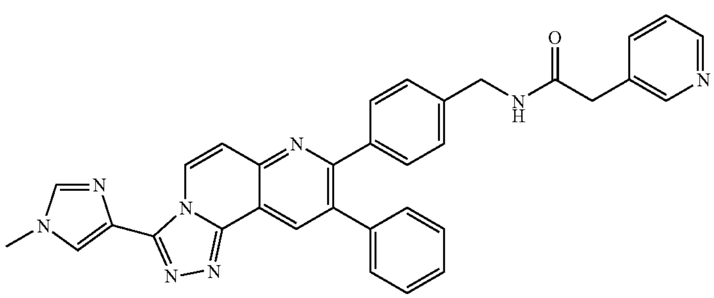 | 3-(1-methyl-1H-imidazol-4-yl)-9-phenyl-8-(4-{[(pyridin-3-ylacetyl) amino]methyl}phenyl)[1,2,4]triazolo[3,4-f]-1,6-naphthyridine; isolated as an HCl salt | Calc'd: 551.2303 Observed: 551.2326 |
| 39-39 (16-22) | 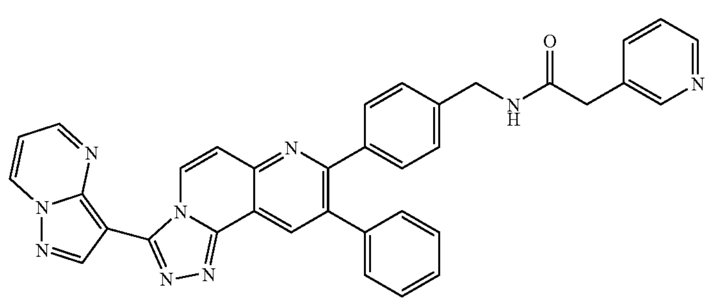 | 9-phenyl-3-pyrazolo[1,5-a]pyrimidin-3-yl-8-(4-{[(pyridin-3-ylacetyl) amino]methyl}phenyl)[1,2,4]triazolo[3,4-f]-1,6-naphthyridine; isolated as an HCl salt | Calc'd: 588.2255 Observed: 588.2276 |

TABLE 14-continued

| Cmp (amine) | Structure | Name | HRMS m/z (M + H) |
|---|---|---|---|
| 39-40 (13-10) | 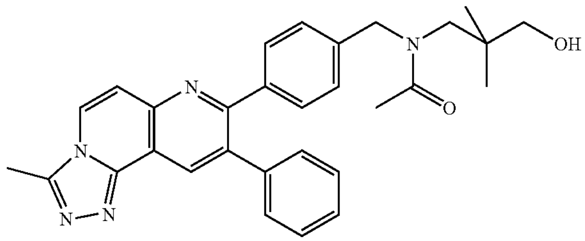 | N-(3-hydroxy-2,2-dimethylpropyl)-N-[4-(3-methyl-9-phenyl[1,2,4]triazolo[3,4-f]-1,6-naphthyridin-8-yl)benzyl]acetamide | Calc'd: 494.2551 Observed: 494.2557 |
| 39-41 (13-16) | 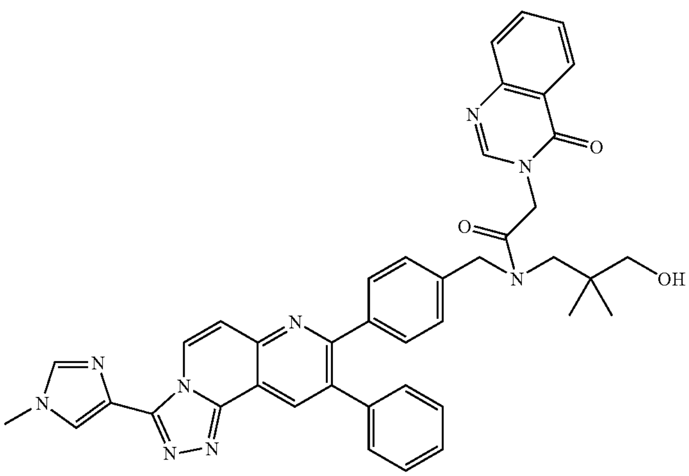 | N-(3-hydroxy-2,2-dimethylpropyl)-N-{4-[3-(1-methyl-1H-imidazol-4-yl)-9-phenyl[1,2,4]triazolo[3,4-f]-1,6-naphthyridin-8-yl]benzyl}-2-(4-oxoquinazolin-3(4H)-yl)acetamide | LRMS (M + 1) = Observed: 704.3 |
| 39-42 (13-20) | 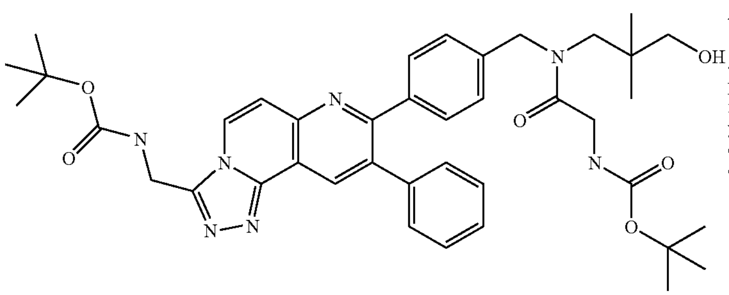 | tert-butyl {2-[[4-(3-{[(tert-butoxycarbonyl)amino]methyl}-9-phenyl[1,2,4]triazolo[3,4-f]-1,6-naphthyridin-8-yl)benzyl](3-hydroxy-2,2-dimethylpropyl)amino]-2-oxoethyl}carbamate | Calc'd: 724.3817 Observed: 724.3822 |
| 39-43 (33-5) | 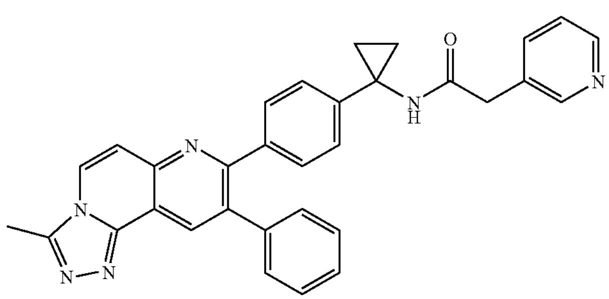 | 3-methyl-9-phenyl-8-(4-{1-[(pyridin-3-ylacetyl)amino]cyclopropyl}phenyl)[1,2,4]triazolo[3,4-f]-1,6-naphthyridine; isolated as a TFA salt | Calc'd: 511.2241 Observed: 511.2264 |
| 39-44 (33-5) | 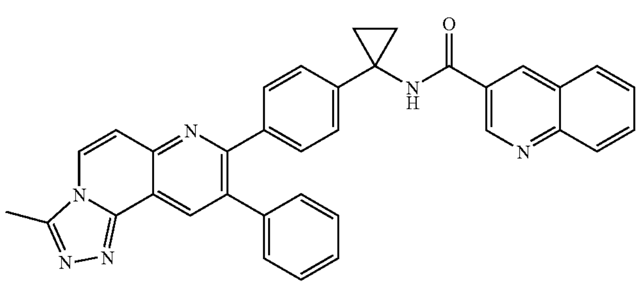 | 3-methyl-9-phenyl-8-(4-{1-[(quinolin-3-ylcarbonyl)amino]cyclopropyl}phenyl)[1,2,4]triazolo[3,4-f]-1,6-naphthyridine; isolated as a TFA salt | Calc'd: 547.2241 Observed: 547.2225 |

TABLE 14-continued

| Cmp (amine) | Structure | Name | HRMS m/z (M + H) |
|---|---|---|---|
| 39-45 (33-5) | 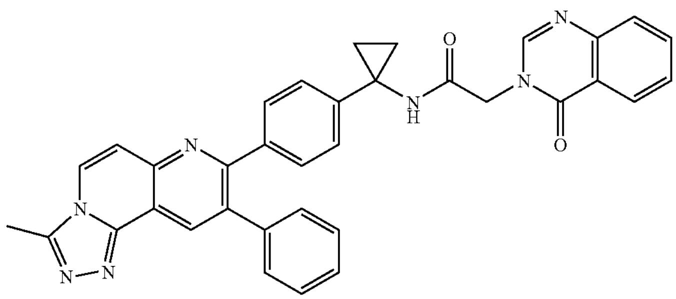 | N-{1-[4-(3-methyl-9-phenyl[1,2,4]triazolo[3,4-f]-1,6-naphthyridin-8-yl)phenyl]cyclopropyl}-2-(4-oxoquinazolin-3(4H)-yl)acetamide | Calc'd: 578.2299 Observed: 578.2276 |
| 39-46 (33-6) | 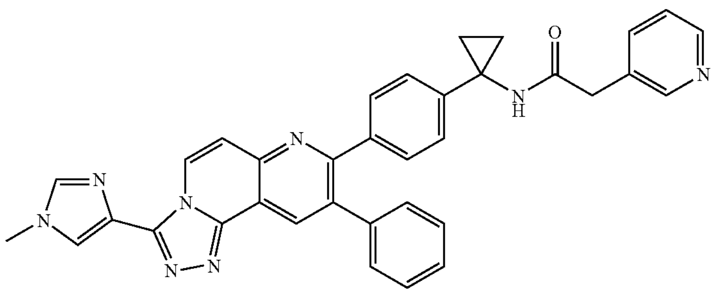 | 3-(1-methyl-1H-imidazol-4-yl)-9-phenyl-8-(4-{1-[(pyridin-3-ylacetyl) amino]cyclopropyl} phenyl)[1,2,4]triazolo[3,4-f]-1,6-naphthyridine; isolated as a TFA salt | Calc'd: 577.2459 Observed: 577.2488 |
| 39-47 (34-5) | 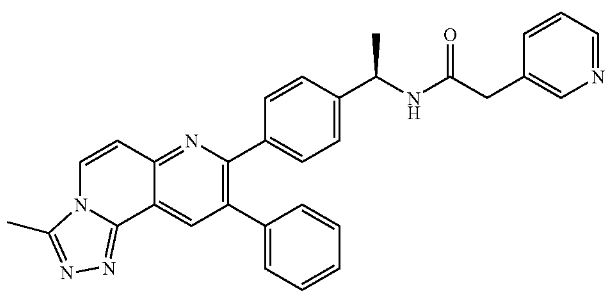 | N-{(1R)-1-[4-(3-methyl-9-phenyl[1,2,4]triazolo [3,4-f]-1,6-naphthyridin-8-yl)phenyl]ethyl}-2-pyridin-3-ylacetamide; isolated as a HCl salt | LRMS (M + 1) = Observed: 498.8 |
| 39-48 (34-5) | 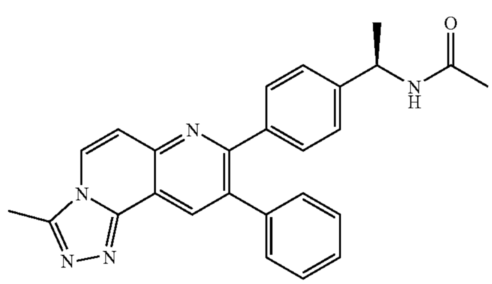 | N-{(1R)-1-[4-(3-methyl-9-phenyl[1,2,4]triazolo [3,4-f]-1,6-naphthyridin-8-yl)phenyl]ethyl} acetamide | LRMS (M + 1) = Observed: 422.2 |
| 39-49 (34-5) | 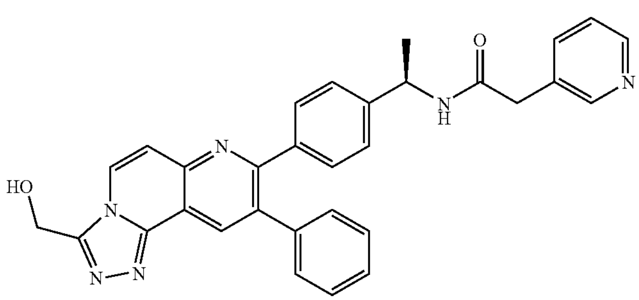 | N-((1R)-1-{4-[3-(hydroxymethyl)-9-phenyl[1,2,4]triazolo[3,4-f]-1,6-naphthyridin-8-yl]phenyl}ethyl)-2-pyridin-3-ylacetamide; isolated as a HCl salt | LRMS (M + 1) = Observed: 514.8 |

TABLE 14-continued

| Cmp (amine) | Structure | Name | HRMS m/z (M + H) |
|---|---|---|---|
| 39-50 (38) | 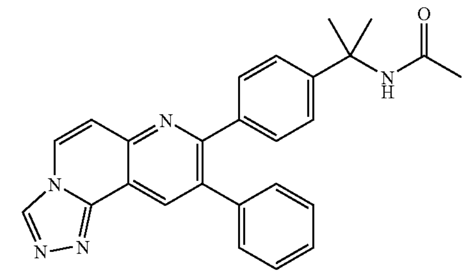 | N-{1-methyl-1-[4-(9-phenyl[1,2,4]triazolo[3,4-f]-1,6-naphthyridin-8-yl)phenyl]ethyl}acetamide | LRMS (M + 1) = Observed: 422.3 |
| 39-51 (37-4) | 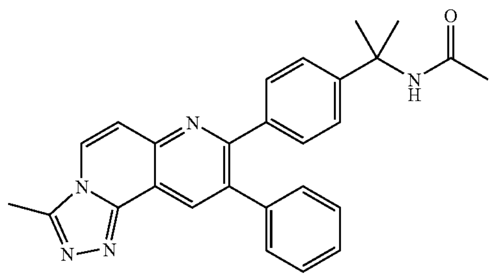 | N-{1-methyl-1-[4-(3-methyl-9-phenyl[1,2,4]triazolo[3,4-f]-1,6-naphthyridin-8-yl)phenyl]ethyl}acetamide | LRMS (M + 1) = Observed: 435.8 |

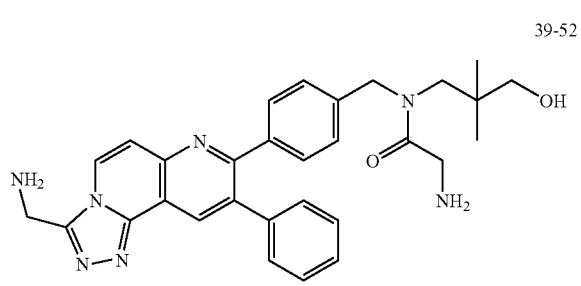

2-[{4-[3-(ammoniomethyl)-9-phenyl[1,2,4]triazolo[3,4-f]-1,6-naphthyridin-8-yl]benzyl}(3-hydroxy-2,2-dimethylpropyl)amino]-2-oxoethanamine (39-52)

The title compound was prepared according to the procedures of Scheme 27 from 39-42; MS (M+H$^+$): Calc'd: 524.2769, Observed: 524.2777. Compound 39-52 was isolated as an HCl salt.

Example 1

Cloning of the Human Akt Isoforms and ΔPH-Akt1

The pS2neo vector (deposited in the ATCC on Apr. 3, 2001 as ATCC PTA-3253) was prepared as follows: The pRmHA3 vector (prepared as described in *Nucl. Acid Res.* 16:1043-1061 (1988)) was cut with BglII and a 2734 bp fragment was isolated. The pUChsneo vector (prepared as described in *EMBO J.* 4:167-171 (1985)) was also cut with BglII and a 4029 bp band was isolated. These two isolated fragments were ligated together to generate a vector termed pS2neo-1. This plasmid contains a polylinker between a metallothionine promoter and an alcohol dehydrogenase poly A addition site. It also has a neo resistance gene driven by a heat shock promoter. The pS2neo-1 vector was cut with Psp5II and BsiWI. Two complementary oligonucleotides were synthesized and then annealed (CTGCGGCCGC (SEQ. ID. NO.: 1) and GTACGCGGCCGCAG (SEQ. ID. NO.: 2)). The cut pS2neo-1 and the annealed oligonucleotides were ligated together to generate a second vector, pS2neo. Added in this conversion was a NotI site to aid in the linearization prior to transfection into S2 cells.

Human Akt1 gene was amplified by PCR (Clontech) out of a human spleen cDNA (Clontech) using the 5' primer: 5'CGCGAATTCAGATCTACCATGAGCGACGTGGCTATTGTG 3' (SEQ. ID. NO.: 3), and the 3' primer: 5' CGCTCTAGAGGATCCTCAGGCCGTGCTGCTGGC3' (SEQ. ID. NO.: 4). The 5' primer included an EcoRI and BglII site. The 3' primer included an XbaI and BamHI site for cloning purposes. The resultant PCR product was subcloned into pGEM3Z (Promega) as an EcoRI/Xba I fragment. For expression/purification purposes, a middle T tag was added to the 5' end of the full length Akt1 gene using the PCR primer: 5'GTACGATGCTGAACGATATCTTCG 3' (SEQ. ID. NO.: 5). The resulting PCR product encompassed a 5' KpnI site and a 3' BamHI site which were used to subclone the fragment in frame with a biotin tag containing insect cell expression vector, pS2neo.

For the expression of a pleckstrin homology domain (PH) deleted (Δaa 4-129, which includes deletion of a portion of the Akt1 hinge region) version of Akt1, PCR deletion mutagenesis was done using the full length Akt1 gene in the pS2neo vector as template. The PCR was carried out in 2 steps using overlapping internal primers (5'GAATACATGCCGATGGAAAGCGACGGGGCTGAA-GAGATGGAGGTG 3' (SEQ. ID. NO.: 6), and 5'CCCCTCCATCTCTTCAGCCCCGTCGCTTTCCATCGGCATGTATTC 3' (SEQ. ID. NO.: 7)) which encompassed the deletion and 5' and 3' flanking primers which encompassed the KpnI site and middle T tag on the 5' end. The final PCR product was digested with KpnI and SmaI and ligated into the pS2neo full length Akt1 KpnI/SmaI cut vector, effectively replacing the 5' end of the clone with the deleted version.

Human Akt3 gene was amplified by PCR of adult brain cDNA (Clontech) using the amino terminal oligo primer: 5'

GAATTCAGATCTACCATGAGCGATGTTACCATTGTG 3' (SEQ. ID. NO.: 8); and the carboxy terminal oligo primer: 5' TCTAGATCTTATTCTCGTCCACTTGCAGAG 3'(SEQ. ID. NO.: 9). These primers included a 5' EcoRI/BglII site and a 3' XbaI/BglII site for cloning purposes. The resultant PCR product was cloned into the EcoRI and XbaI sites of pGEM4Z (Promega). For expression/purification purposes, a middle T tag was added to the 5' end of the full length Akt3 clone using the PCR primer: 5'GGTACCATGGAATACATGCCGATG-GAAAGCGATGTTACCATTGTGAAG 3' (SEQ. ID. NO.: 10). The resultant PCR product encompassed a 5' KpnI site which allowed in frame cloning with the biotin tag containing insect cell expression vector, pS2neo.

Human Akt2 gene was amplified by PCR from human thymus cDNA (Clontech) using the amino terminal oligo primer: 5' AAGCTTAGATCTACCATGAATGAGGT-GTCTGTC 3' (SEQ. ID. NO.: 11); and the carboxy terminal oligo primer: 5'GAATTCGGATCCTCACTCGCGGAT-GCTGGC 3' (SEQ. ID. NO.: 12). These primers included a 5' HindIII/BglII site and a 3' EcoRI/BamHI site for cloning purposes. The resultant PCR product was subcloned into the HindIII/EcoRI sites of pGem3Z (Promega). For expression/purification purposes, a middle T tag was added to the 5' end of the full length Akt2 using the PCR primer: 5'GGTAC-CATGGAATACATGCCGATGGAAAATGAG-GTGTCTGTCATCAAAG 3' (SEQ. ID. NO.: 13). The resultant PCR product was subcloned into the pS2neo vector as described above.

Example 2

Expression of Human Akt Isoforms and ΔPH-Akt1

The DNA containing the cloned Akt1, Akt2, Akt3 and ΔPH-Akt1 genes in the pS2neo expression vector was purified and used to transfect Drosophila S2 cells (ATCC) by the calcium phosphate method. Pools of antibiotic (G418, 500 µg/ml) resistant cells were selected. Cell were expanded to a 1.0 L volume (~7.0×10$^6$/ml), biotin and CuSO$_4$ were added to a final concentration of 50 µM and 50 mM respectively. Cells were grown for 72 h at 27° C. and harvested by centrifugation. The cell paste was frozen at −70° C. until needed.

Example 3

Purification of Human Akt Isoforms and ΔPH-Akt1

Cell paste from one liter of S2 cells, described in Example 2, was lysed by sonication with 50 mls 1% CHAPS in buffer A: (50 mM Tris pH 7.4, 1 mM EDTA, 1 mM EGTA, 0.2 mM AEBSF, 10 µg/ml benzamidine, 5 µg/ml of leupeptin, aprotinin and pepstatin each, 10% glycerol and 1 mM DTT). The soluble fraction was purified on a Protein G Sepharose fast flow (Pharmacia) column loaded with 9 mg/ml anti-middle T monoclonal antibody and eluted with 75 µM EYMPME (SEQ. ID. NO.: 14) peptide in buffer A containing 25% glycerol. Akt/PKB containing fractions were pooled and the protein purity evaluated by SDS-PAGE. The purified protein was quantitated using a standard Bradford protocol. Purified protein was flash frozen on liquid nitrogen and stored at −70° C.

Akt and Akt pleckstrin homology domain deletions purified from S2 cells required activation. Akt and Akt pleckstrin homology domain deletions were activated (Alessi et al. *Current Biology* 7:261-269) in a reaction containing 10 nM PDK1 (Upstate Biotechnology, Inc.), lipid vesicles (10 µM phosphatidylinositol-3,4,5-trisphosphate—Metreya, Inc, 100 µM phosphatidylcholine and 100 µM phosphatidylserine—Avanti Polar lipids, Inc.) and activation buffer (50 mM Tris pH7.4, 1.0 mM DTT, 0.1 mM EGTA, 1.0 µM Microcystin—LR, 0.1 mM ATP, 10 mM MgCl$_2$, 333 µg/ml BSA and 0.1 mM EDTA). The reaction was incubated at 22° C. for 4 hours. Aliquots were flash frozen in liquid nitrogen.

Example 4

Akt Kinase Assays

Activated Akt isoforms and pleckstrin homology domain deletion constructs were assayed utilizing a GSK-derived biotinylated peptide substrate. The extent of peptide phosphorylation was determined by Homogeneous Time Resolved Fluorescence (HTRF) using a lanthanide chelate (Lance)-coupled monoclonal antibody specific for the phosphopeptide in combination with a streptavidin-linked allophycocyanin (SA-APC) fluorophore which will bind to the biotin moiety on the peptide. When the Lance and APC are in proximity (i.e. bound to the same phosphopeptide molecule), a non-radiative energy transfer takes place from the Lance to the APC, followed by emission of light from APC at 665 nm. Materials required for the assay:

A. Activated Akt isozyme or pleckstrin homology domain deleted construct

B. Akt peptide substrate: GSK3α (S21) Peptide #3928 biotin-GGRARTSSFAEPG (SEQ. ID. NO.:15), Macromolecular Resources.

C. Lance labeled anti-phospho GSK3a monoclonal antibody (Cell Signaling Technology, clone #27).

D. SA-APC (Prozyme catalog no. PJ25S lot #896067).

E. Microfluor®B U Bottom Microtiter Plates (Dynex Technologies, Catalog no. 7205).

F. Discovery® HTRF Microplate Analyzer, Packard Instrument Company.

G. 100× Protease Inhibitor Cocktail (PIC): 1 mg/ml benzamidine, 0.5 mg/ml pepstatin, 0.5 mg/ml leupeptin, 0.5 mg/ml aprotinin.

H. 10× Assay Buffer: 500 mM HEPES, pH 7.5, 1% PEG, mM EDTA, 1 mM EGTA, 1% BSA, 20 mM σ-Glycerol phosphate.

I. Quench Buffer: 50 mM HEPES pH 7.3, 16.6 mM EDTA, 0.1% BSA, 0.1% Triton X-100, 0.17 nM Lance labeled monoclonal antibody clone #27, 0.0067 mg/ml SA-APC J. ATP/MgCl$_2$ working solution: 1× Assay buffer, 1 mM DTT, 1×PIC, 125 mM KCl, 5% Glycerol, 25 mM MgCl$_2$, 375 TM ATP K. Enzyme working solution: 1× Assay buffer, 1 mM DTT, 1×PIC, 5% Glycerol, active Akt. The final enzyme concentrations were selected so that the assay was in a linear response range.

L. Peptide working solution: 1× Assay buffer, 1 mM DTT, 1×PIC, 5% Glycerol, 2 TM GSK3 biotinylated peptide #3928

The reaction is assembled by adding 16 TL of the ATP/MgCl$_2$ working solution to the appropriate wells of a 96-well microtiter plate. Inhibitor or vehicle (1.0 Ti) is added followed by 10 Ti of peptide working solution. The reaction is started by adding 13 Tl of the enzyme working solution and mixing. The reaction is allowed to proceed for 50 mM and then stopped by the addition of 60 Tl HTRF quench buffer. The stopped reactions were incubated at room temperature for at least 30 mM and then read on the Discovery instrument. Procedure for Streptavidin Flash Plate Assay:

Step 1:

A 1 µl solution of the test compound in 100% DMSO was added to 20 pa of 2× substrate solution (20 uM GSK3 Peptide, 300 µM ATP, 20 mM MgCl$_2$, 20 µCi/ml [γ$^{33}$P] ATP, 1× Assay Buffer, 5% glycerol, 1 mM DTT, 1×PIC, 0.1% BSA and 100 mM KCl). Phosphorylation reactions were initiated by adding 19 μl of 2× Enzyme solution (6.4 nM active Akt/PKB, 1× Assay Buffer, 5% glycerol, 1 mM DTT, 1×PIC and 0.1% BSA). The reactions were then incubated at room temperature for 45 minutes.

Step 2:

The reaction was stopped by adding 170 μl of 125 mM EDTA. 200 μl of stopped reaction was transferred to a Streptavidin Flashplate® PLUS (NEN Life Sciences, catalog no. SMP103). The plate was incubated for ≧10 minutes at room temperature on a plate shaker. The contents of each well was aspirated, and the wells rinsed 2 times with 200 μl TBS per well. The wells were then washed 3 times for 5 minutes with 200 μl TBS per well with the plates incubated at room temperature on a platform shaker during wash steps.

The plates were covered with sealing tape and counted using the Packard TopCount with the appropriate settings for counting [$^{33}$P] in Flashplates.

Procedure for Streptavidin Filter Plate Assay:

Step 1:

The enzymatic reactions as described in Step 1 of the Streptavidin Flash Plate Assay above were performed.

Step 2:

The reaction was stopped by adding 20 μl of 7.5M Guanidine Hydrochloride. 50 μl of the stopped reaction was transferred to the Streptavidin filter plate (SAM$^{2™}$ Biotin Capture Plate, Promega, catalog no. V7542) and the reaction was incubated on the filter for 1-2 minutes before applying vacuum.

The plate was then washed using a vacuum manifold as follows: 1) 4×200 μl/well of 2M NaCl; 2) 6×200 μl/well of 2M NaCl with 1% H$_3$PO$_4$; 3) 2×200 μl/well of diH$_2$O; and 4) 2×100 μl/well of 95% Ethanol. The membranes were then allowed to air dry completely before adding scintillant.

The bottom of the plate was sealed with white backing tape, 30 μl/well of Microscint 20 (Packard Instruments, catalog no. 6013621) was added. The top of the plate was sealed with clear sealing tape, and the plate then counted using the Packard TopCount with the appropriate settings for [$^{33}$P] with liquid scintillant.

Procedure for Phosphocellulose Filter Plate Assay:

Step 1:

The enzymatic reactions were performed as described in Step 1 of the Streptavidin Flash Plate Assay (above) utilizing KKGGRARTSSFAEPG (SEQ. ID. NO.: 16) as the substrate in place of biotin-GGRARTSSFAEPG.

Step 2:

The reaction was stopped by adding 20 μl of 0.75% H$_3$PO$_4$. 50 μl of stopped reaction was transferred to the filter plate (UNIFILTER™, Whatman P81 Strong Cation Exchanger, White Polystyrene 96 Well Plates, Polyfiltronics, catalog no. 7700-3312) and the reaction incubated on the filter for 1-2 minutes before applying vacuum.

The plate was then washed using a vacuum manifold as follows: 1) 9×200 Owen of 0.75% H$_3$PO$_4$; and 2) 2×200 μl/well of diH$_2$O. The bottom of the plate was sealed with white backing tape, then 30 μl/well of Microscint 20 was added. The top of the plate was sealed with clear sealing tape, and the plate counted using the Packard TopCount with the appropriate settings for [$^{33}$P] and liquid scintillant.

PKA assay:

Each individual PKA assay consists of the following components:

A. 5×PKA assay buffer (200 mM Tris pH7.5, 100 mM MgCl$_2$, 5 mM σ-mercaptoethanol, 0.5 mM EDTA)

B. 50 μM stock of Kemptide (Sigma) diluted in water

C. $^{33}$P-ATP prepared by diluting 1.0 μl $^{33}$P-ATP [10 mCi/ml] into 200 Tl of a 50 μM stock of unlabeled ATP D. 10 μl of a 70 nM stock of PKA catalytic subunit (UBI catalog #14-114) diluted in 0.5 mg/ml BSA E. PKA/Kemptide working solution: equal volumes of 5×PKA assay buffer, Kemptide solution and PKA catalytic subunit.

The reaction is assembled in a 96 deep-well assay plate. The inhibitor or vehicle (10 Ti) is added to 10 Ti of the $^{33}$P-ATP solution. The reaction is initiated by adding 30 Tl of the PKA/Kemptide working solution to each well. The reactions were mixed and incubated at room temperature for 20 min. The reactions were stopped by adding 50 Tl of 100 mM EDTA and 100 mM sodium pyrophosphate and mixing.

The enzyme reaction product (phosphorylated Kemptide) was collected on p81 phosphocellulose 96 well filter plates (Millipore). To prepare the plate, each well of a p81 filter plate was filled with 75 mM phosphoric acid. The wells were emptied through the filter by applying a vacuum to the bottom of the plate. Phosphoric acid (75 mM, 170 μl) was added to each well. A 30 μl aliquot from each stopped PKA reaction was added to corresponding wells on the filter plate containing the phosphoric acid. The peptide was trapped on the filter following the application of a vacuum and the filters were washed 5 times with 75 mM phosphoric acid. After the final wash, the filters were allowed to air dry. Scintillation fluid (30 μl) was added to each well and the filters counted on a TopCount (Packard).

PKC assay:

Each PKC assay consists of the following components:

A. 10×PKC co-activation buffer: 2.5 mM EGTA, 4 mM CaCl$_2$

B. 5×PKC activation buffer: 1.6 mg/ml phosphatidylserine, 0.16 mg/ml diacylglycerol, 100 mM Tris pH 7.5, 50 mM MgCl$_2$, 5 mM 14-mercaptoethanol C. $^{33}$P-ATP prepared by diluting 1.0 μl $^{33}$P-ATP [10 mCi/ml] into 100 μl of a 100 μM stock of unlabeled ATP D. Myelin basic protein (350 μg/ml, UBI) diluted in water E. PKC (50 ng/ml, UBI catalog #14-115) diluted into 0.5 mg/ml BSA F. PKC/Myelin Basic Protein working solution: Prepared by mixing 5 volumes each of PKC co-activation buffer and Myelin Basic protein with 10 volumes each of PKC activation buffer and PKC.

The assays were assembled in 96 deep-well assay plates. Inhibitor or vehicle (10 Ti) was added to 5.0 ul of $^{33}$P-ATP. Reactions were initiated with the addition of the PKC/Myelin Basic Protein working solution and mixing. Reactions were incubated at 30° C. for 20 min. The reactions were stopped by adding 50 Tl of 100 mM EDTA and 100 mM sodium pyrophosphate and mixing. Phosphorylated Mylein Basic Protein was collected on PVDF membranes in 96 well filter plates and quantitated by scintillation counting.

Compounds of the instant invention described in the Schemes and Tables were tested in the assay described above and were found to have IC$_{50}$ of ≦50 μM against one or more of Akt1, Akt2 and Akt3.

Example 5

Cell Based Assays to Determine Inhibition of Akt/PKB

Cells (for example LnCaP or a PTEN$^{(-/-)}$ tumor cell line with activated Akt/PKB) were plated in 100 mM dishes. When the cells were approximately 70 to 80% confluent, the cells were refed with 5 mls of fresh media and the test compound added in solution. Controls included untreated cells, vehicle treated cells and cells treated with either LY294002 (Sigma) or wortmanin (Sigma) at 20 μM or 200 nM, respectively. The cells were incubated for 2, 4 or 6 hrs, and the media removed, the cells were washed with PBS, scraped and transferred to a centrifuge tube. They were pelleted and washed again with PBS. Finally, the cell pellet was resuspended in lysis buffer (20 mM Tris pH8, 140 mM NaCl, 2 mM EDTA, 1% Triton, 1 mM Na Pyrophosphate, 10 mM σ-Glycerol Phosphate, 10 mM NaF, 0.5 mm NaVO$_4$, 1 μM Microsystine, and 1× Protease Inhibitor Cocktail), placed on ice for 15 minutes and gently vortexed to lyse the cells. The lysate was spun in a Beckman tabletop ultra centrifuge at 100,000×g at 4° C. for 20 min. The supernatant protein was quantitated by a standard Bradford protocol (BioRad) and stored at −70° C. until needed.

Proteins were immunoprecipitated (IP) from cleared lysates as follows: For Akt1/PKBI, lysates are mixed with Santa Cruz sc-7126 (D-17) in NETN (100 mM NaCl, 20 mM Tris pH 8.0, 1 mM EDTA, 0.5% NP-40) and Protein A/G Agarose (Santa Cruz sc-2003) was added. For Akt2/PKBσ, lysates were mixed in NETN with anti-Akt2 agarose (Upstate Biotechnology #16-174) and for Akt3/PKBK, lysates were mixed in NETN with anti-Akt3 agarose (Upstate Biotechnology #16-175). The IPs were incubated overnight at 4° C., washed and separated by SDS-PAGE.

Western blots were used to analyze total Akt, pThr308 Akt1, pSer473 Akt1, and corresponding phosphorylation sites on Akt2 and Akt3, and downstream targets of Akt using specific antibodies (Cell Signaling Technology): Anti-Total Akt (cat. no. 9272), Anti-Phospho Akt Serine 473 (cat. no. 9271), and Anti-Phospho Akt Threonine 308 (cat. no. 9275). After incubating with the appropriate primary antibody diluted in PBS+0.5% non-fat dry milk (NFDM) at 4° C. overnight, blots were washed, incubated with Horseradish peroxidase (HRP)-tagged secondary antibody in PBS+0.5% NFDM for 1 hour at room temperature. Proteins were detected with ECL Reagents (Amersham/Pharmacia Biotech RPN2134).

Example 6

Heregulin Stimulated Akt Activation

MCF7 cells (a human breast cancer line that is PTENn were plated at 1×10$^6$ cells per 100 mM plate. When the cells were 70-80% confluent, they were refed with 5 ml of serum free media and incubated overnight. The following morning, compound was added and the cells were incubated for 1-2 hrs, after which time heregulin was added (to induce the activation of Akt) for 30 minutes and the cells were analyzed as described above.

Example 7

Inhibition Of Tumor Growth

In vivo efficacy of an inhibitor of the growth of cancer cells may be confirmed by several protocols well known in the art.

Human tumor cell lines which exhibit a deregulation of the PI3K pathway (such as LnCaP, PC3, C33a, OVCAR-3, MDA-MB-468, A2780 or the like) are injected subcutaneously into the left flank of 6-10 week old female nude (also male mice [age 10-14 weeks] are used for prostate tumor xenografts [LnCaP and PC3]) mice (Harlan) on day 0. The mice are randomly assigned to a vehicle, compound or combination treatment group. Daily subcutaneous administration begins on day 1 and continues for the duration of the experiment. Alternatively, the inhibitor test compound may be administered by a continuous infusion pump. Compound, compound combination or vehicle is delivered in a total volume of 0.2 ml. Tumors are excised and weighed when all of the vehicle-treated animals exhibited lesions of 0.5-1.0 cm in diameter, typically 4 to 5.5 weeks after the cells were injected. The average weight of the tumors in each treatment group for each cell line is calculated.

Example 8

Spot Multiplex Assay

This procedure describes a sandwich immunoassay used to detect multiple phosphorylated proteins in the same well of a 96 well format plate. Cell lysates are incubated in 96-well plates on which different capture antibodies are placed on spatially distinct spots in the same well. Phoshorylation-specific rabbit polyclonal antibodies are added and the complex is detected by an anti-rabbit antibody labeled with an electrochemiluminescent tag.
96-Well LNCaP Plates+/−Compounds:
Spin in Beckman J6 1200 rpm 10 min, aspirate media. Add 50/21/well: TBS (Pierce #28376-20 mM Tris pH 7.5, 150 mM NaCl)+1% Triton X-100+Protease and Phosphatase Inhibitors. Wrap in plastic wrap, place in −70° C. freezer until completely frozen. Block Multiplex Plates (Meso Scale Discovery, Gaithersburg, Md.) with 3% Blocker A in 1× Tris Wash Buffer, 150 μl/well. Cover with plate sealer, incubate on Micromix shaker RT 2 h (minimum). Wash with 1×RCM 51 (TTBS). Thaw cell lysate plates on ice, add 40 μl lysate/well into blocked plates. Cover with plate sealer, incubate on Micromix shaker 4° C., O/N, Wash with 1×RCM 51. Dilute Secondary Antibodies in 1% Blocker A in 1× Tris Wash Buffer: Anti phospho AKT (T308), Anti phospho Tuberin (T1462), alone or in combination. Add 25 μl/well, cover with plate sealer, incubate on Micromix shaker RT 3 h. Wash with 1×RCM 51. Dilute Ru-GAR in 1% Blocker A in 1× Tris Wash Buffer. Add 25 μl/well, cover with plate sealer, incubate on Micromix shaker RT 1 h. Wash with 1×RCM 51. Dilute 4× Read Buffer T to 1× with Water, add 200 μl diluted Read Buffer/well
Read on Sector 6000 Imager.
Protease and Phosphatase Inhibitors:
Microcystin-LR, Calbiochem #475815 to 1 μM final concentration (stock=500 μM)
Calbiochem #524624, 100× Set I
biochem #524625, 100× Set II
Calbiochem #539134, 100× Set III
Anti Phospho AKT (T308):
Cell Signaling Technologies #9275
Anti Phospho Tuberin (T1462):
Covance Affinity Purified (Rabbits MS 2731/2732)
Ru-GAR=Ruthenylated Goat anti Rabbit
10× Tris Wash Buffer, Blocker A and 4× Read Buffer T
10×RCM 51 (10×TTBS, RCM 51)
1×=20 mM Tris pH 7.5, 140 mM NaCl, 0.1% Tween-20

Example 9

Cell-Based (In-Vivo) Assay

This procedure describes a cell-based (in vivo) activity assay for the Akt serine/threonine kinase. Activated endogenous Akt is capable of phosphorylating a specific Akt substrate (GSK3(3) peptide which is biotinylated. Detection is performed by Homogeneous Time Resolved Fluorescence (HTRF) using a Europium Kryptate [Eu(K)] coupled antibody specific for the phosphopeptide and streptavidin linked XL665 fluorophore which will bind to the biotin moiety on the peptide. When the [Eu(K)] and XL665 are in proximity (i.e. bound to the same phosphopeptide molecule) a non-radiative energy transfer takes place from the Eu(K) to the XL665, followed by emission of light from XL665 at 665 nm.

The assay can be used to detect inhibitors of all three Akt isozymes (Akt1, Akt2, and Akt3) from multiple different species if specific antibodies to each exist.

Materials and Reagents

A. Cell Culture Microtiter Flat Bottom 96 well plates, Corning Costar, Catalog no. 3598

B. Reacti-Bind Protein A Coated 96-well plates, Pierce, Catalog no 15130.

C. Reacti-Bind Protein G Coated 96-well plates, Pierce, Catalog no 15131.

D. Micromix 5 Shaker.

E. Microfluor®B U Bottom Microtiter Plates, Dynex Technologies, Catalog no. 7205.

F. 96 Well Plate Washer, Bio-Tek Instruments, Catalog no. EL 404.

G. Discovery® HTRF Microplate Analyzer, Packard Instrument Company.

Buffer Solutions

A. IP Kinase Cell Lysis Buffer: 1×TBS; 0.2% Tween 20; 1× Protease Inhibitor Cocktail III (Stock is 100×, Calbiochem, 539134); 1× Phosphatase Inhibitor Cocktail I (Stock is 100×, Calbiochem, 524624); and 1× Phosphatase Inhibitor Cocktail II (Stock is 100×, Calbiochem, 524625).

B. 10× Assay Buffer: 500 mM Hepes pH 7.5; 1% PEG; 1 mM EDTA; 1 mM EGTA; and 20 mM β-glycerophosphate.

C. IP Kinase Assay Buffer: 1× Assay Buffer; 50 mM KCl; 150 μM ATP; 10 mM $MgCl_2$; 5% Glycerol; 1 mM DTT; 1 Tablet Protease Inhibitor Cocktail per 50 ml Assay Buffer; and 0.1% BSA D. GSK3β Substrate Solution: IP Kinase Assay Buffer; and 500 nM Biotinylated GSK30 peptide.

E. Lance Buffer: 50 mM Hepes pH 7.5; 0.1% BSA; and 0.1% Triton X-100.

F. Lance Stop Buffer: Lance Buffer; and 33.3 mM EDTA.

G. Lance Detection Buffer: Lance Buffer; 13.3 μg/ml SA-APC; and 0.665 nM EuK Ab a-phospho (Ser-21) GSK3B Multi-Step Immunoprecipitation Akt Kinase Assay Day 1

A. Seed C33a cells Step: Plate 60,000 C33a cells/well in 96 well microtiter plate.

B. Incubate cells overnight at 37° C.

Day 2

D. Compound Addition Step: Add compounds in fresh media (alpha-MEM/10% FBS, room temp) to 96 well plate from above and incubate for 5 hrs in tissue culture incubator.

E. Cell Lysis Step: Aspirate media and add 100 μl of IP Kinase Cell Lysis Buffer.

F. Freeze 96 well microtiter plate at −70° C. (NOTE: This step can be done for a minimum of 1 hour or overnight.)

Day 3

G. Coat Protein A/G 96 well plate Step: Add appropriate concentration of α-Akt antibody (Akt1, Akt2, or Akt3) in a 100 μl of PBS to the following wells:

| | |
|---|---|
| α-Akt 1 (20 ng/well/100 ul) | B2 >>>>>> B10/rows B-G/Akt1 plate |
| α-Akt 2 (50 ng/well/100 ul) | B2 >>>>>> B10/rows B-G/Akt2 plate |
| Rabbit-IgG (150 ng/well/100 ul): | B11-G11 on every plate (Akt1 and Akt2) |

H. Incubate in the cold room (+4° C.) for 4 hours on the Micromix 5 (Form 20; Attitude 2) (NOTE: Attitude depends on which Micromix 5 machine).

I. Aspirate off α-Akt antibody solution and add 100 μl of PBS to each well.

J. Akt Immunoprecipitation Step: To the 100 μl of PBS from Step (I) add 5 μl of thawed cell lysate for Akt1 plates and 10 μl of thawed cell lysate for Akt2 plates. NOTE: Thaw cell lysate on ice. Mix thawed lysate by pipetting up & down 10× before transferring to antibody plates. Keep the cell lysate plates on ice. After transfer of cell lysate to the antibody plates refreeze the cell lysate plates at −70° C.

K. Incubate in the cold room (+4° C.) overnight on Micromix 5 shaker (form 20, attitude 3).

Day 4

L. Immunoprecipitation Plate Wash Step: Wash 96 well plates 1× with TTBS (RCM 51, 1×=2 cycles) using the 96-Well Plate Washer. Fill wells with TTBS and incubate for 10 minutes. Wash 96 well plates 2× with TTBS. (NOTE: Prime plate washer before use: 1. Check buffer reservoirs, making sure they are full and 2. empty waste containers.

M. Manual Plate Wash Step: Add 180 μl of IP Kinase Assay buffer.

N. Start Akt Enzyme Reaction: Aspirate supernatant. Add 60 μl of GSK3β Substrate Solution.

O. Incubate for 2.5 hours on Micromix 5 shaker @ RT. NOTE: Time of incubation should be adjusted so that the ratio of Column 10/Column 11 is not >10.

P. Combine 30 μl of Lance Detection Buffer with 30 μl of Lance Stop Buffer (60 μl total/well) and add to Microfluor U bottom 96 well black plates.

Q. Stop Akt Enzyme Reaction: Transfer 40 μl of Akt Enzyme Reaction Mix from Protein A/G 96 well plate from Step (O) to Microfluor U bottom 96 well black plates from Step (P).

U. Incubate at room temperature for 1-2 hrs on Micromix 5 shaker (form 20, attitude 3), then read with the Discovery HTRF Microplate Analyzer using Akt program.

IP Kinase Cell Lysis Buffer

100 μl per well

| | 8 ml (1 Plate) | 45 ml (6 Plates) |
|---|---|---|
| 1X TBS | 7744 μl | NA |
| Tween 20 | 20 μl | NA |
| 1X Protease Inhibitor Cocktail III | 80 μl | NA |
| 1X Phosphatase Inhibitor Cocktail I | | 450 μl |
| 1X Phosphatase Inhibitor Cocktail II | 80 μl | 450 μl |
| Microcystin LR (500X) | | 450 μl |
| | 80 μl | |
| | | 90 μl |

IP Kinase Assay Buffer

100 μl per well

| | 8 ml (1 Plate) | 50 ml (3 Plates) |
|---|---|---|
| 10X Assay Buffer | 800 μl | 5 ml |
| 1 M KCl | 400 μl | 2.5 ml |

-continued

|  | 8 ml (1 Plate) | 50 ml (3 Plates) |
|---|---|---|
| 250 mM ATP | 4.8 μl | 30 μl |
| 1M MgCl$_2$ | 80 μl | 500 μl |
| Glycerol | 400 μl | 2.5 ml |
| 1M DTT | 8 μl | 50 μl |
| Protease Inhibitor Cocktail | 1 tablet/50 ml | 1 |
| 10% BSA | 80 μl | 500 μl |
| di dH$_2$0 | 6227.2 μl | 38.9 ml |

GSK3β Substrate Solution
60 μl per well

|  | 5 ml (1 Plate) | 7 ml |
|---|---|---|
| IP Kinase Assay Buffer | 5 ml | — |
| 1 mM GSK3β peptide | 2.5 μl | 3.5 μl |

Lance Stop Buffer
30 μl per well

|  | 3 ml (1 Plate) | 5 ml | 5 ml |
|---|---|---|---|
| 1X Lance Buffer | 2800.2 μl |  |  |
| EDTA 0.5 M | 199.8 μl |  |  |

Lance Detection Buffer
30 μl per well

|  | 3 ml (1 Plate) | 5 ml |
|---|---|---|
| SA-APC (1 mg/ml in ddH2O, dilute 1/75.2 in Lance Buffer) | 40 μl | 66.7 μl |
| EuK Ab a-phospho (Ser 21)GSK3β (680 nM, dilute 1/1133 in Lance Buffer) | 2.7 μl | 4.5 μl |

What is claimed is:

1. A compound according to Formula E:

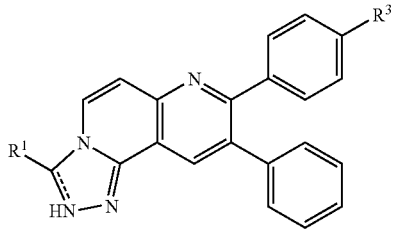

wherein:
a is 0 or 1; b is 0 or 1; m is 0, 1 or 2;
the dashed line represents an optional double bond;
$R^1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_a O_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;
$R^3$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_a O_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one or more substituents selected from $R^6$;
$R^6$ is: $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_bNR^7R^8$, oxo, CHO, $(N=O)R^7R^8$, $S(O)_m NR^7R^8$, SH, $S(O)_m-(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one or more substituents selected from $R^{6a}$;
$R^{6a}$ is selected from: $(C=O)_aO_b(C_1-C_{10})$alkyl, $O_a(C_1-C_3)$perfluoroalkyl, $(C_0-C_6)$alkylene-$S(O)_mR^a$; SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(R^b)_2$, $C(O)R^a$, $(C_0-C_6)$alkylene-$CO_2R^a$, $C(O)H$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$;
$R^7$ and $R^8$ are independently selected from: H, $(C=O)_aO_b (C_1-C_{10})$alkyl, $(C=O)_aO_b(C_3-C_8)$cycloalkyl, $(C=O)_a O_b$-aryl, $(C=O)_aO_b$-heterocyclyl, $(C_2-C_{10})$alkenyl, $(C_2-C_{10})$alkynyl, SH, $SO_2R^a$, and $(C=O)_aNR^b_2$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{6a}$;

$R^a$ is $(C_1-C_6)$alkyl, $(C_3-C_6)$cycloalkyl, aryl, or heterocyclyl; and
$R^b$ is independently: H, $(C_1-C_6)$alkyl, aryl, heterocyclyl, $(C_3-C_6)$cycloalkyl, $(C=O)_aO_b(C_1-C_6)$alkyl, or $S(O)_m R^a$;
or a pharmaceutically acceptable salt, tautomer, or a stereoisomer thereof.

2. A compound according to Formula J:

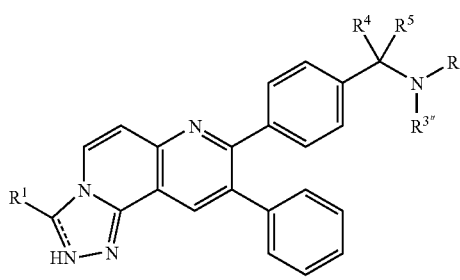

wherein:
a is 0 or 1; b is 0 or 1; m is 0, 1 or 2;
the dashed line represents an optional double bond;
$R^1$ is selected from: $CF^3$, H, oxo, $(C=O)_aO_b(C_1-C_{10})$alkyl, $(C=O)_aO_{b\text{-aryl}}$, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b (C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one to six substituents selected from $R^6$;
$R^{3'}$ and $R^{3''}$ are independently selected from: $CF^3$, H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl, $(C_1-C_6)$alkyl-heterocyclyl and $(C=O)_aO_b$-heterocyclyl, said alkyl, aryl, alkenyl, alkynyl, cycloalkyl, and heterocyclyl is optionally substituted with one to five substituents selected from $R^6$; or $R^{3'}$ and $R^{3''}$ can be taken together with the nitrogen to which they are attached to form a piperidine or pyrrolidine which may be optionally substituted with one to five substituents selected from $R^6$;
$R^4$ and $R^5$ are independently: H, $(C_1-C_6)$alkyl, $(C_1-C_6)$alkenyl, $(C_1-C_6)$alkynyl, wherein said alkyl is optionally substituted with up to three substituents selected from: OH and halo; and wherein $R^4$ and $R^5$ can be taken together to form a $(C_3-C_7)$cycloalkyl, wherein said cycloalkyl is optionally substituted with up to three substituents selected from $R^6$;
$R^6$ is: $CF^3$, $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, halo, CN, OH, $O_bC_1-C_6$ perfluoroalkyl, $O_a(C=O)_bNR^7R^8$, oxo, CHO, $(N=O)R^7R^8$, $S(O)_m NR^7R^8$, SH, $S(O)_m-(C_1-C_{10})$alkyl or $(C=O)_aO_bC_3-C_8$ cycloalkyl, said alkyl, aryl, alkenyl, alkynyl, heterocyclyl, and cycloalkyl optionally substituted with one to five substituents selected from $R^{6a}$;
$R^{6a}$ is selected from: $CF_3$, $(C=O)_aO_b(C_1-C_{10})$alkyl, $O_a(C_1-C_3)$perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$ alkylene-heterocyclyl, $(C_0-C_6)$alkylene-$N(R^b)_2$, $(C=O)_a NR^b_2$, $C(O)R^a$, $(C_0-C_6)$alkylene-$CO_2R^a$, $C(O)H$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O_a(C=O)_b(C_1-C_6)$alkyl, oxo, and $N(R^b)_2$;

$R^7$ and $R^8$ are independently selected from: $CF^3$, H, $(C=O)_a O_b(C_1-C_{10})$alkyl, $(C=O)_a O_b(C_3-C_8)$cycloalkyl, $(C=O)_a O_b$-aryl, $(C=O)_a O_b$-heterocyclyl, $(C_2-C_{10})$alkenyl, $(C_2-C_{10})$alkynyl, SH, $SO_2R^a$, and $(C=O)_a NR^b_2$, said alkyl, cycloalkyl, aryl, heterocyclyl, alkenyl, and alkynyl is optionally substituted with one to five substituents selected from $R^{6a}$, or $R^7$ and $R^8$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one to six substituents selected from $R^{6a}$;

$R^a$ is $(C_1-C_6)$alkyl, $NR^b_2$, $(C_3-C_6)$cycloalkyl, aryl, or heterocyclyl; and $R^b$ is independently: H, $(C_1-C_6)$alkyl, $NH_2$, aryl, heterocyclyl, $(C_3-C_6)$cycloalkyl, $(C=O)_a O_b(C_1-C_6)$alkyl, or $S(O)_m R^a$;

or a pharmaceutically acceptable salt, tautomer, or a stereoisomer thereof.

3. A compound which is selected from:

9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-amine;

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-ol;

9-phenyl-8-(4-{[4-(4-pyridin-2-yl-1H-imidazol-1-yl)piperidin-1-yl]methyl}phenyl) [1,2,4]triazolo[3,4-f]-1,6-naphthyridin-3-amine;

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridin-3-thiol;

3-methyl-9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine;

9-phenyl-8-(4-{[4-(5-pyridin-2-yl-1H-1,2,4-triazol-3-yl)piperidin-1-yl]methyl}phenyl)[1,2,4]triazolo[3,4-f]-1,6-naphthyridine;

3-(chloromethyl)-9-phenyl-8-(4-{[4-(4-pyridin-2-yl-1H-imidazol-1-yl)piperidin-1-yl]methyl}phenyl) [1,2,4]triazolo[3,4-f]-1,6-naphthyridine;

3-[(4-methylpiperazin-1-yl)methyl]-9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridine;

2-({[9-phenyl-8-(4-{[4-(5-pyridin-2-yl-1H-1,2,4-triazol-3-yl)piperidin-1-yl]methyl}phenyl) [1,2,4]triazolo[3,4-f]-1,6-naphthyridin-3-yl]methyl}amino)ethanol;

8-(4-Aminomethyl-phenyl)-9-phenyl-[1,2,4]triazolo[3,4-f][1,6]naphthyridin-3-ol;

1-[4-(9-Phenyl[1,2,4]triazolo[3,4-f]-1,6-naphthyridin-8-yl)phenyl]methanamine;

4-(3-Methyl-9-phenyl-[1,2,4]triazolo[3,4-f][1,6]naphthyridin-8-yl)-benzylamine;

8-[4-(Aminomethyl)phenyl]-9-phenyl[1,2,4]triazolo[3,4-f]-1,6-naphthyridin-3-amine;

1-[4-(9-Phenyl[1,2,4]triazolo[3,4-f]-1,6-naphthyridin-8-yl)phenyl]ethanamine;

9-Phenyl-8-{4-[4-(5-pyridin-2-yl-4H-[1,2,4]triazol-3-yl)-piperidin-1-ylmethyl]-phenyl}-[1,2,4]triazolo[3,4-f][1,6]naphthyridine;

9-phenyl-8-(4-{[4-(5-pyridin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine;

3-(1H-imidazol-4-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine;

tert-butyl[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methylcarbamate;

[9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridin-3-yl]methanol;

5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]-2,4-dihydro-3H-1,2,4-triazol-3-one;

3-(3-methyl-1H-1,2,4-triazol-5-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine;

3-imidazo[2,1-b][1,3]thiazol-6-yl-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine;

9-phenyl-8-(4-{[4-(5-pyridin-2-yl-4H-1,2,4-triazol-3-yl)piperidin-1-yl]methyl}phenyl)-3-[1,2,4]triazolo[1,5-a]pyrimidin-2-yl[1,2,4]triazolo[3,4-f]-1,6-naphthyridine;

3-imidazo[1,2-a]pyridin-2-yl-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

9-phenyl-8-(4-{[4-(5-pyridin-2-yl-4H-1,2,4-triazol-3-yl)piperidin-1-yl]methyl}phenyl)-3-(1H-1,2,4-triazol-5-yl)[1,2,4]triazolo[3,4-f]-1,6-naphthyridine;

3-(1H-benzimidazol-6-yl)-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

3-(1,5-dimethyl-1H-pyrazol-3-yl)-9-phenyl-8-(4-{[4-(5-pyridin-2-yl-4H-1,2,4-triazol-3-yl)piperidin-1-yl]methyl}phenyl)[1,2,4]triazolo[3,4-f]-1,6-naphthyridine;

3-imidazo[1,2-a]pyrimidin-2-yl-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

5-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine;

9-phenyl-3-pyrazolo[1,5-a]pyrimidin-3-yl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

3-(5-methyl-1H-pyrazol-3-yl)-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]pyridin-2-amine;

4-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol;

3-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol;

2-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]phenol;

1-{4-[3-(5-oxo-4,5-dihydro-1H-1,2,4-triazol-3-yl)-9-phenyl[1,2,4]triazolo[3,4-f]-1,6-naphthyridin-8-yl]benzyl}piperidine-4-carboxamide;

1-[4-(3-imidazo[1,2-a]pyridin-2-yl-9-phenyl[1,2,4]triazolo[3,4-f]-1,6-naphthyridin-8-yl)benzyl]piperidine-4-carboxamide;

9-phenyl-8-(4-{[4-(5-pyrazin-2-yl-4H-1,2,4-triazol-3-yl)piperidin-1-yl]methyl}phenyl) [1,2,4]triazolo[3,4-f]-1,6-naphthyridine;

9-phenyl-8-(4-{[4-(5-pyrimidin-2-yl-4H-1,2,4-triazol-3-yl)piperidin-1-yl]methyl}phenyl)-3-(1H-1,2,3-triazol-4-yl)[1,2,4]triazolo[3,4-f]-1,6-naphthyridine;

3-(1-methyl-1H-imidazol-4-yl)-9-phenyl-8-(4-{[4-(5-pyrimidin-2-yl-4H-1,2,4-triazol-3-yl)piperidin-1-yl]methyl}phenyl) [1,2,4]triazolo[3,4-f]-1,6-naphthyridine;

3-(1-methyl-1H-imidazol-4-yl)-9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridine;

3-(1-methyl-1H-imidazol-4-yl)-9-phenyl-8-(4-{[4-(5-pyrazin-2-yl-4H-1,2,4-triazol-3-yl)piperidin-1-yl]methyl}phenyl) [1,2,4]triazolo[3,4-f]-1,6-naphthyridine;

N-[2-(4-methyl-1H-imidazol-2-yl)ethyl]-N-{4-[3-(1-methyl-1H-imidazol-4-yl)-9-phenyl[1,2,4]triazolo[3,4-f]-1,6-naphthyridin-8-yl]benzyl}amine;

$N^1$-(2-hydroxyphenyl)-$N^3$-{4-[3-(1-methyl-1H-imidazol-4-yl)-9-phenyl[1,2,4]triazolo[3,4-f]-1,6-naphthyridin-8-yl]benzyl}-beta-alaninamide;

1-{4-[3-(1-methyl-1H-imidazol-4-yl)-9-phenyl[1,2,4]triazolo[3,4-f]-1,6-naphthyridin-8-yl]benzyl}piperidine-4-carboxamide;

5-[({4-[3-(1-methyl-1H-imidazol-4-yl)-9-phenyl[1,2,4]triazolo[3,4-f]-1,6-naphthyridin-8-yl]benzyl}amino)methyl]pyridin-2-ol;

$N^1,N^1$,2,2-tetramethyl-$N^3$-{4-[3-(1-methyl-1H-imidazol-4-yl)-9-phenyl[1,2,4]triazolo[3,4-f]-1,6-naphthyridin-8-yl]benzyl}propane-1,3-diamine;

3-hydroxy-2,2-dimethyl-N-[4-(3-methyl-9-phenyl[1,2,4]triazolo[3,4-f]-1,6-naphthyridin-8-yl)benzyl]propan-1-amine;

2-fluoro-3-hydroxy-N-[4-(3-methyl-9-phenyl[1,2,4]triazolo[3,4-f]-1,6-naphthyridin-8-yl)benzyl]propan-1-amine;

2,2-difluoro-3-hydroxy-N-[4-(3-methyl-9-phenyl[1,2,4]triazolo[3,4-f]-1,6-naphthyridin-8-yl)benzyl]propan-1-amine;

2,3-dihydroxy-N-[4-(3-methyl-9-phenyl[1,2,4]triazolo[3,4-f]-1,6-naphthyridin-8-yl)benzyl]propan-1-amine;

4-hydroxy-N-[4-(3-methyl-9-phenyl[1,2,4]triazolo[3,4-f]-1,6-naphthyridin-8-yl)benzyl]cyclohexanamine;

4-hydroxy-N-[4-(3-methyl-9-phenyl[1,2,4]triazolo[3,4-f]-1,6-naphthyridin-8-yl)benzyl]cyclohexanamine;

3-hydroxy-2,2-dimethyl-N-{4-[3-(1-methyl-1H-imidazol-4-yl)-9-phenyl[1,2,4]triazolo[3,4-f]-1,6-naphthyridin-8-yl]benzyl}propan-1-amine;

3-hydroxy-2,2-dimethyl-N-[4-(9-phenyl-3-[1,2,4]triazolo[1,5-a]pyrimidin-2-yl[1,2,4]triazolo[3,4-f]-1,6-naphthyridin-8-yl)benzyl]propan-1-amine;

3-hydroxy-2,2-dimethyl-N-[4-(9-phenyl-3-pyrazolo[1,5-a]pyrimidin-2-yl[1,2,4]triazolo[3,4-f]-1,6-naphthyridin-8-yl)benzyl]propan-1-amine;

3-hydroxy-2,2-dimethyl-N-{4-[9-phenyl-3-(1H-1,2,3-triazol-4-yl) [1,2,4]triazolo[3,4-f]-1,6-naphthyridin-8-yl]benzyl}propan-1-amine;

tert-butyl {[8-(4-{[(3-hydroxy-2,2-dimethylpropyl)amino]methyl}phenyl)-9-phenyl[1,2,4]triazolo[3,4-f]-1,6-naphthyridin-3-yl]methyl}carbamate;

N-{4-[3-(ammoniomethyl)-9-phenyl[1,2,4]triazolo[3,4-f]-1,6-naphthyridin-8-yl]benzyl}-3-hydroxy-2,2-dimethylpropan-1-amine;

[9-phenyl-8-(4-{[4-(5-pyrazin-2-yl-4H-1,2,4-triazol-3-yl)piperidin-1yl]methyl}phenyl)[1,2,4]triazolo[3,4-f]-1,6-naphthyridin-3-yl]methanol;

$N^3$-{4-[3-(hydroxymethyl)-9-phenyl[1,2,4]triazolo[3,4-f]-1,6-naphthyridin-8-yl]benzyl}-$N^1$-(2-hydroxyphenyl)-beta-alaninamide;

(8-{4-[(cyclohexylamino)methyl]phenyl}-9-phenyl[1,2,4]triazolo[3,4-f]-1,6-naphthyridin-3-yl)methanol;

$N^3$-{4-[3-(hydroxymethyl)-9-phenyl[1,2,4]triazolo[3,4-f]-1,6-naphthyridin-8-yl]benzyl}-$N^1$-(4-hydroxyphenyl)-beta-alaninamide;

[9-phenyl-8-(4-{[4-(5-pyridin-3-yl-4H-1,2,4-triazol-3-yl)piperidin-1-yl]methyl}phenyl)[1,2,4]triazolo[3,4-f]-1,6-naphthyridin-3-yl]methanol;

1-{4-[3-(hydroxymethyl)-9-phenyl[1,2,4]triazolo[3,4-f]-1,6-naphthyridin-8-yl]benzyl}piperidine-4-carboxamide;

{8-[4-(1-aminocyclopropyl)phenyl]-9-phenyl[1,2,4]triazolo[3,4-f]-1,6-naphthyridin-3-yl}methanol;

1-[4-(9-phenyl-3-pyridin-4-yl[1,2,4]triazolo[3,4-f]-1,6-naphthyridin-8-yl)phenyl]methanamine;

1-{4-[3-(1-oxidopyridin-3-yl)-9-phenyl[1,2,4]triazolo[3,4-f]-1,6-naphthyridin-8-yl]phenyl}methanamine;

1-[4-(3,9-diphenyl[1,2,4]triazolo[3,4-f]-1,6-naphthyridin-8-yl)phenyl]methanamine;

1-{4-[3-(4-fluorophenyl)-9-phenyl[1,2,4]triazolo[3,4-f]-1,6-naphthyridin-8-yl]phenyl}methanamine;

4-{8-[4-(aminomethyl)phenyl]-9-phenyl[1,2,4]triazolo[3,4-f]-1,6-naphthyridin-3-yl}benzonitrile;

4-(9-phenyl-3-pyrimidin-4-yl[1,2,4]triazolo[3,4-f]-1,6-naphthyridin-8-yl)benzylamine;

1-{4-[3-(1-oxidopyridin-2-yl)-9-phenyl[1,2,4]triazolo[3,4-f]-1,6-naphthyridin-8-yl]phenyl}methanamine;

5-{8-[4-(aminomethyl)phenyl]-9-phenyl[1,2,4]triazolo[3,4-f]-1,6-naphthyridin-3-yl}yridine-2-ol;

1-[4-(9-phenyl-3-pyridin-3-yl[1,2,4]triazolo[3,4-f]-1,6-naphthyridin-8-yl)phenyl]methanamine;

4-(9-phenyl-3-pyrimidin-2-yl[1,2,4]triazolo[3,4-f]-1,6-naphthyridin-8-yl)benzylamine;

1-[4-(9-phenyl-3-pyridin-2-yl[1,2,4]triazolo[3,4-f]-1,6-naphthyridin-8-yl)phenyl]methanamine;

1-[4-(9-phenyl-3-pyrazin-2-yl[1,2,4]triazolo[3,4-f]-1,6-naphthyridin-8-yl)phenyl]methanamine;

1-{4-[9-phenyl-3-(1H-1,2,4-triazol-3-yl)[1,2,4]triazolo[3,4-f]-1,6-naphthyridin-8-yl]phenyl}methanamine;

1-{4-[9-phenyl-3-(1,3-thiazol-4-yl)[1,2,4]triazolo[3,4-f]-1,6-naphthyridin-8-yl]phenyl}methanamine;

1-{4-[9-phenyl-3-(1H-pyrazol-4-yl) [1,2,4]triazolo[3,4-f]-1,6-naphthyridin-8-yl]phenyl}methanamine;

1-{4-[3-(3-methyl-1H-pyrazol-4-yl)-9-phenyl[1,2,4]triazolo[3,4-f]-1,6-naphthyridin-8-yl]phenyl}methanamine;

1-{4-[3-(3-methyl-1H-1,2,4-triazol-5-yl)-9-phenyl[1,2,4]triazolo[3,4-f]-1,6-naphthyridin-8-yl]phenyl}methanamine;

1-{4-[3-(1-methyl-1H-pyrazol-4-yl)-9-phenyl[1,2,4]tria-zolo[3,4-f]-1,6-naphthyridin-8-yl]phenyl}methanamine;
1-{4-[9-phenyl-3-(1,2,5-thiadiazol-3-yl) [1,2,4]triazolo[3,4-f]-1,6-naphthyridin-8-yl]phenyl}methanamine;
1-{4-[9-phenyl-3-(1,2,3-thiadiazol-4-yl) [1,2,4]triazolo[3,4-f]-1,6-naphthyridin-8-yl]phenyl}methanamine;
1-[4-(9-phenyl-3-pyrazolo[1,5-a]pyrimidin-3-yl[1,2,4]triazolo[3,4-f]-1,6-naphthyridin-8-yl)phenyl]methanamine;
{8-[4-(aminomethyl)phenyl]-9-phenyl[1,2,4]triazolo[3,4-f]-1,6-naphthyridin-3-yl}methanamine;
{8-[4-(aminomethyl)phenyl]-9-phenyl[1,2,4]triazolo[3,4-f]-1,6-naphthyridin-3-yl}methanol;
1-{4-[9-phenyl-3-(2,2,2-trifluoroethyl)[1,2,4]triazolo[3,4-f]-1,6-naphthyridin-8-yl]phenyl}methanamine;
1-{4-[9-phenyl-3-(1H-tetraazol-1-ylmethyl) [1,2,4]triazolo[3,4-f]-1,6-naphthyridin-8-yl]phenyl}methanamine;
8-[4-(aminomethyl)phenyl]-9-phenyl[1,2,4]triazolo[3,4-f]-1,6-naphthyridine-3-carboxamide;
1-{4-[3-(1H-imidazol-1-ylmethyl)-9-phenyl[1,2,4]triazolo[3,4-f]-1,6-naphthyridin-8-yl]phenyl}methanamine;
1-(4-{3-[(methylsulfonyl)methyl]-9-phenyl[1,2,4]triazolo[3,4-f]-1,6-naphthyridin-8-yl}phenyl)methanamine;
{8-[4-(aminomethyl)phenyl]-9-phenyl[1,2,4]triazolo[3,4-f]-1,6-naphthyridin-3-yl}acetonitrile;
2-{8-[4-(aminomethyl)phenyl]-9-phenyl[1,2,4]triazolo[3,4-f]-1,6-naphthyridin-3-yl}ethanol;
N-({8-[4-(aminomethyl)phenyl]-9-phenyl[1,2,4]triazolo[3,4-f]-1,6-naphthyridin-3-yl}methyl)acetamide;
4-[3-(2-methylimidazo[1,2-a]pyridin-3-yl)-9-phenyl[1,2,4]triazolo[3,4-f]-1,6-naphthyridin-8-yl]benzylamine;
1-[4-(9-phenyl-3-pyrazolo[1,5-a]pyridin-3-yl[1,2,4]triazolo[3,4-f]-1,6-naphthyridin-8-yl)phenyl]methanamine;
1-[4-(3-imidazo[1,2-a]pyridin-2-yl-9-phenyl[1,2,4]triazolo[3,4-f]-1,6-naphthyridin-8-yl)phenyl]methanamine;
1-{4-[9-phenyl-3-(4,5,6,7-tetrahydro-1,2-benzisoxazol-3-yl)[1,2,4]triazolo[3,4-f]-1,6-naphthyridin-8-yl]phenyl}methanamine;
1-[4-(3-imidazo[2, 1-b][1,3]thiazol-6-yl-9-phenyl[1,2,4]triazolo[3,4-f]-1,6-naphthyridin-8-yl)phenyl]methanamine;
1-{4-[3-(1-methyl-1H-imidazol-5-yl)-9-phenyl[1,2,4]triazolo[3,4-f]-1,6-naphthyridin-8-yl]phenyl}methanamine;
1-{4-[3-(1-methyl-1H-imidazol-4-yl)-9-phenyl[1,2,4]triazolo[3,4-f]-1,6-naphthyridin-8-yl]phenyl}methanamine;
4-[3-(1-methyl-5-phenyl-1H-pyrazol-4-yl)-9-phenyl[1,2,4]triazolo[3,4-f]-1,6-naphthyridin-8-yl]benzylamine;
1-{4-[9-phenyl-3-(4,5,6,7-tetrahydro-1-benzothien-3-yl)[1,2,4]triazolo[3,4-f]-1,6-naphthyridin-8-yl]phenyl}methanamine;
1-{4-[3-(1-isopropyl-1H-pyrazol-4-yl)-9-phenyl[1,2,4]triazolo[3,4-f]-1,6-naphthyridin-8-yl]phenyl}methanamine;
1-{4-[9-phenyl-3-(1,4,5,6-tetrahydrocyclopenta[c]pyrazol-3-yl) [1,2,4]triazolo[3,4-f]-1,6-naphthyridin-8-yl]phenyl}methanamine;
1-(4-{9-phenyl-3-[(2S)-pyrrolidin-2-yl][1,2,4]triazolo[3,4-f]-1,6-naphthyridin-8-yl}phenyl)methanamine;
4-[3-(1-aminoethyl)-9-phenyl[1,2,4]triazolo[3,4-f]-1,6-naphthyridin-8-yl]benzylamine;
1-{4-[3-(1H-imidazol-2-yl)-9-phenyl[1,2,4]triazolo[3,4-f]-1,6-naphthyridin-8-yl]phenyl}methanamine;
1-[4-(3-cyclopropyl-9-phenyl[1,2,4]triazolo[3,4-f]-1,6-naphthyridin-8-yl)phenyl]methanamine;
1-{4-[9-phenyl-3-(trifluoromethyl) [1,2,4]triazolo[3,4-f]-1,6-naphthyridin-8-yl]phenyl}methanamine;
1-{4-[3-(5-methyl-1H-pyrazol-3-yl)-9-phenyl[1,2,4]triazolo[3,4-f]-1,6-naphthyridin-8-yl]phenyl}methanamine;
1-{4-[3-(1,5-dimethyl-1H-pyrazol-3-yl)-9-phenyl[1,2,4]triazolo[3,4-f]-1,6-naphthyridin-8-yl]phenyl}methanamine;
4-[3-(1H-indol-2-yl)-9-phenyl[1,2,4]triazolo[3,4-f]-1,6-naphthyridin-8-yl]benzylaminen;
1-{4-[3-(1-methyl-1H-imidazol-2-yl)-9-phenyl[1,2,4]triazolo[3,4-f]-1,6-naphthyridin-8-yl]phenyl}methanamine;
1-{4-[3-(3-methyl-2H-3lambda$^5$-imidazol-4-yl)-9-phenyl[1,2,4]triazolo[3,4-f]-1,6-naphthyridin-8-yl]phenyl}methanamine;
4-[3-(6-chloroimidazo[1,2-a]pyridin-2-yl)-9-phenyl[1,2,4]triazolo[3,4-f]-1,6-naphthyridin-8-yl]benzylamine;
1-{4-[3-(1H-benzimidazol-2-yl)-9-phenyl[1,2,4]triazolo[3,4-f]-1,6-naphthyridin-8-yl]phenyl}methanamine;
4-[3-(5-cyclopropyl-4H-pyrazol-3-yl)-9-phenyl[1,2,4]triazolo[3,4-f]-1,6-naphthyridin-8-yl]benzylamine;
1-{4-[9-phenyl-3-(4,5,6,7-tetrahydro-1H-indazol-3-yl)[1,2,4]triazolo[3,4-f]-1,6-naphthyridin-8-yl]phenyl}methanamine;
4-[9-phenyl-3-(3-phenyl-1H-pyrazol-5-yl)[1,2,4]triazolo[3,4-f]-1,6-naphthyridin-8-yl]benzylamine;
1-(4-{9-phenyl-3-[3-(trifluoromethyl)-1H-pyrazol-5-yl][1,2,4]triazolo[3,4-f]-1,6-naphthyridin-8-yl}phenyl)methanamine;
1-[4-(9-phenyl-3-pyrazolo[1,5-a]pyrimidin-2-yl[1,2,4]triazolo[3,4-f]-1,6-naphthyridin-8-yl)phenyl]methanamine;
1-{4-[3-(1-benzyl-1H-pyrazol-4-yl)-9-phenyl[1,2,4]triazolo[3,4-f]-1,6-naphthyridin-8-yl]phenyl}methanamine;
1-[4-(9-phenyl-3-[1,2,4]triazolo[1,5-a]pyrimidin-2-yl[1,2,4]triazolo[3,4-f]-1,6-naphthyridin-8-yl)phenyl]methanamine;
4-[9-phenyl-3-(1-phenyl-1H-pyrazol-4-yl)[1,2,4]triazolo[3,4-f]-1,6-naphthyridin-8-yl]benzylamine;
1-{4-[9-phenyl-3-(4,5,6,7-tetrahydro-2-benzothien-1-yl)[1,2,4]triazolo[3,4-f]-1,6-naphthyridin-8-yl]phenyl}methanamine;
1-{4-[9-phenyl-3-(5,6,7,8-tetrahydroimidazo[1,2-a]pyridin-2-yl)[1,2,4]triazolo[3,4-f]-1,6-naphthyridin-8-yl]phenyl}methanamine;
2-{8-[4-(aminomethyl)phenyl]-9-phenyl[1,2,4]triazolo[3,4-f]-1,6-naphthyridin-3-yl}propan-2-amine;
1-{8-[4-(aminomethyl)phenyl]-9-phenyl[1,2,4]triazolo[3,4-f]-1,6-naphthyridin-3-yl}ethane-1,2-diol;
4-{8-[4-(aminomethyl)phenyl]-9-phenyl[1,2,4]triazolo[3,4-f]-1,6-naphthyridin-3-yl}imidazolidin-2-one;
(2R)-2-amino-2-{8-[4-(aminomethyl)phenyl]-9-phenyl[1,2,4]triazolo[3,4-f]-1,6-naphthyridin-3-yl}ethanol;
(2R)-2-{8-[4-(aminomethyl)phenyl]-9-phenyl[1,2,4]triazolo[3,4-f]-1,6-naphthyridin-3-yl}-2-(methylamino)ethanol;
1-{4-[3-(5-ethylisoxazol-3-yl)-9-phenyl[1,2,4]triazolo[3,4-f]-1,6-naphthyridin-8-yl]phenyl}methanamine;

5-{8-[4-(aminomethyl)phenyl]-9-phenyl[1,2,4]triazolo[3,4-f]-1,6-naphthyridin-3-yl}-2,4-dihydro-3H-1,2,4-triazol-3-one;
6-{8-[4-(aminomethyl)phenyl]-9-phenyl[1,2,4]triazolo[3,4-f]-1,6-naphthyridin-3-yl}-4,5-dihydropyridazin-3(2H)-one;
6-{8-[4-(aminomethyl)phenyl]-9-phenyl[1,2,4]triazolo[3,4-f]-1,6-naphthyridin-3-yl}pyridazin-3(2H)-one;
N-(4-{8-[4-(aminomethyl)phenyl]-9-phenyl[1,2,4]triazolo[3,4-f]-1,6-naphthyridin-3-yl}phenyl)acetamide;
1-{4-[3-(4-phenoxyphenyl)-9-phenyl[1,2,4]triazolo[3,4-f]-1,6-naphthyridin-8-yl]phenyl}methanamine;
1-{4-[3-(1H-benzimidazol-5-yl)-9-phenyl[1,2,4]triazolo[3,4-f]-1,6-naphthyridin-8-yl]phenyl}methanamine;
(4-{8-[4-(aminomethyl)phenyl]-9-phenyl[1,2,4]triazolo[3,4-f]-1,6-naphthyridin-3-yl}phenyl)methanol;
4-[3-(4-cyclohexylphenyl)-9-phenyl[1,2,4]triazolo[3,4-f]-1,6-naphthyridin-8-yl]benzylamine;
4-{8-[4-(aminomethyl)phenyl]-9-phenyl[1,2,4]triazolo[3,4-f]-1,6-naphthyridin-3-yl}-1,3-dihydro-2H-imidazol-2-one;
1-{4-[3-(4-methyl-1H-imidazol-5-yl)-9-phenyl[1,2,4]triazolo[3,4-f]-1,6-naphthyridin-8-yl]phenyl}methanamine;
4-[9-phenyl-3-(1-propyl-1H-imidazol-4-yl)[1,2,4]triazolo[3,4-f]-1,6-naphthyridin-8-yl]benzylamine;
1-{4-[3-(1-isopropyl-1H-imidazol-4-yl)-9-phenyl[1,2,4]triazolo[3,4-f]-1,6-naphthyridin-8-yl]phenyl}methanamine;
1-{4-[3-(1-butyl-1H-imidazol-4-yl)-9-phenyl[1,2,4]triazolo[3,4-f]-1,6-naphthyridin-8-yl]phenyl}methanamine;
1-[4-(3-imidazo[1,2-a]pyrimidin-2-yl-9-phenyl[1,2,4]triazolo[3,4-f]-1,6-naphthyridin-8-yl)phenyl]methanamine;
5-({[4-(3-methyl-9-phenyl[1,2,4]triazolo[3,4-f]-1,6-naphthyridin-8-yl)benzyl]amino}methyl)pyridin-2-ol;
1-(6-methoxypyridin-3-yl)-N-[4-(3-methyl-9-phenyl[1,2,4]triazolo[3,4-f]-1,6-naphthyridin-8-yl)benzyl]methanamine;
N-[(2-methoxypyrimidin-5-yl)methyl]-N-[4-(3-methyl-9-phenyl[1,2,4]triazolo[3,4-f]-1,6-naphthyridin-8-yl)benzyl]amine;
1-[4-(3-ethyl-9-phenyl[1,2,4]triazolo[3,4-f]-1,6-naphthyridin-8-yl)phenyl]methanamine;
1-[4-(9-phenyl-3-propyl[1,2,4]triazolo[3,4-f]-1,6-naphthyridin-8-yl)phenyl]methanamine;
N-[4-(9-phenyl[1,2,4]triazolo[3,4-f]-1,6-naphthyridin-8-yl)benzyl]acetamide;
4-({[4-(9-phenyl[1,2,4]triazolo[3,4-f]-1,6-naphthyridin-8-yl)benzyl]amino}methyl)phenol;
1-[9-phenyl-8-(4-{[4-(5-pyridin-2-yl-4H-1,2,4-triazol-3-yl)piperidin-1-yl]methyl}phenyl) [1,2,4]triazolo[3,4-f]-1,6-naphthyridin-3-yl]methanamine;
9-phenyl-3-(1H-1,2,3-triazol-4-yl)-8-(4-{[4-(4H-1,2,4-triazol-3-yl)piperidin-1-yl]methyl}phenyl) [1,2,4]triazolo[3,4-f]-1,6-naphthyridine;
1-{4-[3-(1H-Imidazol-4-yl)-9-phenyl[1,2,4]triazolo[3,4-f]-1,6-naphthyridin-8-yl]phenyl}methanamine;
1-{4-[9-phenyl-3-(3H-1 lambda$^4$,3-thiazol-5-yl) [1,2,4]triazolo[3,4-f]-1,6-naphthyridin-8-yl]phenyl}methanamine;
1-{4-[9-phenyl-3-(1H-pyrazol-3-yl)-2H-4lambda$^5$-[1,2,4]triazolo[3,4-f]-1,6-naphthyridin-8-yl]phenyl}methanamine;
1-{4-[9-phenyl-3-(1,3-thiazol-4-yl)[1,2,4]triazolo[3,4-f]-1,6-naphthyridin-8-yl]phenyl}methanamine;
4-[9-Phenyl-3-(pyrrolidin-1-ylmethyl)[1,2,4]triazolo[3,4-f]-1,6-naphthyridin-8-yl]benzylamine;
1-{4-[3-(azetidin-1-ylmethyl)-9-phenyl[1,2,4]triazolo[3,4-f]-1,6-naphthyridin-8-yl]phenyl}methanamine;
1-({8-[4-(aminomethyl)phenyl]-9-phenyl[1,2,4]triazolo[3,4-f]-1,6-naphthyridin-3-yl}methyl)piperidine-4-carboxamide;
1-{4-[3-(morpholin-4-ylmethyl)-9-phenyl[1,2,4]triazolo[3,4-f]-1,6-naphthyridin-8-yl]phenyl}methanamine;
2-[({8-[4-(aminomethyl)phenyl]-9-phenyl[1,2,4]triazolo[3,4-f]-1,6-naphthyridin-3-yl}methyl)amino]ethanol;
1-(4-{3-[(4-methyl piperazin-1-yl)methyl]-9-phenyl[1,2,4]triazolo[3,4-f]-1,6-naphthyridin-8-yl}phenyl)methanamine;
4-[9-phenyl-3-(piperazin-1-ylmethyl)[1,2,4]triazolo[3,4-f]-1,6-naphthyridin-8-yl]benzylamine;
N-({8-[4-(aminomethyl)phenyl]-9-phenyl[1,2,4]triazolo[3,4-f]-1,6-naphthyridin-3-yl}methyl)-N-methylamine;
N-({8-[4-(aminomethyl)phenyl]-9-phenyl[1,2,4]triazolo[3,4-f]-1,6-naphthyridin-3-yl}methyl)-N,N-dimethylamine;
[4-(3-Methyl-9-phenyl[1,2,4]triazolo[3,4-f]-1,6-naphthyridin-8-yl)phenyl]methanol;
{4-[3-(1-Methyl-1H-imidazol-4-yl)-9-phenyl[1,2,4]triazolo[3,4-f]-1,6-naphthyridin-8-yl]phenyl}methanol;
1-[4-(9-Phenyl-3-[1,2,4]triazolo[1,5-a]pyrimidin-2-yl[1,2,4]triazolo[3,4-f]-1,6-naphthyridin-8-yl]phenyl]ethanol;
9-phenyl-8-(4-{[4-(4H-1,2,4-triazol-3-yl)piperidin-1-yl]methyl}phenyl)[1,2,4]triazolo[3,4-f]-1,6-naphthyridine;
3-methyl-9-phenyl-8-(4-{[4-(4H-1,2,4-triazol-3-yl)piperidin-1-yl]methyl}phenyl) [1,2,4]triazolo[3,4-f]-1,6-naphthyridine;
9-phenyl-8-(4-{[4-(4H-1,2,4-triazol-3-yl)piperidin-1-yl]methyl}phenyl)[1,2,4]triazolo[3,4-f]-1,6-naphthyridin-3-ol;
1-[4-(3-Methyl-9-phenyl[1,2,4]triazolo[3,4-f]-1,6-naphthyridin-8-yl)phenyl]cyclopropanamine;
1-{4-[3-(1-methyl-1H-imidazol-4-yl)-9-phenyl[1,2,4]triazolo[3,4-f]-1,6-naphthyridin-8-yl]phenyl}cyclopropanamine;
1-[4-(9-phenyl-3-[1,2,4]triazolo[1,5-a]pyrimidin-2-yl[1,2,4]triazolo[3,4-f]-1,6-naphthyridin-8-yl]phenyl]cyclopropanamine;
1-{4-[9-phenyl-3-(5,6,7,8-tetrahydro imidazo[1,2-a]pyridin-2-yl) [1,2,4]triazolo[3,4-f]-1,6-naphthyridin-8-yl]phenyl}cyclopropanamine;
1-[4-(9-phenyl-3-pyrimidin-2-yl[1,2,4]triazolo[3,4-f]-1,6-naphthyridin-8-yl)phenyl]cyclopropanamine;
1-{4-[3-(1,5-dimethyl-1H-pyrazol-3-yl)-9-phenyl[1,2,4]triazolo[3,4-f]-1,6-naphthyridin-8-yl]phenyl}cyclopropanamine;
(1R)-1-[4-(3-Methyl-9-phenyl[1,2,4]triazolo[3,4-f]-1,6-naphthyridin-8-yl)phenyl]ethanamine;
(1R)-1-[4-(9-phenyl[1,2,4]triazolo[3,4-f]-1,6-naphthyridin-8-yl)phenyl]ethanamine;
(1R)-1-{4-[9-Phenyl-3-(5-pyridin-2-yl-1H-pyrazol-3-yl) [1,2,4]triazolo[3,4-f]-1,6-naphthyridin-8-yl]phenyl}ethanamine;
(1R)-1-{4-[3-(hydroxymethyl)-9-phenyl[1,2,4]triazolo[3,4-f]-1,6-naphthyridin-8-yl]phenyl}ethanamine;
(1R)-1-{4-[3-(1-methyl-1H-imidazol-4-yl)-9-phenyl[1,2,4]triazolo[3,4-f]-1,6-naphthyridin-8-yl]phenyl}ethanamine;

(1R)-1-[4-(9-phenyl-3-[1,2,4]triazolo[1,5-a]pyrimidin-2-yl[1,2,4]triazolo[3,4-f]-1,6-naphthyridin-8-yl)phenyl]ethanamine;
(1R)-1-[4-(3-imidazo[2,1-b][1,3]thiazol-6-yl-9-phenyl[1,2,4]triazolo[3,4-f]-1,6-naphthyridin-8-yl)phenyl]ethanamine;
(1R)-1-[4-(9-phenyl-3-pyrimidin-2-yl[1,2,4]triazolo[3,4-f]-1,6-naphthyridin-8-yl)phenyl]ethanamine;
(1R)-1-[4-(9-Phenyl[1,2,4]triazolo[3,4-f]-1,6-naphthyridin-8-yl)phenyl]propan-1-amine;
2-[4-(3-methyl-9-phenyl[1,2,4]triazolo[3,4-f]-1,6-naphthyridin-8-yl)phenyl]propan-2-amine;
2-[4-(9-phenyl[1,2,4]triazolo[3,4-f]-1,6-naphthyridin-8-yl)phenyl]propan-2-amine;
3-(2-{[4-(3-methyl-9-phenyl[1,2,4]triazolo[3,4-f]-1,6-naphthyridin-8-yl)benzyl]amino}-2-oxoethyl)pyridine;
N-[4-(3-methyl-9-phenyl[1,2,4]triazolo[3,4-f]-1,6-naphthyridin-8-yl)benzyl]-5-pyridin-4-yl-2-furamide;
N-[4-(3-methyl-9-phenyl[1,2,4]triazolo[3,4-f]-1,6-naphthyridin-8-yl)benzyl]-5-pyridin-3-yl-2-furamide;
N-[4-(3-methyl-9-phenyl[1,2,4]triazolo[3,4-f]-1,6-naphthyridin-8-yl)benzyl]-5-pyridin-3-yl-1H-pyrrole-3-carboxamide;
2-hydroxy-N-[4-(3-methyl-9-phenyl[1,2,4]triazolo[3,4-f]-1,6-naphthyridin-8-yl)benzyl]acetamide;
tert-butyl (2-{[4-(3-methyl-9-phenyl[1,2,4]triazolo[3,4-f]-1,6-naphthyridin-8-yl)benzyl]amino}-2-oxoethyl)carbamate;
4-(2-{[4-(3-methyl-9-phenyl[1,2,4]triazolo[3,4-f]-1,6-naphthyridin-8-yl)benzyl]amino}-2-oxoethyl)morpholine;
2-{[4-(3-methyl-9-phenyl[1,2,4]triazolo[3,4-f]-1,6-naphthyridin-8-yl)benzyl]amino}-2-oxoethanamine;
4-(2-{[4-(3-methyl-9-phenyl[1,2,4]triazolo[3,4-f]-1,6-naphthyridin-8-yl)benzyl]amino}-2-oxoethyl)pyridine;
2,4-dihydroxy-6-(2-{[4-(3-methyl-9-phenyl[1,2,4]triazolo[3,4-f]-1,6-naphthyridin-8-yl)benzyl]amino}-2-oxoethyl)pyrimidine;
2-(2-{[4-(3-methyl-9-phenyl[1,2,4]triazolo[3,4-f]-1,6-naphthyridin-8-yl)benzyl]amino}-2-oxoethyl)pyridine;
3-(2-{[4-(3-methyl-9-phenyl[1,2,4]triazolo[3,4-f]-1,6-naphthyridin-8-yl)benzyl]amino}-2-oxoethyl)pyridine;
N-[4-(3-methyl-9-phenyl[1,2,4]triazolo[3,4-f]-1,6-naphthyridin-8-yl)benzyl]-2-pyrazin-2-ylacetamide;
3-methyl-9-phenyl-8-[4-({[(pyridin-3-ylamino)carbonyl]amino}methyl)phenyl][1,2,4]triazolo[3,4-f]-1,6-naphthyridine;
2-(2-hydroxyphenyl)-N-[4-(3-methyl-9-phenyl[1,2,4]triazolo[3,4-f]-1,6-naphthyridin-8-yl)benzyl]acetamide;
2-(3-hydroxyphenyl)-N-[4-(3-methyl-9-phenyl[1,2,4]triazolo[3,4-f]-1,6-naphthyridin-8-yl)benzyl]acetamide;
2-(4-hydroxyphenyl)-N-[4-(3-methyl-9-phenyl[1,2,4]triazolo[3,4-f]-1,6-naphthyridin-8-yl)benzyl]acetamide;
2-(3,4-dihydroxyphenyl)-N-[4-(3-methyl-9-phenyl[1,2,4]triazolo[3,4-f]-1,6-naphthyridin-8-yl)benzyl]acetamide;
N-[4-(3-methyl-9-phenyl[1,2,4]triazolo[3,4-f]-1,6-naphthyridin-8-yl)benzyl]-2-phenylacetamide;
3-methyl-9-phenyl-8-(4-{[(pyridin-3-ylcarbonyl)amino]methyl}phenyl)[1,2,4]triazolo[3,4-f]-1,6-naphthyridine;
2-hydroxy-N-[4-(3-methyl-9-phenyl[1,2,4]triazolo[3,4-f]-1,6-naphthyridin-8-yl)benzyl]benzamide;
2-(4-hydroxyphenyl)-2-methyl-N-[4-(3-methyl-9-phenyl[1,2,4]triazolo[3,4-f]-1,6-naphthyridin-8-yl)benzyl]propanamide;
methyl 4-{[4-(3-methyl-9-phenyl[1,2,4]triazolo[3,4-f]-1,6-naphthyridin-8-yl)benzyl]amino}-4-oxobutanoate;
2-hydroxy-N-(2-{[4-(3-methyl-9-phenyl[1,2,4]triazolo[3,4-f]-1,6-naphthyridin-8-yl)benzyl]amino}-2-oxoethyl)benzamide;
N-[4-(3-methyl-9-phenyl[1,2,4]triazolo[3,4-f]-1,6-naphthyridin-8-yl)benzyl]-2-(5-phenyl-4H-1,2,4-triazol-3-yl)acetamide;
3-methyl-9-phenyl-8-(4-{[(quinolin-3-ylcarbonyl)amino]methyl}phenyl)[1,2,4]triazolo[3,4-f]-1,6-naphthyridine;
N-[4-(3-methyl-9-phenyl[1,2,4]triazolo[3,4-f]-1,6-naphthyridin-8-yl)benzyl]-2-(4-oxoquinazolin-3(4H)-yl)acetamide;
N-[4-(3-methyl-9-phenyl[1,2,4]triazolo[3,4-f]-1,6-naphthyridin-8-yl)benzyl]-2-(2-oxo-1,3-benzoxazol-3(2H)-yl)acetamide;
8-(4-{[(1H-benzimidazol-1-ylacetyl)amino]methyl}phenyl)-3-methyl-9-phenyl[1,2,4]triazolo[3,4-f]-1,6-naphthyridine;
8-(4-{[(1H-benzimidazol-2-ylacetyl)amino]methyl}phenyl)-3-methyl-9-phenyl[1,2,4]triazolo[3,4-f]-1,6-naphthyridine;
2-(4-methyl-1,2,5-oxadiazol-3-yl)-N-[4-(3-methyl-9-phenyl[1,2,4]triazolo[3,4-f]-1,6-naphthyridin-8-yl)benzyl]acetamide;
2-(1H-indazol-1-yl)-N-[4-(3-methyl-9-phenyl[1,2,4]triazolo[3,4-f]-1,6-naphthyridin-8-yl)benzyl]acetamide;
2-(5,6-dimethyl-4-oxothieno[2,3-d]pyrimidin-3(4H)-yl)-N-[4-(3-methyl-9-phenyl[1,2,4]triazolo[3,4-f]-1,6-naphthyridin-8-yl)benzyl]acetamide;
3-methyl-8-[4-({[(6-morpholin-4-ylpyridin-3-yl)carbonyl]amino}methyl)phenyl]-9-phenyl[1,2,4]triazolo[3,4-f]-1,6-naphthyridine;
2-(6-chloropyridin-3-yl)-N-[4-(3-methyl-9-phenyl[1,2,4]triazolo[3,4-f]-1,6-naphthyridin-8-yl)benzyl]acetamide;
3-cyano-N-[4-(3-methyl-9-phenyl[1,2,4]triazolo[3,4-f]-1,6-naphthyridin-8-yl)benzyl]propanamide;
3-methyl-9-phenyl-8-(4-{[(3-pyridin-3-ylpropanoyl)amino]methyl}phenyl)[1,2,4]triazolo[3,4-f]-1,6-naphthyridine;
3-(1-methyl-1H-imidazol-4-yl)-9-phenyl-8-(4-{[(pyridin-3-ylacetyl)amino]methyl}phenyl)[1,2,4]triazolo[3,4-f]-1,6-naphthyridine;
9-phenyl-3-pyrazolo[1,5-a]pyrimidin-3-yl-8-(4-{[(pyridin-3-ylacetyl)amino]methyl}phenyl)[1,2,4]triazolo[3,4-f]-1,6-naphthyridine;
N-(3-hydroxy-2,2-dimethylpropyl)-N-[4-(3-methyl-9-phenyl[1,2,4]triazolo[3,4-f]-1,6-naphthyridin-8-yl)benzyl]acetamide;
N-(3-hydroxy-2,2-dimethylpropyl)-N-{4-[3-(1-methyl-1H-imidazol-4-yl)-9-phenyl[1,2,4]triazolo[3,4-f]-1,6-naphthyridin-8-yl]benzyl}-2-(4-oxoquinazolin-3(4H)-yl)acetamide;
tert-butyl {2-[[4-(3-{[(tert-butoxycarbonyl)amino]methyl}-9-phenyl[1,2,4]triazolo[3,4-f]-1,6-naphthyridin-8-yl)benzyl](3-hydroxy-2,2-dimethylpropyl)amino]-2-oxoethyl}carbamate;
3-methyl-9-phenyl-8-(4-{1-[(pyridin-3-ylacetyl)amino]cyclopropyl}phenyl)[1,2,4]triazolo[3,4-f]-1,6-naphthyridine;

3-methyl-9-phenyl-8-(4-{1-[(quinolin-3-yl carbonyl)amino]cyclopropyl}phenyl)[1,2,4]triazolo[3,4-f]-1,6-naphthyridine;

N-{1-[4-(3-methyl-9-phenyl[1,2,4]triazolo[3,4-f]-1,6-naphthyridin-8-yl)phenyl]cyclopropyl}-2-(4-oxoquinazolin-3(4H)-yl)acetamide;

3-(1-methyl-1H-imidazol-4-yl)-9-phenyl-8-(4-{1-[(pyridin-3-ylacetyl)amino]cyclopropyl}phenyl)[1,2,4]triazolo[3,4-f]-1,6-naphthyridine;

N-{(1R)-1-[4-(3-methyl-9-phenyl[1,2,4]triazolo[3,4-f]-1,6-naphthyridin-8-yl)phenyl]ethyl}-2-pyridin-3-ylacetamide;

N-{(1R)-1-[4-(3-methyl-9-phenyl[1,2,4]triazolo[3,4-f]-1,6-naphthyridin-8-yl)phenyl]ethyl}acetamide;

N-((1R)-1-{4-[3-(hydroxymethyl)-9-phenyl[1,2,4]triazolo[3,4-f]-1,6-naphthyridin-8-yl]phenyl}ethyl)-2-pyridin-3-ylacetamide;

N-{1-methyl-1-[4-(9-phenyl[1,2,4]triazolo[3,4-f]-1,6-naphthyridin-8-yl)phenyl]ethyl}acetamide; and N-{1-methyl-1-[4-(3-methyl-9-phenyl[1,2,4]triazolo[3,4-f]-1,6-naphthyridin-8-yl)phenyl]ethyl}acetamide;

or a pharmaceutically acceptable salt or stereoisomer thereof.

4. A pharmaceutical composition comprising a pharmaceutical carrier, and dispersed therein, a therapeutically effective amount of a compound of claim 1.

* * * * *

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Completely Synthetic DNA Sequence

<400> SEQUENCE: 1
ctgcggccgc                                                         10

<210> SEQ ID NO 2
<211> LENGTH: 14
<212> TYPE: DNA
<213> ORGANISM: Artificial Sequence
<220> FEATURE:
<223> OTHER INFORMATION: Completely Synthetic DNA Sequence

<400> SEQUENCE: 2
gtacgcggcc gcag                                                    14

<210> SEQ ID NO 3
<211> LENGTH: 39
<212> TYPE: DNA
<213> ORGANISM: Artificial Sequence
<220> FEATURE:
<223> OTHER INFORMATION: Completely Synthetic DNA Sequence

<400> SEQUENCE: 3
cgcgaattca gatctaccat gagcgacgtg gctattgtg                         39

<210> SEQ ID NO 4
<211> LENGTH: 33
<212> TYPE: DNA
<213> ORGANISM: Artificial Sequence
<220> FEATURE:
<223> OTHER INFORMATION: Completely Synthetic DNA Sequence

<400> SEQUENCE: 4
cgctctagag gatcctcagg ccgtgctgct ggc                               33

```
<210> SEQ ID NO 5
<211> LENGTH: 24
<212> TYPE: DNA
<213> ORGANISM: Artificial Sequence
<220> FEATURE:
<223> OTHER INFORMATION: Completely Synthetic DNA Sequence

<400> SEQUENCE: 5
gtacgatgct gaacgatatc ttcg                                          24

<210> SEQ ID NO 6
<211> LENGTH: 45
<212> TYPE: DNA
<213> ORGANISM: Artificial Sequence
<220> FEATURE:
<223> OTHER INFORMATION: Completely Synthetic DNA Sequence

<400> SEQUENCE: 6
gaatacatgc cgatggaaag cgacggggct gaagagatgg aggtg                   45

<210> SEQ ID NO 7
<211> LENGTH: 45
<212> TYPE: DNA
<213> ORGANISM: Artificial Sequence
<220> FEATURE:
<223> OTHER INFORMATION: Completely Synthetic DNA Sequence

<400> SEQUENCE: 7
cccctccatc tcttcagccc cgtcgctttc catcggcatg tattc                   45

<210> SEQ ID NO 8
<211> LENGTH: 36
<212> TYPE: DNA
<213> ORGANISM: Artificial Sequence
<220> FEATURE:
<223> OTHER INFORMATION: Completely Synthetic DNA Sequence

<400> SEQUENCE: 8
gaattcagat ctaccatgag cgatgttacc attgtg                             36

<210> SEQ ID NO 9
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 9
tctagatctt attctcgtcc acttgcagag                                    30

<210> SEQ ID NO 10
<211> LENGTH: 48
<212> TYPE: DNA
<213> ORGANISM: Artificial Sequence
<220> FEATURE:
<223> OTHER INFORMATION: Completely Synthetic DNA Sequence

<400> SEQUENCE: 10
ggtaccatgg aatacatgcc gatggaaagc gatgttacca ttgtgaag                48

<210> SEQ ID NO 11
<211> LENGTH: 33
<212> TYPE: DNA
<213> ORGANISM: Artificial Sequence
<220> FEATURE:
<223> OTHER INFORMATION: Completely Synthetic DNA Sequence
```

```
<400> SEQUENCE: 11
aagcttagat ctaccatgaa tgaggtgtct gtc                          33

<210> SEQ ID NO 12
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 12
gaattcggat cctcactcgc ggatgctggc                              30

<210> SEQ ID NO 13
<211> LENGTH: 49
<212> TYPE: DNA
<213> ORGANISM: Artificial Sequence
<220> FEATURE:
<223> OTHER INFORMATION: Completely Synthetic DNA Sequence

<400> SEQUENCE: 13
ggtaccatgg aatacatgcc gatggaaaat gaggtgtctg tcatcaaag         49

<210> SEQ ID NO 14
<211> LENGTH: 6
<212> TYPE: PRT
<213> ORGANISM: Artificial Sequence
<220> FEATURE:
<223> OTHER INFORMATION: Completely Synthetic Amino Acid Sequence

<400> SEQUENCE: 14

Glu Tyr Met Pro Met Glu
  1               5

<210> SEQ ID NO 15
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 15

Gly Gly Arg Ala Arg Thr Ser Ser Phe Ala Glu Pro Gly
  1               5                  10

<210> SEQ ID NO 16
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 16

Lys Lys Gly Gly Arg Ala Arg Thr Ser Ser Phe Ala Glu Pro Gly
  1               5                  10                  15
```